(12) United States Patent
Cramp et al.

(10) Patent No.: US 7,858,640 B2
(45) Date of Patent: Dec. 28, 2010

(54) QUINOLINES AND THEIR THERAPEUTIC USE

(75) Inventors: Michael Colin Cramp, Essex (GB); Rosa Arienzo, Essex (GB); George Hynd, Essex (GB); Peter Crackett, Hertfordshire (GB); Yann Griffon, Essex (GB); Trevor Keith Harrison, Essex (GB); Nicholas Charles Ray, Essex (GB); Harry Finch, Essex (GB); John Gary Montana, Essex (GB)

(73) Assignee: Pulmagen Therapeutics (Asthma) Limited, Slough (GB)

( * ) Notice: Subject to any disclaimer, the term of this patent is extended or adjusted under 35 U.S.C. 154(b) by 11 days.

(21) Appl. No.: 12/066,603

(22) PCT Filed: Sep. 29, 2006

(86) PCT No.: PCT/GB2006/003644

§ 371 (c)(1),
(2), (4) Date: Aug. 4, 2008

(87) PCT Pub. No.: WO2007/036743

PCT Pub. Date: Apr. 5, 2007

(65) Prior Publication Data

US 2009/0156600 A1  Jun. 18, 2009

(30) Foreign Application Priority Data

Sep. 30, 2005 (GB) .................... 0519969.0
May 26, 2006 (GB) .................... 0610551.4

(51) Int. Cl.
*A01N 43/42* (2006.01)
*A61K 31/47* (2006.01)
*C07D 215/00* (2006.01)
*C07D 215/38* (2006.01)

(52) U.S. Cl. ............... 514/311; 514/312; 514/313; 546/152; 546/153; 546/159

(58) Field of Classification Search ............... 514/311, 514/312, 313; 546/152, 159
See application file for complete search history.

(56) References Cited

U.S. PATENT DOCUMENTS

2004/0127708 A1* 7/2004 Fuji et al. ................... 544/281

FOREIGN PATENT DOCUMENTS

| EP | 0 101 330 | 2/1984 |
|---|---|---|
| EP | 0 556 060 | 8/1993 |
| EP | 1 413 306 | 4/2004 |
| WO | WO 03/066046 | 8/2003 |
| WO | WO 2004106302 | * 5/2004 |

OTHER PUBLICATIONS

Vippagunta et. al., Advanced Drug Delivery Reviews, 2001, Elsevier, vol. 48, pp. 3-26.*
Lloyd, J. et al., "Quinoline-4-carboxylic acids as angiotensin II receptor antagonists," *Bioorganic & Medicinal Chemistry Letters*, 1994, vol. 4, No. 1, pp. 195-200.

* cited by examiner

*Primary Examiner*—Sreeni Padmanabhan
*Assistant Examiner*—Sarah Pihonak
(74) *Attorney, Agent, or Firm*—Saliwanchik, Lloyd & Saliwanchik

(57) ABSTRACT

Compounds of formula [1] are CRTH2 antagonists, useful in the treatment of conditions having an inflammatory components; in which: $R^1$-$R^9$ are various substituents; A is —CHR$^{10}$—, —C(O)—, —S(O)n—, —O—, or —NR$^{10}$— wherein n is an integer from 0-1 and $R^{10}$ is selected from various substituents; B is a direct bond or a divalent radical; $R^{11}$ and $R^{12}$ are selected from cvarious substituents; X is a carboxylic acid, tetrazole, 3-hydroxyisoxazole, hydroxamic acid, phosphinate, phosphonate, phosphonamide, sulfonic acid group, or a group of formula C=(O)NHSO$_2$R$^6$ or SO$_2$NHC(=O)R$^6$; and Y is aryl, heteroaryl, aryl-fused-heterocycloalkyl, heteroaryl-fused-cycloalkyl, heteroaryl-fused-heterocycloalkyl or aryl-fused-cycloalkyl group.

(1)

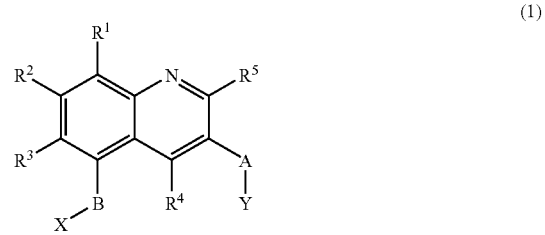

5 Claims, No Drawings

QUINOLINES AND THEIR THERAPEUTIC USE

CROSS-REFERENCE TO A RELATED APPLICATION

This application is a National Stage Application of International Application Number PCT/GB2006/003644, filed Sep. 29, 2006; which claims priority to Great Britain Application Nos. 0519969.0, filed Sep. 30, 2005 and 0610551.4, filed May 26, 2006, in their entirety.

FIELD OF THE INVENTION

This invention relates to a class of quinoline compounds which are ligands of the CRTH2 receptor (Chemoattractant Receptor-homologous molecule expressed on T Helper cells type 2), and their use in therapy, in particular the treatment of diseases responsive to modulation of CRTH2 receptor activity, principally diseases having a significant inflammatory component. The invention also relates to novel members of that class of ligands and pharmaceutical compositions containing them.

BACKGROUND TO THE INVENTION

Mast cells are known to play an important role in allergic and immune responses through the release of a number of mediators, such as histamine leukotrienes, cytokines, prostaglandin $D_2$, etc (Boyce; Allergy Asthma Proc., 2004, 25, 27-30). Prostaglandin $D_2$ ($PGD_2$) is the major metabolite produced by the action of cyclooxygenase on arachadonic acid by mast cells in response to allergen challenge (Lewis et al; J. Immunol., 1982, 129, 1627-1631). It has been shown that $PGD_2$ production is increased in patients with systemic mastocytosis (Roberts; N. Engl. J. Med., 1980, 303, 1400-1404), allergic rhinitis (Naclerio et al; Am. Rev. Respir. Dis., 1983, 128, 597-602; Brown et al; Arch. Otolarynol. Head Neck Surg., 1987, 113, 179-183; Lebel et al; J. Allergy Clin. Immunol., 1988, 82, 869-877), bronchial asthma (Murray et al; N. Engl. J. Med., 1986, 315, 800-804; Liu et al; Am. Rev. Respir. Dis., 1990, 142, 126-132; Wenzel et al; J. Allergy Clin. Immunol., 1991, 87, 540-548), and urticaria (Heavey et al; J. Allergy Clin. Immunol., 1986, 78, 458-461). $PGD_2$ mediates it effects through two receptors, the $PGD_2$ (or DP) receptor (Boie et al; J. Biol. Chem., 1995, 270, 18910-18916) and the chemoattractant receptor-homologous molecule expressed on Th2 (or CRTH2) (Nagata et al; J. Immunol., 1999, 162, 1278-1289; Powell; Prostaglandins Luekot. Essent. Fatty Acids, 2003, 69, 179-185). Therefore, it has been postulated that agents that antagonise the effects of $PGD_2$ at its receptors may have beneficial effects in number of disease states.

The CRTH2 receptor has been shown to be expressed on cell types associated with allergic inflammation, such as basophils, eosinophils, and Th2-type immune helper cells (Hirai et al; J. Exp. Med., 2001, 193, 255-261). The CRTH2 receptor has been shown to mediate $PGD_2$-mediated cell migration in these cell types (Hirai et al; J. Exp. Med., 2001, 193, 255-261), and also to play a major role in neutrophil and eosinophil cell recruitment in a model of contact dermatitis (Takeshita et al; Int. Immunol., 2004, 16, 947-959). Ramatroban {(3R)-3-[(4-fluorophenyl)sulphonyl-amino]-1,2,3,4-tetrahydro-9H-carbazole-9-propanoic acid}, a dual CRTH2 and thromboxane $A_2$ receptor antagonist, has been shown to attenuate these responses (Sugimoto et al; J. Pharmacol. Exp. Ther., 2003, 305, 347-352; Takeshita et al; op. cit.). The potential of $PGD_2$ both to enhance allergic inflammation and induce an inflammatory response has been demonstrated in mice and rats. Transgenic mice over expressing $PGD_2$ synthase exhibit an enhanced pulmonary eosinophilia and increased levels of Th2 cytokines in response to allergen challenge (Fujitani et al, J. Immunol., 2002, 168, 443-449). In addition, exogenously administered CRTH2 agonists enhance the allergic response in sensitised mice (Spik et al; J. Immunol., 2005, 174, 3703-3708). In rats exogenously applied CRTH2 agonists cause a pulmonary eosinophilia but a DP agonist (BW 245C) or a TP agonist (I-BOP) showed no effect (Shirashi et al; J. Pharmacol. Exp Ther., 2005, 312, 954-960). These observations suggest that CRTH2 antagonists may have valuable properties for the treatment of diseases mediated by $PGD_2$.

In addition to ramatroban a number of other CRTH2 antagonists have been described. Examples include: indole-acetic acids (WO2003/022813; WO2003/066046; WO2003/066047; WO2003/097042; WO2003/097598; WO2003/101961; WO2003/101981; WO2004/007451; WO2004/078719; WO2004/106302; WO2005/019171; GB2407318; WO2005/040112; WO2005/040114; WO2005/044260); tetrahydroquinolines (EP1413306; EP1435356; WO2004/032848; WO2004/035543; WO2005/007094), and phenylacetic acids (WO2004/058164; WO2004/089884; WO2004/089885; WO2005/018529).

The quinoline template is a common one in compounds proposed for use as pharmaceuticals. However the compounds with which the present invention is concerned have a substitution pattern on the quinoline template which distinguishes them from specific known quinoline-type pharmaceuticals or known generally proposed classes of quinoline-type pharmaceuticals.

DETAILED DESCRIPTION OF THE INVENTION

Use of a compound of formula [1] or a pharmaceutically acceptable salt, N-oxide, hydrate or solvate thereof:

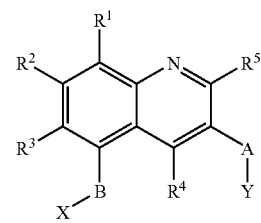

[1]

in which:

$R^1$, $R^2$, $R^3$, $R^4$ and $R^5$ are independently hydrogen, $C_1$-$C_6$alkyl, fully or partially fluorinated $C_1$-$C_6$alkyl, cyclopropyl, halo, —S(O)$_n$R$^6$, —SO$_2$NR$^7$R$^8$, —NR$^7$R$^8$, —NR$^7$C(O)R$^6$, —CO$_2$R$^7$, —C(O)NR$^7$R$^8$, —C(O)R$^6$, —NO$_2$, —CN or a group —OR$^9$;

wherein each $R^6$ is independently $C_1$-$C_6$alkyl, fully or partially fluorinated $C_1$-$C_6$alkyl, cycloalkyl, aryl, or heteroaryl;

$R^7$, $R^8$ are independently $C_1$-$C_6$alkyl, fully or partially fluorinated $C_1$-$C_6$alkyl, cycloalkyl, cycloalkyl-($C_1$-$C_6$alkyl)-, aryl, heteroaryl or hydrogen;

$R^9$ is hydrogen, $C_1$-$C_6$alkyl, fully or partially fluorinated $C_1$-$C_6$alkyl, cycloalkyl, cylcoalkyl-($C_1$-$C_6$alkyl)-, or a group —SO$_2$R$^6$;

A is —CHR$^{10}$—, —C(O)—, —S(O)$_n$—, —O—, or —NR$^{10}$— wherein n is an integer from 0-2 and R$^{10}$ is hydrogen, C$_1$-C$_3$alkyl, or fully or partially fluorinated C$_1$-C$_3$alkyl group;

B is a direct bond, or a divalent radical selected from —CH$_2$—, —CH$_2$CH$_2$—, —CHR$^{11}$—, —CR$^{11}$R$^{12}$—, —CH$_2$CHR$^{11}$— in either orientation, —CH$_2$CR$^{11}$R$^{12}$— in either orientation, —CHR$^{11}$CHR$^{12}$— in either orientation, and divalent radicals of formula —(CR$^{11}$R$^{12}$)$_p$—Z— wherein Z is attached to the ring carrying R$^1$, R$^2$ and R$^3$; wherein R$^{11}$ is C$_1$-C$_3$alkyl, cyclopropyl, or fully or partially fluorinated C$_1$-C$_3$alkyl;

R$^{12}$ is methyl or fully or partially fluorinated methyl;

p is independently 1 or 2; and

Z is —O—, —NH—, or —S(O)$_n$—, wherein n is an integer from 0-2;

X is a carboxylic acid, tetrazole, 3-hydroxyisoxazole, hydroxamic acid, phosphinate, phosphonate, phosphonamide, or sulfonic acid group, or a group of formula C(=O)NHSO$_2$R$^6$ or SO$_2$NHC(=O)R$^6$;

Y is aryl, heteroaryl, aryl-fused-heterocycloalkyl, heteroaryl-fused-cycloalkyl, heteroaryl-fused-heterocycloalkyl or aryl-fused-cycloalkyl group;

for the manufacture of a medicament for use in the treatment of conditions responsive to modulation of CRTH2 receptor activity.

Compounds (1) with which the invention is concerned are CRTH2 receptor antagonists, and are selective over the DP receptor.

A second aspect of the invention is a method of treatment of conditions responsive to modulation of CRTH2 receptor activity, comprising administering to a patient suffering such disease an effective amount of a compound (I) as defined above, or a pharmaceutically acceptable salt, N-oxide, hydrate or solvate thereof.

Important conditions responsive to modulation of CRTH2 receptor activity include asthma, chronic obstructive pulmonary disease, allergic airway syndrome, bronchitis, cystic fibrosis, emphysema and rhinitis, Other conditions responsive to modulation of CRTH2 receptor activity include psoriasis, dermatitis (atopic and non-atopic), Crohn's disease, ulcerative colitis, and irritable bowel disease.

Compounds (1) as defined above except that R$^4$ and R$^5$ are not simultaneously hydrogen and B is not a direct bond, and their pharmaceutically acceptable salts, N-oxides, hydrates and solvates, are believed to be novel in their own right, and such novel compounds form a third aspect of the invention. Pharmaceutical composition comprising such compounds, in admixture with a pharmaceutically acceptable carrier or excipient, and the use of such compounds in therapy, are also aspects of the invention.

Terminology

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein, the term "fully or partially fluorinated C$_a$-C$_b$alkyl" wherein a and b are integers refers to a straight or branched chain alkyl radical having from a to b carbon atoms in which the hydrogen atoms all replaced by fluorine (fully fluorinated) or in which some of the hydrogen atoms are replaced by fluorine (partially fluorinated). The term includes, for example —CF$_3$, —CHF$_2$, —CFH$_2$, and CF$_3$CH$_2$—.

As used herein the term "carbocyclic" refers to an optionally substituted mono-, bi- or tricyclic radical having up to 16 ring atoms, all of which are carbon, and includes aryl and cycloalkyl.

As used herein the term "cycloalkyl" refers to an optionally substituted monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to an optionally substituted mono-, bi- or tri-cyclic carbocyclic aromatic radical, and includes radicals having two monocyclic carbocyclic aromatic rings which are directly linked by a covalent bond. Aryl radicals may have, for example, from 6 to 14 ring carbon atoms, preferably from 6 to 10 carbon atoms. Illustrative of aryl radicals are phenyl, biphenyl and napthyl.

As used herein, the term "aryl-fused-cycloalkyl" refers to a carbocyclic radical consisting of a monocyclic aryl ring, such as phenyl, fused to a cycloalkyl group, in which the aryl and cycloalkyl parts are as defined herein. Exemplary aryl-fused-cycloalkyl groups include tetrahydronaphthyl and indanyl. The aryl-fused-cycloalkyl radical may be attached to the remainder of the molecule by any available carbon atom.

As used herein the unqualified term "heteroaryl" refers to an optionally substituted mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocycloalkyl" or "heterocyclyl" or "heterocycloalkyl" includes "heteroaryl" as defined above, and in addition means an optionally substituted mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, quinolyl, morpholinyl, benzfuranyl, pyranyl, isoxazolyl, benzimidazolyl, methylenedioxyphenyl, ethylenedioxyphenyl, maleimido and succinimido groups.

As used herein, the term "heteroaryl-fused-cycloalkyl" means a heterocyclic radical consisting of monocyclic heteroaryl group, such as pyridyl or furanyl, fused to a cycloalkyl group, in which the heteroaryl and cycloalkyl parts are as defined herein. Exemplary heteroaryl-fused-cycloalkyl groups include tetrahydroquinolinyl and tetrahydrobenzofuranyl. The heteroaryl-fused-cycloalkyl group may be attached to the remainder of the molecule by any available carbon or nitrogen atom.

As used herein, the term "aryl-fused-heterocycloalkyl" refers to a heterocyclic radical consisting of a monocyclic aryl ring, such as phenyl, fused to a heterocycloalkyl group, in which the aryl and heterocycloalkyl parts are as defined above. Exemplary aryl-fused-heterocycloalkyl groups include tetrahydroquinolinyl, indolinyl, benzodioxinyl, benxodioxolyl, dihydrobenzofuranyl and isoindolonyl. The aryl-fused-heterocycloalkyl radical may be attached to the remainder of molecule by any available carbon or nitrogen atom.

As used herein, the term "heteroaryl-fused-heterocycloalkyl" refers to a heterocyclic radical consisting of a monocyclic heteroaryl group, such as pyridyl or furanyl, fused to a heterocycloalkyl group, in which the heteroaryl and heterocycloalkyl parts are as defined herein. Exemplary heteroaryl-fused-heterocycloalkyl groups include dihydrodioxinopyridinyl, dihydropyrrolopyridinyl, dihydrofuranopyridinyl and dioxolopyridinyl. The heteroaryl-fused-heterocycloalkyl group may be attached to the remainder of the molecule by any available carbon or nitrogen atom.

Unless otherwise specified in the context in which it occurs, the term "substituted" as applied to any moiety herein means substituted with up to four compatible substituents, each of which independently may be, for example, $(C_1-C_6)$ alkyl, cycloalkyl, $(C_1-C_6)$alkoxy, hydroxy, hydroxy$(C_1-C_6)$ alkyl, mercapto, mercapto$(C_1-C_6)$alkyl, $(C_1-C_6)$alkylthio, phenyl, monocyclic heteroaryl having 5 or 6 ring atoms, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$ cycloalkyl, phenyl, or monocyclic heterocyclic group having 5 or 6 ring atoms, or R$^A$ and R$^B$ when attached to the same nitrogen atom may form a ring with that nitrogen of 5 or 6 ring atoms, optionally containing further heteroatoms selected from N, O or S (examples being morpholinyl, piperidinyl, piperizinyl, 4-methylpiperizinyl, and tetrahydropyrrolyl). An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Specific salts with bases include the benzathine, calcium, diolamine, meglumine, olamine, potassium, procaine, sodium, tromethamine and zinc salts. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. Additional salt forms are detailed in the "Handbook of Pharmaceutical Salts. Properties, selection and use", P. Heinrich Stahl & Camille G. Wermuth, Wiley-VCH, 2002.

Also as used herein:
The term "phosphinate" refers to a group of formula —P(O)R(OR) group in which R is hydrogen or $C_1-C_4$ alkyl. Exemplary groups are —P(O)(OH)CH$_3$ and —P(O)(OH)H.

The term "phosphonate" refers to a group of formula —P(O)(OH)OR in which R is hydrogen or $C_1-C_4$ alkyl. Exemplary groups are —P(O)(OH)$_2$ and —P(O)(OH) OC$_2$H$_5$.

The term "phosphonamide" refers to a group of formula —P(O)(OR)NR$_2$ in which R is hydrogen or $C_1-C_4$ alkyl. An exemplary group is —P(O)(OH)NH$_2$.

Compounds with which the invention is concerned which may exist in one or more stereoisomeric form, because of the presence of asymmetric atoms or rotational restrictions, and in such cases can exist as a number of stereoisomers with R or S stereochemistry at each chiral centre or as atropisomeres with R or S stereochemistry at each chiral axis. The invention includes all such enantiomers and diastereoisomers and mixtures thereof.

Use of prodrugs, such as esters, of compounds (I) with which the invention is concerned is also part of the invention. "Prodrug" means a compound which is convertible in vivo by metabolic means (e.g. by hydrolysis, reduction or oxidation) to a compound of formula (1). For example an ester prodrug of a compound of formula (1) may be convertible by hydrolysis in vivo to the parent molecule. Suitable esters of compounds of formula (1) are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluene-sulphonates, cyclohexylsulphamates and quinates. Examples of ester prodrugs are those described by F. J. Leinweber, Drug Metab. Res., 1987, 18, 379. As used in herein, references to the compounds of formula (1) are meant to also include the prodrug forms.

The Variables $R^1$-$R^5$, A, B, X and Y

For use in accordance with the invention, the following structural characteristics are currently preferred, in any compatible combination, in the compounds (1):

$R^1$, $R^2$, $R^3$, $R^4$ and $R^5$ are independently hydrogen; $C_1-C_6$alkyl, for example methyl, ethyl, or n- or iso-propyl; fully or partially fluorinated $C_1-C_6$alkyl, for example trifluoromethyl or difluoromethyl; cycloalkyl, for example cyclopropyl or cyclobutyl; halo, for example fluoro, chloro or bromo; —NO$_2$; —CN; or a group selected from —S(O)$_n$R$^6$, —SO$_2$NR$^7$R$^8$, —NR$^7$R$^8$, —NR$^7$C(O)R$^6$, —CO$_2$R$^7$, —C(O) NR$^7$R$^8$, —C(O)R$^6$, or a group —OR$^9$;

wherein each $R^6$ is independently $C_1-C_6$alkyl, for example methyl, ethyl, or n- or iso-propyl; fully or partially fluorinated $C_1-C_6$alkyl, for example trifluoromethyl or difluoromethyl; cycloalkyl for example cyclopropyl, cyclobutyl, cyclopentyl or cyclohexyl; aryl, for example phenyl; or heteroaryl, for example pyridyl, thienyl or furanyl;

$R^7$, $R^8$ are independently $C_1-C_6$alkyl, for example methyl, ethyl, or n- or iso-propyl; fully or partially fluorinated $C_1-C_6$alkyl, for example trifluoromethyl or difluoromethyl; cycloalkyl for example cyclopropyl, cyclobutyl, cyclopentyl or cyclohexyl; cycloalkyl-($C_1-C_6$alkyl)-, for example cyclopropylmethyl, cyclopentylmethyl, cyclohexylmethyl, cyclopropylethyl, cyclopentylethyl, cyclohexylethyl; aryl, for example phenyl; or heteroaryl, for example pyridyl, thienyl or furanyl; or hydrogen;

$R^9$ is hydrogen, $C_1-C_6$alkyl, for example methyl, ethyl, or n- or iso-propyl; fully or partially fluorinated $C_1-C_6$alkyl, for example trifluoromethyl or difluoromethyl; cycloalkyl for example cyclopropyl, cyclobutyl, cyclopentyl or cyclohexyl; cycloalkyl-($C_1-C_6$alkyl)-, for example cyclopropylmethyl, cyclopentylmethyl, cyclohexylmethyl, cyclopropylethyl, cyclopentylethyl, cyclohexylethyl; or a group —$SO_2R^6$.

Currently preferred instances of $R^1$-$R^5$ are:
$R^1$ is fluoro or chloro;
$R^2$ is hydrogen, chloro or methyl;
$R^3$ is hydrogen;
$R^4$ is methyl, ethyl, methoxy or difluoromethoxy;
$R^5$ is methyl, ethyl, ethoxy, isopropoxy, difluoromethoxy or cyano;

A is —$CHR^{10}$—, —C(O)—, —S(O)$_n$—, —O—, or —$NR^{10}$— wherein n is an integer from 0-2 and $R^{10}$ is hydrogen, $C_1$-$C_6$alkyl, for example methyl, ethyl, or n- or isopropyl; fully or partially fluorinated $C_1$-$C_6$alkyl, for example trifluoromethyl or difluoromethyl. Currently preferred instances of A are —$CH_2$—, —O—, or —S(O)$_n$— wherein n is 0, 1 or 2.

B is a direct bond, or a divalent radical selected from —$CH_2$—, —$CH_2CH_2$—, —$CHR^{11}$—, —$CR^{11}R^{12}$—, —$CH_2CHR^{11}$— in either orientation, —$CH_2CR^{11}R^{12}$— in either orientation, —$CHR^{11}CHR^{12}$— in either orientation, and divalent radicals of formula —$(CR^{11}R^{12})_p$—Z— wherein Z is attached to the ring carrying $R^1$, $R^2$ and $R^3$; wherein $R^{11}$ is $C_1$-$C_6$alkyl, for example methyl, ethyl, or n- or iso-propyl; fully or partially fluorinated $C_1$-$C_6$alkyl, for example trifluoromethyl or difluoromethyl; or cyclopropyl;
$R^{12}$ is methyl or fully or partially fluorinated methyl, for example trifluoromethyl or difluoromethyl;
p is independently 1 or 2; and
Z is —O—NH—, or —S(O)$_n$—, wherein n is an integer from 0-2;

Currently preferred instances of B are —$CH_2$—, —OCH($CH_3$)— or —$OCH_2$— wherein the oxygen is attached to the ring carrying $R^1$, $R^2$ and $R^3$.

X is a carboxylic acid, tetrazole, 3-hydroxyisoxazole, hydroxamic acid, phosphinate, phosphonate, phosphonamide, or sulfonic acid group, or a group of formula C(=O)NHSO$_2R^6$ or SO$_2$NHC(=O)$R^6$. Currently preferred are compounds wherein X is a carboxylic acid group. Of course, prodrugs of such compounds include those wherein the carboxylic acid group is esterified as an ester which is hydrolysed in vivo to release the carboxylic acid.

Y is aryl, such as phenyl; heteroaryl for example quinolinyl, pyridyl, thienyl, furanyl, azolyl, thiazolyl, diazolyl, or imidazolyl, aryl-fused-heterocycloalkyl, for example tetrahydroquinolinyl, indolinyl, benzodioxinyl, benxodioxolyl, dihydrobenzofuranyl and isoindolonyl; heteroaryl-fused-cycloalkyl, for example tetrahydroquinolyl; heteroaryl-fused-heterocycloalkyl, for example indolinyl, benzodioxinyl, benzodioxolyl, dihydrobenzofuranyl or isoindolonyl; or aryl-fused-cycloalkyl group such as tetrahydronaphthyl and indanyl. Currently it is preferred that Y be optionally substituted. Currently preferred examples of Y include:

4-fluorophenyl, 4-chlorophenyl, 4-methanesulfonylphenyl, 4-ethanesulfonylphenyl, 4-(morpholine-4-sulfonyl)phenyl, 4-(pyrrolidine-1-carbonyl)phenyl, 2,4-difluorophenyl, 2,4-dichlorophenyl, 2-chloro-2-fluorophenyl, 2-chloro-4-fluorophenyl, 2-chloro-4-methanesulfonylphenyl, 2-chloro-4-(pyrrolidine-1-carbonyl)phenyl and 2-chloro-4-cyclobutylcarbamoyl.

A particularly preferred subclass of compounds (1) of the invention consists of those wherein $R^1$ is fluoro or chloro; $R^2$ and $R^3$ are hydrogen; $R^4$ is methyl, ethyl, methoxy or difluoromethoxy; $R^5$ is methyl, ethyl, ethoxy, isopropoxy, difluoromethoxy or cyano; A is —$CH_2$—, —O—, or —S(O)$_n$— wherein n is 0, 1 or 2; B is —$CH_2$—, —OCH($CH_3$)— or —$OCH_2$— wherein the oxygen is attached to the ring carrying $R^1$, $R^2$ and $R^3$; X is —$CO_2H$; and Y is 4-fluorophenyl, 4-chlorophenyl, 4-methanesulfonylphenyl, 4-ethanesulfonylphenyl, 4-(morpholine-4-sulfonyl)phenyl, 4-(pyrrolidine-1-carbonyl)phenyl, 2,4-difluorophenyl, 2,4-dichlorophenyl, 2-chloro-2-fluorophenyl, 2-chloro-4-fluorophenyl, 2-chloro-4-methanesulfonylphenyl, 2-chloro-4-(pyrrolidine-1-carbonyl)phenyl and 2-chloro-4-cyclobutylcarbamoyl, and pharmaceutically acceptable salts, N-oxides, hydrates or solvates thereof.

Specific compounds with which the invention is concerned include those of the Examples herein, and pharmaceutically acceptable salts, N-oxides, hydrates or solvates thereof.

Compositions

As mentioned above, the compounds with which the invention is concerned are CRTH2 receptor antagonists, and are useful in the treatment of diseases which benefit from such modulation. Examples of such diseases are referred to above, and include asthma, rhinitis, allergic airway syndrome, and bronchitis.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range will lie within the range of from about 0.001 mg to about 100 mg per kg body weight of a mammal, often 0.01 mg to about 50 mg per kg, for example 0.1 to 10 mg per kg, in single or divided doses. On the other hand, it may be necessary to use dosages outside these limits in some cases.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The drug may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Other compounds may be combined with compounds of this invention of formula [I] for the prevention and treatment of prostaglandin-mediated diseases. Thus the present invention is also concerned with pharmaceutical compositions for preventing and treating $PGD_2$-mediated diseases comprising a therapeutically effective amount of a compound of the invention of formula [I] and one or more other therapeutic agents. Suitable therapeutic agents for a combination therapy with compounds of formula [1] include, but are not limited to: (1) corticosteroids, such as fluticasone, ciclesonide or budesonide; (2) β2-adrenoreceptor agonists, such as salmeterol, indacaterol or formoterol; (3) leukotriene modulators, for example leukotriene antagonists such as montelukast, zafirulast or pranlukast or leukotriene biosynthesis inhibitors such as Zileuton or BAY-1005; (4) anticholinergic agents, for example muscarinic-3 (M3) receptor antagonists such as tiotropium bromide; (5) phosphodiesterase-IV (PDE-IV) inhibitors, such as roflumilast or cilomilast; (6) antihistamines, for example selective histamine-1 (H1) receptor antagonists, such as fexofenadine, citirizine, loratidine or astemizole; (7) antitussive agents, such as codeine or dextramorphan; (8) non-selective COX-1/COX-2 inhibitors, such as ibuprofen or ketoprofen; (9) COX-2 inhibitors, such as celecoxib and rofecoxib; (10) VLA-4 antagonists, such as those described in WO97/03094 and WO97/02289; (11) TACE inhibitors and TNF-α inhibitors, for example anti-TNF monoclonal antibodies, such as Remicade and CDP-870 and TNF receptor immunoglobulin molecules, such as Enbrel; (12) inhibitors of matrix metalloprotease, for example MMP12; (13) human neutrophil elastase inhibitors, such as those described in WO2005/026124, WO2003/053930 and WO06/082412; (14) A2a agonists such as those described in EP1052264 and EP1241176 (15) A2b antagonists such as those described in WO2002/42298; (16) modulators of chemokine receptor function, for example antagonists of CCR3 and CCR8; (17) compounds which modulate the action of other prostanoid receptors, for example a DP receptor antagonist or a thromboxane $A_2$ antagonist; and (18) agents that modulate Th2 function, such as PPAR agonists The weight ratio of the compound of the invention to the second active ingredient may be varied and will depend upon the effective dose of each ingredient. Generally, an effective dose of each will be used.

Methods of Synthesis

The present invention is also concerned with processes for preparing the compounds of this invention.

The compounds of formula [1] of the present invention can be prepared according to the procedures of the following schemes and examples, using appropriate materials, and are further exemplified by the following specific examples. Moreover, by utilizing the procedures described with the disclosure contained herein, one of ordinary skill in the art can readily prepare additional compounds of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

Compounds of the invention of formula [1a], in which group B is represented by a group of formula O-(optionally substituted)alkylene, and $R^{1-5}$, A, X and Y are as defined above, may conveniently be prepared by the reaction between a compound of formula [2] and a suitable alkylating agent of formula [3], where group LG represents a suitable leaving group (for example, chloro, bromo, or methanesulfonyloxy). Typically, the alkylation reaction is carried out in the presence of a base (for example, potassium carbonate) in an inert solvent (for example, acetone or N,N-dimethylformamide). It will be understood by those who are practiced in the art that it may be convenient to carry out the transformation of intermediate [2] to final compound [1a] using a form of alkylating agent [3] in which one or other of the functionalities on either component is suitably protected. For example, if group X represents a carboxylic acid it may be convenient to carry out the reaction using an alkylating agent in which the acid group is protected as an ester (for example, an ethyl or tert-butyl ester). It is to be understood that if the reaction is carried out on a protected form of alkylating agent [3] an appropriate deprotection step will be required to obtain the desired compound [1a] of the invention (Scheme 1).

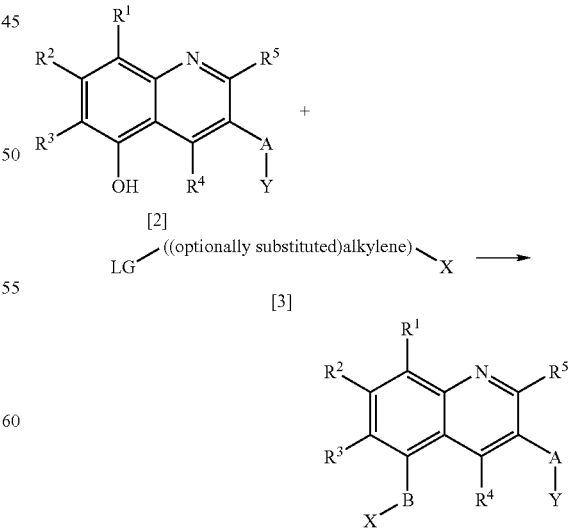

Intermediate compounds of formula [2] may conveniently be prepared by the reaction between an aminophenol of formula [4] and a 1,3-dicarbonyl compound of formula [5] (Scheme 2). The reaction may be carried out neat or in the presence of a suitable dehydrating agent, such as polyphosphoric acid, p-toluenesulfonic acid or methanesulfonic acid. Compounds of formula [4] and [5] are commercially available or prepared by known methods.

Scheme 2

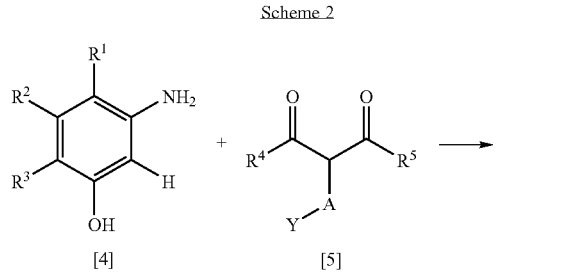

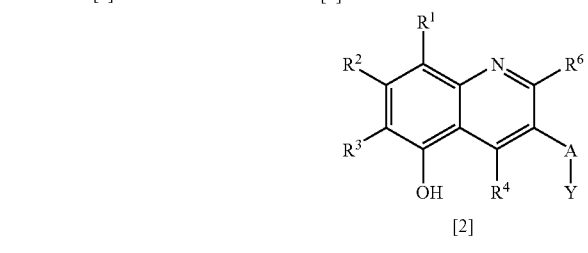

Compounds of formula [1a] in which $R^4$ is an alkoxy group, such as difluoromethoxy, may be conveniently be prepared from the reaction of aniline of formula [6] and a β-ketoester of formula [7], in which PG represents an appropriate alkyl group (such as methyl and ethyl), followed by alkylation with chlorodifluoromethane (Scheme 3). It is to be understood that if the reaction is carried out on a protected form of intermediate [6] an appropriate deprotection step will be required to obtain the desired compound [1a]. Ketoesters of formula [7] are known or may be prepared from known compounds according to methods known to those skilled in the art.

Scheme 3

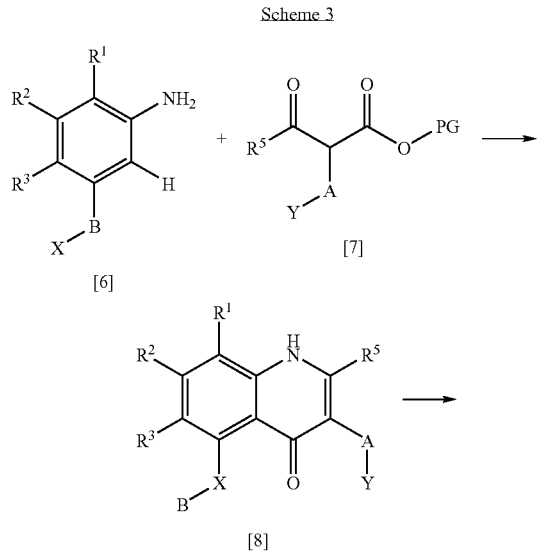

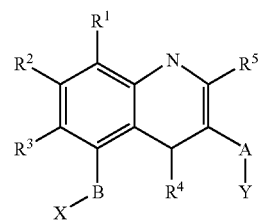

[1a] B = O-(optionally substituted)alkylene
$R^4$ = OCHF$_2$

Compound of formula [6] may be prepared from compounds of formula [4] by treatment with an alkylating agent of formula [3] (Scheme 4), using methods described above for the preparation of compounds of formula [1a] from compounds of formula [2] (Scheme 1).

Scheme 4

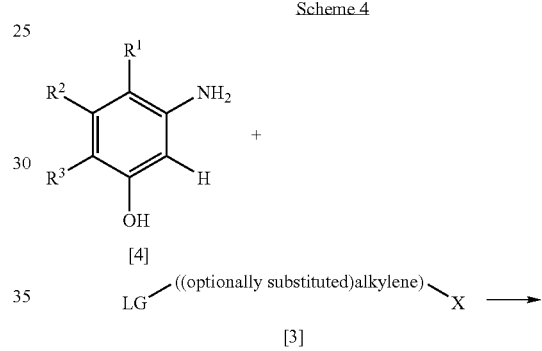

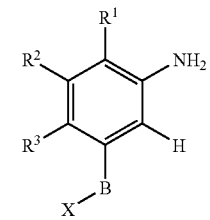

[6] B = O-(optionally substituted)alkylene

Compounds of formula [1a] in which $R^5$ is an alkoxy group, such as difluoromethoxy, may conveniently be prepared from intermediate compounds of formula [11] using methods described above for the preparation of compounds of formula [1a] from compounds of formula [2] (Scheme 1) and compounds of formula [1a] from compounds of formula [8] (Scheme 3).

Compounds of formula [11] may conveniently be prepared from compounds of formula [10]. The reaction may be carried in the presence of a suitable dehydrating agent, for example methanesulfonic acid or p-toluenesulfonic acid.

Intermediate compounds of formula [10] may be prepared from reaction of aminophenols of formula [4] with β-ketothioesters of formula [9] in the presence of silver trifluoroacetate. Compounds of formula [4] and [9] are commercially available or prepared by known methods.

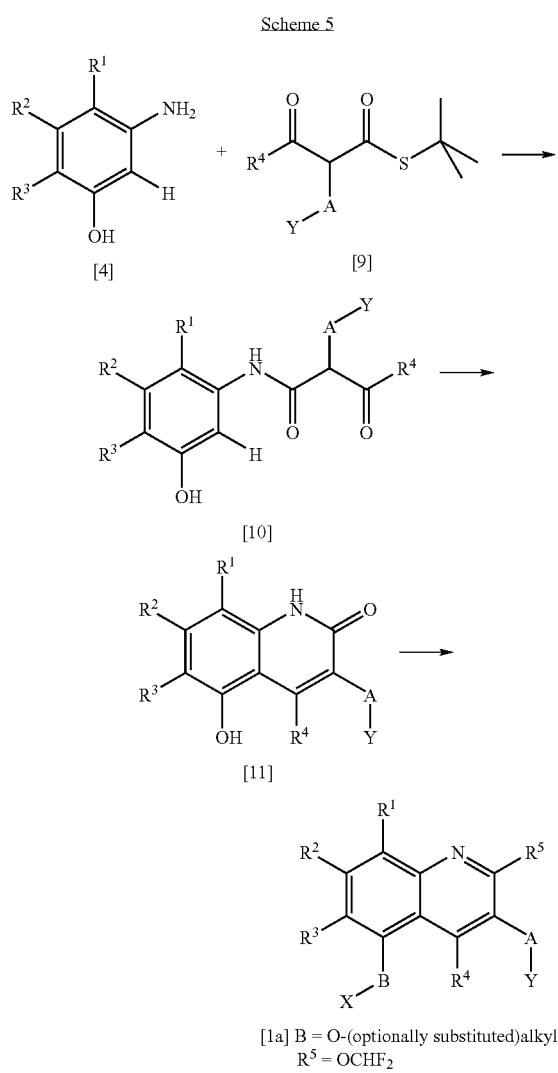

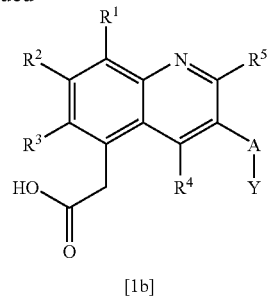

Compounds of the invention of formula [1b], wherein R[1-5], A and Y are as defined above, may be prepared by the reaction between an intermediate compound of formula [12], in which group T represents a chloro, bromo, or iodo atom, or a trifluoro-methanesulfonyloxy group, and 1-(tert-butyldimethylsilyloxy)-1-methoxyethane (Scheme 6). The reaction may conveniently be carried out in the presence of a suitable catalyst (for example a palladium compound) and a base, such as sodium acetate.

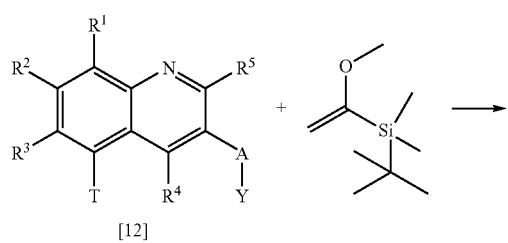

Intermediates of formula [12], in which T is trifluoromethanesulfonyloxy, may be prepared from the reaction of intermediates of formula [2] with N-phenyl-trifluoromethanesulfonimide in the presence of a base, such as potassium carbonate.

It will be understood by those practiced in the art that compounds of the invention may be prepared by transformations of other compounds of the invention. For example, compounds of the invention of formula [1c], in which group A represents a sulfonyl group, may conveniently be prepared by the oxidation of compounds of the invention of formula [1a], in which group A represents a sulfanyl group, with a suitable oxidising agent such as potassium peroxymonosulfate, meta-chloroperoxybenzoic acid or other well known oxidising agents.

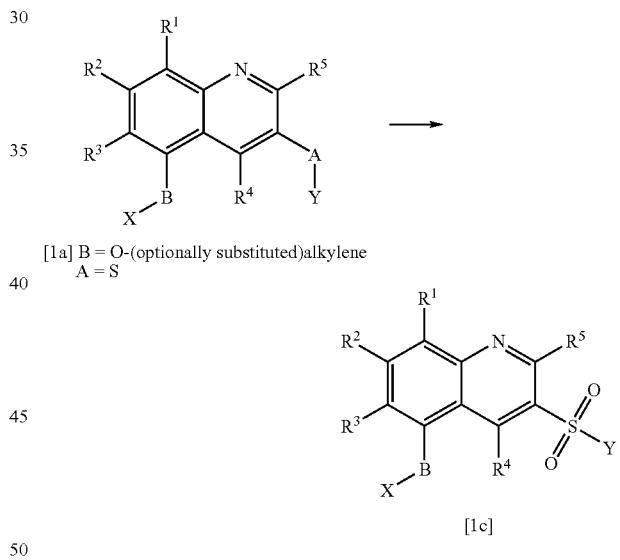

In a further example, compounds of formula [1b], in which group R[5] represents a hydrogen atom may conveniently be prepared by the reduction of compounds of formula [1b], in which group R[5] represents a halo group such as chloro or bromo. The transformation may conveniently be achieved by reduction with hydrogen in the presence of a suitable catalyst, such as palladium supported on carbon.

EXAMPLES

The invention will now be described with reference to the following examples. It will be appreciated that the invention is described by way of example only and modification of detail may be made without departing from the scope of the invention.

$^1$H NMR spectra were recorded at ambient temperature using a Varian Unity Inova (400 MHz) spectrometer with a triple resonance 5 mm probe spectrometer. Chemical shifts are expressed in ppm relative to tetramethylsilane. The following abbreviations have been used: br s=broad singlet, s=singlet, d=doublet, dd=double doublet, t=triplet, q=quartet, m=multiplet.

Mass Spectrometry (LCMS) experiments to determine retention times and associated mass ions were performed using the following methods:

Method A: experiments were performed on a Micromass Platform LCT spectrometer with positive ion electrospray and single wavelength UV 254 nm detection using a Higgins Clipeus C18 5 μm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Method B: experiments were performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes Microwave experiments were carried out using a Personal Chemistry Smith Synthesizer™, which uses a single-mode resonator and dynamic field tuning, both of which give reproducibility and control. Temperatures from 40-250° C. can be achieved, and pressures of up to 20 bar can be reached. Two types of vial are available for this processor, 0.5-2.0 mL and 2.0-5.0 mL.

Reverse-phase preparative HPLC purifications were carried out using Genesis 7 micron C-18 bonded silica stationary phase in columns 10 cm in length and 2 cm internal diameter. The mobile phase used was mixtures of acetonitrile and water (both buffered with 0.1% v/v trifluoroacetic acid) with a flow rate of 10 mL per minute and typical gradients of 40 to 90% organic modifier ramped up over 30 to 40 minutes. Fractions containing the required product (identified by LC-MS analysis) were pooled, the organic fraction removed by evaporation, and the remaining aqueous fraction lyophilised, to give the final product.

Example 1

[8-chloro-3-(4-chlorobenzyl)-4-methoxy-2-methylquinolin-5-yloxy]acetic Acid

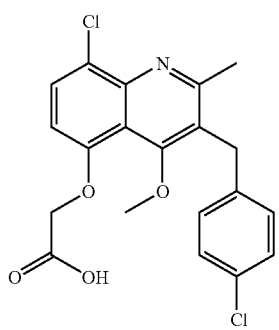

Preparation 1a 8-chloro-3-(4-chlorobenzyl)-5-hydroxy-2-methyl-1H-quinolin-4-one

A mixture of 3-amino-4-chlorophenol (2.5 g), 2-(4-chlorobenzyl)-3-oxobutyric acid ethyl ester (4.7 g) and toluene-4-sulfonic acid (0.3 g) was heated at 160° C. under nitrogen for 10 hours. The mixture was cooled to room temperature and the residue triturated with methanol and then crystallised from butan-1-ol to afford a beige powder. Purification by column chromatography on silica gel, eluting with a mixture of ethyl acetate and dichloromethane (0:1 to 1:0 by volume) gave title compound as a yellow solid, 0.77 g.

$^1$H NMR (DMSO-d6): δ 2.50 (s, 3H), 3.90 (s, 2H), 6.90 (d, J=8.6 Hz, 1H), 7.20-7.30 (m, 4H), 7.60 (d, J=8.6 Hz, 1H), 11.05 (s, 1H), 14.90 (s, 1H).

MS: ESI (+ve) (Method B): 334 (M+H)$^+$, Retention time 3.8 min.

Preparation 1b

[8-chloro-3-(4-chlorobenzyl)-2-methyl-4-oxo-1,4-dihydroquinolin-5-yloxy]acetic Acid Methyl Ester A solution of 8-chloro-3-(4-chlorobenzyl)-5-hydroxy-2-methyl-1H-quinolin-4-one (0.56 g) in tetrahydrofuran (7.0 mL) was flushed with nitrogen and cooled to −40° C. A 1.0 M solution of sodium bis(trimethylsilyl)amide in tetrahydrofuran (1.7 mL) was added and the resulting mixture warmed to 0° C. over 1 hour. The mixture was cooled to −30° C. and a solution of bromoacetic acid methyl ester (0.26 g) in tetrahydrofuran (1.0 mL) was added and the resulting mixture warmed to room temperature over 2 hours and then stirred at this temperature for 3 days. The mixture was diluted with 1.0 M aqueous hydrochloric acid and extracted with ethyl acetate and the combined extracts were washed with saturated aqueous sodium chloride solution and then dried over magnesium sulfate. The solvent was removed under reduced pressure and purification of the residue by column chromatography on silica gel, eluting with a mixture of ethyl acetate and dichloromethane (1:19 to 19:1 by volume) gave title compound as a gum, 0.13 g.

MS: ESI (+ve) (Method B): 406 (M+H)$^+$, Retention time 3.1 min.

Preparation 1c

[8-chloro-3-(4-chlorobenzyl)-4-methoxy-2-methylquinolin-5-yloxy]acetic Acid Methyl Ester A mixture of [8-chloro-3-(4-chlorobenzyl)-2-methyl-4-oxo-1,4-dihydroquinolin-5-yloxy]acetic acid methyl ester (0.13 g), iodomethane (0.20 mL), N,N-dimethylformamide (1.0 mL) and potassium carbonate (0.14 g) were stirred at room temperature for 22 hours. The mixture was diluted with water and extracted with ethyl acetate and the combined extracts were washed with saturated aqueous sodium chloride solution and dried over magnesium sulfate. The solvent was removed under reduced pressure and purification of the residue by column chromatography on silica gel, eluting with a mixture of ethyl acetate and dichloromethane (1:19 to 19:1 by volume) gave title compound as a gum, 0.059 g.

MS: ESI (+ve) (Method B): 420 (M+H)$^+$, Retention time 4.0 min.

Preparation 1d

[8-chloro-3-(4-chlorobenzyl)-4-methoxy-2-methylquinolin-5-yloxy]acetic Acid

A mixture of [8-chloro-3-(4-chlorobenzyl)-4-methoxy-2-methylquinolin-5-yloxy]acetic acid methyl ester (0.059 g), methanol (2.0 mL), saturated aqueous lithium hydroxide solution (0.25 mL) and water (0.4 mL) was stirred at room temperature for 15 hours, The methanol was removed under reduced pressure and the pH of the residue adjusted to 1 by the addition of 1.0 M aqueous hydrochloric acid. Purification by preparative reverse-phase HPLC using a gradient over 30 minutes of acetonitrile in water (20% to 80% of organic modifier) gave title compound as a yellow solid, 0.060 g.

$^1$H NMR (DMSO-d6): δ 2.55 (s, 3H), 3.80 (s, 3H), 4.20 (s, 2H), 4.90 (s, 2H), 6.90 (d, J=8.6 Hz, 1H), 7.15 (d, J=8.6 Hz, 2H), 7.30 (d, J=8.6 Hz, 2H), 7.80 (d, J=8.6 Hz, 1H).

MS: ESI (+ve) (Method A): 406 (M+H)$^+$, Retention time 11.0 min.

MS: ESI (+ve) (Method B): 406 (M+H)$^+$, Retention time 3.5 min.

Example 2

[8-chloro-3-(4-chlorobenzyl)-2,4-dimethylquinolin-5-yloxy]acetic Acid

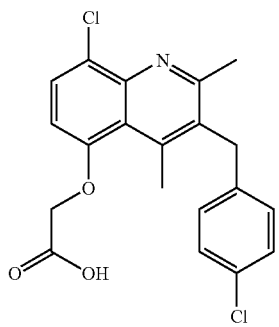

Preparation 2a

[8-chloro-3-(4-chlorobenzyl)-2,4-dimethylquinolin-5-yloxy]acetic Acid Methyl Ester A mixture of 8-chloro-3-(4-chlorobenzyl)-2,4-dimethylquinolin-5-ol (0.23 g), N,N-dimethylformamide (5.0 mL), potassium carbonate (0.11 g) and bromoacetic acid methyl ester (0.075 mL) was stirred at room temperature for 17 hours. The mixture was concentrated under reduced pressure and the residue diluted with ethyl acetate and this mixture was washed with saturated aqueous sodium chloride solution and then dried over magnesium sulfate. The solvent was removed under reduced pressure and purification of the residue by column chromatography on silica gel, eluting with a mixture of ethyl acetate and cyclohexane (1:1 by volume) gave title compound, 0.11 g.

$^1$H NMR (CDCl$_3$): δ 2.75 (s, 3H), 2.85 (s, 3H), 4.25 (s, 2H), 4.75 (s, 2H), 6.60 (d, J=8.6 Hz, 1H), 6.95 (d, J=8.6 Hz, 1H), 7.20 (d, J=8.3 Hz, 2H), 7.65 (d, J=8.3 Hz, 2H).

MS: ESI (+ve) (Method B): 404 (M+H)$^+$, Retention time 4.1 min.

Preparation 2b

[8-chloro-3-(4-chlorobenzyl)-2,4-dimethylquinolin-5-yloxy]acetic Acid

A solution of [8-chloro-3-(4-chlorobenzyl)-2,4-dimethylquinolin-5-yloxy]acetic acid methyl ester (0.11 g), acetonitrile (2.0 mL) and 4.0 M aqueous lithium hydroxide solution (2.0 mL) was stirred at room temperature for 1 hour. The acetonitrile was removed under reduced pressure and the pH of the residue adjusted to 5 by the addition of saturated aqueous sodium dihydrogenphosphate solution. The resulting mixture was extracted with ethyl acetate and the combined extracts dried over magnesium sulfate and concentrated under reduced pressure. Purification of the residue by column chromatography on a flash NH$_2$ cartridge, eluting with methanol and then 2.0 M ammonia in methanol, gave title compound, 0.10 g.

$^1$H NMR (DMSO-d6): δ 2.60 (s, 3H), 2.85 (s, 3H), 4.25 (s, 2H), 4.75 (s, 2H), 6.80 (d, J=8.6 Hz, 1H), 7.00 (d, J=8.6 Hz, 2H), 7.25 (d, J=8.6 Hz, 2H), 7.65 (d, J=8.6 Hz, 1H).

MS: ESI (+ve) (Method A): 390 (M+H)$^+$, Retention time 11.0 min.

MS: ESI (+ve) (Method B): 390 (M+H)$^+$, Retention time 3.5 min.

Example 3

[3-(4-chlorobenzyl)-2-ethoxy-4,7-dimethylquinolin-5-yl]acetic Acid

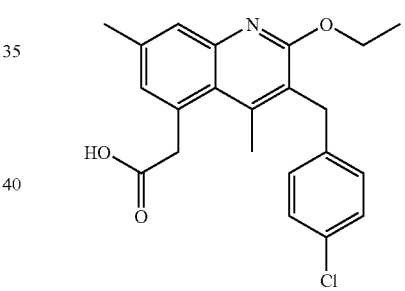

Preparation 3a 3-amino-5-methylphenol

A mixture of 5-methylbenzene-1,3-diol (6.0 g), ammonium chloride (3.0 g), water (9.0 mL), and ammonium hydroxide (6.8 mL, 33% in water) were sealed in a bomb and heated at 180° C. for 17 hours. The mixture was cooled to room temperature and the resulting precipitate collected by filtration. Crystallisation from water gave title compound, 1.7 g.

$^1$H NMR (DMSO-d6): δ 2.05 (s, 3H), 4.75 (br s, 2H), 5.75-5.80 (m, 3H), 8.70 (s, 1H).

Preparation 3b 3-(4-chlorobenzyl)-5-hydroxy-4,7-dimethyl-1H-quinolin-2-one

A mixture of 3-amino-5-methylphenol (0.25 g) and 2-(4-chlorobenzyl)-3-oxobutyric acid ethyl ester (0.52 g) was heated at 150° C. under nitrogen for 7 hours. The mixture was cooled to room temperature and the residue triturated with methanol to afford the title compound as an off-white solid, 0.32 g.

$^1$H NMR (DMSO-d6): δ 2.20 (s, 3H), 2.55 (s, 3H), 4.00 (s, 2H), 6.40 (m, 1H), 6.55 (m, 1H), 7.20 (2H, d, J=8.6 Hz), 7.30 (2H, d, J=8.6 Hz), 10.00 (1H, brs), 11.50 (1H, br s).

MS: ESI (+ve) (Method B): 314 (M+H)$^+$, Retention time 3.14 min.

Preparation 3c

Trifluoromethanesulfonic Acid 3-(4-chlorobenzyl)-4,7-dimethyl-2-oxo-1,2-dihydroquinolin-5-yl Ester A mixture of 3-(4-chlorobenzyl)-5-hydroxy-4,7-dimethyl-1H-quinolin-2-one (1.4 g), N-phenyltrifluoromethanesulfonimide (1.75 g), potassium carbonate (1.85 g) and tetrahydrofuran (7.0 mL) was heated by microwave irradiation at 120° C. for 12 minutes. The mixture was filtered and the filtrate concentrated under reduced pressure. Purification of the residue by column chromatography on silica gel, eluting with a mixture of ethyl acetate and dichloromethane (1:25 to 1:5 by volume) gave title compound as an off-white solid, 3.3 g.

$^1$H NMR (DMSO-d6): δ 2.40 (3H, s), 2.60 (s, 3H), 4.15 (s, 2H), 6.95 (m, 1H), 7.15-7.20 (m, 4H), 7.30 (m, 1H), 12.0 (s, 1H).

MS: ESI (+ve) (Method B): 446 (M+H)$^+$, Retention time 4.1 min.

Preparation 3d

[3-(4-chlorobenzyl)-4,7-dimethyl-2-oxo-1,2-dihydroquinolin-5-yl]acetic Acid Methyl Ester A mixture of trifluoromethanesulfonic acid 3-(4-chlorobenzyl)-4,7-dimethyl-2-oxo-1,2-dihydroquinolin-5-yl ester (1.1 g), 1-(tert-butyldimethylsilyloxy)-1-methoxyethene (2.7 mL), sodium acetate (0.25 g), bis(dibenzylideneacetone) palladium (0.07 g) and 1,1'-bis(diphenylphospino)ferrocene (0) (0.07 g) in N,N-dimethylformamide (15.0 mL) was heated by microwave irradiation at 120° C. for 15 minutes. The mixture was diluted with ethyl acetate, washed with saturated aqueous ammonium chloride solution, water and saturated aqueous sodium chloride solution and then dried over magnesium sulfate. The solvent was removed under reduced pressure and purification of the residue by column chromatography on silica gel, eluting with a mixture of ethyl acetate and dichloromethane (0:1 to 1:3 by volume) gave title compound as a pale orange oil, 1.75 g.

$^1$H NMR (DMSO-d6): δ 2.30 (s, 3H), 2.40 (s, 3H), 3.60 (s, 3H), 4.00 (s, 2H), 4.15 (s, 2H), 6.85 (s, 1H), 7.10 (s, 1H), 7.20 (d, J=8.3 Hz, 2H), 7.30 (d, J=8.3 Hz, 2H), 11.75 (s, 1H).

MS: ESI (+ve) (Method B): 370 (M+H)$^+$, Retention time 3.4 min.

Preparation 3e

[3-(4-chlorobenzyl)-2-ethoxy-4,7-dimethylquinolin-5-yl]acetic Acid Methyl Ester

A mixture of [3-(4-chlorobenzyl)-4,7-dimethyl-2-oxo-1,2-dihydroquinolin-5-yl]acetic acid methyl ester (1.0 g), bromoethane (0.24 mL), potassium carbonate (1.1 g) and N,N-dimethylformamide (10 mL) was heated at 40° C. for 17 hours. The mixture was diluted with ethyl acetate and washed with water and saturated aqueous sodium chloride solution and then dried over magnesium sulfate. The solvent was removed under reduced pressure and purification of the residue by column chromatography on silica gel, eluting with a mixture of ethyl acetate and dichloromethane (0:1 to 1:5 by volume) gave title compound as a gum, 0.28 g.

$^1$H NMR (DMSO-d6): δ 1.25 (t, J=7.0 Hz, 3H), 2.35 (s, 3H), 2.40 (s, 3H), 3.60 (s, 3H), 4.05 (s, 2H), 4.15 (s, 2H), 4.35 (q, J=7.0 Hz, 2H), 7.00 (s, 1H), 7.15 (d, J=8.6 Hz, 2H), 7.30 (d, J=8.6 Hz, 2H), 7.35 (s, 1H).

MS: ESI (+ve) (Method B): 398 (M+H)$^+$, Retention time 4.7 min.

Preparation 3f

[3-(4-chlorobenzyl)-2-ethoxy-4,7-dimethylquinolin-5-yl]acetic Acid

A solution of [3-(4-chlorobenzyl)-2-ethoxy-4,7-dimethylquinolin-5-yl]acetic acid methyl ester (0.10 g), methanol (2.0 mL), saturated aqueous lithium hydroxide solution (0.20 mL) and water (0.4 mL) was stirred at 50° C. for 5 hours. The methanol was removed under reduced pressure and the residue acidified by the addition of trifluoroacetic acid. The resulting precipitate was collected by filtration, washed with water and dried to afford title compound as a white solid, 0.095 g.

$^1$H NMR (DMSO-d6): δ 1.30 (t, J=7.0 Hz, 3H), 2.40 (s, 3H), 2.60 (s, 3H), 4.10 (s, 2H), 4.15 (s, 2H), 4.40 (q, J=7.0 Hz, 2H), 7.10 (m, 1H), 7.15 (m, 2H), 7.30 (m, 2H), 7.50 (m, 1H), 12.50 (br s, 1H).

MS: ESI (+ve) (Method A): 384 (M+H)$^+$, Retention time 13.4 min.

MS: ESI (+ve) (Method B): 384 (M+H)$^+$, Retention time 4.2 min.

Example 4

[3-(4-chlorobenzyl)-2,4,7-trimethylquinolin-5-yloxy]acetic Acid

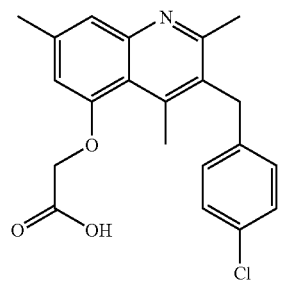

Preparation 4a

[3-(4-chlorobenzyl)-2,4,7-trimethylquinolin-5-yloxy]acetic Acid Methyl Ester

A mixture of 3-(4-chlorobenzyl)-2,4,7-trimethylquinolin-5-ol (0.24 g), N,N-dimethylformamide (2.0 mL), potassium carbonate (0.12 g) and bromoacetic acid methyl ester (0.12 mL) was stirred at room temperature for 17 hours. The mixture was filtered and the filtrate concentrated under reduced pressure. The residue was triturated with diethyl ether and further purification by column chromatography on silica gel, eluting with a mixture of methyl tert-butyl ether and dichloromethane (1:4 to 3:7 by volume) gave title compound, 0.078 g.

$^1$H NMR (CDCl$_3$): δ 2.50 (s, 3H), 2.60 (s, 3H), 2.85 (s, 3H), 3.85 (s, 3H), 4.20 (s, 2H), 4.75 (s, 2H), 6.55 (m, 1H), 6.95 (m, 2H), 7.30 (m, 2H), 7.50 (m, 1H).

MS: ESI (+ve) (Method B): 384 (M+H)$^+$, Retention time 2.5 min.

Preparation 4b

[3-(4-chlorobenzyl)-2,4,7-trimethylquinolin-5-yloxy] acetic Acid

A solution of [3-(4-chlorobenzyl)-2,4,7-trimethylquinolin-5-yloxy]acetic acid methyl ester (0.045 g), acetonitrile (2.0 mL), tetrahydrofuran (1.0 mL) and 4.0 M aqueous lithium hydroxide solution (2.0 mL) was stirred at room temperature for 2 hours. The organic solvents were removed under reduced pressure and the pH of the residue adjusted to 5-6 by the addition of saturated aqueous sodium dihydrogenphosphate solution. The resulting mixture was extracted with chloroform and the combined extracts dried over magnesium sulfate. The solvent was removed under reduced pressure and trituration of the residue with diethyl ether and then methanol gave title compound, 0.025 g.

$^1$H NMR (DMSO-d6): δ 2.40 (s, 3H), 2.50 (s, 3H), 2.80 (s, 3H), 4.20 (s, 2H), 4.60 (s, 2H), 6.70 (m, 1H), 7.05 (d, J=8.6 Hz, 2H), 7.25 (m, 1H), 7.30 (d, J=8.6 Hz, 2H).

MS: ESI (+ve) (Method A): 370 (M+H)$^+$, Retention time 7.5 min.

MS: ESI (+ve) (Method B): 370 (M+H)$^+$, Retention time 2.3 min.

Example 5

[3-(4-chlorobenzyl)-2,4,7-trimethylquinolin-5-yl] acetic Acid

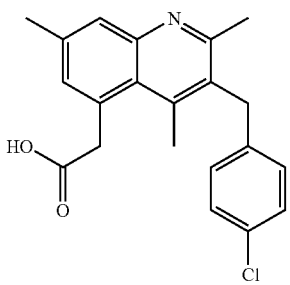

Preparation 5a 3-(4-chlorobenzyl)-2,4,7-trimethylquinolin-5-ol

A mixture of 3-amino-5-methylphenol (1.0 g), 3-(4-chlorobenzyl)pentane-2,4-dione (1.7 g) and toluene-4-sulfonic acid (0.30 g) was heated at 160° C. under nitrogen for 3 hours. The mixture was cooled to room temperature and the residue triturated with methanol to give title compound, 1.5 g.

MS: ESI (+ve) (Method B): 312 (M+H)$^+$, Retention time 2.3 min.

Preparation 5b

Trifluoromethanesulfonic Acid 3-(4-chlorobenzyl)-2,4,7-trimethylquinolin-5-yl Ester A mixture of 3-(4-chlorobenzyl)-2,4,7-trimethylquinolin-5-ol (0.32 g), N-phenyltrifluoromethanesulfonimide (0.36 g), potassium carbonate (0.42 g) and tetrahydrofuran (5.0 mL) was heated by microwave irradiation at 120° C. for 20 minutes. The mixture was filtered and the filtrate concentrated under reduced pressure. Purification of the residue by column chromatography on silica gel, eluting with a mixture of dichloromethane and methyl tert-butyl ether (9:1 by volume) gave title compound, 0.39 g.

$^1$H NMR (CDCl$_3$): δ 2.55 (s, 3H), 2.65 (s, 3H), 2.75 (s, 3H), 4.25 (s, 2H), 6.90 (m, 2H), 7.25-7.40 (m, 4H).

Preparation 5c

[3-(4-chlorobenzyl)-2,4,7-trimethylquinolin-5-yl] acetic Acid Methyl Ester

A mixture of trifluoromethanesulfonic acid 3-(4-chlorobenzyl)-2,4,7-trimethylquinolin-5-yl ester (0.39), 1-(tert-butyldimethylsilyloxy)-1-methoxyethene (0.95 mL), sodium acetate (0.086 g), tris(dibenzylideneacetone) dipalladium (0) (0.080 g) and 1,1'-bis(diphenylphospino) ferrocene (0) (0.048 g) in N,N-dimethylformamide (3.0 mL) was heated by microwave irradiation at 120° C. for 10 minutes. The mixture was diluted with saturated aqueous ammonium chloride solution and extracted with ethyl acetate. The combined extracts were dried over sodium sulfate and the solvent removed under reduced pressure. Purification of the residue by column chromatography on silica gel, eluting with a mixture of ethyl acetate and cyclohexane (1:1 by volume) gave title compound, 0.11 g.

$^1$H NMR (CD$_3$OD): δ 2.50 (s, 3H), 2.55 (s, 3H), 2.65 (s, 3H), 3.65 (s, 3H), 4.25 (s, 2H), 4.30 (s, 2H), 7.00 (d, J=8.6 Hz, 2H), 7.25 (m, 3H), 7.70 (m, 1H).

Preparation 5d

[3-(4-chlorobenzyl)-2,4,7-trimethylquinolin-5-yl] acetic Acid

A solution of [3-(4-chlorobenzyl)-2,4,7-trimethylquinolin-5-yl]acetic acid methyl ester (0.10 g), methanol (2.0 mL) and 4.0 M aqueous lithium hydroxide solution (2.0 mL) was stirred at room temperature for 2 hours. The methanol was removed under reduced pressure and the pH of the residue adjusted to 5-6 by the addition of saturated aqueous sodium dihydrogenphosphate solution. The resulting mixture was extracted with ethyl acetate and the combined extracts dried over magnesium sulfate and the solvent removed under reduced pressure. Trituration of the residue with acetonitrile gave title compound, 0.010 g.

$^1$H NMR (DMSO-d6): δ 2.55 (s, 3H), 2.80 (s, 3H), 3.05 (s, 3H), 4.25 (s, 2H), 5.30 (s, 2H), 6.85 (m, 2H), 7.25 (m, 2H), 7.40 (m, 1H), 8.70 (m, 1H).

MS: ESI (+ve) (Method A): 354 (M+H)$^+$, Retention time 7.0 min.

MS: ESI (+ve) (Method B): 354 (M+H)$^+$, Retention time 2.4 min.

Example 6

[8-chloro-3-(4-chlorobenzyl)-2,4-dimethylquinolin-5-yl]acetic Acid

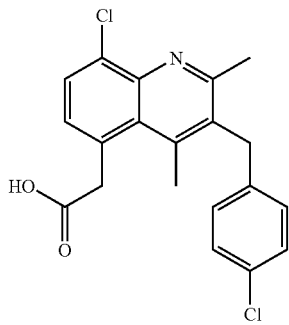

Preparation 6a

8-chloro-3-(4-chlorobenzyl)-2,4-dimethylquinolin-5-ol

A mixture of 3-amino-4-chlorophenol (2.2 g), 3-(4-chlorobenzyl)pentane-2,4-dione (3.4 g) and toluene-4-sulfonic acid (few crystals) was heated at 170° C. under nitrogen for 10 hours. The mixture was cooled to room temperature and purification by column chromatography on silica gel, eluting with a mixture of methanol and dichloromethane (1:19 by volume), followed by trituration with diethyl ether gave title compound as a pale brown solid, 0.41 g.

$^1$H NMR (DMSO-d6): δ 2.55 (s, 3H), 2.80 (s, 3H), 4.25 (s, 2H), 6.85 (d, J=8.3 Hz, 1H), 7.05 (d, J=8.3 Hz, 2H), 7.30 (d, J=8.3 Hz, 2H), 7.60 (d, J=8.3 Hz, 1H), 10.50 (s, 1H).

MS: ESI (+ve) (Method B): 332 (M+H)$^+$, Retention time 3.4 min.

Preparation 6b

Trifluoromethanesulfonic Acid 8-chloro-3-(4-chlorobenzyl)-2,4-dimethylquinolin-5-yl Ester A mixture of 8-chloro-3-(4-chlorobenzyl)-2,4-dimethylquinolin-5-ol (0.20 g), N-phenyltrifluoromethanesulfonimide (0.26 g), potassium carbonate (0.25 g) and tetrahydrofuran (2.0 mL) was heated by microwave irradiation at 120° C. for 10 minutes. The mixture was diluted with water and extracted with ethyl acetate. The combined extracts were washed with saturated aqueous sodium chloride solution and dried over sodium sulfate. The solvent was removed under reduced pressure and purification of the residue by column chromatography on silica gel, eluting with a mixture of ethyl acetate and cyclohexane (1:19 by volume) gave title compound as a beige solid, 0.25 g.

$^1$H NMR (CDCl$_3$): δ 2.70 (s, 3H), 2.75 (s, 3H), 4.30 (s, 2H), 6.90 (d, J=8.8 Hz, 2H), 7.25 (d, J=8.8 Hz, 2H), 7.40 (d, J=8.4 Hz, 1H), 7.80 (d, J=8.4 Hz, 1H).

Preparation 6c

[8-chloro-3-(4-chlorobenzyl)-2,4-dimethylquinolin-5-yl]acetic Acid Methyl Ester A mixture of trifluoromethanesulfonic acid 8-chloro-3-(4-chlorobenzyl)-2,4-dimethylquinolin-5-yl ester (0.24 g), 1-(tert-butyldimethylsilyloxy)-1-methoxyethene (0.56 mL), sodium acetate (0.053 g), tris(dibenzylideneacetone) dipalladium (0) (0.024 g) and 1,1'-bis(diphenylphospino) ferrocene (0) (0.014 g) in N,N-dimethylformamide (2 mL) was heated by microwave irradiation at 120° C. for 10 minutes. The mixture was diluted with ethyl acetate, washed with water and saturated aqueous sodium chloride solution and then dried over sodium sulfate. The solvent was removed under reduced pressure and the residue purified by column chromatography on silica gel, eluting with a mixture of ethyl acetate and cyclohexane (1:9 to 1:6 by volume) to afford title compound as a pink solid, 0.12 g.

$^1$H NMR (CDCl$_3$): δ 2.60 (s, 3H), 2.70 (s, 3H), 3.70 (s, 3H), 4.20 (s, 2H), 4.25 (s, 2H), 6.90 (d, J=8.6 Hz, 2H), 7.20-7.25 (m, 3H), 7.70 (d, J=7.8 Hz, 1H).

MS: ESI (+ve) (Method B): 388 (M+H)$^+$, Retention time 4.3 min.

Preparation 6d

[8-chloro-3-(4-chlorobenzyl)-2,4-dimethylquinolin-5-yl]acetic Acid

A solution of [8-chloro-3-(4-chlorobenzyl)-2,4-dimethylquinolin-5-yl]acetic acid methyl ester (0.11 g), methanol (5.0 mL) and 1.0 M aqueous lithium hydroxide solution (0.84 mL) was stirred at room temperature for 17 hours. The solvent was removed under reduced pressure and the residue diluted with water. The pH of the mixture was adjusted to 3-4 by the addition of 1.0 M aqueous hydrochloric acid and the resulting precipitate collected by filtration and washed with water. Crystallisation from industrial methylated spirits gave title compound as a white solid, 0.056 g.

$^1$H NMR (DMSO-d6): δ 2.55 (s, 3H), 2.60 (s, 3H), 4.20 (s, 2H), 4.30 (s, 2H), 7.05 (d, J=8.6 Hz, 2H), 7.30 (d, J=8.6 Hz, 2H), 7.35 (d, J=8.1 Hz, 1H), 7.80 (d, J=8.1 Hz, 1H).

MS: ESI (+ve) (Method A): 374 (M+H)$^+$, Retention time 10.9 min.

Example 7

[8-chloro-3-(4-chlorophenoxy)-2,4-dimethylquinolin-5-yloxy]acetic Acid

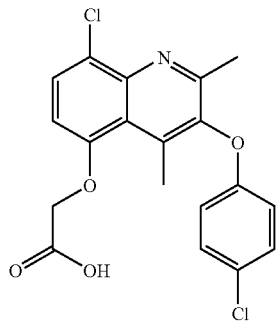

Preparation 7a

8-chloro-3-(4-chlorophenoxy)-2,4-dimethylquinolin-5-ol

A mixture of 3-amino-4-chlorophenol (0.36 g), 3-(4-chlorophenoxy)pentane-2,4-dione (0.57 g) and p-toluenesulfonic acid monohydrate (0.020 g) was heated at 125° C. for 3 hours. The mixture was cooled to room temperature and purified by column chromatography on silica gel, eluting with a mixture of dichloromethane and ethyl acetate (1:0 to 0:1 by volume) to afford title compound as a brown oil, 0.16 g.

$^1$H NMR (CDCl$_3$): δ 2.55 (s, 3H), 2.70 (s, 3H), 6.70 (d, J=9.0 Hz, 1H), 6.75 (d, J=9.0 Hz, 2H), 7.20 (d, J=9.0 Hz, 2H), 7.25 (d, J=9.0 Hz, 1H).

MS: ESI (+ve) (Method B): 334 (M+H)$^+$, Retention time 4.2 min.

Preparation 7b

[8-chloro-3-(4-chlorophenoxy)-2,4-dimethylquinolin-5-yloxy]acetic acid methyl ester A mixture of 8-chloro-3-(4-chlorophenoxy)-2,4-dimethylquinolin-5-ol (0.16 g), N,N-dimethylformamide (3.0 mL), potassium carbonate (0.20 g) and bromoacetic acid methyl ester (0.88 g) was stirred at room temperature for 15 hours. The mixture was diluted with dichloromethane, washed with water and dried over magnesium sulfate. The solvent was removed under reduced pressure and purification of the residue by column chromatography on silica gel, eluting with a mixture of dichloromethane and ethyl acetate (1:0 to 5:1 by volume) gave title compound as an off-white solid, 0.20 g.

MS: ESI (+ve) (Method B): 406 (M+H)$^+$, Retention time 4.5 min.

Preparation 7c

[8-chloro-3-(4-chlorophenoxy)-2,4-dimethylquinolin-5-yloxy]acetic Acid

A solution of [8-chloro-3-(4-chlorophenoxy)-2,4-dimethylquinolin-5-yloxy]acetic acid methyl ester (0.20 g), methanol (5.0 mL), water (1.0 mL) and 5.0 M aqueous sodium hydroxide solution (1.0 mL) was stirred at room temperature for 3 hours. The pH of the solution was adjusted to 1 by the addition of 1.0 M hydrochloric acid and the methanol removed under reduced pressure. The residue was purified by preparative reverse-phase HPLC using a gradient over 30 minutes of acetonitrile in water (40% to 98% of organic modifier) to afford title compound as a yellow-green solid, 0.025 g.

$^1$H NMR (DMSO-d6): δ 2.45 (s, 3H), 2.70 (s, 3H), 3.55 (s, 2H), 4.85 (s, 2H), 6.85 (d, J=9.0 Hz, 2H), 7.00 (d, J=8.6 Hz, 1H), 7.35 (d, J=9.0 Hz, 2H), 7.80 (d, J=8.6 Hz 1H), 13.15 (brs, 1H).

MS: ESI (+ve) (Method A): 392 (M+H)$^+$, Retention time 12.3 min.

Example 8

[8-chloro-3-(4-chlorophenylsulfanyl)-2,4-dimethylquinolin-5-yloxy]acetic Acid

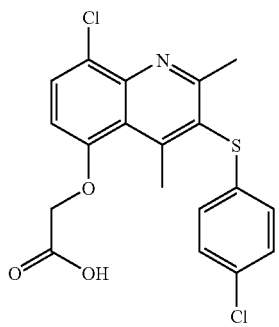

Preparation 8a 8-chloro-3-(4-chlorophenylsulfanyl)-2,4-dimethylquinolin-5-ol

A mixture of 3-amino-4-chlorophenol (0.36 g), 3-(4-chlorophenylsulfanyl)pentane-2,4-dione (0.61 g) and p-toluenesulfonic acid monohydrate (0.040 g) was heated at 140° C. for 10 hours. The mixture was cooled to room temperature and purified by column chromatography on silica gel, eluting with a mixture of dichloromethane and ethyl acetate (1:0 to 0:1 by volume) to afford title compound as a brown oil, 0.050 g.

MS: ESI (−ve) (Method B): 348 (M−H)$^−$, Retention time 4.4 min.

Preparation 8b

[8-chloro-3-(4-chlorophenylsulfanyl)-2,4-dimethylquinolin-5-yloxy]acetic Acid Methyl Ester A mixture of 8-chloro-3-(4-chlorophenylsulfanyl)-2,4-dimethylquinolin-5-ol (0.050 μg), N,N-dimethylformamide (2.0 mL), potassium carbonate (0.059 g) and bromoacetic acid methyl ester (0.031 g) was stirred at room temperature for 15 hours. The mixture was diluted with dichloromethane and this solution was washed with water and then dried over magnesium sulfate. The solvent was removed under reduced pressure to afford title compound as brown solid, 0.11 g.

MS: ESI (+ve) (Method B): 422 (M+H)$^+$, Retention time 4.8 min.

Preparation 8c

[8-chloro-3-(4-chlorophenylsulfanyl)-2,4-dimethylquinolin-5-yloxy]acetic Acid

A solution of [8-chloro-3-(4-chlorophenylsulfanyl)-2,4-dimethylquinolin-5-yloxy]acetic acid methyl ester (0.11 g), methanol (5.0 mL), water (1.0 mL) and 5.0 M aqueous sodium hydroxide solution (0.5 mL) was stirred at room temperature for 3 hours. The pH of the solution was adjusted to 1 by the addition of 1.0 M aqueous hydrochloric acid. The resulting mixture was purified by preparative reverse-phase HPLC using a gradient over 30 minutes of acetonitrile in water (30% to 90% of organic modifier) to afford title compound as a white solid, 0.045 g.

$^1$H NMR (DMSO-d6): δ 2.70 (s, 3H), 3.15 (s, 3H), 5.35 (s, 2H), 6.85 (d, J=8.5 Hz, 1H), 7.00 (d, J=8.5 Hz, 2H), 7.35 (d, J=8.5 Hz, 2H), 7.80 (d, J=8.5 Hz, 1H).

MS: ESI (+ve) (Method A): 408 (M+H)$^+$, Retention time 13.1 min.

Example 9

[8-chloro-3-(4-chlorobenzyl)-4-difluoromethoxy-2-methylquinolin-5-yloxy]acetic Acid

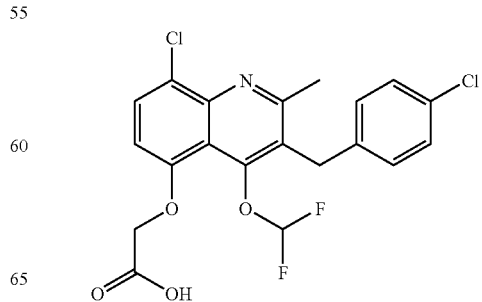

Preparation 9a

[8-chloro-3-(4-chlorobenzyl)-4-difluoromethoxy-2-methylquinolin-5-yloxy]acetic Acid Methyl Ester To a mixture of [8-chloro-3-(4-chlorobenzyl)-2-methyl-4-oxo-1,4-dihydroquinolin-5-yloxy]acetic acid methyl ester (0.080 g), N,N-dimethylformamide (2.0 mL) and potassium carbonate (0.080 g) at −80° C. was added chlorodifluoromethane (0.4 mL). The flask was sealed and the resulting mixture warmed to room temperature and then stirred at this temperature for 17 hours. The excess chlorodifluoromethane was allowed to evaporate and the residue diluted with water and extracted with ethyl acetate. The combined extracts were washed with saturated aqueous sodium chloride solution and dried over magnesium sulfate. The solvent was removed under reduced pressure to afford title compound as a light brown solid, 0.10 g.

MS: ESI (+ve) (Method B): 456 $(M+H)^+$, Retention time 4.3 min.

Example 9b

[8-chloro-3-(4-chlorobenzyl)-4-difluoromethoxy-2-methylquinolin-5-yloxy]acetic acid A solution of [8-chloro-3-(4-chlorobenzyl)-4-difluoromethoxy-2-methylquinolin-5-yloxy]acetic acid methyl ester (0.10 g), methanol (6.0 mL), water (0.6 mL) and saturated aqueous lithium hydroxide solution (0.3 mL) was stirred at room temperature for 17 hours. The methanol was removed under reduced pressure and the pH of the residue adjusted to 4 by the addition of glacial acetic acid. The resulting precipitate was collected by filtration and washed with water. Purification of the solid by preparative reverse-phase HPLC using a gradient over 37 minutes of acetonitrile in water (20% to 95% of organic modifier) gave title compound as a cream solid, 0.020 g.

$^1$H NMR (DMSO-d6): δ 2.55 (s, 3H), 4.30 (s, 2H), 4.95 (s, 2H), 7.05 (d, J=8.7 Hz, 1H), 7.10 (d, J=8.5 Hz, 2H), 7.25 (t, J=75 Hz, 1H); 7.35 (d, J=8.5 Hz, 2H), 7.85 (d, J=8.7 Hz, 1H), 13.50 (br s, 1H).

MS: ESI (+ve) (Method A): 442 $(M+H)^+$, Retention time 12.5 min.

MS: ESI (+ve) (Method B): 442 $(M+H)^+$, Retention time 3.9 min.

Example 10

[8-chloro-3-(4-chlorobenzyl)-2-methylquinolin-5-yloxy]acetic Acid

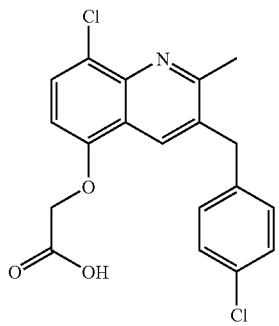

Preparation 10a

[4,8-dichloro-3-(4-chlorobenzyl)-2-methylquinolin-5-yloxy]acetic Acid Methyl Ester A solution of [8-chloro-3-(4-chlorobenzyl)-2-methyl-4-oxo-1,4-dihydroquinolin-5-yloxy]acetic acid methyl ester (0.13 g) in phosphorus oxychloride (5.0 mL) was heated at 180° C. in a microwave reactor for 15 minutes. The mixture was poured into ice and the pH of the solution adjusted to 3 by the addition of sodium acetate. The mixture was extracted with ethyl acetate and the combined extracts washed with saturated aqueous sodium hydrogen carbonate solution and dried over magnesium sulfate. The solvent removed under reduced pressure to afford title compound as a beige solid, 0.12 g.

Preparation 10b

[8-chloro-3-(4-chlorobenzyl)-2-methylquinolin-5-yloxy]acetic Acid Methyl Ester

A mixture of [4,8-dichloro-3-(4-chlorobenzyl)-2-methylquinolin-5-yloxy]acetic acid methyl ester (0.12 g), palladium, 5 wt. % on activated carbon (0.010 g), ethanol, and 1.0 M aqueous hydrochloric acid (1.0 mL) was stirred at room temperature for 17 hours under an atmosphere of hydrogen. The mixture was filtered through hyflo, washing with ethanol and water and the solvent removed under reduced pressure to afford title compound, 0.11 g.

Preparation 10c

[8-chloro-3-(4-chlorobenzyl)-2-methylquinolin-5-yloxy]acetic Acid

A solution of [8-chloro-3-(4-chlorobenzyl)-2-methylquinolin-5-yloxy]acetic acid methyl ester (0.10 g), ethanol (6.0 mL), water (2.0 mL) and saturated aqueous lithium hydroxide solution (2.0 mL) was stirred at room temperature for 5 hours. The ethanol was removed under reduced pressure and the pH of the residue adjusted to 4 by the addition of glacial acetic acid. The resulting precipitate was collected by filtration, washed with water and purification by preparative reverse-phase HPLC using a gradient over 37 minutes of acetonitrile in water (20% to 95% of organic modifier) gave title compound as an off-white solid, 0.039 mg.

$^1$H NMR (DMSO-d6): δ 2.60 (s, 3H), 4.25 (s, 2H), 4.90 (s, 2H), 6.90 (d, J=8.6 Hz, 1H), 7.20 (d, J=8.6 Hz, 2H), 7.35 (d, J=8.6 Hz, 2H), 7.75 (d, J=8.6 Hz, 1H), 8.30 (s, 1H), 13.15 (br s, 1H).

MS: ESI (+ve) (Method A): 376 $(M+H)^+$, Retention time 11.3 min.

MS: ESI (+ve) (Method B): 376 $(M+H)^+$, Retention time 3.6 min.

Example 11

[7-chloro-3-(4-chlorobenzyl)-2,4-dimethylquinolin-5-yl]acetic acid

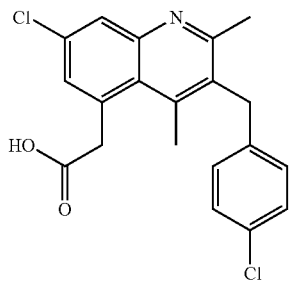

Preparation 11a 7-chloro-3-(4-chlorobenzyl)-2,4-dimethylquinolin-5-ol

A mixture of 3-amino-5-chlorophenol (0.46 g), 3-(4-chlorobenzyl)pentane-2,4-dione (0.72 g), and p-toluenesulfonic acid monohydrate (0.26 g) was heated at 160° C. for 2 hours. The mixture was cooled to room temperature, diluted with methanol (5.0 mL) and sonicated. The resulting precipitate was collected by filtration, washed with methanol and dried to afford a 50:50 mixture of title compound and 5-chloro-3-(4-chlorobenzyl)-2,4-dimethylquinolin-7-ol as an off-white solid, 0.67 g.

MS: ESI (+ve) (Method B): 332 (M+H)$^+$, Retention time 2.4 min.

Preparation 11b

Trifluoromethanesulfonic Acid 7-chloro-3-(4-chlorobenzyl)-2,4-dimethylquinolin-5-yl Ester A mixture of 7-chloro-3-(4-chlorobenzyl)-2,4-dimethylquinolin-5-ol and 5-chloro-3-(4-chlorobenzyl)-2,4-dimethylquinolin-7-ol (0.66 g), N-phenyltrifluoromethanesulfonimide (0.86 g), potassium carbonate (0.82 g) and tetrahydrofuran (10 mL) was heated by microwave irradiation at 130° C. for 20 minutes. The mixture was filtered and the filtrate concentrated under reduced pressure. Purification of the residue by column chromatography on silica gel, eluting with 1,2-dichloroethane gave a 50:50 mixture of title compound and trifluoromethanesulfonic acid 5-chloro-3-(4-chlorobenzyl)-2,4-dimethylquinolin-7-yl ester as a honey coloured gum, 0.86 g.

MS: ESI (+ve) (Method B): 464 (M+H)$^+$, Retention time 4.9 min.

Preparation 11c

[7-chloro-3-(4-chlorobenzyl)-2,4-dimethylquinolin-5-yl]acetic Acid Methyl Ester

A mixture of trifluoromethanesulfonic acid 7-chloro-3-(4-chlorobenzyl)-2,4-dimethylquinolin-5-yl ester and trifluoromethanesulfonic acid 5-chloro-3-(4-chlorobenzyl)-2,4-dimethylquinolin-7-yl ester (0.86 g), tert-butyl-(1-methoxyvinyloxy)-dimethyl silane (2.0 mL), sodium acetate (0.18 g), bis(dibenzylideneacetone) palladium (0.05 g) and 1,1'-bis(diphenylphospino) ferrocene (0) (0.05 g) in N,N-dimethylformamide (11.0 mL) was heated by microwave irradiation at 120° C. for 15 minutes. The mixture was diluted with ethyl acetate and this solution was washed with saturated aqueous ammonium chloride solution and saturated aqueous sodium chloride solution and then dried over-magnesium sulfate. The solvent was removed under reduced pressure and purification of the residue by column chromatography on silica gel, eluting with a mixture of dichloromethane, ethyl acetate and pentane (4:0:1 to 1:0:0 to 50:1:0 to 25:1:0 to 12.5:1:0 by volume) gave title compound as a honey coloured gum, 0.25 g.

$^1$H NMR (DMSO-d6): δ 2.50 (s, 3H), 2.55 (s, 3H), 3.60 (s, 3H), 4.25 (s, 2H), 4.40 (s, 2H), 7.00 (d, J=8.6 Hz, 2H), 7.35 (d, J=8.6 Hz, 2H), 7.50 (d, J=2.4 Hz, 1H), 7.90 (d, J=2.4 Hz, 1H).

MS: ESI (+ve) (Method B): 388 (M+H)$^+$, Retention time 3.2 min.

Preparation 11d

[7-chloro-3-(4-chlorobenzyl)-2,4-dimethylquinolin-5-yl]acetic Acid

A mixture of [7-chloro-3-(4-chlorobenzyl)-2,4-dimethylquinolin-5-yl]acetic acid methyl ester (0.24 g), methanol (10 mL), water (2.0 mL) and saturated aqueous lithium hydroxide solution (1.0 mL) was stirred at room temperature for 17 hours. The pH of the solution was adjusted to 5 by the addition of glacial acetic acid and the methanol removed under reduced pressure. The resulting precipitate was collected by filtration and washed with water. Crystallisation of the solid from ethyl, acetate gave title compound as a fluffy white solid, 0.16 g $^1$H NMR (DMSO-d6): δ 2.45 (s, 3H), 2.70 (s, 3H), 3.75 (s, 2H), 4.15 (s, 2H), 7.00 (d, J=8.5 Hz, 2H), 7.25 (d, J=2.4 Hz, 1H), 7.35 (d, J=8.5 Hz, 2H), 7.70 (d, J=2.4 Hz, 1H).

MS: ESI (+ve) (Method A): 374 (M+H)$^+$, Retention time 7.8 min.

MS: ESI (+ve) (Method B): 374 (M+H)$^+$, Retention time 2.6 min.

Example 12

[8-chloro-3-(4-chlorophenylsulfanyl)-2,4-dimethylquinolin-5-yl]acetic Acid

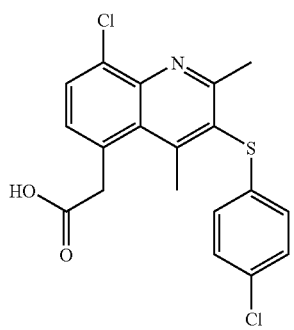

Preparation 12a

8-chloro-3-(4-chlorophenylsulfanyl)-2,4-dimethylquinolin-5-ol

A mixture of 3-amino-4-chlorophenol (5.0 g), 3-(4-chlorophenylsulfanyl)pentane-2,4-dione (8.4 g), p-toluenesulfonic acid monohydrate (12 g) was heated at 140° C. for 6 hours. The mixture was cooled to room temperature and purified by column chromatography on silica gel, eluting with a mixture of dichloromethane and ethyl acetate (1:0 to 1:1 by volume) to afford title compound as a brown solid, 1.3 g.

MS: ESI (+ve) (Method B): 350 (M+H)$^+$, Retention time 4.4 min.

Preparation 12b

Trifluoromethanesulfonic Acid 8-chloro-3-(4-chlorophenylsulfanyl)-2,4-dimethylquinolin-5-yl Ester A mixture of 8-chloro-3-(4-chlorophenylsulfanyl)-2,4-dimethylquinolin-5-ol (1.3 g), N-phenyltrifluoromethanesulfonimide (1.7 g), potassium carbonate (1.6 g) and tetrahydrofuran (10 mL) was heated by microwave irradiation at 120° C. for 20 minutes. The mixture was filtered and the filtrate concentrated under reduced pressure. Purification of the residue by column chromatography on silica gel, eluting with a mixture of pentane and dichloromethane (9:1 to 0:1 by volume) gave title compound, 0.27 g.

MS: ESI (+ve) (Method B): 482 (M+H)$^+$, Retention time 5.1 min.

Preparation 12c

[8-chloro-3-(4-chlorophenylsulfanyl)-2,4-dimethylquinolin-5-yl]acetic Acid Methyl Ester A mixture of trifluoromethanesulfonic acid 8-chloro-3-(4-chlorophenylsulfanyl)-2,4-dimethylquinolin-5-yl ester (0.31 g), tert-butyl-(1-methoxyvinyloxy)dimethyl silane (0.71 mL), sodium acetate (0.064 g), bis(dibenzylideneacetone) palladium (0.018 g) and 1,1'-bis(diphenylphospino) ferrocene (0) (0.018 g) in N,N-dimethylformamide (4.0 mL) was heated by microwave irradiation at 120° C. for 15 minutes. The mixture was diluted with ethyl acetate, and this solution was washed with saturated aqueous ammonium chloride solution and saturated aqueous sodium chloride solution and then dried over magnesium sulfate. The solvent was removed under reduced pressure and purification of the residue by column chromatography on silica gel, eluting with a mixture of dichloromethane and cyclohexane (1:1 to 2:0 by volume) gave title compound as a pale yellow solid, 0.15 g.

$^1$H NMR (DMSO-d6): δ 2.75, (s, 3H), 2.90 (s, 3H), 3.60, (s, 3H), 4.40 (s, 2H), 7.00 (d, J=8.7 Hz, 2H), 7.35 (d, J=8.7 Hz, 2H), 7.50 (d, J=7.7 Hz, 1H), 7.95 (d, J=7.7 Hz, 1H).

MS: ESI (+ve) (Method B): 406 (M+H)$^+$, Retention time 4.5 min.

Preparation 12d

[8-chloro-3-(4-chlorophenylsulfanyl)-2,4-dimethylquinolin-5-yl]acetic Acid

A mixture of [8-chloro-3-(4-chlorophenylsulfanyl)-2,4-dimethylquinolin-5-yl]acetic acid methyl ester (0.040 g), methanol (2.0 mL), water (0.4 mL) and saturated aqueous lithium hydroxide solution (0.2 mL) was stirred at room temperature for 17 hours. The solvent was removed under reduced pressure and the residue diluted with water (2.0 mL) and then the pH adjusted to 4 by the addition of glacial acetic acid. The resulting precipitate was collected by filtration, washed with water and dried to afford title compound as a grey-brown solid, 0.038 g.

$^1$H NMR (DMSO-d6): δ 2.70 (s, 3H), 3.00 (s, 3H), 4.15 (s, 2H), 7.00 (d, J=8.6 Hz, 2H), 7.30 (d, J=8.6 Hz, 2H), 7.45 (d, J=7.8 Hz, 1H), 7.85 (d, J=7.8 Hz, 1H).

MS: ESI (+ve) (Method A): 392 (M+H)$^+$, Retention time 12.4 min.

MS: ESI (+ve) (Method B): 392 (M+H)$^+$, Retention time 4.1 min.

Example 13

N-{2-[8-chloro-3-(4-chlorobenzyl)-2,4-dimethylquinolin-5-yloxy]-acetyl}methanesulfonamide

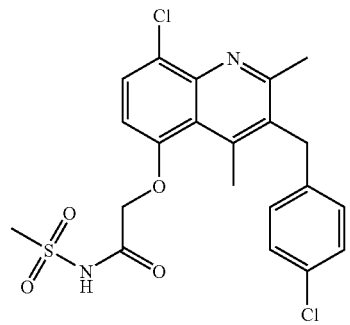

Preparation 13a

N-{2-[8-chloro-3-(4-chlorobenzyl)-2,4-dimethylquinolin-5-yloxy]acetyl}methanesulfonamide A mixture of [8-chloro-3-(4-chlorobenzyl)-2,4-dimethylquinolin-5-yloxy]acetic acid (0.050 g), 1-(3-dimethylaminopropyl)-3-ethylcarbodiimide hydrochloride (0.037 g), methanesulfonamide (0.020 g), and 4-(N,N-dimethylamino)pyridine (0.005 g) in dichloromethane (5.0 mL) was stirred at room temperature 1 hour. The mixture was diluted with dichloromethane and this solution was washed with water and then dried over magnesium sulfate. The solvent was removed under reduced pressure and purification of the residue by preparative reverse-phase HPLC using a gradient over 30 minutes of acetonitrile in water (40% to 95% of organic modifier) gave title compound as a yellow solid, 0.010 g $^1$H NMR (DMSO-d6): δ 2.60 (s, 3H), 2.80 (s, 3H), 3.30 (s, 3H), 4.30 (s, 2H), 4.90 (s, 2H), 6.85 (d, J=8.8 Hz, 1H), 7.05 (d, J=8.4 Hz, 2H), 7.35 (d, J=8.4 Hz, 2H), 7.75 (d, J=8.8 Hz, 1H), 12.15 (br s, 1H).

MS: ESI (+ve) (Method A): 467 (M+H)$^+$, Retention time 11.0 min.

Example 14

N-{2-[8-chloro-3-(4-chlorobenzyl)-2,4-dimethylquinolin-5-yloxy]-acetyl}benzenesulfonamide

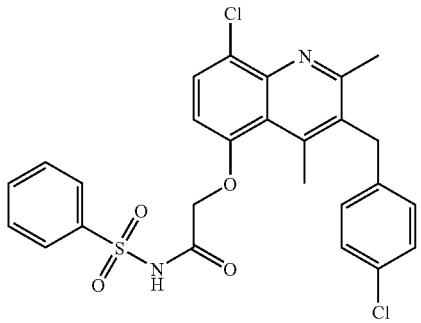

Preparation 14a

N-{2-[8-chloro-3-(4-chlorobenzyl)-2,4-dimethylquinolin-5-yloxy]acetyl}benzenesulfonamide A mixture of [8-chloro-3-(4-chlorobenzyl)-2,4-dimethylquinolin-5-yloxy]acetic acid (0.050 g), 1-(3-dimethylaminopropyl)-3-ethylcarbodiimide hydrochloride (0.037 g), benzenesulfonamide (0.030 g), and 4-(N,N-dimethylamino)pyridine (0.005 g) in dichloromethane (5.0 mL) was stirred at room temperature 1 hour. The mixture was purified by column chromatography on silica gel, eluting with a mixture of methanol and dichloromethane (1:19 by volume), followed by trituration with cyclohexane containing a small amount of diethyl ether to afford title compound as a buff solid, 0.020 g.

$^1$H NMR (DMSO-d6): δ 2.55 (s, 3H), 2.70 (s, 3H), 4.25 (s, 2H), 4.80 (s, 2H), 6.70 (d, J=8.6 Hz, 1H), 7.00 (d, J=8.6 Hz, 2H), 7.35 (d, J=8.6 Hz, 2H), 7.60-7.70 (m, 4H), 7.90 (d, J=8.6 Hz, 2H), 12.55 (br s, 1H).

MS: ESI (+ve) (Method A): 529 (M+H)+ Retention time 12.4 min.

Example 15

[8-chloro-3-(4-chlorophenoxy)-2,4-dimethylquinolin-5-yl]acetic Acid

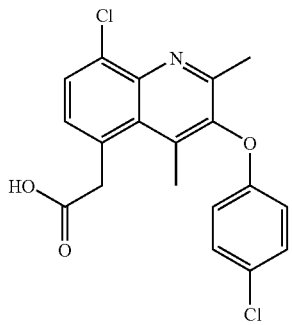

Preparation 15a

Trifluoromethanesulfonic Acid 8-chloro-3-(4-chlorophenoxy)-2,4-dimethylquinolin-5-yl Ester A mixture of 8-chloro-3-(4-chlorophenoxy)-2,4-dimethylquinolin-5-ol (0.50 g), N-phenyltrifluoromethanesulfonimide (0.68 g), potassium carbonate (0.62 g) and tetrahydrofuran (3.0 mL) was heated by microwave irradiation at 120° C. for 20 minutes. The mixture was diluted with dichloromethane and this solution was washed with water and saturated aqueous sodium chloride solution and then dried over magnesium sulfate. The solvent was removed under reduced pressure and the residue purified by column chromatography on silica gel, eluting with a mixture of ethyl acetate and pentane (1:9 by volume) to afford title compound as a yellow solid, 0.36 g.

MS: ESI (+ve) (Method B): 466 (M+H)$^+$, Retention time 5.1 min.

Preparation 15b

[8-chloro-3-(4-chlorophenoxy)-2,4-dimethylquinolin-5-yloxy]acetic Acid Methyl Ester A mixture of trifluoromethanesulfonic acid 8-chloro-3-(4-chlorophenoxy)-2,4-dimethylquinolin-5-yl ester (0.20 g), tert-butyl-(1-methoxyvinyloxy)dimethyl silane (0.40 g), sodium acetate (0.044 g), tris(dibenzylideneacetone) dipalladium (0.020 g) and 1,1'-bis(diphenylphospino) ferrocene (0) (0.012 g) in N,N-dimethylformamide (5.0 mL) was heated by microwave irradiation at 120° C. for 15 minutes. The mixture was purified by column chromatography on silica gel, eluting with a mixture of pentane and dichloromethane (9:1 to 0:1 by volume) to afford title compound as a yellow oil, 0.034 g.

MS: ESI (+ve) (Method B): 390 (M+H)$^+$, Retention time 4.4 min.

Preparation 15c

[8-chloro-3-(4-chlorophenoxy)-2,4-dimethylquinolin-5-yl]acetic Acid

A mixture of [8-chloro-3-(4-chlorophenoxy)-2,4-dimethylquinolin-5-yloxy]acetic acid methyl ester (0.035 g), methanol (5.0 mL), and 5.0 M aqueous sodium hydroxide solution (0.36 mL) was stirred at room temperature for 4 hours. The solvent was removed under reduced pressured and the residue purified by preparative reverse-phase HPLC using a gradient over 30 minutes of acetonitrile in water (30% to 95% of organic modifier) to afford title compound as a white solid, 0.0050 g.

$^1$H NMR (DMSO-d6): δ 2.45 (s, 3H), 2.55 (s, 3H), 4.25 (s, 2H), 6.85 (d, J=9.1 Hz, 2H), 7.35 (d, J=9.1 Hz, 2H), 7.45 (d, J=7.8 Hz, 1H), 7.85 (d, J=7.8 Hz, 1H).

MS: ESI (+ve) (Method A): 376 (M+H)$^+$, Retention time 11.6 min.

MS: ESI (+ve) (Method B): 376 (M+H)$^+$, Retention time 4.0 min.

Example 16 and 17

[8-chloro-3-(4-chlorobenzyl)-4-ethyl-2-methylquinolin-5-yloxy]acetic acid and [8-chloro-3-(4-chlorobenzyl)-2-ethyl-4-methylquinolin-5-yloxy]acetic Acid

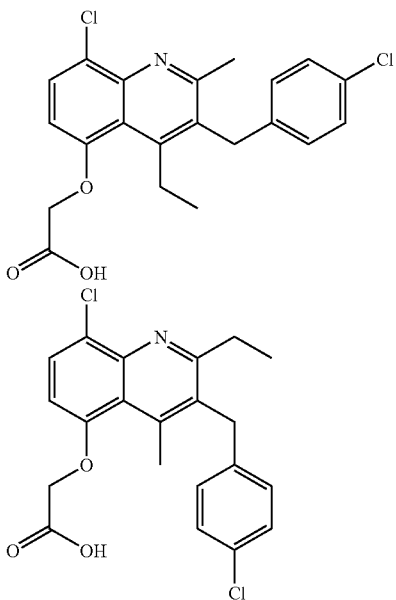

Preparation 16a

3-(4-chlorobenzyl)hexane-2,4-dione

A solution of hexane-2,4-dione (5.7 g) in N,N-dimethylformamide (20 mL) was added dropwise over a period of 15 minutes to a stirred suspension of sodium hydride (60% in oil, 2.2 g) in N,N-dimethylformamide (60 mL) at −5° C. The mixture was stirred a room temperature for 30 minutes and then a solution of 1-bromomethyl-4-chlorobenzene (11 g) in N,N-dimethylformamide (20 mL) was added dropwise over a period of 20 minutes. The resulting mixture Was stirred at room temperature for 17 hours and then diluted with 1.0 M aqueous hydrochloric acid (100 mL). The mixture was extracted with diethyl ether and the combined extracts, washed with 1.0 M aqueous hydrochloric acid and saturated aqueous sodium chloride solution and then dried over magnesium sulfate. The solvent was removed under reduced pressure and purification of the residue by column chromatography on silica gel, eluting with a mixture of pentane and toluene (1:1 to 1:2 to 0:1 by volume) gave title compound (55:45 mixture of keto-enol tautomers) as a white solid, 2.6 g.

$^1$H NMR (CDCl$_3$): δ 1.00 (t, J=7.3 Hz, 3H), 1.05 (t, J=7.3 Hz, 3H), 2.05 (s, 3H), 2.15 (s, 3H), 2.25-2.50 (m, 4H), 3.05-3.25 (M, 2H), 3.65 (s, 2H), 3.95 (t, J=7.5 Hz, 1H), 7.05-7.10 (m, 4H), 7.20-7.30 (m, 4H).

Preparation 16b and 17a

8-chloro-3-(4-chlorobenzyl)-4-ethyl-2-methylquinolin-5-ol and 8-chloro-3-(4-chlorobenzyl)-2-ethyl-4-methylquinolin-5-ol A mixture of 3-amino-4-chlorophenol (0.72 g), 3-(4-chlorobenzyl)hexane-2,4-dione (1.2 g) and p-toluenesulfonic acid monohydrate (0.10 g) was heated at 160° C. for 1.5 hours. The mixture was cooled to room temperature and then purified by column chromatography on silica gel, eluting with a mixture of toluene and dichloromethane (2:1 to 3:2 to 1:1 to 2:3 to 1:2 to 1:4 to 0:1 by volume) to afford title compounds, 0.25 g.

MS: ESI (+ve) (Method B): 346 (M+H)$^+$, Retention time 3.6 and 3.9 min.

Preparation 16c and 17b

[8-chloro-3-(4-chlorobenzyl)-4-ethyl-2-methylquinolin-5-yloxy]acetic Acid Methyl Ester and [8-chloro-3-(4-chlorobenzyl)-2-ethyl-4-methylquinolin-5-yloxy]acetic Acid Methyl Ester A mixture of 8-chloro-3-(4-chlorobenzyl)-4-ethyl-2-methylquinolin-5-ol and 8-chloro-3-(4-chlorobenzyl)-2-ethyl-4-methylquinolin-5-ol (0.25 g), N,N-dimethylformamide (4.0 mL), potassium carbonate (0.12 g) and bromoacetic acid methyl ester (0.12 g) was stirred at room temperature for 4 hours. The mixture was diluted with ethyl acetate and this mixture was washed with saturated aqueous sodium chloride solution and then dried over magnesium sulfate. The solvent was removed under reduced pressure to afford title compounds as a honey coloured semi-solid, 0.26 g.

MS: ESI (+ve) (Method B): 418 (M+H)$^+$, Retention time 4.5 and 4.8 min.

Preparation 16d and 17c

[8-chloro-3-(4-chlorobenzyl)-4-ethyl-2-methylquinolin-5-yloxy]acetic Acid and [8-chloro-3-(4-chlorobenzyl)-2-ethyl-4-methylquinolin-5-yloxy]acetic Acid A solution of [8-chloro-3-(4-chlorobenzyl)-4-ethyl-2-methylquinolin-5-yloxy]acetic acid methyl ester and [8-chloro-3-(4-chlorobenzyl)-2-ethyl-4-methylquinolin-5-yloxy]acetic acid methyl ester (0.26 g), methanol (15 mL), water (1.5 mL) and saturated aqueous lithium hydroxide solution (1.5 mL) was stirred at room temperature for 3 hours. The pH of the solution was adjusted to 4 by the addition of glacial acetic acid and the methanol removed under reduced pressure. The resulting precipitate was collected by filtration and purified by preparative reverse-phase HPLC using a gradient over 30 minutes of acetonitrile in water (40% to 98% of organic modifier) to afford [8-chloro-3-(4-chlorobenzyl)-4-ethyl-2-methylquinolin-5-yloxy]acetic acid as a yellow foam, 0.049 g and [8-chloro-3-(4-chlorobenzyl)-2-ethyl-4-methylquinolin-5-yloxy]acetic acid as a yellow foam, 0.10 g.

[8-chloro-3-(4-chlorobenzyl)-4-ethyl-2-methylquinolin-5-yloxy]acetic acid $^1$H NMR (DMSO-d6): δ 1.15 (t, J=7.3 Hz, 3H), 2.55 (s, 3H), 3.55 (m, 2H), 4.30 (s, 2H), 4.90 (s, 2H), 6.95 (d, J=8.6 Hz, 1H), 7.05 (d, J=8.5 Hz, 2H), 7.35 (d, J=8.5 Hz, 2H), 7.75 (d, J=8.6 Hz, 1H), 13.05 (br s, 1H).

MS: ESI (+ve) (Method A): 404 (M+H)$^+$, Retention time 11.7 min.

[8-chloro-3-(4-chlorobenzyl)-2-ethyl-4-methylquinolin-5-yloxy]acetic acid $^1$H NMR (DMSO-d6): δ 1.25 (t, J=7.4 Hz, 3H), 2.80 (s, 3H), 2.90 (q, J=7.4 Hz, 2H), 4.30 (s, 2H), 4.85 (s, 2H), 6.90 (d, J=8.5 Hz, 1H), 7.05 (d, J=8.5 Hz, 2H), 7.35 (d, J=8.5 Hz, 2H), 7.75 (d, J=8.5 Hz, 1H).

MS: ESI (+ve) (Method A): 404 (M+H)$^+$, Retention time 12.6 min.

Example 18 and 19

[8-chloro-4-difluoromethoxy-3-(4-fluorobenzyl)-2-methylquinolin-5-yloxy]acetic acid and [8-chloro-2-difluoromethoxy-3-(4-fluorobenzyl)-4-methylquinolin-5-yloxy]acetic acid

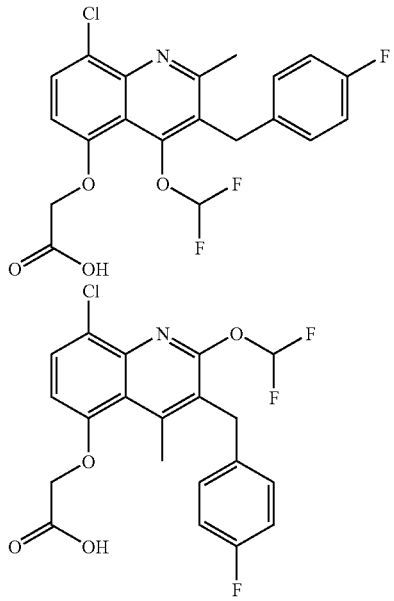

Preparation 18a 2-(4-fluorobenzyl)-3-oxobutyric Acid Ethyl Ester

A suspension of potassium tert-butoxide (11.2 g) in anhydrous tetrahydrofuran (200 mL) at 0° C. was treated with a mixture of tert-butanol (0.2 mL) and 3-oxobutyric acid ethyl ester (12.7 mL). The mixture was warmed to 15° C. over a period of 40 minutes and a solution of 1-chloromethyl-4-fluorobenzene (11.9 mL) in tetrahydrofuran (40 mL) was added and the resulting mixture heated at 70° C. for 20 hours. The mixture was cooled to room temperature, diluted with water and the tetrahydrofuran removed under reduced pressure. The residue was extracted with ethyl acetate and the combined extracts washed with water and saturated aqueous sodium chloride solution and then dried over magnesium sulfate. The solvent was removed under reduced pressure and the residue purified by distillation under reduced pressure (boiling point, 102-104° C. at 0.42 mbar) to afford title compound as a colourless oil, 12.4 g.

$^1$H NMR (CDCl$_3$): δ 1.20 (t, J=7.2 Hz, 3H), 2.20 (s, 3H), 3.15 (m, 2H), 3.75 (t, J=7.6 Hz, 1H), 4.15 (m, 2H), 6.95-7.00 (m, 2H), 7.10-7.15 (m, 2H).

Preparation 18b and 19b

[8-chloro-3-(4-fluorobenzyl)-2-methyl-4-oxo-1,4-dihydroquinolin-5-yloxy]acetic Acid Methyl Ester and [8-chloro-3-(4-fluorobenzyl)-4-methyl-2-oxo-1,2-dihydroquinolin-5-yloxy]acetic Acid Methyl Ester A mixture of (3-amino-4-chlorophenoxy)acetic acid methyl ester (1.3 g), 2-(4-fluorobenzyl)-3-oxobutyric acid ethyl ester (7.4 g), polyphosphoric acid (15 g) and dioxane (8.0 mL) was heated at 112° C. for 5 hours. The mixture was cooled to room temperature, diluted with water and extracted with ethyl acetate. The combined extracts were washed with water and dried over magnesium sulfate. The solvent was removed under reduced pressure and the residue purified by column chromatography on silica gel, eluting with a mixture of dichloromethane and methanol (19:1 by volume) to afford title compounds, 0.39 g.

$^1$H NMR (CDCl$_3$): δ 2.75 (s, 6H), 3.80 (s, 3H), 3.85 (s, 3H), 4.05 (s, 2H), 4.15 (s, 2H), 4.70 (s, 2H), 4.85 (s, 2H), 6.50-7.55 (m, 12), 9.00 (br s, 1H), 9.10 (br s, 1H).

Preparation 18c and 19c

[8-chloro-4-difluoromethoxy-3-(4-fluorobenzyl)-2-methylquinolin-5-yloxy]acetic Acid Methyl Ester and [8-chloro-2-difluoromethoxy-3-(4-fluorobenzyl)-4-methylquinolin-5-yloxy]acetic Acid Methyl Ester A mixture of [8-chloro-3-(4-fluorobenzyl)-2-methyl-4-oxo-1,4-dihydroquinolin-5-yloxy]acetic acid methyl ester and [8-chloro-3-(4-fluorobenzyl)-4-methyl-2-oxo-1,2-dihydroquinolin-5-yloxy]acetic acid methyl ester (0.39 g), N,N-dimethylformamide (70 mL), potassium carbonate (0.41 g) and acetic acid chlorodifluoromethyl ester (0.22 mL) was stirred at 80° C. for 2 hour. The mixture was diluted with water, extracted with ethyl acetate and the combined extracts dried over magnesium sulfate. The solvent was removed under reduced pressure and the residue purified by column chromatography on silica gel, eluting with a mixture of cyclohexane and ethyl acetate (4:1 by volume) to afford title compounds as a mixture, 0.26 g.

$^1$H NMR (CDCl$_3$): δ 2.65 (s, 3H), 2.95 (s, 3H), 3.80 (s, 3H), 3.85 (s, 3H), 4.20 (s, 2H), 4.35 (s, 2H), 4.75 (s, 2H), 4.85 (s, 2H), 6.60-8.05 (m, 14H).

Preparation 18d and 19d

[8-chloro-4-difluoromethoxy-3-(4-fluorobenzyl)-2-methylquinolin-5-yloxy]acetic Acid and [8-chloro-2-difluoromethoxy-3-(4-fluorobenzyl)-4-methylquinolin-5-yloxy]acetic Acid A solution of [8-chloro-4-difluoromethoxy-3-(4-fluorobenzyl)-2-methylquinolin-5-yloxy]acetic acid methyl ester and [8-chloro-2-difluoromethoxy-3-(4-fluorobenzyl)-4-methylquinolin-5-yloxy]acetic acid methyl ester (0.26 g), methanol (5.0 mL), water (3.0 mL) and lithium hydroxide solution (0.13 g mL) was stirred at room temperature for 1 hour. The solution was acidified by the addition of hydrochloric acid, extracted with ethyl acetate and the combined extracts dried over magnesium sulfate. The solvent was removed under reduced pressure and the residue purified by preparative reverse-phase HPLC using a gradient over 30 minutes of acetonitrile—(in water to afford [8-chloro-4-difluoromethoxy-3-(4-fluorobenzyl)-2-methylquinolin-5- yloxy]acetic acid as a white solid, 0.032 g and [8-chloro-2-difluoromethoxy-3-(4-fluorobenzyl)-4-methylquinolin-5-yloxy]acetic acid as a white solid, 0.029 g.

[8-chloro-4-difluoromethoxy-3-(4-fluorobenzyl)-2-methylquinolin-5-yloxy]acetic acid $^1$H NMR (DMSO-d6): δ 2.55 (s, 3H), 4.30 (s, 2H), 4.90 (s, 2H), 7.05 (d, J=8.6 Hz, 1H), 7.05-7.15 (m, 4H), 7.25 (t, J=75 Hz, 1H), 7.85 (d, J=8.6 Hz, 1H), 13.50 (br s, 1H).

MS: ESI (+ve) (Method A): 426 (M+H)$^+$, Retention time 11.6 min.

[8-chloro-2-difluoromethoxy-3-(4-fluorobenzyl)-4-methylquinolin-5-yloxy]acetic acid $^1$H NMR (DMSO-d6): δ 2.90 (s, 3H), 4.20 (s, 2H), 4.85 (s, 2H), 7.00 (d, J=8.7 Hz, 1H), 7.00-7.25 (m, 4H), 7.80 (d, J=8.7 Hz, 1H), 7.90 (t, J=72 Hz, 1H), 13.20 (br s, 1H).

MS: ESI (+ve) (Method A): 426 (M+H)$^+$, Retention time 12.6 min.

Example 20

[8-chloro-3-(4-methanesulfonylbenzyl)-2,4-dimethylquinolin-5-yloxy]acetic Acid

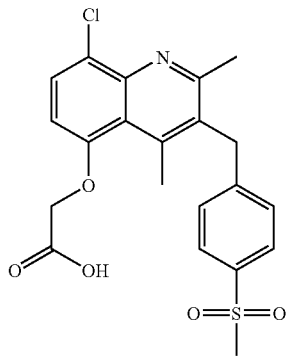

Preparation 20a 3-(4-methanesulfonylbenzyl)pentane-2,4-dione

A solution of pentane-2,4-dione (4.4 g) in N,N-dimethylformamide (10 mL) was added dropwise over a period of 15 minutes to a stirred suspension of sodium hydride (60% in oil, 1.7 g) in N,N-dimethylformamide (50 mL) at −5° C. The mixture was warmed to room temperature over 20 minutes and a solution of 1-bromomethyl-4-methanesulfonylbenzene (10 g) in N,N-dimethylformamide (20 mL) was added dropwise over a period of 10 minutes. The resulting mixture was stirred at room temperature for 17 hours and then diluted with 1.0 M aqueous hydrochloric acid (100 mL). The resulting mixture was extracted with a mixture of diethyl ether and ethyl acetate (1:1 by volume) and the combined extracts washed with a saturated aqueous sodium chloride solution and then dried over magnesium sulfate. The solvent was removed under reduced pressure and purification of the residue by column chromatography on silica gel, eluting with a mixture of cyclohexane and ethyl acetate (2:1 to 1:2 by volume) gave title compound as a colourless gum, 3.7 g.

$^1$H NMR (CDCl$_3$): δ 2.05 (s, 6H), 2.15 (s, 6H), 3.00 (s, 3H), 3.05 (s, 3H), 3.25 (d, J=7.3 Hz, 2H), 3.75 (s, 2H), 4.00 (t, J=7.3 Hz, 1H), 7.35-7.40 (m, 4H), 7.85-7.90 (m, 4H).

Preparation 20b 8-chloro-3-(4-methanesulfonylbenzyl)-2,4-dimethylquinolin-5-ol

A mixture of 3-amino-4-chlorophenol (0.36 g), 3-(4-methanesulfonylbenzyl)pentane-2,4-dione (0.5 g) and p-toluenesulfonic acid monohydrate (0.05 g) was heated at 160° C. for 2.5 hours. The mixture was cooled to room temperature and purified by column chromatography on silica gel, eluting with a mixture of dichloromethane and ethyl acetate (50:1 to 2:1 by volume) to afford title compound (7:10 mixture of keto-enol tautomers) as a beige solid, 0.32 g.

MS: ESI (+ve) (Method B): 376 (M+H)$^+$, Retention time 2.5 min.

Preparation 20c

[8-chloro-3-(4-methanesulfonylbenzyl)-2,4-dimethylquinolin-5-yloxy]acetic Acid Methyl Ester A mixture of 8-chloro-3-(4-methanesulfonylbenzyl)-2,4-dimethylquinolin-5-ol (0.31 g), N,N-dimethylformamide (5.0 mL), potassium carbonate (0.46 g) and bromoacetic acid methyl ester (0.35 g) was stirred at room temperature for 17 hours. The mixture was diluted with ethyl acetate and this solution washed with water and saturated aqueous sodium chloride solution and then dried over magnesium sulfate. The solvent was removed under reduced pressure and purification of the residue by column chromatography on silica gel, eluting with a mixture of toluene, dichloromethane and ethyl acetate (1:1:0 to 0:1:0 and 0:1:1 by volume) gave title compound as a white solid, 0.20 g.

$^1$H NMR (DMSO-d6): δ 2.60 (s, 3H), 2.80 (s, 3H), 3.20 (s, 3H), 3.70 (s, 3H), 4.45 (s, 2H), 5.00 (s, 2H), 6.95 (d, J=8.7 Hz, 1H), 7.30 (d, J=8.3 Hz, 2H), 7.75 (d, J=8.7 Hz, 1H), 7.85 (d, J=8.3 Hz, 2H).

MS: ESI (+ve) (Method B): 448 (M+H)$^+$, Retention time 3.4 min.

Preparation 20d

[8-chloro-3-(4-methanesulfonylbenzyl)-2,4-dimethylquinolin-5-yloxy]acetic acid

A solution of [8-chloro-3-(4-methanesulfonylbenzyl)-2,4-dimethylquinolin-5-yloxy]-acetic acid methyl ester (0.11 g), methanol (5.0 mL), water (1.0 mL) and saturated aqueous lithium hydroxide solution (0.5 mL) was stirred at room temperature for 3 days. The pH of the solution was adjusted to 4 by the addition of glacial acetic acid and the methanol removed under reduced pressure. The resulting precipitate was collected by filtration, washed with water and dried to afford title compound as a white solid, 0.08 g.

$^1$H NMR (DMSO-d6): δ 2.60 (s, 3H), 2.85 (s, 3H), 3.15 (s, 3H), 4.30 (s, 2H), 4.40 (s, 2H), 6.75 (d, J=8.5 Hz, 1H), 7.30 (d, J=8.3 Hz, 2H), 7.65 (d, J=8.5 Hz, 1H), 7.85 (d, J=8.3 Hz, 2H).

MS: ESI (+ve) (Method A): 434 (M+H)$^+$, Retention time 8.1 min.

MS: ESI (+ve) (Method B): 434 (M+H)$^+$, Retention time 2.8 min.

Example 21

[8-chloro-3-(4-chlorobenzenesulfonyl)-2,4-dimethylquinolin-5-yloxy]acetic Acid

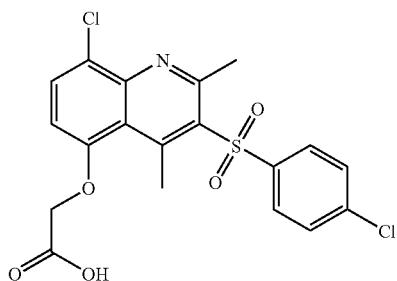

Preparation 21a 8-chloro-3-(4-chlorophenylsulfanyl)-2,4-dimethylquinolin-5-ol A mixture of 3-amino-4-chlorophenol (5.0 g), 3-(4-chlorophenylsulfanyl)pentane-2,4-dione (8.4 g), p-toluenesulfonic acid monohydrate (3.20 g) and toluene (150 mL) was heated at reflux for 2 days. The mixture was cooled to room temperature and the solvent removed under reduced pressure. The residue was dissolved in ethyl acetate, washed with water and saturated aqueous sodium chloride solution and dried over magnesium sulfate. The solvent was removed under reduced pressure and purification of the residue by column chromatography on silica gel, eluting with a mixture of dichloromethane and cyclohexane (1:9 by volume) gave title compound as a pale yellow solid, 0.99 g.

$^1$H NMR (DMSO-d6): δ 2.70 (s, 3H), 3.05 (s, 3H), 6.95 (d, J=8.4 Hz, 1H), 7.00 (d, J=8.4 Hz, 2H), 7.35 (d, J=8.4 Hz, 2H), 7.75 (d, J=8.4 Hz, 1H).

MS: ESI (+ve) (Method B): 350 (M+H)$^+$, Retention time 4.5 min.

Preparation 21b

[8-chloro-3-(4-chlorophenylsulfanyl)-2,4-dimethylquinolin-5-yloxy]acetic Acid Methyl Ester A mixture of 8-chloro-3-(4-chlorophenylsulfanyl)-2,4-dimethylquinolin-5-ol (0.99 g), N,N-dimethylformamide (40 mL), potassium carbonate (0.60 g) and bromoacetic acid methyl ester (0.32 mL) was stirred at room temperature for 24 hours. The solvent was removed under reduced pressure and the residue diluted with water and this mixture was extracted with ethyl acetate. The combined extracts were washed with water and saturated aqueous sodium chloride solution and dried over magnesium sulfate. The solvent was removed under reduced pressure and purification of the residue by column chromatography on silica gel, eluting with a mixture of ethyl acetate and cyclohexane (1:9 by volume) gave title compound as a white solid, 0.26 g.

$^1$H NMR (CDCl$_3$): δ 2.85 (s, 3H), 3.20 (s, 3H), 3.80 (s, 3H), 4.76 (s, 2H), 6.70 (d, J=8.4 Hz, 1H), 6.90 (d, J=8.9 Hz, 2H), 7.15 (d, J=8.9 Hz, 2H), 7.70 (d, J=8.4 Hz, 1H).

MS: ESI (+ve) (Method B): 421 (M+H)$^+$, Retention time 4.2 min.

Preparation 21c

[8-chloro-3-(4-chlorobenzenesulfonyl)-2,4-dimethylquinolin-5-yloxy]acetic Acid Methyl Ester and [8-chloro-3-(4-chlorobenzenesulfinyl)-2,4-dimethylquinolin-5-yloxy]acetic Acid Methyl Ester A mixture of [8-chloro-3-(4-chlorophenylsulfanyl)-2,4-dimethylquinolin-5-yloxy]acetic acid methyl ester (0.050 g), 3-chloroperoxybenzoic acid (0.040 g) and chloroform was stirred at room temperature for 2 hours. After evaporation of solvents the mixture was purified by column chromatography on silica gel, eluting with a mixture of dichloromethane and methanol (99:1 by volume) to afford [8-chloro-3-(4-chlorobenzenesulfonyl)-2,4-dimethylquinolin-5-yloxy]acetic acid methyl ester as a white sold, 0.020 g and [8-chloro-3-(4-chlorobenzenesulfinyl)-2,4-dimethylquinolin-5-yloxy]acetic acid methyl ester as a cream solid, 0.056 g.

[8-chloro-3-(4-chlorobenzenesulfonyl)-2,4-dimethylquinolin-5-yloxy]acetic acid Methyl Ester MS: ESI (+ve) (Method B): 454 (M+H)$^+$, Retention time 4.3 min.

[8-chloro-3-(4-chlorobenzenesulfinyl)-2,4-dimethylquinolin-5-yloxy]acetic Acid Methyl Ester MS: ESI (+ve) (Method B): 438 (M+H)$^+$, Retention time 4.1 min.

Preparation 21d

[8-chloro-3-(4-chlorobenzenesulfonyl)-2,4-dimethylquinolin-5-yloxy]acetic Acid

A solution of [8-chloro-3-(4-chlorobenzenesulfonyl)-2,4-dimethylquinolin-5-yloxy]acetic acid methyl ester (0.020 g), methanol (3.0 mL) and 1.0 M aqueous sodium hydroxide solution (0.22 mL) was stirred at room temperature for 3 hours. The pH of the solution was adjusted to 5 by the addition of formic acid and the solvent removed under reduced pressure. Purification of the residue by preparative reverse-phase HPLC using a gradient over 30 minutes of acetonitrile in water gave title compound as a pale yellow solid, 0.0025 g.

$^1$H NMR (DMSO-d6): δ 3.00 (s, 3H), 3.10 (s, 3H), 4.65 (s, 2H), 6.90 (d, J=8.9 Hz, 1H), 7.60 (d, J=8.5 Hz, 2H), 7.80 (d, J=8.9 Hz, 1H), 7.85 (d, J=8.5 Hz, 2H), 8.25 (br s, 1H).

MS: ESI (+ve) (Method A): 440 (M+H)$^+$, Retention time 11.4 min.

Example 22

[8-chloro-3-(4-chlorobenzenesulfinyl)-2,4-dimethylquinolin-5-yloxy]acetic Acid

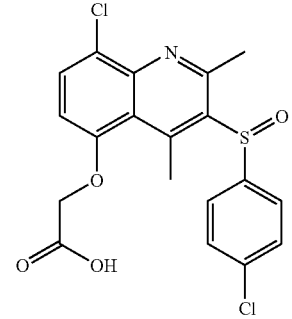

Preparation 22a

[8-chloro-3-(4-chlorobenzenesulfinyl)-2,4-dimethylquinolin-5-yloxy]acetic Acid

A mixture of [8-chloro-3-(4-chlorobenzenesulfinyl)-2,4-dimethylquinolin-5-yloxy]acetic acid methyl ester (0.050 g), methanol (3.0 mL) and 1.0 M aqueous sodium hydroxide solution (0.57 mL) was stirred at room temperature for 3 hours. The pH of the mixture was adjusted to 5 by the addition of formic acid and the solvent removed under reduced pressure. Purification of the residue by preparative reverse-phase HPLC using a gradient over 30 minutes of acetonitrile in water gave title compound as a pale yellow solid, 0.029 g.

$^1$H NMR (DMSO-d6): δ 2.65 (s, 3H), 3.30 (s, 3H), 4.85 (s, 2H), 7.00 (d, J=8.7 Hz; 1H), 7.50 (d, J=8.3 Hz, 2H), 7.55 (d, J=8.3 Hz, 2H), 7.80 (d, J=8.7 Hz, 1H).

MS: ESI (+ve) (Method A): 424 (M+H)$^+$, Retention time 10.6 min.

Example 23

8-chloro-3-(4-chlorobenzyl)-2,4-dimethyl-5-(1H-tetrazol-5-ylmethoxy)quinoline

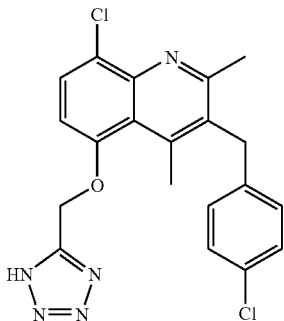

Preparation 23a

[8-chloro-3-(4-chlorobenzyl)-2,4-dimethylquinolin-5-yloxy]acetonitrile

A mixture of 8-chloro-3-(4-chlorobenzyl)-2,4-dimethylquinolin-5-ol (0.80 g), N,N-dimethylformamide (10 mL), potassium carbonate (1.0 g) and bromoacetonitrile (0.25 mL) was stirred at room temperature for 2 hours. The mixture was diluted with ethyl acetate and this mixture was washed with water and saturated aqueous sodium chloride solution and then dried over magnesium sulfate. The solvent was removed under reduced pressure to afford title compound as a light brown solid, 0.90 g.

$^1$H NMR (DMSO-d6): δ 2.60 (s, 3H), 2.75 (s, 3H), 4.30 (s, 2H), 5.35 (s, 2H), 7.05 (d, J=8.3 Hz, 2H), 7.15 (d, J=8.7 Hz, 1H), 7.35 (d, J=7.3 Hz, 2H), 7.85 (d, J=8.7 Hz, 1H).

MS: ESI (+ve) (Method B): 371 (M+H)$^+$, Retention time 4.3 min.

Preparation 23b 8-chloro-3-(4-chlorobenzyl)-2,4-dimethyl-5-(1H-tetrazol-5-ylmethoxy)quinoline A mixture of [8-chloro-3-(4-chlorobenzyl)-2,4-dimethylquinolin-5-yloxy]acetonitrile (0.10 g), sodium azide (0.026 g), ammonium chloride (0.022 g) and N,N-dimethylformamide (1.5 mL) was heated by microwave irradiation at 100° C. for 45 minutes. The mixture was diluted with ethyl acetate (20 mL) and saturated aqueous sodium chloride solution (20 mL). The resulting precipitate was collected by filtration, washed with water and ethyl acetate and dried to afford title compound as a white solid, 0.14 g.

$^1$H NMR (DMSO-d6): δ 2.55 (s, 3H), 2.70 (s, 3H), 4.25 (s, 2H), 5.30 (s, 2H), 7.05 (d, J=8.4 Hz, 2H), 7.30 (d, J=8.4 Hz, 1H), 7.35 (d, J=8.4 Hz, 2H), 7.75 (d, J=8.4 Hz, 1H).

MS: ESI (+ve) (Method B): 414 (M+H)$^+$, Retention time 11.0 min.

Example 24

[8-chloro-3-(4-chlorophenylsulfanyl)-4-difluoromethoxy-2-methyl-quinolin-5-yloxy]acetic Acid

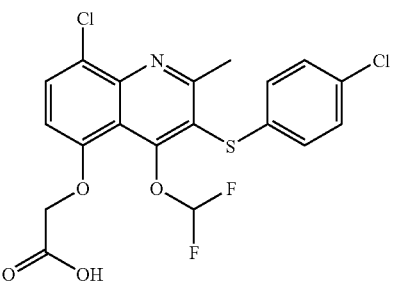

Preparation 24a 2-(4-chlorophenylsulfanyl)-3-oxobutyric Acid Methyl Ester

To a solution of 2-chloro-3-oxobutyric acid methyl ester (3.5 g) and 4-chlorobenzenethiol (4.1 g) in dichloromethane (60 mL) at 0° C. was added triethylamine (4.0 mL). The mixture was warmed to room temperature and then stirred at this temperature for 3 days. The solvent was removed under reduced pressure and the residue diluted with ethyl acetate and this mixture was washed with saturated aqueous sodium chloride solution and then dried over magnesium sulfate. The solvent was removed under reduced pressure and the residue purified by column chromatography on silica gel, eluting with a mixture of ethyl acetate and cyclohexane (1:4 by volume) to afford title compound as a waxy solid, 7.2 g.

$^1$H NMR (CDCl$_3$): δ 2.35 (s, 3H), 3.75 (s, 3H), 7.05 (d, J=8.7 Hz, 2H), 7.25 (d, J=8.7 Hz, 2H).

Preparation 24b

[8-chloro-3-(4-chlorophenylsulfanyl)-2-methyl-4-oxo-1,4-dihydroquinolin-5-yloxy]acetic Acid Methyl Ester A mixture of (3-amino-4-chlorophenoxy)acetic acid methyl ester (2.1 g), 2-(4-chlorophenylsulfanyl)-3-oxobutyric acid methyl ester (2.5 g), polyphosphoric acid (10 g) and dioxane (30 mL) was heated at 130° C. for 2 days. The mixture was cooled to room temperature and the solvent removed under reduced pressure. The residue was diluted with water and the resulting precipitate collected by filtration, washed with water and dichloromethane and dried to afford title compound, 1.6 g.

MS: ESI (+ve) (Method B): 424 (M+H)$^+$, Retention time 3.4 min.

Preparation 24c

[8-chloro-3-(4-chlorophenylsulfanyl)-4-difluoromethoxy-2-methylquinolin-5-yloxy]acetic Acid Methyl Ester A mixture of [8-chloro-3-(4-chlorophenylsulfanyl)-2-methyl-4-oxo-1,4-dihydroquinolin-5-yloxy]acetic acid methyl ester (0.26 g), N,N-dimethylformamide (5.0 mL), potassium carbonate (0.25 g) and acetic acid chlorodifluoromethyl ester (0.13 mL) was stirred at 80° C. for 17 hour. The mixture was diluted with water and extracted with ethyl acetate. The combined extracts were washed with saturated aqueous sodium chloride solution and dried over magnesium sulfate. The solvent was removed under reduced pressure and the residue purified by column chromatography on silica gel, eluting with a mixture of dichloromethane and cyclohexane (7:3 by volume) to afford title compound, 0.044 g.

MS: ESI (+ve) (Method B): 474 (M+H)$^+$, Retention time 4.5 min.

Preparation 24d

[8-chloro-3-(4-chlorophenylsulfanyl)-4-difluoromethoxy-2-methyl-quinolin-5-yloxy]acetic Acid A solution of [8-chloro-3-(4-chlorophenylsulfanyl)-4-difluoromethoxy-2-methylquinolin-5-yloxy]acetic acid methyl ester (0.044 g), tetrahydrofuran (3.0 mL) and 1.0 M aqueous sodium hydroxide solution (0.15 mL) was stirred at room temperature for 1 hour. The solution was acidified by the addition of 1.0 M aqueous hydrochloric acid and the solvent removed under reduced pressured. The residue was diluted with ethyl acetate and this mixture washed with water and then dried over magnesium sulfate. The solvent was removed under reduced pressure and the resulting solid washed with dichloromethane and dried to afford title compound, 0.024 g.

$^1$H NMR (DMSO-d6): δ 2.65 (s, 3H), 4.90 (s, 2H), 7.05-7.15 (m, 3H), 7.30 (t, J=74 Hz, 1H), 7.35 (d, J=8.6 Hz, 2H), 7.95 (d, J=8.9 Hz, 1H), 13.5 (br s, 1H).

MS: ESI (+ve) (Method A): 460 (M+H)$^+$, Retention time 12.7 min.

Example 25

[8-chloro-3-(4-chlorobenzyl)-4-difluoromethoxy-2-methylquinolin-5-yl]acetic acid

Preparation 25a

[8-chloro-3-(4-chlorobenzyl)-2-methyl-4-oxo-1,4-dihydroquinolin-5-yl]acetic Acid A mixture of (3-amino-4-chlorophenyl)acetic acid methyl ester (1.0 g), 2-(4-chlorobenzyl)-3-oxobutyric acid ethyl ester (1.3 g), polyphosphoric acid (5 mL) and dioxane (10 mL) was heated at 130° C. for 1.5 hours. The mixture was diluted with water and the pH of this solution adjusted to 3 by the addition of sodium acetate. The resulting precipitate was collected by filtration and purified by column chromatography on silica gel, eluting with a mixture of dichloromethane, ethyl acetate and methanol (1:0:0 to 10:1:0 to 1:1:0 to 20:0:1 and 0:0:1 by volume) to afford title compound, 0.60 g.

$^1$H NMR (DMSO-d6): δ2.40 (s, 3H), 3.35 (s, 3H), 3.90 (s, 2H), 4.10 (s, 2H), 7.00 (d, J=7.9 Hz, 1H), 7.20 (d, J=8.5 Hz, 2H), 7.25 (d, J=8.5 Hz, 2H), 7.65 (d, J=7.9 Hz, 1H), 10.35 (br s, 1H).

MS: ESI (+ve) (Method B): 376 (M+H)$^+$, Retention time 3.6 min.

Preparation 25b

[8-chloro-3-(4-chlorobenzyl)-4-difluoromethoxy-2-methylquinolin-5-yl]acetic Acid A mixture of [8-chloro-3-(4-chlorobenzyl)-2-methyl-4-oxo-1,4-dihydroquinolin-5-yl]acetic acid (0.45 g), tetraethylammonium bromide (0.025 g), 7.5 M aqueous sodium hydroxide solution (1.6 mL) and dioxane (25 mL) was heated at 80° C. and then chlorodifluoromethane was bubbled through this solution for 30 minutes. The mixture was Cooled to room temperature and the pH of the solution adjusted to 5 by the addition of glacial acetic acid. The mixture was extracted with ethyl acetate and the combined extracts washed with saturated aqueous sodium chloride solution and then dried over sodium sulfate. The solvent was removed under reduced pressure and purification of the residue by preparative reverse-phase HPLC using a gradient over 30 minutes of acetonitrile in water (40% to 95% of organic modifier) gave title compound as an off-white solid, 0.003 g.

$^1$H NMR (DMSO-d6): δ 2.40 (s, 3H), 3.85 (s, 2H), 4.05 (s, 2H), 7.15 (d, J=8.4 Hz, 2H), 7.30 (d, J=8.4 Hz, 2H), 7.35 (d, J=8.1 Hz, 1H), 7.65 (t, J=57 Hz, 1H), 7.85 (d, J=8.1 Hz, 1H), 12.10 (br s, 1H).

MS: ESI (+ve) (Method A): 426 (M+H)$^+$, Retention time 11.8 min.

MS: ESI (+ve) (Method B): 426 (M+H)$^+$, Retention time 3.9 min.

Example 26

[8-chloro-4-difluoromethoxy-3-(4-methanesulfonylbenzyl)-2-methylquinolin-5-yloxy]acetic acid

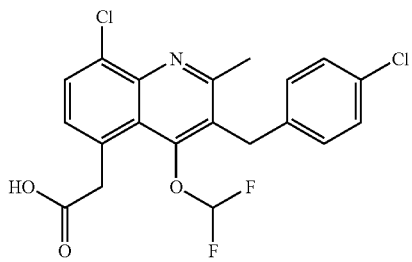

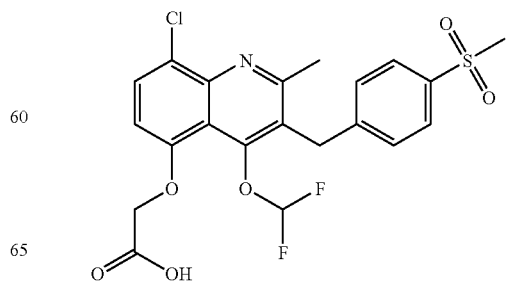

Preparation 26a

2-(4-methanesulfonylbenzyl)-3-oxobutyric Acid Ethyl Ester

A suspension of potassium tert-butoxide (4.5 g) in anhydrous tetrahydrofuran (70 mL) at 0° C. was treated with a mixture of tert-butanol (0.2 mL) and 3-oxobutyric acid ethyl ester (5.2 g). After stirring at 15° C. for 15 minutes a solution of 1-bromomethyl-4-methanesulfonylbenzene (10 g) in tetrahydrofuran (30 mL) was added and the resulting mixture heated at 70° C. for 17 hours. The mixture was diluted with saturated aqueous citric acid solution (20 mL) and extracted with ethyl acetate. The combined extracts were washed with saturated aqueous sodium chloride solution and dried over magnesium sulfate. The solvent was removed under reduced pressure and the residue purified by column chromatography on silica gel, eluting with a mixture of pentane and dichloromethane (2:1 to 0:1 by volume) to afford title compound as a gum, 3.5 g.

$^1$H NMR (CDCl$_3$): δ 1.20 (t, J=6.5 Hz, 3H), 2.25 (s, 3H), 3.05 (s, 3H), 3.25 (m, 2H), 3.85 (t, J=7.6 Hz, 1H), 4.10-4.25 (m, 2H), 7.40 (d, J=8.4 Hz, 2H), 7.85 (d, J=8.4 Hz, 2H).

Preparation 26b

[8-chloro-3-(4-methanesulfonylbenzyl)-2-methyl-4-oxo-1,4-dihydroquinolin-5-yloxy]acetic Acid Methyl Ester A mixture of (3-amino-4-chlorophenoxy)acetic acid methyl ester (0.54 g), 2-(4-methanesulfonylbenzyl)-3-oxobutyric acid ethyl ester (0.75 g), polyphosphoric acid (2.5 mL) and dioxane (10 mL) was heated at 130° C. for 20 hours. The mixture was diluted with water and the pH of this solution this solution was adjusted to 3 by the addition of sodium acetate. The resulting precipitate was collected by filtration and dried to afford title compound as a white solid, 1.0 g.

$^1$H NMR (DMSO-d6): δ 2.45 (s, 3H), 3.15 (s, 3H), 3.70 (s, 3H), 3.95 (s, 2H), 4.85 (s, 2H), 6.70 (d, J=8.1 Hz, 1H), 7.45 (d, J=8.1 Hz, 2H), 7.65 (d, J=8.1 Hz, 1H), 7.80 (d, J=8.1 Hz, 2H), 10.15 (br s, 1H).

MS: ESI (+ve) (Method B): 450 (M+H)$^+$, Retention time 2.7 min.

Preparation 26c

[8-chloro-4-difluoromethoxy-3-(4-methanesulfonylbenzyl)-2-methylquinolin-5-yloxy]acetic Acid Methyl Ester A stirred mixture of [8-chloro-3-(4-methanesulfonylbenzyl)-2-methyl-4-oxo-1,4-dihydroquinolin-5-yloxy]acetic acid methyl ester (0.40 g), N,N-dimethylformamide (15 mL) and potassium carbonate (0.37 g) was cooled to −80° C. and chlorodifluoromethane was bubbled through this solution for 30 minutes. The flask was sealed and the resulting mixture warmed to room temperature over 30 minutes and then stirred at this temperature for 3 days and then at 50° C. for 6 hours. The excess chlorodifluoromethane was allowed to evaporate and the residue diluted with ethyl acetate. The mixture was washed with water and saturated aqueous sodium chloride solution and dried over magnesium sulfate. The solvent was removed under reduced pressure and the residue purified by column chromatography on silica gel, eluting with a mixture of dichloromethane and ethyl acetate (1:0 to 1:2 by volume) to afford title compound as a colourless gum, 0.41 g.

$^1$H NMR (DMSO-d6): δ 2.65 (s, 3H), 3.00 (s, 3H), 3.85 (s, 3H), 4.50 (s, 2H), 4.85 (s, 2H), 6.75 (d, J=8.3 Hz, 1H), 7.00 (t, J=75 Hz, 1H), 7.30 (d, J=8.3 Hz, 2H), 7.75 (d, J=8.3 Hz, 1H), 7.85 (d, J=8.3 Hz, 2H).

MS: ESI (+ve) (Method B): 500 (M+H)$^+$, Retention time 3.6 min.

Preparation 26d

[8-chloro-4-difluoromethoxy-3-(4-methanesulfonylbenzyl)-2-methylquinolin-5-yloxy]acetic Acid A solution of [8-chloro-4-difluoromethoxy-3-(4-methanesulfonylbenzyl)-2-methylquinolin-5-yloxy]acetic acid methyl ester (0.13 g), methanol (20 mL), saturated, aqueous lithium hydroxide solution (1.0 mL) and water (2.0 mL) was stirred at room temperature for 45 minutes. The pH of the solution was adjusted to 5 by the addition of glacial acetic acid and the methanol removed under reduced pressured. The resulting precipitate was collected by filtration and purified by preparative reverse-phase HPLC using a gradient over 45 minutes of acetonitrile in water (10% to 95% of organic modifier) to afford title compound as a pale yellow solid, 0.014 g.

$^1$H NMR (DMSO-d6): δ 2.55 (s, 3H), 3.15 (s, 3H), 4.45 (s, 2H), 4.95 (s, 2H), 7.05 (d, J=8.6 Hz, 2H), 7.25 (t, J=75 Hz, 1H), 7.35 (d, J=8.4 Hz, 2H), 7.85 (d, J=8.4 Hz, 2H), 7.90 (d, J=8.6 Hz, 1H), 13.35 (br s, 1H).

MS: ESI (+ve) (Method A): 486 (M+H)$^+$, Retention time 9.6 min.

MS: ESI (+ve) (Method B): 486 (M+H)$^+$, Retention time 3.6 min.

Example 27

[3-(4-chlorobenzyl)-4-difluoromethoxy-8-fluoro-2-methylquinolin-5-yloxy]acetic acid

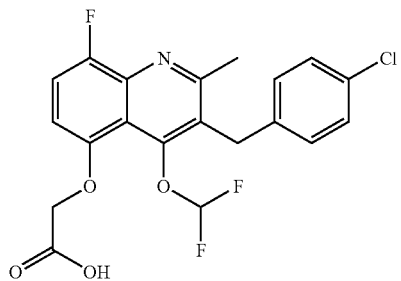

Preparation 27a

[3-(4-chlorobenzyl)-8-fluoro-2-methyl-4-oxo-1,4-dihydroquinolin-5-yloxy]acetic acid methyl ester A mixture of (3-amino-4-fluorophenoxy)acetic acid methyl ester (0.50 g), 2-(4-chlorobenzyl)-3-oxobutyric acid ethyl ester (7.4 g) and polyphosphoric acid (1.1 g) was heated at 130° C. for 2 hours. The mixture was cooled to room temperature, diluted with water and extracted with ethyl acetate. The combined extracts were washed with water and dried over sodium sulfate. The solvent was removed under reduced pressure and the residue purified by column chromatography on silica gel, eluting with a mixture of dichloromethane and methanol (19:1 by volume) to afford title compound, 0.29 g.

¹H NMR (CDCl₃): δ 2.60 (s, 3H), 3.90 (s, 3H), 4.10 (s, 2H), 4.80 (s, 2H), 6.60 (dd, J=3.6, 8.7 Hz, 1H), 7.15-7.25 (m, 5H).

Preparation 27b

[3-(4-chlorobenzyl)-4-difluoromethoxy-8-fluoro-2-methylquinolin-5-yloxy]acetic Acid Methyl Ester A mixture of [3-(4-chlorobenzyl)-8-fluoro-2-methyl-4-oxo-1,4-dihydroquinolin-5-yloxy]acetic acid methyl ester (0.29 g), N,N-dimethylformamide (10 mL), potassium carbonate (0.62 g) and acetic acid chlorodifluoromethyl ester (0.31 mL) was stirred at 70° C. for 17 hours. The mixture was cooled to room temperature, diluted with water and extracted with ethyl acetate. The combined extracts were dried over sodium sulfate and the solvent removed under reduced pressure. Purification of the residue by column chromatography on silica gel, eluting with a mixture of cyclohexane and ethyl acetate (4:1 by volume) gave title compound, 0.18 g.

MS: ESI (+ve) (Method B): 439 (M+H)⁺, Retention time 4.1 min.

Preparation 27c

[3-(4-chlorobenzyl)-4-difluoromethoxy-8-fluoro-2-methylquinolin-5-yloxy]acetic Acid A solution of [3-(4-chlorobenzyl)-4-difluoromethoxy-8-fluoro-2-methylquinolin-5-yloxy]acetic acid methyl ester (0.18 g), methanol (3.5 mL), water (2.0 mL), tetrahydrofuran (3.5 mL) and lithium hydroxide solution (0.036 g) was stirred at room temperature for 30 minutes. The solution was acidified by the addition of 1.0 M aqueous hydrochloric acid, extracted with ethyl acetate and the combined extracts dried over sodium sulfate. The solvent was removed under reduced pressure and purification of the residue by preparative reverse-phase HPLC, using a gradient over 30 minutes of acetonitrile in water, gave title compound as a yellow solid, 0.088 g.

¹H NMR (DMSO-d6): δ 2.50 (s, 3H), 4.30 (s, 2H), 4.90 (s, 2H), 7.00 (dd, J=3.7, 8.8 Hz, 1H), 7.10 (d, J=8.5 Hz, 2H), 7.25 (t, J=75 Hz, 1H), 7.35 (d, J=8.5 Hz, 2H), 7.50 (dd, J=8.8, 10.2 Hz, 1H), 13.35 (br s, 1H).

MS: ESI (+ve) (Method A): 425 (M+H)⁺, Retention time 11.2 min.

Example 28

[8-chloro-3-(4-methanesulfonylbenzyl)-2,4-dimethylquinolin-5-yl]acetic acid

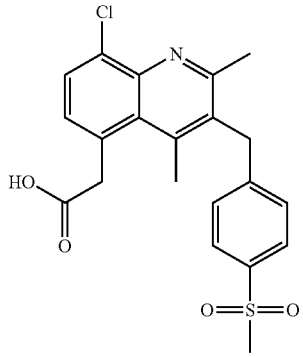

Preparation 28a 8-chloro-3-(4-methanesulfonylbenzyl)-2,4-dimethylquinolin-5-ol

A mixture of 3-amino-4-chlorophenol (1.0 g), 3-(4-methanesulfonylbenzyl)pentane-2,4-dione (0.53 g), methanesulfonic acid (3 drops) and toluene (20 mL) was heated at reflux for 3 hours. The mixture was cooled to room temperature and the solvent removed under reduced pressure. The residue was diluted with ethyl acetate and then washed with water and saturated aqueous sodium chloride solution and dried over magnesium sulfate. The solvent was removed under reduced pressure and purification of the residue by column chromatography on silica gel, eluting with a mixture of dichloromethane and methanol (1:0 to 99:1 by volume) gave title compound as a pale yellow solid, 0.32 g.

MS: ESI (+ve) (Method B): 376 (M+H)⁺, Retention time 2.5 min.

Preparation 28b

Trifluoromethanesulfonic acid 8-chloro-3-(4-methanesulfonylbenzyl)-2,4-dimethylquinolin-5-yl Ester A mixture of 8-chloro-3-(4-methanesulfonylbenzyl)-2,4-dimethylquinolin-5-ol (0.10 g), N-phenyltrifluoromethanesulfonimide (0.11 g), potassium carbonate (0.11 g) and tetrahydrofuran (3.0 mL) was heated by microwave irradiation at 130° C. for 5 minutes. The mixture was filtered and the filtrate concentrated under reduced pressure. Purification of the residue by column chromatography on silica gel, eluting with dichloromethane gave title compound as a cream solid, 0.11 g.

MS: ESI (+ve) (Method B): 508 (M+H)⁺, Retention time 4.1 min.

Preparation 28c

[8-chloro-3-(4-methanesulfonylbenzyl)-2,4-dimethylquinolin-5-yl]acetic Acid Methyl Ester A mixture of trifluoromethanesulfonic acid 8-chloro-3-(4-methanesulfonylbenzyl)-2,4-dimethylquinolin-5-yl ester (0.11 g), 1-(tert-butyldimethylsilyloxy)-1-methoxyethene (0.22 mL), sodium acetate (0.019 g), bis(dibenzylideneacetone) palladium (0.006 g) and 1,1'-bis(diphenylphospino)ferrocene (0) (0.006 g) in N,N-dimethylformamide (1.0 mL) was heated by microwave irradiation at 120° C. for 20 minutes. The mixture was diluted with ethyl acetate and this solution was washed with saturated aqueous sodium chloride solution and then dried over magnesium sulfate. The solvent was removed under reduced pressure and purification of the residue by column chromatography on silica gel, eluting with a mixture of dichloromethane and methanol (1:0 to 99:1 by volume) gave title compound as a brown oil, 0.050 g.

MS: ESI (+ve) (Method B): 431 (M+H)⁺, Retention time 3.3 min.

Preparation 28d

[8-chloro-3-(4-methanesulfonylbenzyl)-2,4-dimethylquinolin-5-yl]acetic Acid

A solution of [8-chloro-3-(4-methanesulfonylbenzyl)-2,4-dimethylquinolin-5-yl]acetic acid methyl ester (0.050 g), methanol (3.0 mL) and 1.0 M aqueous sodium hydroxide solution (0.63 mL) was stirred at room temperature for 18 hours. The pH of the solution was adjusted to 5 by the addition of formic acid and the solvent removed under reduced pressure. Purification of the residue by preparative reverse-phase HPLC using a gradient over 30 minutes of acetonitrile in water (30% to 70% of organic modifier) gave title compound as a white solid, 0.0060 g.

$^1$H NMR (CD$_3$OD): δ 2.65 (s, 3H), 2.70 (s, 3H), 3.10 (s, 3H), 4.25 (s, 2H), 4.45 (s, 2H), 7.30 (d, J=8.6 Hz, 2H), 7.35 (d, J=7.7 Hz, 1H), 7.75 (d, J=7.7 Hz, 1H), 7.85 (d, J=8.6 Hz, 2H).

MS: ESI (+ve) (Method B): 418 (M+H)$^+$, Retention time 8.1 min.

Example 29

[8-chloro-4-difluoromethoxy-2-ethyl-3-(4-methanesulfonylbenzyl)-quinolin-5-yloxy]acetic acid

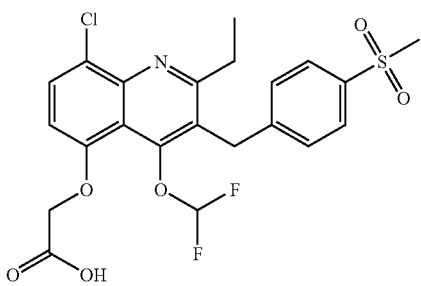

Preparation 29a

2-(4-methanesulfonylbenzyl)-3-oxopentanoic Acid Ethyl Ester

A suspension of potassium tert-butoxide (3.9 g) in anhydrous tetrahydrofuran (60 mL) at 0° C. was treated with a mixture of tert-butanol (0.15 mL) and 3-oxopentanoic acid ethyl ester (5.0 g). The mixture was warmed to room temperature and after 30 minutes a solution of 1-bromomethyl-4-methanesulfonylbenzene (8.6 g) in tetrahydrofuran (20 mL) was added and the resulting mixture heated at 70° C. for 17 hours. The mixture was cooled to room temperature and diluted with water (20 mL) and this mixture was extracted with ethyl acetate. The combined extracts were washed with saturated aqueous sodium chloride solution and dried over magnesium sulfate. The solvent was removed under reduced pressure and the residue purified, by column chromatography on silica gel, eluting with a mixture of dichloromethane and ethyl acetate (1:0 to 4:1 by volume) to afford title compound as a white solid, 3.6 g.

MS: ESI (+ve) (Method B): 313 (M+H)$^+$, Retention time 3.2 min.

Preparation 29b

[8-chloro-2-ethyl-3-(4-methanesulfonylbenzyl)-4-oxo-1,4-dihydroquinolin-5-yloxy]acetic Acid Methyl Ester A mixture of (3-amino-4-chlorophenoxy)acetic acid methyl ester (0.54 g), 2-(4-methanesulfonylbenzyl)-3-oxopentanoic acid ethyl ester (0.78 g), polyphosphoric acid (2.5 mL) and dioxane (10 mL) was heated at 130° C. for 17 hours. The mixture was diluted with water (100 mL) and the pH of this solution adjusted to 4 by the addition of sodium acetate. The mixture was extracted with ethyl acetate and the combined extracts were washed with saturated aqueous sodium chloride solution and dried over magnesium sulfate. The solvent was removed under reduced pressure to afford title compound as a honey coloured solid, 1.2 g.

MS: ESI (+ve) (Method B): 462 (M+H)$^+$, Retention time 2.9 min.

Preparation 29c

[8-chloro-4-difluoromethoxy-2-ethyl-3-(4-methanesulfonylbenzyl)quinolin-5-yloxy]acetic Acid Methyl Ester A mixture of [8-chloro-2-ethyl-3-(4-methanesulfonylbenzyl)-4-oxo-1,4-dihydroquinolin-5-yloxy]acetic acid methyl ester (1.2 g), N,N-dimethylformamide (15 mL) and potassium carbonate (1.1 g) was cooled to −80° C. and chlorodifluoromethane was bubbled through this solution for 30 minutes. The flask was sealed and the resulting mixture warmed to room temperature over 30 minutes and then heated at 50° C. for 17 hours. The excess chlorodifluoromethane was allowed to evaporate and the residue diluted with ethyl acetate and this mixture was washed with saturated aqueous sodium chloride solution and then dried over magnesium sulfate. The solvent was removed under reduced pressure and the residue purified by column chromatography on silica gel, eluting with a mixture of dichloromethane and ethyl acetate (1:0 to 4:1 by volume) to afford title compound as a clear gum, 0.27 g.

MS: ESI (+ve) (Method B): 514 (M+H)$^+$, Retention time 3.9 min.

Preparation 29d

[8-chloro-4-difluoromethoxy-2-ethyl-3-(4-methanesulfonylbenzyl)quinolin-5-yloxy]acetic Acid A solution of [8-chloro-4-difluoromethoxy-2-ethyl-3-(4-methanesulfonylbenzyl)quinolin-5-yloxy]acetic acid methyl ester (0.10 g), methanol (5.0 mL), water (1.0 mL) and saturated aqueous lithium hydroxide solution (0.5 mL) was stirred at room temperature for 45 minutes. The pH of the solution was adjusted to 5 by the addition of glacial acetic acid and the methanol removed under reduced pressured. The residue was diluted with water (2.0 mL) and the resulting precipitate collected by filtration, washed with water and dried to afford title compound as a white solid, 0.075 g.

$^1$H NMR (DMSO-d6): δ 1.25 (t, J=7.2 Hz, 3H), 2.85 (q, J=7.2 Hz, 2H), 3.15 (s, 3H), 4.40 (s, 2H), 4.45 (s, 2H), 6.90 (d, J=8.4 Hz, 1H), 7.35 (d, J=8.4 Hz, 2H), 7.80 (d, J=8.4 Hz, 1H), 7.85 (d, J=8.4 Hz, 2H), 8.10 (t, J=75 Hz, 1H).

MS: ESI (+ve) (Method A): 500 (M+H)+, Retention time 10.7 min.

MS: ESI (+ve) (Method B): 500 (M+H)+, Retention time 3.6 min.

Example 30

[3-(4-chlorobenzyl)-2-difluoromethoxy-8-fluoro-4-methylquinolin-5-yloxy]-acetic Acid

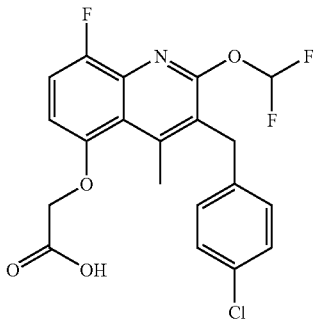

Preparation 30a 2-(4-chlorobenzyl)-3-oxothiobutyric Acid S-tert-butyl Ester

The title compound was prepared by the method of Preparation 34a using 1-bromomethyl-4-chlorobenzene and 3-oxothiobutyric acid S-tert-butyl ester.

$^1$H NMR (CDCl$_3$): δ1.40 (s, 9H), 2.20 (s, 3H), 3.05-3.20 (m, 2H), 3.80 (m, 1H), 7.10 (d, J=8.5 Hz, 2H), 7.25 (d, J=8.5 Hz, 2H).

Preparation 30b 2-(4-chlorobenzyl)-N-(2-fluoro-5-hydroxyphenyl)-3-oxobutyramide

The title compound was prepared by the method of Preparation 34b using 3-amino-4-fluorophenol and 2-(4-chlorobenzyl)-3-oxothiobutyric acid S-tert-butyl ester.

$^1$H NMR (DMSO-d6): δ 2.20 (s, 3H), 3.05 (m, 2H), 4.15 (m 1H), 6.50 (m 1H), 7.00 (dd, J=9.0, 10.6 Hz, 1H), 7.25 (m, 3H), 7.35 (d, J=8.3 Hz, 2H), 9.40 (s, 1H), 9.95 (s, 1H).

MS: ESI (+ve) (Method B): 336 (M+H)+, Retention time 3.2 min.

Preparation 30c 3-(4-chlorobenzyl)-8-fluoro-5-hydroxy-4-methyl-1H-quinolin-2-one The title compound was prepared by the method of Preparation 34c using 2-(4-chlorobenzyl)-N-(2-fluoro-5-hydroxyphenyl)-3-oxobutyramide.

$^1$H NMR (DMSO-d6): δ 2.60 (s, 3H), 4.00 (s, 2H), 6.50 (dd, J=4.4, 8.9 Hz, 1H), 7.15-7.25 (m, 3H), 7.30 (m, 2H), 10.15 (s, 1H), 11.40 (s, 1H).

MS: ESI (+ve) (Method B): 318 (M+H)+, Retention time 3.3 min.

Preparation 30d

[3-(4-chlorobenzyl)-8-fluoro-4-methyl-2-oxo-1,2-dihydroquinolin-5-yloxy]acetic Acid Methyl Ester The title compound was prepared by the method of Preparation 34d using 3-(4-chlorobenzyl)-8-fluoro-5-hydroxy-4-methyl-1H-quinolin-2-one.

Preparation 30e

[3-(4-chlorobenzyl)-2-difluoromethoxy-8-fluoro-4-methylquinolin-5-yloxy]acetic Acid Methyl Ester A mixture of [3-(4-chlorobenzyl)-8-fluoro-4-methyl-2-oxo-1,2-dihydroquinolin-5-yloxy]acetic acid methyl ester (1.0 g), N,N-dimethylformamide (15 mL), potassium carbonate (0.89 g) and acetic acid chlorodifluoromethyl ester (1.1 mL) was stirred at 70° C. for 18 hours. The mixture was diluted with water, extracted with ethyl acetate and the combined extracts dried over magnesium sulfate. The solvent was removed under reduced pressure and purification of the residue by column chromatography on silica gel, eluting with a mixture of pentane and dichloromethane (4:1 by volume) gave title compound as a white solid, 0.49 g.

$^1$H NMR (DMSO-d6): 8.2.85 (s, 3H), 3.70 (s, 3H), 4.2 (s, 2H), 5.0 (s, 2H), 6.95 (dd, J=4.1, 8.8 Hz, 1H), 7.15 (d, J=8.5 Hz, 2H), 7.35 (d, J=8.5 Hz, 2H), 7.50 (dd, J=8.8, 9.8 Hz, 1H), 7.85 (t, J=72 Hz, 1H).

MS: ESI (+ve) (Method B): 440 (M+H)+, Retention time 4.5 min.

Preparation 30f

[3-(4-chlorobenzyl)-2-difluoromethoxy-8-fluoro-4-methylquinolin-5-yloxy]-acetic Acid A solution of [3-(4-chlorobenzyl)-2-difluoromethoxy-8-fluoro-4-methylquinolin-5-yloxy]acetic acid methyl ester (0.45 g), tetrahydrofuran (5.0 mL), methanol (5.0 mL) and 1.0 M aqueous lithium hydroxide solution (1.3 mL) was stirred at room temperature for 18 hours. The solution was acidified by the addition of 1.0 M aqueous hydrochloric acid and extracted with ethyl acetate. The combined extracts were dried over magnesium sulfate and the solvent removed under reduced pressure. Crystallisation of the residue from a mixture of water and propan-2-ol gave title compound as a white solid, 0.33 g.

$^1$H NMR (DMSO-d6): δ 2.95 (s, 3H), 4.25 (s, 2H), 4.75 (s, 2H), 6.85 (dd, J=4.0, 9.0 Hz, 1H), 7.10 (d, J=8.6 Hz, 2H), 7.25 (d, J=8.6 Hz, 2H), 7.30 (m, 1H), 7.80 (t, J=72 Hz, 1H).

MS: ESI (+ve) (Method A): 426 (M-C$_3$H$_6$)+, Retention time 12.6 min.

Example 31

[8-chloro-3-(4-fluorobenzyl)-2-isopropoxy-4-methylquinolin-5-yloxy]acetic Acid

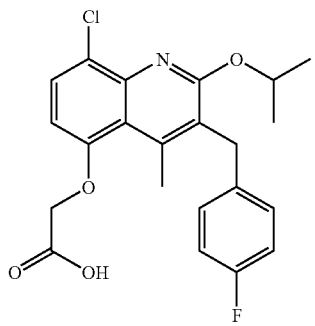

Preparation 31a

[8-chloro-3-(4-fluorobenzyl)-4-methyl-2-oxo-1,2-dihydroquinolin-5-yloxy]acetic Acid Methyl Ester and [8-chloro-3-(4-fluorobenzyl)-2-methyl-4-oxo-1,4-dihydroquinolin-5-yloxy]acetic Acid Methyl Ester A mixture of (3-amino-4-chlorophenoxy)acetic acid methyl ester (1.5 g), 2-(4-fluorobenzyl)-3-oxobutyric acid ethyl ester (1.7 g) and polyphosphoric acid (15 g) was heated at 100° C. for 3 hours. The mixture was cooled to room temperature, diluted with water and extracted with ethyl acetate. The combined extracts were washed with water and saturated aqueous sodium chloride solution and then dried over magnesium sulfate. The solvent was removed under reduced pressure and the residue purified by column chromatography on silica gel, eluting with a mixture of ethyl acetate and cyclohexane (3:7 by volume) to afford [8-chloro-3-(4-fluorobenzyl)-4-methyl-2-oxo-1,2-dihydroquinolin-5-yloxy]acetic acid methyl ester as a yellow-brown solid, 0.13 g and [8-chloro-3-(4-fluorobenzyl)-2-methyl-4-oxo-1,4-dihydroquinolin-5-yloxy]acetic acid methyl ester as a brown oil, 0.21 g.

[8-chloro-3-(4-fluorobenzyl)-4-methyl-2-oxo-1,2-dihydroquinolin-5-yloxy]acetic Acid Methyl Ester $^1$H NMR (CDCl$_3$): δ 2.75 (s, 3H), 3.80 (s, 3H), 4.15 (s, 2H), 4.70 (s, 2H), 6.50 (d, J=8.8 Hz, 1H), 6.95 (m, 2H), 7.20 (m, 2H), 7.70 (d, J=8.8 Hz, 1H), 9.2 (br s, 1H).

MS: ESI (+ve) (Method B): 390 (M+H)$^+$, Retention time 3.7 min.

[8-chloro-3-(4-fluorobenzyl)-2-methyl-4-oxo-1,4-dihydroquinolin-5-yloxy]acetic Acid Methyl Ester $^1$H NMR (CDCl$_3$): δ 2.50 (s, 3H), 3.85 (s, 3H), 4.05 (s, 2H), 4.80 (s, 2H), 6.60 (d, J=8.5 Hz, 1H), 6.90 (m, 2H), 7.20 (m, 2H), 7.55 (d, J=8.5 Hz, 1H).

MS: ESI (+ve) (Method B): 390 (M+H)$^+$, Retention time 3.2 min.

Preparation 31b

[8-chloro-3-(4-fluorobenzyl)-2-isopropoxy-4-methylquinolin-5-yloxy]acetic Acid Methyl Ester A mixture of [8-chloro-3-(4-fluorobenzyl)-4-methyl-2-oxo-1,2-dihydroquinolin-5-yloxy]acetic acid methyl ester (0.020 g), N,N-dimethylformamide (1.0 mL), potassium carbonate (0.020 g) and 2-iodopropane (0.050 g) was stirred at room temperature for 4 hour. The mixture was diluted with water (20 mL), extracted with ethyl acetate and the combined extracts washed with water and saturated aqueous sodium chloride solution and then dried over magnesium sulfate. The solvent removed under reduced pressure and the residue purified by column chromatography on silica gel, eluting with a mixture of ethyl acetate and cyclohexane (1:9 by volume) to afford title compound as a cream solid, 0.023 g.

$^1$H NMR (CDCl$_3$): δ 1.35 (d, J=6.2 Hz, 6H), 2.85 (s, 3H), 3.80 (s, 3H), 4.15 (s, 2H), 4.70 (s, 2H), 5.60 (m, 1H), 6.50 (d, J=8.4 Hz, 1H), 6.90 (m, 2H), 7.10 (m 2H), 7.55 (d, J=8.4 Hz, 1H).

MS: ESI (+ve) (Method B): 432 (M+H)$^+$, Retention time 5.0 min.

Preparation 31c

[8-chloro-3-(4-fluorobenzyl)-2-isopropoxy-4-methylquinolin-5-yloxy]acetic Acid

A solution of [8-chloro-3-(4-fluorobenzyl)-2-isopropoxy-4-methylquinolin-5-yloxy]acetic acid methyl ester (0.020 g), methanol (1.0 mL) and 1.0 M aqueous sodium hydroxide solution (0.25 mL) was stirred at room temperature for 3 hours. The pH of the solution was adjusted to 5 by the addition of formic acid and the solvent removed under reduced pressure. Purification of the residue by preparative reverse-phase HPLC using a gradient over 30 minutes of acetonitrile in water (30% to 90% of organic modifier) gave title compound as a white solid, 0.0085 g.

$^1$H NMR (CDCl$_3$): δ 1.35 (d, J=6.4 Hz, 6H), 2.85 (s, 3H), 4.15 (s, 2H), 4.75 (s, 2H), 5.60 (m, 1H), 6.55 (d, J=8.3 Hz, 1H), 6.90 (m, 2H), 7.10 (m, 2H), 7.55 (d, J=8.3 Hz, 1H).

MS: ESI (+ve) (Method A): 376 (M-C$_3$H$_6$)$^+$, Retention time 14.3 min.

Example 32

[8-chloro-3-(4-fluorobenzyl)-4-isopropoxy-2-methylquinolin-5-yloxy]acetic Acid

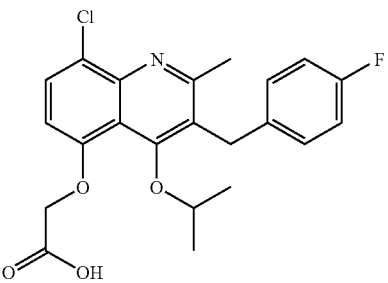

Preparation 32a

[8-chloro-3-(4-fluorobenzyl)-4-isopropoxy-2-methylquinolin-5-yloxy]acetic Acid Methyl Ester A mixture of [8-chloro-3-(4-fluorobenzyl)-2-methyl-4-oxo-1,4-dihydroquinolin-5-yloxy]acetic acid methyl ester (0.020 g), N,N-dimethylformamide (1.0 mL), potassium carbonate (0.020 g) and 2-iodopropane (0.050 g) was stirred at room temperature for 2 days. The mixture was diluted with water, extracted with ethyl acetate and the combined extracts washed with water and saturated aqueous sodium chloride solution and then dried over magnesium sulfate. The solvent was removed under reduced pressure and the residue purified by column chromatography on silica gel, eluting with a mixture of ethyl acetate and cyclohexane (1:9 by volume) to afford title compound as a light brown oil, 0.024 g.

$^1$H NMR (CDCl$_3$): δ 1.25 (d, J=6.8 Hz, 6H), 2.60 (s, 3H), 3.80 (s, 3H), 4.25 (s, 2H), 4.60 (m, 1H), 4.80 (s, 2H), 6.70 (d, J=8.4 Hz, 1H), 6.90 (m, 2H), 7.05 (m, 2H), 7.65 (d, J=8.4 Hz, 1H).

MS: ESI (+ve) (Method B): 432 (M+H)$^+$, Retention time 4.2 min.

Preparation 32b

[8-chloro-3-(4-fluorobenzyl)-4-isopropoxy-2-methylquinolin-5-yloxy]acetic Acid A solution of [8-chloro-3-(4-fluorobenzyl)-4-isopropoxy-2-methylquinolin-5-yloxy]acetic acid methyl ester (0.020 g), methanol (1.0 mL) and 1.0 M aqueous sodium hydroxide solution (0.25 mL) was stirred at room temperature for 3 hours. The pH of the solution was adjusted to 5 by the addition of formic acid and the solvent removed under reduced pressure. Purification of the residue by preparative reverse-phase HPLC using a gradient over 30 minutes of acetonitrile in water (30% to 90% of organic modifier) gave title compound as a pale yellow solid, 0.012 g.

$^1$H NMR (CDCl$_3$): δ 1.30 (d, J=6.2 Hz, 6H), 2.60 (s; 3H), 4.25 (s, 2H), 4.45 (m, 1H), 4.80 (s, 2H), 6.85 (d, J=8.3 Hz, 1H), 6.95 (m, 2H), 7.00 (m, 2H), 7.70 (d, J=8.3 Hz, 1H).

MS: ESI (+ve) (Method A): 376 (M-C$_3$H$_6$)$^+$, Retention time 10.3 min.

Example 33

2-[8-chloro-3-(4-chlorobenzyl)-2,4-dimethylquinolin-5-yloxy]propionic Acid

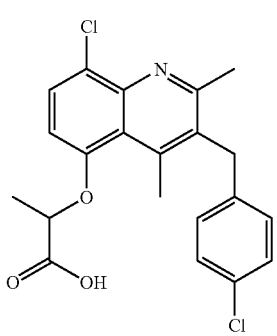

Preparation 33a

2-[8-chloro-3-(4-chlorobenzyl)-2,4-dimethylquinolin-5-yloxy]propionic Acid Methyl Ester A mixture of 8-chloro-3-(4-chlorobenzyl)-2,4-dimethylquinolin-5-ol (0.18 g), N,N-dimethylformamide (2.0 mL), potassium carbonate (0.092 g) and 2-bromopropionic acid methyl ester (0.11 g) was stirred at room temperature for 3 hours. The mixture was diluted with water, extracted with ethyl acetate and the combined extracts washed with water and saturated aqueous sodium chloride solution and then dried over magnesium sulfate. The solvent removed under reduced pressure and the residue purified by column chromatography on silica gel, eluting with a mixture of ethyl acetate and cyclohexane (1:9 to 1:4 by volume) to afford title compound, 0.092 g.

$^1$H NMR (CDCl$_3$): δ 1.70 (d, J=6.8 Hz, 3H), 2.70 (s, 3H), 2.85 (s, 3H), 3.75 (s, 3H), 4.25 (s, 2H), 4.90 (q, J=6.8 Hz, 1H), 6.60 (d, J=8.4 Hz, 1H), 6.95 (d, J=8.4 Hz, 2H), 7.25 (d, J=8.4 Hz, 2H), 7.60 (d, J=8.4 Hz, 1H).

MS: ESI (+ve) (Method B): 418 (M+H)$^+$, Retention time 4.5 min.

Preparation 33b

2-[8-chloro-3-(4-chlorobenzyl)-2,4-dimethylquinolin-5-yloxy]propionic Acid

A solution of 2-[8-chloro-3-(4-chlorobenzyl)-2,4-dimethylquinolin-5-yloxy]propionic acid methyl ester (0.092 g), tetrahydrofuran (2.0 mL) and 1.0 M aqueous lithium hydroxide solution (0.25 mL) was stirred at room temperature for 30 minutes. The tetrahydrofuran was removed under reduced pressure and pH of the residue was adjusted to 2 by the addition of 1.0 M aqueous hydrochloric acid. The mixture was extracted with ethyl acetate and the combined extracts washed with saturated aqueous sodium chloride solution and dried over magnesium sulfate. The solvent was removed under reduced pressure and the resulting solid washed with pentane to afford title compound, 0.080 g.

$^1$H NMR (CDCl$_3$): δ 1.75 (d, J=6.7 Hz, 3H), 2.75 (s, 3H), 2.85 (s, 3H), 4.25 (s, 2H), 4.95 (q, J=6.7 Hz, 1H), 6.65 (d, J=8.6 Hz, 1H), 6.90 (d, J=8.4 Hz, 2H), 7.20 (d, J=8.4 Hz, 2H), 7.55 (d, J=8.6 Hz, 1H).

MS: ESI (+ve) (Method A): 404 (M-C$_3$H$_6$)$^+$, Retention time 11.4 min.

Example 34

[8-chloro-2-difluoromethoxy-3-(4-methanesulfonylbenzyl)-4-methylquinolin-5-yloxy]acetic Acid

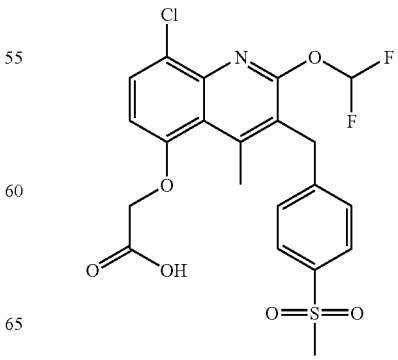

Preparation 34a

2-(4-methanesulfonylbenzyl)-3-oxothiobutyric acid S-tert-butyl Ester

A solution of 3-oxothiobutyric acid S-tert-butyl ester (7.5 g) in 1,2-dimethoxyethane (10 mL) was added to a stirred suspension of sodium hydride (60% in oil, 1.9 g) in 1,2-dimethoxyethane (100 mL) at −20° C. The mixture was warmed to 0° C. for 10 minutes and then a solution of 1-bromomethyl-4-methanesulfonylbenzene (12.9 g) in 1,2-dimethoxyethane (30 mL) was added dropwise over a period of 10 minutes. The resulting mixture was warmed to room temperature over 30 minutes and then stirred at this temperature for 17 hours. The mixture was diluted with saturated aqueous ammonium chloride solution (70 mL) and the phases separated. The aqueous phase was extracted with diethyl ether and the combined organic phases were dried over magnesium sulfate. The solvent was removed under reduced pressure and purification of the residue by column chromatography on silica gel, eluting with a mixture of dichloromethane and ethyl acetate (1:0 to 4:1 by volume) gave title compound, 7.1 g.

$^1$H NMR (CDCl$_3$): δ 1.40 (s, 9H), 2.25 (s, 3H), 3.05 (s, 3H), 3.20-3.30 (m, 2H), 3.85 (m, 1H), 7.40 (d, J=8.5 Hz, 2H), 7.85 (d, J=8.5 Hz, 2H).

Preparation 34b

N-(2-chloro-5-hydroxyphenyl)-2-(4-methanesulfonylbenzyl)-3-oxo-butyramide

Silver trifluoroacetate (1.3 g) was added in two portions over 20 minutes to a stirred solution of 3-amino-4-chlorophenol (0.5 g) and 2-(4-methanesulfonylbenzyl)-3-oxothiobutyric acid S-tert-butyl ester (0.8 g) in 1,2-dimethoxyethane (10 mL) at room temperature. The mixture was stirred at room temperature for 15 hours and then filtered through hyflo, washing with 1,2-dimethoxyethane. The solvent was removed under reduced pressure and purification of the residue by column chromatography on silica gel, eluting with a mixture of dichloromethane and ethyl acetate (1:0 to 0:1 by volume) gave title compound as a pale peach solid, 0.75 g.

MS: ESI (+ve) (Method B): 396 (M+H)$^+$, Retention time 2.7 min.

Preparation 34c

8-chloro-5-hydroxy-3-(4-methanesulfonylbenzyl)-4-methyl-1H-quinolin-2-one

A mixture of N-(2-chloro-5-hydroxyphenyl)-2-(4-methanesulfonylbenzyl)-3-oxo-butyramide (0.25 g) and methanesulfonic acid (1.1 g) was heated at 100° C. for 10 minutes. The mixture cooled to room temperature and poured into a saturated aqueous solution of sodium acetate (20 mL). The resulting precipitate was collected by filtration, washed with water and dried to afford title compound as a pale pink solid, 0.21 g.

MS: ESI (+ve) (Method B): 378 (M+H)$^+$, Retention time 2.8 min.

Preparation 34d

[8-chloro-3-(4-methanesulfonylbenzyl)-4-methyl-2-oxo-1,2-dihydroquinolin-5-yloxy]acetic Acid Methyl Ester A mixture of 8-chloro-5-hydroxy-3-(4-methanesulfonylbenzyl)-4-methyl-1H-quinolin-2-one (0.20 g), N,N-dimethylformamide (4.0 mL), potassium carbonate (0.091 g) and bromoacetic acid methyl ester (0.079 g) was stirred at room temperature for 1 hour. The mixture was diluted with water (20 mL) and the pH adjusted to 4 by the addition of glacial acetic acid. The resulting precipitate was collected by filtration and purified by column chromatography on silica gel, eluting with a mixture of dichloromethane and ethyl acetate (1:0 to 1:1 by volume) to afford title compound as a white solid, 0.14 g.

$^1$H NMR (CDCl$_3$): δ 2.65 (s, 3H), 3.15 (s, 3H), 3.70 (s, 3H), 4.20 (s, 2H), 4.95 (s, 2H), 6.80 (d, J=8.9 Hz, 1H), 7.45 (d, J=8.9 Hz, 2H), 7.55 (d, J=8.9 Hz, 1H), 7.80 (d, J=8.9 Hz, 2H), 10.70 (br s, 1H).

Preparation 34e

[8-chloro-2-difluoromethoxy-3-(4-methanesulfonylbenzyl)-4-methylquinolin-5-yloxy]acetic Acid Methyl Ester A stirred mixture of [8-chloro-3-(4-methanesulfonylbenzyl)-4-methyl-2-oxo-1,2-dihydroquinolin-5-yloxy]acetic acid methyl ester (0.13 g), N,N-dimethylformamide (5.0 mL) and potassium carbonate (0.12 g) was cooled to −80° C. and then chlorodifluoromethane was bubbled through this solution for 30 minutes. The flask was sealed and the resulting mixture warmed to room temperature over 30 minutes and then heat at 40° C. for 15 hours. The excess chlorodifluoromethane was allowed to evaporate and the residue diluted with water. The resulting precipitate was collected by filtration, washed with water and dried to afford title compound as a white solid, 0.15 g.

$^1$H NMR (DMSO-d6): δ 2.90 (s, 3H), 3.20 (s, 3H), 3.70 (s, 3H), 4.35 (s, 2H), 5.00 (s, 2H), 7.05 (d, J=8.7 Hz, 1H), 7.40 (d, J=8.7 Hz, 2H), 7.80 (m, 3H), 7.90 (t, J=72 Hz, 1H).

MS: ESI (+ve) (Method B): 400 (M+H)$^+$, Retention time 4.0 min.

Preparation 34f

[8-chloro-2-difluoromethoxy-3-(4-methanesulfonylbenzyl)-4-methylquinolin-5-yloxy]acetic Acid A solution of [8-chloro-2-difluoromethoxy-3-(4-methanesulfonylbenzyl)-4-methylquinolin-5-yloxy]acetic acid methyl ester (0.14 g), methanol (5.0 mL), saturated aqueous lithium hydroxide solution (0.5 mL) and water (0.4 mL) was stirred at room temperature for 35 minutes. The pH of the solution was adjusted to 5 by the addition of glacial acetic acid and the methanol removed under reduced pressure. The resulting precipitate was collected by filtration, washed with water and dried to afford title compound as a white solid 0.13 g.

$^1$H NMR (DMSO-d6): δ 2.90 (s, 3H), 3.15 (s, 3H), 4.30 (s, 2H), 4.35 (s, 2H), 6.80 (d, J=8.6 Hz, 1H), 7.40 (d, J=8.0 Hz, 2H), 7.75 (d, J=8.6 Hz, 1H), 7.85 (d, J=8.0 Hz, 2H), 7.90 (t, J=72 Hz, 1H).

MS: ESI (+ve) (Method A): 486 (M+H)$^+$, Retention time 10.9 min.

MS: ESI (+ve) (Method B): 486 (M+H)+, Retention time 3.7 min.

Example 35

[8-chloro-3-(2-chloro-4-methanesulfonylbenzyl)-4-difluoro-methoxy-2-methylquinolin-5-yloxy]acetic Acid

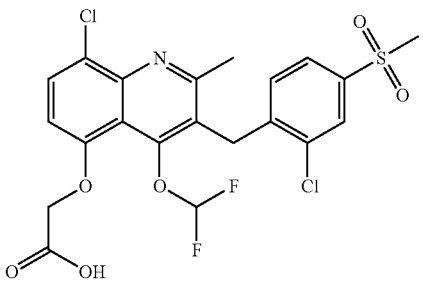

Preparation 35a (4-chloro-3-nitrophenoxy)acetic Acid Methyl Ester

A mixture of 4-chloro-3-nitrophenol (25 g), N,N-dimethylformamide (200 mL), potassium carbonate (60 g) and bromoacetic acid methyl ester (15.5 mL) was stirred at room temperature for 2.5 hours. The mixture was partitioned between ethyl acetate and water and the aqueous phase extracted with ethyl acetate. The combined extracts were dried over sodium sulfate and the solvent removed under reduced pressure. The residue was washed with diethyl ether to afford title compound as a white solid, 30 g.

$^1$H NMR (CDCl$_3$): δ 3.85 (s, 3H), 4.70 (s, 2H), 7.10 (dd, J=3.0, 8.9 Hz, 1H), 7.40 (dd, J=3.0 Hz, 1H), 7.45 (d, J=8.9 Hz, 1H).

Preparation 35b (3-amino-4-chlorophenoxy)acetic Acid Methyl Ester

A solution of (4-chloro-3-nitrophenoxy)acetic acid methyl ester (30 g) in methanol (100 mL) was added to a mixture of iron (26 g), ammonium chloride (33 g) and water (400 mL) at room temperature. The resulting mixture was heated in an ultrasonic bath at 60° C. for 4 hours. The mixture was basified by the addition of sodium hydroxide and then extracted with ethyl acetate. The combined extracts were washed with 1.0 M aqueous hydrochloric acid and the pH of the combined aqueous phases were adjusted to 7-8 by the addition of sodium hydroxide. The resulting precipitate was collected by filtration and dried to afford title compound, 14 g.

$^1$H NMR (DMSO-d6): δ 3.70 (s, 3H), 4.60 (s, 2H), 5.35 (br s, 2H), 6.10 (dd, J=3.0, 8.8 Hz, 1H), 6.35 (d, J=3.0 Hz, 1H), 7.05 (d, J=8.8 Hz, 1H).

Preparation 35c 2-(2-chloro-4-methanesulfonylbenzyl)-3-oxobutyric Acid Ethyl Ester The title compound was prepared by the method of Preparation 34a using 1-bromomethyl-2-chloro-4-methanesulfonylbenzene and 3-oxobutyric acid ethyl ester.

$^1$H NMR (CDCl$_3$): δ1.25 (t, J=7.1 Hz, 3H), 2.30 (s, 3H), 3.05 (s, 3H), 3.25-3.40 (m, 2H), 3.95 (dd, J=6.4, 8.3 Hz, 1H), 4.10-4.25 (m, 2H), 7.50 (d, J=8.2 Hz, 1H), 7.75 (dd, J=1.9, 8.2 Hz, 1H), 7.95 (d, J=1.9 Hz, 1H).

Preparation 35d

[8-chloro-3-(2-chloro-4-methanesulfonylbenzyl)-2-methyl-4-oxo-1,4-dihydroquinolin-5-yloxy]acetic Acid Methyl Ester A mixture of (3-amino-4-chlorophenoxy)acetic acid methyl ester (0.85 g), 2-(2-chloro-4-methanesulfonylbenzyl)-3-oxobutyric acid ethyl ester (2.1 g) and polyphosphoric acid (10 g) was heated at 130° C. for 2 hours. The mixture was cooled to room temperature, diluted with water and extracted with ethyl acetate. The combined extracts were dried over magnesium sulfate and the solvent removed under reduced pressure. The residue was purified by column chromatography on silica gel to afford title compound, 0.35 g.

MS: ESI (+ve) (Method B): 484 (M+H)+, Retention time 3.1 min.

Preparation 35e

[8-chloro-3-(2-chloro-4-methanesulfonylbenzyl)-4-difluoromethoxy-2-methylquinolin-5-yloxy]acetic Acid Methyl Ester A mixture of [8-chloro-3-(2-chloro-4-methanesulfonylbenzyl)-2-methyl-4-oxo-1,4-dihydroquinolin-5-yloxy]acetic acid methyl ester (0.34 g), N,N-dimethylformamide (15 mL), potassium carbonate (0.58 g) and acetic acid chlorodifluoromethyl ester (0.4 mL) was stirred at 70° C. for 16 hours. The mixture was diluted with water, extracted with ethyl acetate and the combined extracts were dried over sodium sulfate and then the solvent removed under reduced pressure. Purification of the residue by column chromatography on silica gel, eluting with a mixture of cyclohexane and ethyl acetate (7:3 by volume) gave title compound, 0.37 g.

MS: ESI (+ve) (Method B): 534 (M+H)+, Retention time 4.0 min.

Preparation 35f

[8-chloro-3-(2-chloro-4-methanesulfonylbenzyl)-4-difluoromethoxy-2-methylquinolin-5-yloxy]acetic Acid A mixture of [8-chloro-3-(2-chloro-4-methanesulfonylbenzyl)-4-difluoromethoxy-2-methylquinolin-5-yloxy]acetic acid methyl ester (0.034 g), methanol (8.0 mL), tetrahydrofuran (8.0 mL), water (5.0 mL) and lithium hydroxide (0.027 µg) was stirred at room temperature for 1 hour. The solution was acidified by the addition of 1.0 M aqueous hydrochloric acid and extracted with ethyl acetate. The combined extracts were dried over magnesium sulfate and the solvent removed under reduced pressure. Purification of the residue by preparative reverse-phase HPLC using a gradient of acetonitrile in water gave title compound as a yellow solid, 0.09 g.

$^1$H NMR (DMSO-d6): δ 2.55 (s, 3H), 3.15 (s, 3H), 4.55 (s, 2H), 4.90 (s, 2H), 6.95 (d, J=7.9 Hz, 1H), 7.00 (d, J=8.7 Hz, 1H), 7.15 (t, J=75 Hz, 1H), 7.70 (dd, J=1.9, 8.2 Hz, 1H), 7.80 (d, J=8.7 Hz, 1H), 8.05 (d, J=1.9 Hz, 1H).

MS: ESI (+ve) (Method A): 520 (M+H)+, Retention time 10.5 min.

Example 36

[8-chloro-2-difluoromethoxy-3-(4-methanesulfonyl-benzyl)-4-methylquinolin-5-yl]acetic Acid

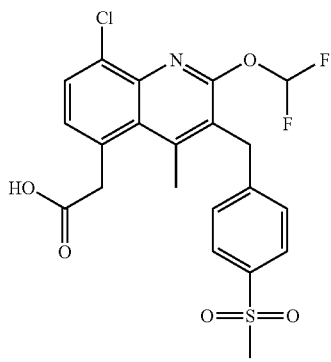

Preparation 36a

Trifluoromethanesulfonic Acid 8-chloro-3-(4-methanesulfonylbenzyl)-4-methyl-2-oxo-1,2-dihydroquinolin-5-yl Ester A mixture of 8-chloro-5-hydroxy-3-(4-methanesulfonylbenzyl)-4-methyl-1H-quinolin-2-one (0.67 g), N-phenyltrifluoromethanesulfonimide (0.63 g), potassium carbonate (0.49 g) and tetrahydrofuran (10 mL) was heated by microwave irradiation at 130° C. for 20 minutes. The mixture was filtered and the filtrate concentrated under reduced pressure. Purification of the residue by column chromatography on silica gel, eluting with a mixture of dichloromethane and ethyl acetate (1:0 to 2:1 by volume) gave title compound as an off-white solid, 0.64 g.

$^1$H NMR (DMSO-d6): δ 2.55 (s, 3H), 3.15 (s, 3H), 4.25 (s, 2H), 7.30 (d, J=8.8 Hz, 1H), 7.45 (d, J=8.3 Hz, 2H), 7.80-7.85 (m, 3H), 11.35 (br s, 1H).

MS: ESI (+ve) (Method B): 510 (M+H)$^+$, Retention time 3.6 min.

Preparation 36b

[8-chloro-3-(4-methanesulfonylbenzyl)-4-methyl-2-oxo-1,2-dihydroquinolin-5-yl]acetic Acid Methyl Ester A mixture of trifluoromethanesulfonic acid 8-chloro-3-(4-methanesulfonylbenzyl)-4-methyl-2-oxo-1,2-dihydroquinolin-5-yl ester (0.042 g), 1-(tert-butyldimethylsilyloxy)-1-methoxyethene (0.10 mL), sodium acetate (0.008 g), bis(dibenzylideneacetone) palladium (0.002 g) and 1,1'-bis(diphenylphospino) ferrocene (0) (0.002 g) in N,N-dimethylformamide (0.8 mL) was heated by microwave irradiation at 120° C. for 15 minutes. The mixture was diluted with ethyl acetate and this solution was washed with saturated aqueous ammonium chloride solution and saturated aqueous sodium chloride solution and then dried over magnesium sulfate. The solvent was removed under reduced pressure and purification of the residue by column chromatography on silica gel, eluting with a mixture of dichloromethane and ethyl acetate (1:0 to 1:1 by volume) gave title compound as an off-white solid, 0.053 g.

MS: ESI (+ve) (Method B): 434 (M+H)$^+$, Retention time 3.0 min.

Preparation 36c

[8-chloro-2-difluoromethoxy-3-(4-methanesulfonylbenzyl)-4-methylquinolin-5-yl]acetic Acid Methyl Ester The title compound was prepared by the method of Preparation 34e using [8-chloro-3-(4-methanesulfonylbenzyl)-4-methyl-2-oxo-1,2-dihydroquinolin-5-yl]acetic acid methyl ester.

MS: ESI (+ve) (Method B): 484 (M+H)$^+$, Retention time 3.9 min.

Preparation 36d

[8-chloro-2-difluoromethoxy-3-(4-methanesulfonylbenzyl)-4-methylquinolin-5-yl]acetic Acid A solution of [8-chloro-2-difluoromethoxy-3-(4-methanesulfonylbenzyl)-4-methylquinolin-5-yl]acetic acid methyl ester (0.030 g), methanol (2.0 mL), saturated aqueous lithium hydroxide solution (0.20 mL) and water (0.40 mL) was stirred at room temperature for 2.5 hours and then at 40° C. for 2 hours. The pH of the solution was adjusted to 5 by the addition of glacial acetic acid and the solvent removed under reduced pressure. The residue was diluted with water and the solid collected by filtration, washed with water and methanol and then dried to afford title compound as a white solid, 0.016 g.

$^1$H NMR (DMSO-d6): δ 2.75 (s, 3H), 3.15 (s, 3H), 4.00 (s, 2H), 4.35 (s, 2H), 7.30 (d, J=8.0 Hz, 1H), 7.40 (d, J=8.5 Hz, 2H), 7.80 (d, J=8.0 Hz, 1H), 7.85 (d, J=8.5 Hz, 2H), 7.90 (t, J=73 Hz, 1H).

MS: ESI (+ve) (Method A): 470 (M+H)$^+$, Retention time 10.5 min.

MS: ESI (+ve) (Method B): 470 (M+H)$^+$, Retention time 3.5 min.

Example 37

[8-chloro-4-difluoromethoxy-2-ethyl-3-(4-fluorobenzyl)quinolin-5-yloxy]acetic Acid

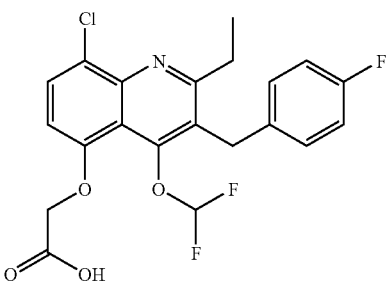

Preparation 37a 2-(4-fluorobenzyl)-3-oxopentanoic Acid Ethyl Ester

The title compound was prepared by the method of Preparation 34a using 1-bromomethyl-4-fluorobenzene and 3-oxopentanoic acid ethyl ester.

$^1$H NMR (CDCl$_3$): δ 1.00 (t, J=7.2 Hz, 3H), 1.20 (t, J=7.2 Hz, 3H), 2.35 (m, 1H), 2.60 (m, 1H), 3.15 (m, 2H), 3.75 (t, J=7.7 Hz; 1H), 4.15 (m, 2H), 6.95 (m, 2H), 7.15 (m, 2H).

Preparation 37b

[8-chloro-2-ethyl-3-(4-fluorobenzyl)-4-hydroxy-1,4-dihydroquinolin-5-yloxy]acetic Acid Methyl Ester A mixture of (3-amino-4-chlorophenoxy)acetic acid methyl ester (1.0 g), 2-(4-fluorobenzyl)-3-oxopentanoic acid ethyl ester (2.1 g) and polyphosphoric acid (10 g) was heated at 130° C. for 4 hours. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of dichloromethane and methanol (1:0 to 19:1 by volume) to afford title compound, 0.25 g.

MS: ESI (+ve) (Method B): 404 (M+H)$^+$, Retention time 3.6 min.

Preparation 37c

[8-chloro-4-difluoromethoxy-2-ethyl-3-(4-fluorobenzyl)quinolin-5-yloxy]acetic Acid Methyl Ester A mixture of [8-chloro-2-ethyl-3-(4-fluorobenzyl)-4-hydroxy-1,4-dihydroquinolin-5-yloxy]acetic acid methyl ester (0.25 g), N,N-dimethylformamide (1.1 mL), potassium carbonate (0.51 g) and acetic acid chlorodifluoromethyl ester (0.33 mL) was stirred at 70° C. for 16 hours. The mixture was diluted with water, extracted with ethyl acetate and the combined extracts dried over sodium sulfate and then the solvent removed under reduced pressure. Purification of the residue by column chromatography on silica gel, eluting with dichloromethane gave title compound, 0.06 g.

MS: ESI (+ve) (Method B): 454 (M+H)$^+$, Retention time 4.6 min.

Preparation 37d

[8-chloro-4-difluoromethoxy-2-ethyl-3-(4-fluorobenzyl)quinolin-5-yloxy]acetic Acid A solution of [8-chloro-4-difluoromethoxy-2-ethyl-3-(4-fluorobenzyl)quinolin-5-yloxy]acetic acid methyl ester (0.060 g), methanol (1.5 mL), tetrahydrofuran (1.5 mL), water (1.0 mL) and lithium hydroxide (0.01 g) was stirred at room temperature for 1 hour. The mixture was acidified by the addition of 1.0 M aqueous hydrochloric acid, extracted with ethyl acetate and the combined extracts dried over magnesium sulfate. The solvent was removed under reduced pressure and purification of the residue by preparative reverse-phase HPLC using a gradient of acetonitrile in water gave title compound as a yellow solid, 0.022 g.

$^1$H NMR (CD$_3$OD): δ 1.25 (t, J=7.5 Hz, 3H), 2.90 (q, J=7.5 Hz, 2H), 4.35 (s, 2H), 4.90 (s, 2H), 6.95-7.00 (m, 3H), 7.10 (m, 2H), 7.15 (t, J=75 Hz, 1H), 7.75 (d, J=8.6 Hz, 1H).

MS: ESI (+ve) (Method A): 440 (M+H)$^+$, Retention time 12.6 min.

Example 38

[8-chloro-3-(2-chloro-4-methanesulfonylbenzyl)-2,4-dimethylquinolin-5-yloxy]acetic Acid

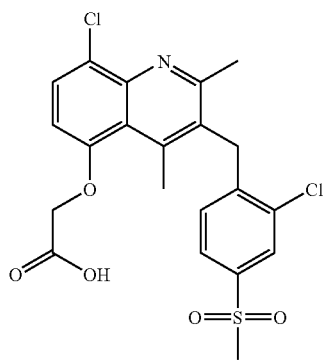

Preparation 38a 3-(2-chloro-4-methanesulfonylbenzyl)pentane-2,4-dione

Sodium hydride (60% in oil, 0.30 g) was added portionwise to a stirred solution of pentane-2,4-dione (0.92 g) in N,N-dimethylformamide (8.0 mL) at 0-10° C. The resulting mixture was stirred at 0-10° C. for 20 minutes and then a solution of 1-bromomethyl-2-chloro-4-methanesulfonylbenzene (2.0 g) in N,N-dimethylformamide (3.0 mL) was added dropwise. The resulting mixture was stirred at room temperature for 5 hours, and then diluted with water and this mixture was extracted with ethyl acetate. The combined extracts were washed with water and saturated aqueous sodium chloride solution and then dried over magnesium sulfate. The solvent was removed under reduced pressure and purification of the residue by column chromatography on silica gel, eluting with a mixture of ethyl acetate and cyclohexane (1:4 to 3:7 by volume) gave title compound as a white solid, 1.2 g.

MS: ESI (+ve) (Method B): 303 (M+H)$^+$, Retention time 2.9 min.

Preparation 38b

[8-chloro-3-(2-chloro-4-methanesulfonylbenzyl)-2,4-dimethylquinolin-5-yloxy]acetic Acid Methyl Ester A mixture of (3-amino-4-chlorophenoxy)acetic acid methyl ester (0.35 g), 3-(2-chloro-4-methanesulfonylbenzyl)pentane-2,4-dione (0.5 g) and polyphosphoric acid (5.0 g) was heated at 100° C. for 3.5 hours. The mixture was cooled to room temperature, diluted with water and extracted with ethyl acetate. The combined extracts were washed with water and saturated aqueous sodium chloride solution and dried over magnesium sulfate. The solvent was removed under reduced pressure and the residue purified by column chromatography on silica gel, eluting with a mixture of ethyl acetate and cyclohexane (2:8 to 3:7 by volume) to afford title compound as a pale yellow waxy solid, 0.36 g.

MS: ESI (+ve) (Method B): 482 (M+H)$^+$, Retention time 3.9 min.

Preparation 38c

[8-chloro-3-(2-chloro-4-methanesulfonylbenzyl)-2,4-dimethylquinolin-5-yloxy]acetic Acid A solution of [8-chloro-3-(2-chloro-4-methanesulfonyl-benzyl)-2,4-dimethylquinolin-5-yloxy]acetic acid methyl ester (0.36 g), methanol (10 mL) and 1.0 M aqueous sodium hydroxide solution (4.0 mL) was stirred at room temperature for 3 hours. The solvent was removed under reduced pressure and the pH of the residue adjusted to 5 by the addition of formic acid. Purification by preparative reverse-phase HPLC using a gradient of acetonitrile in water (50% to 65% of organic modifier) gave title compound as a white solid, 0.035 g.

$^1$H NMR (DMSO-d6): δ 2.55 (s, 3H), 2.75 (s, 3H), 3.25 (s, 3H), 4.35 (s, 2H), 4.80 (s, 2H), 6.85 (d, J=8.2 Hz, 1H), 6.95 (d, J=8.5 Hz, 1H), 7.70 (dd, J=1.9, 8.2 Hz, 1H), 7.75 (d, J=8.5 Hz, 1H), 8.10 (d, J=1.9 Hz, 1H).

MS: ESI (+ve) (Method A): 468 (M+H)$^+$, Retention time 9.6 min.

Example 39

[8-chloro-3-(4-chlorobenzyl)-4-difluoromethoxy-2-ethylquinolin-5-yloxy]acetic Acid

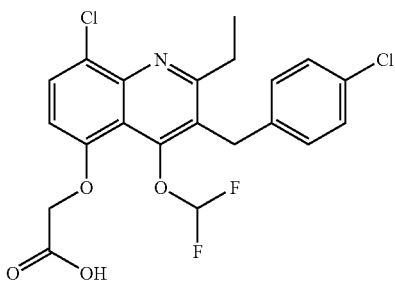

Preparation 39a 2-(4-chlorobenzyl)-3-oxopentanoic Acid Ethyl Ester

A suspension of potassium tert-butoxide (2.8 g) in anhydrous tetrahydrofuran (400 mL) at 0° C. was treated with a mixture of tert-butanol (1.0 mL) and 3-oxopentanoic acid ethyl ester (3.0 g). After stirring at room temperature for 45 minutes a solution of 1-bromomethyl-4-chlorobenzene (4.3 g) in tetrahydrofuran (100 mL) was added and the resulting mixture heated at 70° C. for 24 hours. The mixture was cooled to room temperature, diluted with water and the tetrahydrofuran removed under reduced pressure. The residue was extracted with ethyl acetate and the combined extracts dried over magnesium sulfate and then the solvent removed under reduced pressure. The residue was purified by column chromatography on silica gel, eluting with a mixture of cyclohexane and methyl tert-butyl ether (4:1 by volume) to afford title compound. 4.8 g.

MS: ESI (+ve) (Method B): 269 (M+H)$^+$, Retention time 4.0 min.

Preparation 39b

[8-chloro-3-(4-chlorobenzyl)-2-ethyl-4-oxo-1,4-dihydroquinolin-5-yloxy]acetic Acid Methyl Ester A mixture of (3-amino-4-chlorophenoxy)acetic acid methyl ester (0.53 g), 2-(4-chlorobenzyl)-3-oxopentanoic acid ethyl ester (0.66 g), methanesulfonic acid (0.032 mL) and toluene (20 mL) was heated at reflux for 20 hours. The mixture was cooled to room temperature and the solvent removed under reduced pressure. The residue was diluted with water, extracted with ethyl acetate and the combined extracts dried over magnesium sulfate. The solvent was removed under reduced pressure and the residue purified by column chromatography on silica gel, eluting with a mixture of dichloromethane and ethyl acetate (9:1 by volume) to afford title compound, 0.034 g MS: ESI (+ve) (Method B): 420 (M+H)$^+$, Retention time 3.8 min.

Preparation 39c

[8-chloro-3-(4-chlorobenzyl)-4-difluoromethoxy-2-ethylquinolin-5-yloxy]acetic Acid Methyl Ester The title compound was prepared by the method of Preparation 34e using [8-chloro-3-(4-chlorobenzyl)-2-ethyl-4-oxo-1,4-dihydroquinolin-5-yloxy]acetic acid methyl ester.

MS: ESI (+ve) (Method B): 470 (M+H)$^+$, Retention time 4.8 min.

Preparation 39d

[8-chloro-3-(4-chlorobenzyl)-4-difluoromethoxy-2-ethylquinolin-5-yloxy]acetic Acid A solution of [8-chloro-3-(4-chlorobenzyl)-4-difluoromethoxy-2-ethylquinolin-5-yloxy]acetic acid methyl ester (0.017 g), tetrahydrofuran (3.0 mL) and 1.0 M aqueous lithium hydroxide solution (0.20 mL) was stirred at room temperature for 1 hour. The solvent was removed under reduced pressure and the residue diluted with water. The pH of the resulting mixture was adjusted to 5 by the addition of sodium dihydrogenphosphate and extracted with ethyl acetate. The combined extracts were dried over magnesium sulfate and the solvent removed under reduced pressure. Purification of the residue by preparative reverse-phase HPLC using a gradient of acetonitrile in water (30% to 95% of organic modifier) gave title compound, 0.010 g.

$^1$H NMR (DMSO-d6): δ 1.35 (t, J=7.4 Hz, 3H), 2.90 (q, J=7.4 Hz, 2H), 4.35 (s, 2H), 4.90 (s, 2H), 6.75 (d, J=8.6 Hz, 1H), 6.85 (t, J=75 Hz, 1H), 7.00 (d, J=8.4 Hz, 2H), 7.25 (d, J=8.4 Hz, 2H), 7.70 (d, J=8.6 Hz, 1H).

MS: ESI (+ve) (Method A): 456 (M+H)$^+$, Retention time 13.4 min.

Example 40

[8-chloro-3-(8-chloro-4-methanesulfonylbenzyl)-2-difluoro-methoxy-4-methylquinolin-5-yloxy]acetic acid

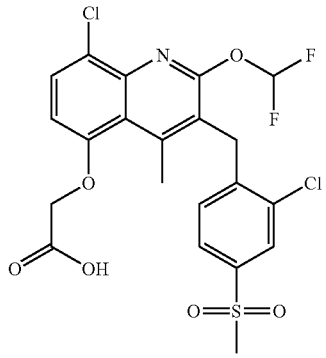

Preparation 40a 2-(2-chloro-4-methanesulfonylbenzyl)-3-oxothiobutyric acid S-tert-butyl Ester The title compound was prepared by the method of Preparation 34a using 1-bromomethyl-2-chloro-4-methanesulfonylbenzene and 3-oxothiobutyric acid S-tert-butyl ester.

$^1$H NMR (CDCl$_3$): δ 1.45 (s, 9H), 1.75 (s, 3H), 3.10 (s, 3H), 3.80 (s, 2H), 7.40 (d, J=8.1 Hz, 1H), 7.75 (dd, J=1.9, 8.1 Hz, 1H), 7.95 (d, J=1.9 Hz, 1H).

MS: ESI (−ve) (Method B): 375 (M−H)$^−$, Retention time 3.7 min.

Preparation 40b

N-(2-chloro-5-hydroxyphenyl)-2-(2-chloro-4-methanesulfonylbenzyl)-3-oxobutyramide The title compound was prepared by the method of Preparation 34b using 3-amino-4-chlorophenol and 2-(2-chloro-4-methanesulfonylbenzyl)-3-oxothiobutyric acid S-tert-butyl ester.

MS: ESI (+ve) (Method B): 430 (M+H)$^+$, Retention time 2.97 min.

Preparation 40c 8-chloro-3-(2-chloro-4-methanesulfonylbenzyl)-5-hydroxy-4-methyl-1H-quinolin-2-one The title compound was prepared by the method of Preparation 34c using N-(2-chloro-5-hydroxyphenyl)-2-(2-chloro-4-methanesulfonylbenzyl)-3-oxobutyramide.

$^1$H NMR (DMSO-d6): δ 2.55 (s, 3H), 3.25 (s, 3H), 4.15 (s, 2H), 6.65 (d, J=8.8 Hz, 1H), 7.15 (d, J=8.2 Hz, 1H), 7.45 (d, J=8.8 Hz, 1H), 7.75 (dd, J=1.9, 8.2 Hz, 1H), 8.00 (d, J=1.9 Hz, 1H), 10.50 (br s, 1H).

MS: ESI (+ve) (Method B): 412 (M+H)$^+$, Retention time 3.1 min.

Preparation 40d

[8-chloro-3-(2-chloro-4-methanesulfonylbenzyl)-4-methyl-2-oxo-1,2-dihydroquinolin-5-yloxy]acetic Acid Methyl Ester The title compound was prepared by the method of Preparation 34d using 8-chloro-3-(2-chloro-4-methanesulfonylbenzyl)-5-hydroxy-4-methyl-1H-quinolin-2-one.

$^1$H NMR (DMSO-d6): δ 2.60, (s, 3H), 3.25 (s, 3H), 3.70 (s, 3H), 4.20 (s, 2H), 4.95 (s, 2H), 6.80 (d, J=8.9 Hz, 1H), 7.15 (d, J=8.2 Hz, 1H), 7.60 (d, J=8.9 Hz, 1H), 7.75 (dd, J=1.9, 8.2 Hz, 1H), 8.05 (d, J=1.9 Hz, 1H), 10.75 (br s, 1H).

MS: ESI (+ve) (Method B): 484 (M+H)$^+$, Retention time 3.4 min.

Preparation 40e

[8-chloro-3-(2-chloro-4-methanesulfonylbenzyl)-2-difluoromethoxy-4-methylquinolin-5-yloxy]acetic Acid Methyl Ester The title compound was prepared by the method of Preparation 34e using [8-chloro-3-(2-chloro-4-methanesulfonylbenzyl)-4-methyl-2-oxo-1,2-dihydroquinolin-5-yloxy]acetic acid methyl ester.

MS: ESI (+ve) (Method B): 534 (M+H)$^+$, Retention time 4.3 min.

Preparation 40f

[8-chloro-3-(2-chloro-4-methanesulfonylbenzyl)-2-difluoromethoxy-4-methylquinolin-5-yloxy]acetic Acid A solution of [8-chloro-3-(2-chloro-4-methanesulfonylbenzyl)-2-difluoromethoxy-4-methylquinolin-5-yloxy]acetic acid methyl ester (0.50 g), methanol (10 mL), saturated aqueous lithium hydroxide solution (0.5 mL) and water (1.0 mL) was stirred at 40° C. for 3 hours. The methanol was removed under reduced pressure and the pH of the residue adjusted to 4 by the addition of glacial acetic acid. The resulting precipitate was collected by filtration, washed with water, methanol and diethyl ether, and then dried to afford title compound as a white solid, 0.15 g.

$^1$H NMR (DMSO-d6): δ 2.85 (s, 3H), 3.25 (s, 3H), 4.30 (s, 2H), 4.35 (s, 2H), 6.80 (d, J=8.6 Hz, 1H), 7.00 (d, J=8.4 Hz, 1H), 7.70 (dd, J=1.8, 8.4 Hz, 1H), 7.75 (d, J=8.6 Hz, 1H), 7.85 (t, J=72 Hz, 1H), 8.05 (d, J=1.8 Hz, 1H).

MS: ESI (+ve) (Method A): 520 (M+H)$^+$, Retention time 11.7 min.

MS: ESI (+ve) (Method B): 520 (M+H)$^+$, Retention time 3.9 min.

Example 41

[8-chloro-2,4-diethyl-3-(4-methanesulfonylbenzyl)quinolin-5-yloxy]acetic Acid

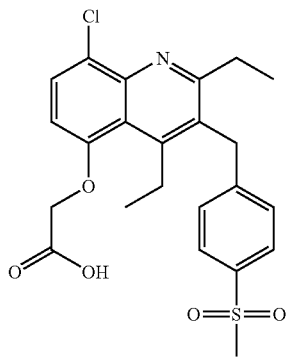

Preparation 41a 4-(4-methanesulfonylbenzyl)heptane-3,5-dione

Sodium hydride (60% in oil, 0.17 g) was added portionwise to a stirred solution of heptane-3,5-dione (0.54 mL) in N,N-dimethylformamide (4.0 mL) at 0-10° C. The resulting mixture was stirred at 0-10° C. for 10 minutes and then a solution of 1-bromomethyl-4-methanesulfonylbenzene (1.2 g) in N,N-dimethylformamide (2.0 mL) was added dropwise. The resulting mixture was stirred at room temperature for 18 hours, diluted with water and extracted with ethyl acetate. The combined extracts were washed with water and saturated aqueous sodium chloride solution and dried over magnesium sulfate. The solvent was removed under reduced pressure and purification of the residue by column chromatography on silica gel, eluting with a mixture of ethyl acetate and cyclohexane (1:4 by volume) gave title compound as a white solid, 0.61 g.

MS: ESI (+ve) (Method B): 297 (M+H)$^+$, Retention time 3.0 and 3.4 min.

Preparation 41b

[8-chloro-2,4-diethyl-3-(4-methanesulfonylbenzyl)quinolin-5-yloxy]acetic Acid Methyl Ester A mixture of (3-amino-4-chlorophenoxy)acetic acid methyl ester (0.35 g), 4-(4-methanesulfonylbenzyl)heptane-3,5-dione (0.49 g) and polyphosphoric acid (5.0 g) was heated at 100° C. for 2 hours. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of dichloromethane and methanol (99.5:0.5 by volume) to afford title compound, 0.20 g.

MS: ESI (+ve) (Method B): 476 (M+H)$^+$, Retention time 4.1 min.

Preparation 41c

[8-chloro-2,4-diethyl-3-(4-methanesulfonylbenzyl)quinolin-5-yloxy]acetic Acid

A mixture of [8-chloro-2,4-diethyl-3-(4-methanesulfonylbenzyl)quinolin-5-yloxy]acetic acid methyl ester (0.20 g), methanol (4.0 mL) and 1.0 M aqueous sodium hydroxide solution (2.0 mL) was stirred at room temperature for 5 hours. The pH of the solution was adjusted to 5 by the addition of formic acid and the solvent removed under reduced pressure. Purification of the residue by preparative reverse-phase HPLC using a gradient of acetonitrile in water (40% to 85% of organic modifier) gave title compound as a pale yellow solid, 0.034 g.

$^1$H NMR (DMSO-d6): δ 1.15 (t, J=7.2 Hz, 3H), 1.25 (t, J=7.2 Hz, 3H), 2.50 (q, J=7.2 Hz, 2H), 2.85 (q, J=7.2 Hz, 2H), 3.15 (s, 3H), 4.45 (s, 2H), 4.85 (s, 2H), 6.95 (d, J=8.7 Hz, 1H), 7.30 (d, J=8.5 Hz, 2H), 7.75 (d, J=8.7 Hz, 1H), 7.85 (d, J=8.5 Hz, 2H).

MS: ESI (+ve) (Method A): 462 (M+H)$^+$, Retention time 10.4 min.

Example 42

8-chloro-3-(4-chlorobenzyl)-2,4-dimethyl-5-(1H-tetrazol-5-yl)quinoline

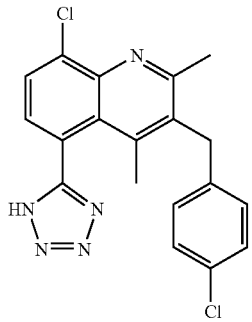

Preparation 42a 8-chloro-3-(4-chlorobenzyl)-2,4-dimethylquinoline-5-carbonitrile A mixture of trifluoromethanesulfonic acid 8-chloro-3-(4-chlorobenzyl)-2,4-dimethyl-quinolin-5-yl ester (0.29 g), zinc cyanide (0.036 g), tetrakis(triphenylphosphine)palladium(0), (0.071 g) in N,N-dimethylformamide (8.0 mL) was heated by microwave irradiation at 125° C. for 10 minutes. The mixture was diluted with water and the resulting precipitate collected by filtration and then purified by column chromatography on silica gel, eluting with a mixture of cyclohexane, dichloromethane and ethyl acetate (1:1:0 to 0:1:0 to 0:20:1 by volume) to afford title compound as a white solid, 0.17 g.

$^1$H NMR (CDCl$_3$): δ 2.75 (s, 3H), 3.00 (s, 3H), 4.30 (s, 2H), 6.90 (m, 2H), 7.25 (m, 2H), 7.80-7.90 (m, 2H).

MS: ESI (+ve) (Method B): 341 (M+H)$^+$, Retention time 4.6 min.

Preparation 42b 8-chloro-3-(4-chlorobenzyl)-2,4-dimethyl-5-(1H-tetrazol-5-yl)quinoline A mixture of 8-chloro-3-(4-chlorobenzyl)-2,4-dimethylquinoline-5-carbonitrile (0.048 g), toluene (1.5 mL), trimethylsilyl azide (0.081 g) and dibutyltin oxide (0.007 g) were sealed in a flask and heated at 100° C. for 66 hours. The mixture was cooled to room temperature and diluted with ethyl acetate. The resulting mixture was washed with saturated aqueous sodium hydrogen carbonate solution and the pH of the aqueous phase was adjusted to 5 by the addition of glacial acetic acid. The resulting precipitate was collected by filtration, washed with diluted aqueous acetic acid solution and dried to afford title compound as a white solid, 0.017 g.

¹H NMR (DMSO-d6): 6.1.75 (s, 3H), 2.65 (s, 3H), 4.25 (s, 2H), 7.00 (d, J=8.7 Hz, 2H), 7.35 (d, J=8.7 Hz, 2H), 7.65 (d, J=7.8 Hz, 1H), 8.05 (d, J=7.8 Hz, 1H).

MS: ESI (+ve) (Method A): 384 (M+H)⁺, Retention time 11.2 min.

MS: ESI (+ve) (Method B): 384 (M+H)⁺, Retention time 3.8 min.

Example 43

[8-chloro-4-difluoromethoxy-2-isopropyl-3-(4-methanesulfonylbenzyl)quinolin-5-yloxy]acetic Acid

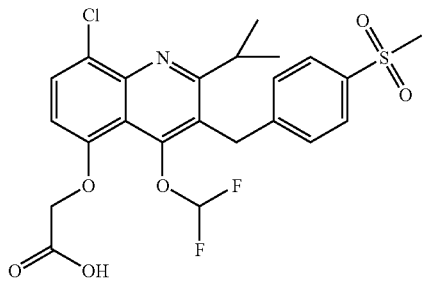

Preparation 43a 2-(4-methanesulfonylbenzyl)-4-methyl-3-oxopentanoic Acid Ethyl Ester A suspension of potassium tert-butoxide (0.54 g) in anhydrous tetrahydrofuran (200 mL) at 0° C. was treated with a mixture of tert-butanol (0.1 mL) and 4-methyl-3-oxopentanoic acid ethyl ester (0.65 mL). After stirring at room temperature for 45 minutes a solution of 1-bromomethyl-4-methanesulfonylbenzene (1.0 g) in tetrahydrofuran (50 mL) was added and the resulting mixture heated at 70° C. for 24 hours. The mixture was cooled to room temperature, diluted with water and the tetrahydrofuran removed under reduced pressure. The residue was extracted with ethyl acetate and the combined extracts dried over magnesium sulfate and then the solvent removed under reduced pressure to afford title compound, 1.4 g.

MS: ESI (+ve) (Method B): 327 (M+H)⁺, Retention time 3.3 min.

Preparation 43b

[8-chloro-2-isopropyl-3-(4-methanesulfonylbenzyl)-4-oxo-1,4-dihydroquinolin-5-yloxy]acetic Acid Methyl Ester A mixture of (3-amino-4-chlorophenoxy)acetic acid methyl ester (0.70 g), 2-(4-methanesulfonylbenzyl)-4-methyl-3-oxopentanoic acid ethyl ester (1.4 g), polyphosphoric acid (3.5 g) and dioxane (50 mL) was heated at 120° C. for 2 days. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of ethyl acetate and cyclohexane (1:1 by volume) to afford title compound. 0.79 g.

MS: ESI (+ve) (Method B): 478 (M+H)⁺, Retention time 3.4 min.

Preparation 43c

[8-chloro-4-difluoromethoxy-2-isopropyl-3-(4-methanesulfonylbenzyl)quinolin-5-yloxy]acetic Acid Methyl Ester The title compound was prepared by the method of Preparation 34e using [8-chloro-2-isopropyl-3-(4-methanesulfonylbenzyl)-4-oxo-1,4-dihydroquinolin-5-yloxy]acetic acid methyl ester.

¹H NMR (CDCl₃): δ 1.25 (d, J=6.7 Hz, 6H), 3.00 (s, 3H), 3.20 (m, 1H), 3.80 (s, 3H), 4.50 (s, 2H), 4.85 (s, 2H), 6.70 (d, J=8.5 Hz, 1H), 6.95 (t, J=75 Hz, 1H), 7.25 (d, J=8.5 Hz, 2H), 7.70 (d, J=8.5 Hz, 1H), 7.85 (d, J=8.5 Hz, 2H).

MS: ESI (+ve) (Method B): 528 (M+H)⁺, Retention 4.2 min.

Preparation 43d

[8-chloro-4-difluoromethoxy-2-isopropyl-3-(4-methanesulfonylbenzyl)quinolin-5-yloxy]acetic Acid A mixture of [8-chloro-4-difluoromethoxy-2-isopropyl-3-(4-methanesulfonylbenzyl)quinolin-5-yloxy]acetic acid methyl ester (0.040 g), tetrahydrofuran (3.0 mL) and 1.0 M aqueous lithium hydroxide solution (0.10 mL) was stirred at room temperature for 1 hour. The solvent was removed under reduced pressure and the residue diluted with water and then the pH adjusted to 5 by the addition of sodium dihydrogenphosphate. The mixture was extracted with ethyl acetate and the combined extracts dried over magnesium sulfate and then the solvent removed under reduced pressure to afford title compound, 0.025 g.

¹H NMR (DMSO-d6): δ 1.15 (d, J=6.4 Hz, 6H), 2.50 (m, 1H), 3.15 (s, 3H), 4.50 (s, 2H), 4.80 (s, 2H), 7.00 (d, J=8.7 Hz, 1H), 7.35 (d, J=8.2 Hz, 2H), 7.50 (t, J=75 Hz, 1H), 7.80-7.85 (m, 3H).

MS: ESI (+ve) (Method A): 514 (M+H)⁺, Retention time 11.7 min.

Example 44

[8-chloro-2-cyano-3-(4-methanesulfonylbenzyl)-4-methylquinolin-5-yloxy]acetic Acid

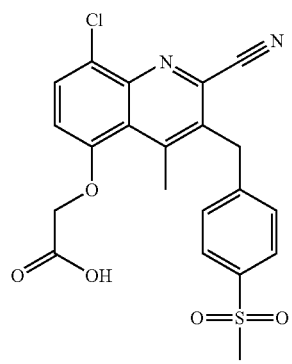

Preparation 44a

[8-chloro-3-(4-methanesulfonylbenzyl)-4-methyl-2-trifluoromethanesulfonyloxyquinolin-5-yloxy]acetic Acid Methyl Ester A mixture of [8-chloro-3-(4-methanesulfonylbenzyl)-4-methyl-2-oxo-1,2-dihydroquinolin-5-yloxy]acetic acid methyl ester (0.22 g), N-phenyltrifluoromethanesulfonimide (0.35 g), potassium carbonate (0.090 g) and N,N-dimethylformamide (5.0 mL) was stirred at room temperature for 17 hours. The mixture was partitioned between dichloromethane and water and the aqueous phase extracted with dichloromethane. The combined organic phases were washed with water, dried over sodium sulfate and the solvent removed under reduced pressure. Purification of the residue by column chromatography on silica gel, eluting with dichloromethane gave title compound, 0.080 g.

MS: ESI (+ve) (Method B): 582 (M+H)$^+$, Retention time 4.1 min.

Preparation 44b

[8-chloro-2-cyano-3-(4-methanesulfonylbenzyl)-4-methylquinolin-5-yloxy]acetic Acid Methyl Ester A mixture of [8-chloro-3-(4-methanesulfonylbenzyl)-4-methyl-2-trifluoromethanesulfonyloxyquinolin-5-yloxy]acetic acid methyl ester, (0.080 g), zinc cyanide (0.010 g), tetrakis(triphenylphosphine)palladium(0) (0.030 g), and lithium chloride (0.001 g) in N,N-dimethylformamide (8.0 mL) was heated by microwave irradiation at 120° C. for 15 minutes. The mixture was diluted with water and the resulting precipitate collected by filtration, washed with water and diethyl ether and then dried to afford title compound, 0.056 g.

MS: ESI (+ve) (Method B): 459 (M+H)$^+$, Retention time 3.7 min.

Preparation 44c

[8-chloro-2-cyano-3-(4-methanesulfonylbenzyl)-4-methylquinolin-5-yloxy]acetic Acid A mixture of [8-chloro-2-cyano-3-(4-methanesulfonylbenzyl)-4-methylquinolin-5-yloxy]acetic acid methyl ester (0.056 g), methanol (1.5 mL), tetrahydrofuran (1.5 mL), water (2.0 mL) and lithium hydroxide (0.60 g) was stirred at room temperature for 1 hour. The mixture was partitioned between ethyl acetate and 1.0 M aqueous hydrochloric acid. The aqueous phase was extracted with ethyl acetate and the combined organic phases were dried over sodium sulfate and the solvent removed under reduced pressure. Purification of the residue by preparative reverse-phase HPLC using a gradient over 30 minutes of acetonitrile in water gave title compound as a white solid, 0.015 g.

$^1$H NMR (DMSO-d6): δ2.90 (s, 3H), 3.20 (s, 3H), 4.60 (s, 2H), 4.90 (s, 2H), 7.20 (d, J=8.5 Hz, 1H), 7.40 (d, J=8.5 Hz, 2H), 7.85 (d, J=8.5 Hz, 2H), 8.00 (d, J=8.5 Hz, 1H).

MS: ESI (+ve) (Method A): 445 (M+H)$^+$, Retention time 9.8 min.

MS: ESI (+ve) (Method B): 445 (M+H)$^+$, Retention time 3.3 min.

Example 45

[4-difluoromethoxy-2-ethyl-8-fluoro-3-(4-methanesulfonylbenzyl)-quinolin-5-yloxy]acetic Acid

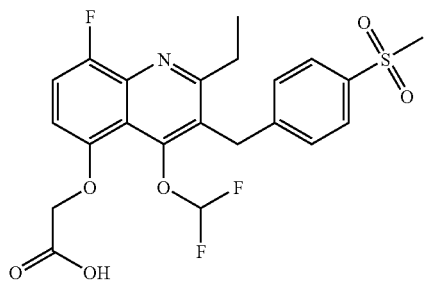

Preparation 45a 2-(4-methanesulfonylbenzyl)-3-oxopentanoic Acid Methyl Ester

A suspension of potassium tert-butoxide (2.7 g) in anhydrous tetrahydrofuran (35 mL) at 0° C. was treated with a mixture of tert-butanol (0.1 mL) and 3-oxopentanoic acid methyl ester (3.2 g). After stirring at room temperature for 15 minutes a solution of 1-chloromethyl-4-methanesulfonylbenzene (5.0 g) in tetrahydrofuran (15 mL) was added and the resulting mixture heated at 70° C. for 16 hours. The mixture was cooled to room temperature, diluted with water and the tetrahydrofuran removed under reduced pressure. The residue was partitioned between ethyl acetate and dilute aqueous ammonium chloride solution. The aqueous phase was extracted with ethyl acetate and the combined organic phases dried over magnesium sulfate. The solvent was removed under reduced pressure and the residue purified by column chromatography on silica gel, eluting with a mixture of toluene, dichloromethane and ethyl acetate (1:1:0 to 0:1:0 to 0:4:1 by volume) to afford title compound as a waxy white solid, 3.0 g.

MS: ESI (+ve) (Method B): 299 (M+H)$^+$, Retention time 3.0 min.

Preparation 45b

[2-ethyl-8-fluoro-3-(4-methanesulfonylbenzyl)-4-oxo-1,4-dihydroquinolin-5-yloxy]acetic Acid Methyl Ester A mixture of (3-amino-4-fluorophenoxy)acetic acid methyl ester (1.0 g), 2-(4-methanesulfonylbenzyl)-3-oxopentanoic acid methyl ester (1.4 g), polyphosphoric acid (5 mL) and dioxane (20 mL) was heated at 130° C. for 17 hours. The mixture was cooled to room temperature, diluted with water and the pH adjusted to 4 by the addition of sodium acetate. The mixture was extracted with ethyl acetate and the combined extracts dried over magnesium sulfate. The solvent was removed under reduced pressure to afford title compound as a honey coloured gum, 2.3 g.

MS: ESI (+ve) (Method B): 448 (M+H)$^+$, Retention time 2.6 min.

Preparation 45c

[4-difluoromethoxy-2-ethyl-8-fluoro-3-(4-methanesulfonylbenzyl)quinolin-5-yloxy]acetic Acid Methyl Ester The title compound was prepared by the method of Preparation 34e using [2-ethyl-8-fluoro-3-(4-methanesulfonylbenzyl)-4-oxo-1,4-dihydroquinolin-5-yloxy]acetic acid methyl ester.
MS: ESI (+ve) (Method B): 498 (M+H)$^+$, Retention time 3.6 min.

Preparation 45d

[4-difluoromethoxy-2-ethyl-8-fluoro-3-(4-methanesulfonylbenzyl)quinolin-5-yloxy]acetic Acid A mixture of [4-difluoromethoxy-2-ethyl-8-fluoro-3-(4-methanesulfonylbenzyl)quinolin-5-yloxy]acetic acid methyl ester (0.82 g), methanol (33 mL), 5.0 M aqueous lithium hydroxide solution (0.7 mL) and water (1.4 mL) was stirred at room temperature for 35 minutes. The pH of the mixture was adjusted to 4 by the addition of glacial acetic acid and the solvent removed under reduced pressure. The residue was diluted with water (4.0 mL) and the solid collected by filtration, washed with water and dried to afford to title compound as a pale cream solid, 0.60 g.
$^1$H NMR (DMSO-d6): δ 1.20 (t, J=7.3 Hz, 3H), 2.80 (q, J=7.3 Hz, 2H), 3.15 (s, 3H), 4.40 (s, 2H), 4.45 (s, 2H), 6.80 (dd, J=3.6, 8.9 Hz, 1H), 7.35 (d, J=8.2 Hz, 2H), 7.45 (dd, J=8.9, 10.2 Hz, 1H), 7.85 (d, J=8.2 Hz, 2H), 8.20 (t, J=75 Hz, 1H).
MS: ESI (+ve) (Method A): 484 (M+H)$^+$, Retention time 9.6 min.
MS: ESI (+ve) (Method B): 484 (M+H)$^+$, Retention time 3.2 min.

Example 46

[3-(2-chloro-4-methanesulfonylbenzyl)-2-difluoromethoxy-8-fluoro-4-methylquinolin-5-yloxy]acetic acid

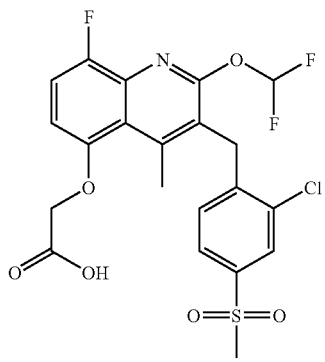

Preparation 46a 2-(2-chloro-4-methanesulfonylbenzyl)-3-oxothiobutyric acid S-tert-butyl Ester The title compound was prepared by the method of Preparation 34a using 1-bromomethyl-2-chloro-4-methanesulfonylbenzene and 3-oxothiobutyric acid S-tert-butyl ester
MS: ESI (+ve) (Method B): 377 (M+H)$^+$, Retention time 3.8 min.

Preparation 46b 2-(2-chloro-4-methanesulfonylbenzyl)-N-(2-fluoro-5-hydroxyphenyl)-3-oxobutyramide The title compound was prepared by the method of Preparation 34b using 3-amino-4-fluorophenol and 2-(2-chloro-4-methanesulfonylbenzyl)-3-oxothiobutyric acid S-tert-butyl ester.
$^1$H NMR (CD$_3$OD): δ 2.30 (s, 3H), 3.10 (s, 3H), 3.50 (m, 1H), 4.15 (m, 1H), 6.55 (m, 1H), 6.90 (dd, J=8.9, 10.5 Hz, 1H), 7.20 (m, 1H), 7.55 (d, J=8.0 Hz, 1H), 7.80 (dd, J=1.9, 8.0 Hz, 1H), 8.00 (d, J=1.9 Hz, 1H).
MS: ESI (+ve) (Method B): 378 (M+H)$^+$, Retention time 2.8 min.

Preparation 46c 3-(2-chloro-4-methanesulfonylbenzyl)-8-fluoro-5-hydroxy-4-methyl-1H-quinolin-2-one The title compound was prepared by the method of Preparation 34c using 2-(2-chloro-4-methanesulfonylbenzyl)-N-(2-fluoro-5-hydroxyphenyl)-3-oxobutyramide.
$^1$H NMR (DMSO-d6): δ 2.55 (s, 3H), 3.25 (s, 3H), 4.10 (s, 2H), 6.55 (dd, J=4.4, 8.9 Hz, 1H), 7.10-7.20 (m, 2H), 7.75 (dd, J=1.9, 8.1 Hz, 1H), 8.00 (d, J=1.9 Hz, 1H), 11.35 (br s, 1H).
MS: ESI (+ve) (Method B): 396 (M+H)$^+$, Retention time 3.0 min.

Preparation 46d

[3-(2-chloro-4-methanesulfonylbenzyl)-8-fluoro-4-methyl-2-oxo-1,2-dihydroquinolin-5-yloxy]acetic Acid Methyl Ester The title compound was prepared by the method of Preparation 34d using 3-(2-chloro-4-methanesulfonylbenzyl)-8-fluoro-5-hydroxy-4-methyl-1H-quinolin-2-one.
MS: ESI (+ve) (Method B): 468 (M+H)$^+$, Retention time 3.2 min.

Preparation 46e

[3-(2-chloro-4-methanesulfonylbenzyl)-2-difluoromethoxy-8-fluoro-4-methylquinolin-5-yloxy]acetic Acid Methyl Ester The title compound was prepared by the method of Preparation 34e using [3-(2-chloro-4-methanesulfonylbenzyl)-8-fluoro-4-methyl-2-oxo-1,2-dihydroquinolin-5-yloxy]acetic acid methyl ester.
$^1$H NMR (DMSO-d6): δ 2.80 (s, 3H), 3.25 (s, 3H), 3.70 (s, 3H), 4.35 (s, 2H), 5.00 (s, 2H), 7.00 (m, 2H), 7.55 (m, 1H), 7.75 (dd, J=1.8, 8.2 Hz, 1H), 7.80 (t, J=72 Hz, 1H), 8.10 (d, J=1.8 Hz, 1H).
MS: ESI (+ve) (Method B): 518 (M+H)$^+$, Retention time 4.1 min.

Preparation 46f

[3-(2-chloro-4-methanesulfonylbenzyl)-2-difluoromethoxy-8-fluoro-4-methylquinolin-5-yloxy]acetic Acid A solution of [3-(2-chloro-4-methanesulfonylbenzyl)-2-difluoromethoxy-8-fluoro-4-methylquinolin-5-yloxy]acetic acid methyl ester (0.22 g), methanol (8.0 mL), 5.0 M aqueous lithium hydroxide solution (0.4 mL) and water (0.8 mL) was stirred at room temperature for 2 hours. The pH of the solution was adjusted to 4 by the addition of glacial acetic acid and the solvent removed under reduced pressure. The residue was diluted with water (4.0 mL) and the solid collected by filtration, washed with water and methanol and dried to afford to title compound as a white solid, 0.17 g.

$^1$H NMR (DMSO-d6): δ 2.85 (s, 3H), 3.25 (s, 3H), 4.25 (s, 2H), 4.30 (s, 2H), 6.75 (dd, J=4.1, 9.0 Hz, 1H), 7.00 (d, J=8.2 Hz, 1H), 7.45 (dd, J=9.0, 9.9 Hz, 1H), 7.75 (dd, J=1.9, 8.2 Hz, 1H), 7.80 (t, J=72 Hz, 1H), 8.05 (d, J=1.9 Hz, 1H).

MS: ESI (+ve) (Method A): 504 (M+H)$^+$, Retention time 11.3 min.

MS: ESI (+ve) (Method B): 504 (M+H)$^+$, Retention time 3.7 min.

Example 47

[3-(2-chloro-4-methanesulfonylbenzyl)-4-difluoromethoxy-2-ethyl-8-fluoroquinolin-5-yloxy]acetic acid

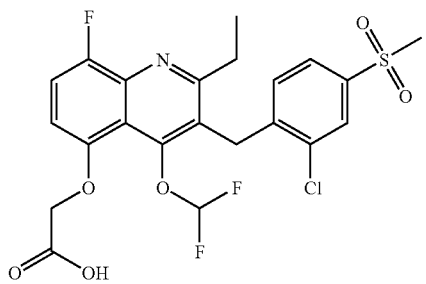

Preparation 47a 3-(2-chloro-4-methanesulfonylbenzyl)-2-ethyl-8-fluoro-5-hydroxy-1H-quinolin-4-one A suspension of potassium tert-butoxide (1.2 g) in anhydrous tetrahydrofuran (200 mL) at 0° C. was treated with a mixture of tert-butanol (1.0 mL) and 3-oxopentanoic acid methyl ester (1.2 g). After stirring at room temperature for 45 minutes a solution of 1-bromomethyl-2-chloro-4-methanesulfonylbenzene (2.5 g) in tetrahydrofuran (50 mL) was added and the resulting mixture stirred at room temperature for 3 days. The mixture was diluted with water and the tetrahydrofuran removed under reduced pressure. The residue was extracted with ethyl acetate and the combined extracts dried over magnesium sulfate. The solvent was removed under reduced pressure and the residue purified by column chromatography on silica gel, eluting with a mixture of cyclohexane, diethyl ether, ethyl acetate and dichloromethane (1:1:0:0 to 0:0:1:9 by volume) to afford title compound, 3.0 g.

MS: ESI (+ve) (Method B): 333 (M+H)$^+$, Retention time 3.2 min.

Preparation 47b

[3-(2-chloro-4-methanesulfonylbenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (1.0 g), 2-(2-chloro-4-methanesulfonylbenzyl)-3-oxopentanoic acid methyl ester (2.1 g), polyphosphoric acid (10 g) and dioxane (10 mL) was heated at 130° C. for 18 hours. The mixture was cooled to room temperature, diluted with water and extracted with ethyl acetate. The combined extracts were washed with saturated aqueous sodium chloride solution and dried over magnesium sulfate. The solvent was removed under reduced pressure and the residue purified by column chromatography on silica gel, eluting with a mixture of dichloromethane and methanol (19:1 by volume) to afford title compound, 1.6 g.

MS: ESI (+ve) (Method B): 482 (M+H)$^+$, Retention time 3.0 min.

Preparation 47c

[3-(2-chloro-4-methanesulfonylbenzyl)-4-difluoromethoxy-2-ethyl-8-fluoroquinolin-5-yloxy]acetic Acid Methyl Ester The title compound was prepared by the method of Preparation 34e using [3-(2-chloro-4-methanesulfonylbenzyl)-2-ethyl-8-fluoro-4-oxo-1,4-dihydroquinolin-5-yloxy]acetic acid methyl ester.

$^1$H NMR (DMSO-d6): δ1.25 (t, J=7.4 Hz, 3H), 2.80 (q, J=7.4 Hz, 2H), 3.30 (s, 3H), 3.75 (s, 3H), 4.45 (s, 2H), 5.00 (s, 2H), 6.90 (d, J=8.2 Hz, 1H), 7.05 (dd, J=3.7, 8.8 Hz, 1H), 7.20 (t, J=75 Hz, 1H), 7.55 (dd, J=8.8, 10.1 Hz, 1H), 7.70 (dd, 1.9, 8.2 Hz, 1H), 8.05 (d, J=1.9 Hz, 1H).

MS: ESI (+ve) (Method B): 532 (M+H)$^+$, Retention time 3.9 min.

Preparation 47d

[3-(2-chloro-4-methanesulfonylbenzyl)-4-difluoromethoxy-2-ethyl-8-fluoroquinolin-5-yloxy]acetic Acid A mixture of [3-(2-chloro-4-methanesulfonylbenzyl)-4-difluoromethoxy-2-ethyl-8-fluoroquinolin-5-yloxy]acetic acid methyl ester (1.0 g), methanol (38 mL), 5.0 M aqueous lithium hydroxide solution (0.8 mL) and water (1.6 mL) was stirred at room temperature for 35 minutes. The pH of the mixture was adjusted to 4 by the addition of glacial acetic acid and the solvent removed under reduced pressure. The residue was diluted with water (4.0 mL) and the solid collected by filtration, washed with water and dried to afford to title compound as a cream solid, 0.66 g.

$^1$H NMR (DMSO-d6): δ 1.25 (t, J=7.6 Hz, 3H), 2.80 (q, J=7.6 Hz, 2H), 3.25 (s, 3H), 4.40 (s, 2H), 4.45 (s, 2H), 6.85 (dd, J=3.7, 8.9 Hz, 1H), 6.90 (d, J=8.1 Hz, 1H), 7.50 (dd, J=8.9, 10.3 Hz, 1H), 7.70 (dd, J=1.9, 8.1 Hz, 1H), 8.00 (d, J=1.9 Hz, 1H), 8.05 (t, J=75 Hz, 1H).

MS: ESI (+ve) (Method A): 518 (M+H)$^+$, Retention time 10.6 min.

MS: ESI (+ve) (Method B): 518 (M+H)+, Retention time 3.5 min.

Example 48

[2-difluoromethoxy-8-fluoro-3-(4-methanesulfonyl-benzyl)-4-methylquinolin-5-yloxy]acetic acid

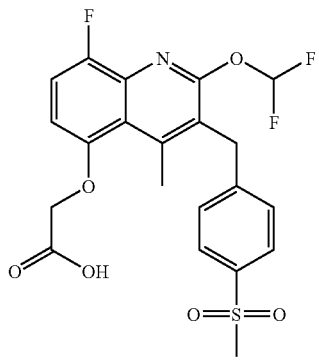

Preparation 48a

N-(2-fluoro-5-hydroxyphenyl)-2-(4-methanesulfonylbenzyl)-3-oxobutyramide

The title compound was prepared by the method of Preparation 34b using 3-amino-4-fluorophenol and 2-(4-methanesulfonylbenzyl)-3-oxothiobutyric acid S-tert-butyl ester.
MS: ESI (+ve) (Method B): 380 (M+H)+, Retention time 2.5 min.

Preparation 48b 8-fluoro-5-hydroxy-3-(4-methanesulfonylbenzyl)-4-methyl-1H-quinolin-2-one The title compound was prepared by the method of Preparation 36c using N-(2-fluoro-5-hydroxyphenyl)-2-(4-methanesulfonylbenzyl)-3-oxobutyramide.
$^1$H NMR (DMSO-d6): δ 2.60 (s, 3H), 3.20 (s, 3H), 4.15 (s, 2H), 6.55 (J=4.3, 8.8 Hz, 1H), 7.20 (dd, J=8.8, 10.1 Hz, 1H), 7.45 (d, J=8.4 Hz, 2H), 7.80 (d, J=8.4 Hz, 2H), 10.15 (s, 1H), 11.45 (s, 1H).
MS: ESI (+ve) (Method B): 362 (M+H)+, Retention time 2.6 min.

Preparation 48c

[8-fluoro-3-(4-methanesulfonylbenzyl)-4-methyl-2-oxo-1,2-dihydroquinolin-5-yloxy]acetic Acid Methyl Ester The title compound was prepared by the method of Preparation 34d using 8-fluoro-5-hydroxy-3-(4-methanesulfonylbenzyl)-4-methyl-1H-quinolin-2-one.
$^1$H NMR (DMSO-d6): δ 2.65 (s, 3H), 3.15 (s, 3H), 3.70 (s, 3H), 4.20 (s, 2H), 4.90 (s, 2H), 6.70 (dd, J=4.1, 9.1 Hz, 1H), 7.30 (m, 1H), 7.45 (d, J=8.3 Hz, 2H), 7.80 (d, J=8.3 Hz, 2H), 11.65 (s, 1H).
MS: ESI (+ve) (Method B): 434 (M+H)+, Retention time 2.9 min.

Preparation 48d

[2-difluoromethoxy-8-fluoro-3-(4-methanesulfonyl-benzyl)-4-methylquinolin-5-yloxy]acetic Acid Methyl Ester The title compound was prepared by the method of Preparation 34e using [8-fluoro-3-(4-methanesulfonylbenzyl)-4-methyl-2-oxo-1,2-dihydroquinolin-5-yloxy]acetic acid methyl ester.
$^1$H NMR (DMSO-d6): δ 2.90 (s, 3H), 3.20 (s, 3H), 3.70 (s, 3H), 4.35 (s, 2H), 5.00 (s, 2H), 6.95 (dd, J=4.0, 8.9 Hz, 1H), 7.40 (d, J=8.4 Hz, 2H), 7.50 (dd, J=8.9, 9.8 Hz, 1H), 7.65-8.05 (m, 3H).
MS: ESI (+ve) (Method B): 484 (M+H)+, Retention time 3.8 min.

Preparation 48e

[2-difluoromethoxy-8-fluoro-3-(4-methanesulfonyl-benzyl)-4-methylquinolin-5-yloxy]acetic Acid A mixture of [2-difluoromethoxy-8-fluoro-3-(4-methanesulfonylbenzyl)-4-methylquinolin-5-yloxy]acetic acid methyl ester (0.57 g), methanol (24 mL), 5.0 M aqueous lithium hydroxide solution (0.5 mL) and water (1.0 mL) was stirred at room temperature for 90 minutes. The pH of the mixture was adjusted to 4 by the addition of glacial acetic acid and the solvent removed under reduced pressure. The residue was diluted with water and the solid collected by filtration, washed with water and dried to afford to title compound as a white solid, 0.53 g.
$^1$H NMR (DMSO-d6): δ 2.90 (s, 3H), 3.15 (s, 3H), 4.25 (s, 2H), 4.35 (s, 2H), 6.75 (dd, J=4.1, 9.1 Hz, 1H), 7.35-7.45 (m, 3H), 7.80 (d, J=8.1 Hz, 2H), 7.85 (t, J=72 Hz, 1H).
MS: ESI (+ve) (Method A): 470 (M+H)+, Retention time 10.4 min.
MS: ESI (+ve) (Method B): 470 (M+H)+, Retention time 3.5 min.

Example 49

[3-(4-chlorobenzyl)-4-difluoromethoxy-2-ethyl-8-fluoroquinolin-5-yloxy]acetic Acid

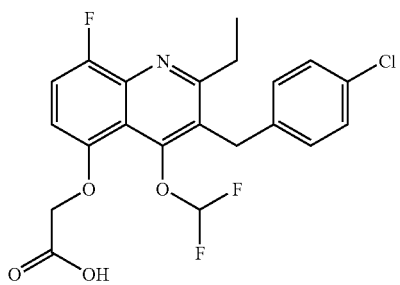

Preparation 49a 2-(4-chlorobenzyl)-3-oxopentanoic Acid Ethyl Ester

A suspension of potassium tert-butoxide (7.8 g) in anhydrous tetrahydrofuran (140 mL) at 0° C. was treated with a mixture of tert-butanol (0.3 mL) and 3-oxopentanoic acid ethyl ester (10 g). After stirring at room temperature for 30 minutes a solution of 1-bromomethyl-4-chlorobenzene (14 g) in tetrahydrofuran (20 mL) was added and the resulting mixture stirred at room temperature for 6 days. The mixture was diluted with water, extracted with ethyl acetate and the combined extracts washed with water and saturated aqueous sodium chloride solution and then dried over magnesium sulfate. The solvent was removed under reduced pressure and the residue purified by column chromatography on silica gel, eluting with a mixture of pentane and ethyl acetate (1:0 to 10:1 by volume) to afford title compound as a yellow oil, 9.3 g.

Preparation 49b

[3-(4-chlorobenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (1.9 g), 2-(4-chlorobenzyl)-3-oxopentanoic acid ethyl ester (0.95 g) and polyphosphoric acid (10 mL) was heated at 120° C. for 5 hours. The mixture was diluted with water, extracted with ethyl acetate and the combined extracts washed with saturated aqueous sodium chloride solution and saturated aqueous sodium hydrogen carbonate solution and then dried over magnesium sulfate. The solvent was removed under reduced pressure and the residue purified by column chromatography on silica gel, eluting with a mixture of dichloromethane and ethyl acetate (1:0 to 10:1 by volume) to afford title compound as a brown solid, 0.10 g.

MS: ESI (+ve) (Method B): 404 (M+H)$^+$, Retention time 3.3 min.

Preparation 49c

[3-(4-chlorobenzyl)-4-difluoromethoxy-2-ethyl-8-fluoroquinolin-5-yloxy]acetic Acid Methyl Ester The title compound was prepared by the method of Preparation 34e using [3-(4-chlorobenzyl)-2-ethyl-8-fluoro-4-oxo-1,4-dihydroquinolin-5-yloxy]acetic acid methyl ester.

MS: ESI (+ve) (Method B): 454 (M+H)$^+$, Retention time 4.4 min.

Preparation 49d

[3-(4-chlorobenzyl)-4-difluoromethoxy-2-ethyl-8-fluoroquinolin-5-yloxy]acetic Acid A solution of [3-(4-chlorobenzyl)-4-difluoromethoxy-2-ethyl-8-fluoroquinolin-5-yloxy]acetic acid methyl ester (0.11 g), methanol (10 mL), and 5.0 M aqueous sodium hydroxide solution (1.0 mL) was stirred at room temperature for 30 minutes. The pH of the solution was adjusted to 5 by the addition of glacial acetic acid. The solvent was removed under reduced pressured and the residue purified by preparative reverse-phase HPLC using a gradient over 30 minutes of acetonitrile in water (40% to 95% of organic modifier) to afford title compound as a white solid, 0.040 g.

$^1$H NMR (DMSO-d6): δ 1.15 (t, J=7.3 Hz, 3H), 2.80 (q, J=7.3 Hz, 2H), 4.30 (s, 2H), 4.40 (s, 2H), 6.80 (dd, J=3.8, 8.9 Hz, 1H), 7.10 (d, J=8.4 Hz, 2H), 7.35 (d, J=8.4 Hz, 2H), 7.45 (dd, J=8.9, 10.4 Hz, 1H), 8.20 (t, J=75 Hz, 1H).

MS: ESI (+ve) (Method A): 440 (M+H)$^+$, Retention time 12.3 min.

MS: ESI (+ve) (Method B): 440 (M+H)$^+$, Retention time 4.1 min.

Example 50

[4-difluoromethoxy-2-ethyl-8-fluoro-3-(4-fluorobenzyl)quinolin-5-yloxy]acetic Acid

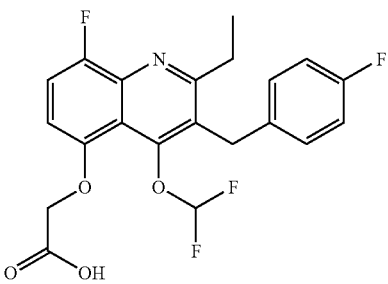

Preparation 50a 2-(4-fluorobenzyl)-3-oxopentanoic Acid Methyl Ester

3-Oxopentanoic acid methyl ester (7.5 g) was added to a stirred suspension of sodium hydride (60% in oil, 4.6 g) in N,N-dimethylformamide (20 mL) and tetrahydrofuran (80 mL) at 0° C. and the resulting mixture stirred at 0° C. for 30 minutes. A solution of 1-bromomethyl-4-fluorobenzene (7.0 mL) in tetrahydrofuran was added and the resulting mixture warmed to room temperature and then stirred at this temperature for 17 hours. The mixture was partitioned between ethyl acetate and water and the aqueous phase extracted with ethyl acetate. The combined organic phases were dried over sodium sulfate and the solvent removed under reduced pressure. The residue was purified by column chromatography on silica gel, eluting with a mixture of cyclohexane and ethyl acetate (19:1 by volume) to afford title compound, 1.0 g.

Preparation 50b

[2-ethyl-8-fluoro-3-(4-fluorobenzyl)-4-oxo-1,4-dihydroquinolin-5-yloxy]acetic Acid Methyl Ester A mixture of (3-amino-4-fluorophenoxy)acetic acid methyl ester (0.80 g), 2-(4-fluorobenzyl)-3-oxopentanoic acid methyl ester (1.0 g), polyphosphoric acid (10 g) and dioxane (10 mL) was heated at 130° C. for 17 hours. The mixture was cooled to room temperature and partitioned between ethyl acetate and water. The aqueous phase was extracted with ethyl acetate and the combined organic phases washed with saturated aqueous sodium chloride solution and dried over magnesium sulfate. The solvent was removed under reduced pressure to afford title compound, 1.5 g.

MS: ESI (+ve) (Method B): 488 (M+H)$^+$, Retention time 3.1 min.

Preparation 50c

[4-difluoromethoxy-2-ethyl-8-fluoro-3-(4-fluorobenzyl)quinolin-5-yloxy]acetic Acid Methyl Ester A mixture of [2-ethyl-8-fluoro-3-(4-fluorobenzyl)-4-oxo-1,4-dihydroquinolin-5-yloxy]acetic acid methyl ester (1.5 g), N/N-dimethylformamide (30 mL), potassium carbonate (5.2 g) and acetic acid chlorodifluoromethyl ester (5.5 mL) was stirred at 70° C. for 4 days. The mixture was diluted with water and extracted with ethyl acetate. The combined extracts were dried over sodium sulfate and the solvent removed under reduced pressure. The residue was purified by column chromatography on silica gel, eluting with a mixture of cyclohexane and ethyl acetate (3:1 by volume) to afford title compounds, 0.50 g.

$^1$H NMR (CDCl$_3$): δ 1.25 (t, J=7.5 Hz, 3H), 2.90 (q, J=7.5 Hz, 2H), 3.85 (s, 3H), 4.35 (s, 2H), 4.80 (s, 2H), 6.70 (dd, J=3.7, 8.7 Hz, 1H), 6.90-7.00 (m, 2H), 7.00-7.10 (m, 2H), 7.20-7.30 (m, 2H).

MS: ESI (+ve) (Method B): 438 (M+H)$^+$, Retention time 4.2 min.

Preparation 50d

[4-difluoromethoxy-2-ethyl-8-fluoro-3-(4-fluorobenzyl)quinolin-5-yloxy]acetic Acid A mixture of [4-difluoromethoxy-2-ethyl-8-fluoro-3-(4-fluorobenzyl)quinolin-5-yloxy]acetic acid methyl ester (050 g), methanol (10 mL); tetrahydrofuran (10 mL), water (8 mL) and lithium hydroxide (0.050 g) was stirred at room temperature for 30 minutes. The mixture was partitioned between ethyl acetate and 1.0 M aqueous hydrochloric acid and the aqueous phase was extracted with ethyl acetate. The combined extracts were dried over magnesium sulfate and the solvent removed under reduced pressure. Purification of the residue by preparative reverse-phase HPLC using a gradient over 30 minutes of acetonitrile in water, followed by washing with diethyl ether gave title compound as a white solid, 0.090 g.

$^1$H NMR (DMSO-d6): δ 1.16 (t, J=7.3 Hz, 3H), 2.80 (q, J=7.3 Hz, 2H), 4.35 (s, 2H), 4.90 (s, 2H), 7.00 (dd, J=3.7, 8.7 Hz, 1H), 7.05-7.15 (m, 4H), 7.30 (t, J=75 Hz, 1H), 7.50 (dd, J=8.8, 10.1 Hz, 1H).

MS: ESI (+ve) (Method A): 424 (M+H)$^+$, Retention time 11.5 min.

Example 51

[3-(2,4-dichlorobenzyl)-2-difluoromethoxy-8-fluoro-4-methylquinolin-5-yloxy]acetic Acid

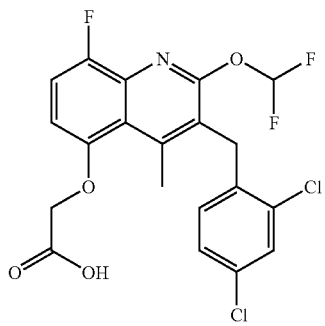

Preparation 51a 2-(2,4-dichlorobenzyl)-N-(2-fluoro-5-hydroxyphenyl)-3-oxobutyramide A mixture of 2-(2,4-dichlorobenzyl)-3-oxobutyric acid ethyl ester (4.6 g) and 3-amino-4-fluorophenol (1.0 g) was heated by microwave irradiation at 120° C. for 20 minutes. The mixture was purified by column chromatography on silica gel, eluting with a mixture of ethyl acetate and pentane (1:19 to 1:1 by volume) to afford title compound, 0.67 g.

Preparation 51b 3-(2,4-dichlorobenzyl)-8-fluoro-5-hydroxy-4-methyl-1H-quinolin-2-one The title compound was prepared by the method of Preparation 34c using 2-(2,4-dichlorobenzyl)-N-(2-fluoro-5-hydroxyphenyl)-3-oxobutyramide.

MS: ESI (+ve) (Method B): 352 (M+H)$^+$, Retention time 3.6 min.

Preparation 51c

[3-(2,4-dichlorobenzyl)-8-fluoro-4-methyl-2-oxo-1,2-dihydro-quinolin-5-yloxy]acetic Acid Methyl Ester The title compound was prepared by the method of Preparation 34d using 3-(2,4-dichlorobenzyl)-8-fluoro-5-hydroxy-4-methyl-1H-quinolin-2-one.

MS: ESI (+ve) (Method B): 424 (M+H)$^+$, Retention time 3.9 min.

Preparation 51d

[3-(2,4-dichlorobenzyl)-2-difluoromethoxy-8-fluoro-4-methylquinolin-5-yloxy]acetic Acid Methyl Ester The title compound was prepared by the method of Preparation 34e using [3-(2,4-dichlorobenzyl)-8-fluoro-4-methyl-2-oxo-1,2-dihydro-quinolin-5-yloxy]acetic acid methyl ester.

MS: ESI (+ve) (Method B): 474 (M+H)$^+$, Retention time 4.8 min.

Preparation 51e

[3-(2,4-dichlorobenzyl)-2-difluoromethoxy-8-fluoro-4-methylquinolin-5-yloxy]acetic Acid A solution of [3-(2,4-dichlorobenzyl)-2-difluoromethoxy-8-fluoro-4-methylquinolin-5-yloxy]acetic acid methyl ester (0.071 g), methanol (10 mL), and 5.0 M aqueous sodium hydroxide solution (0.15 mL) was stirred at room temperature for 1 hour. The solvent was removed under reduced pressure and the pH of the residue adjusted to 4 by the addition of glacial acetic acid. The mixture was diluted in ethyl acetate, washed with water and saturated aqueous sodium chloride solution and dried over magnesium sulfate. The solvent was removed under reduced pressure and the residue purified by column chromatography on silica gel, eluting with a mixture of ethyl acetate and methanol (1:0 to 1:1 by volume) to afford title compound as a white solid, 0.040 g.

$^1$H NMR (DMSO-d6): δ 2.85 (s, 3H), 4.20 (s, 2H), 4.35 (s, 2H), 6.70 (d, J=8.4 Hz, 1H), 6.80 (dd, J=2.1, 8.4 Hz, 1H), 7.25 (t, J=2.1, 8.4 Hz, 1H), 7.40 (t, J=9.4 Hz, 1H), 7.65 (d, J=2.1 Hz, 1H), 7.80 (t, J=72 Hz, 1H).

MS: ESI (+ve) (Method A): 460 (M+H)$^+$, Retention time 13.4 min.

MS: ESI (+ve) (Method B): 460 (M+H)$^+$, Retention time 4.4 min.

Example 52

[2-difluoromethoxy-8-fluoro-3-(4-fluorobenzyl)-4-methylquinolin-5-yloxy]acetic Acid

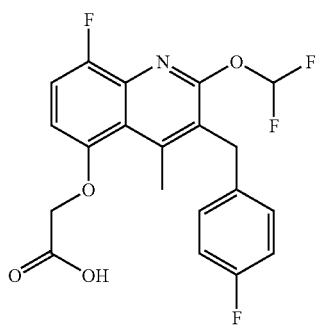

Preparation 52a 2-(4-fluorobenzyl)-3-oxothiobutyric Acid S-tert-butyl Ester

The title compound was prepared by the method of Preparation 34a using 1-bromomethyl-4-fluorobenzene and 3-oxothiobutyric acid S-tert-butyl ester.

$^1$H NMR (CDCl$_3$): δ 1.40 (s, 9H), 2.20 (s, 3H), 3.10 (m, 2H), 3.80 (t, J=7.5 Hz, 1H), 6.95 (m, 2H), 7.10 (m, 2H).

Preparation 52b 2-(4-fluorobenzyl)-N-(2-fluoro-5-hydroxyphenyl)-3-oxobutyramide The title compound was prepared by the method of Preparation 34b using 3-amino-4-fluorophenol and 2-(4-fluorobenzyl)-3-oxothiobutyric acid S-tert-butyl ester.

Preparation 52c 8-fluoro-3-(4-fluorobenzyl)-5-hydroxy-4-methyl-1H-quinolin-2-one The title compound was prepared by the method of Preparation 34c using 2-(4-fluorobenzyl)-N-(2-fluoro-5-hydroxyphenyl)-3-oxobutyramide.

MS: ESI (+ve) (Method B): 302 (M+H)$^+$, Retention time 3.1 min.

Preparation 52d

[8-fluoro-3-(4-fluorobenzyl)-4-methyl-2-oxo-1,2-dihydroquinolin-5-yloxy]acetic Acid Methyl Ester The title compound was prepared by the method of Preparation 34d using 8-fluoro-3-(4-fluorobenzyl)-5-hydroxy-4-methyl-1H-quinolin-2-one.

$^1$H NMR (DMSO-d6): δ 2.65 (s, 3H), 3.70 (s, 3H), 4.05 (s, 2H), 4.90 (s, 2H), 6.65 (dd, J=4.0, 9.1 Hz, 1H), 7.05 (m, 2H), 7.20-7.35 (m, 3H), 11.60 (s, 1H).

MS: ESI (+ve) (Method B): 374 (M+H)$^+$, Retention time 3.5 min.

Preparation 52e

[2-difluoromethoxy-8-fluoro-3-(4-fluorobenzyl)-4-methylquinolin-5-yloxy]acetic Acid Methyl Ester A mixture of [8-fluoro-3-(4-fluorobenzyl)-4-methyl-2-oxo-1,2-dihydroquinolin-5-yloxy]acetic acid methyl ester (0.48 g), N,N-dimethylformamide (6.0 mL), potassium carbonate (0.72 g) and acetic acid chlorodifluoromethyl ester (1.7 mL) was stirred at 70° C. for 5 days. The mixture was diluted with Water, extracted with ethyl acetate and the combined extracts washed with water and then dried over magnesium sulfate. The solvent was removed under reduced pressure and purification of the residue by column chromatography on silica gel, eluting with a mixture of ethyl acetate and cyclohexane (1:6 by volume), followed by washing with diethyl ether gave title compound as a white solid, 0.29 g.

$^1$H NMR (CDCl$_3$): δ 2.95 (s, 3H), 3.80 (s, 3H), 4.20 (s, 2H), 4.70 (s, 2H), 6.60 (dd, J=4.0, 8.7 Hz, 1H), 6.90-7.00 (m, 2H), 7.10 (m, 2H), 7.20 (t, J=9.0 Hz, 1H), 7.80 (t, J=73 Hz, 1H).

Preparation 52f

[2-difluoromethoxy-8-fluoro-3-(4-fluorobenzyl)-4-methylquinolin-5-yloxy]acetic Acid A mixture of [2-difluoromethoxy-8-fluoro-3-(4-fluorobenzyl)-4-methylquinolin-5-yloxy]acetic acid methyl ester (0.20 g), tetrahydrofuran (4.0 mL), methanol (4.0 mL), water (3.0 mL) and lithium hydroxide (0.020 g) was stirred at room temperature for 40 minutes. The mixture was partitioned between ethyl acetate and 1.0 M aqueous hydrochloric acid. The aqueous phase was extracted with ethyl acetate and the combined organic phases were dried over sodium sulfate and the solvent removed under reduced pressure. Purification of the residue by preparative reverse-phase HPLC using a gradient over 30 minutes of acetonitrile in water gave title compound as a white solid, 0.10 g.

$^1$H NMR (DMSO-d6): δ 2.90 (s, 3H), 4.20 (s, 2H), 4.80 (s, 2H), 6.90 (dd, J=4.0, 8.9 Hz, 1H), 7.05-7.20 (m, 4H), 7.50 (m, 1H), 7.85 (t, J=72 Hz, 1H).

MS: ESI (+ve) (Method A): 410 (M+H)$^+$, Retention time 12.2 min.

MS: ESI (+ve) (Method B): 410 (M+H)$^+$, Retention time 3.9 min.

Example 53

[3-(2,4-difluorobenzyl)-4-difluoromethoxy-2-ethyl-8-fluoroquinolin-5-yloxy]acetic Acid

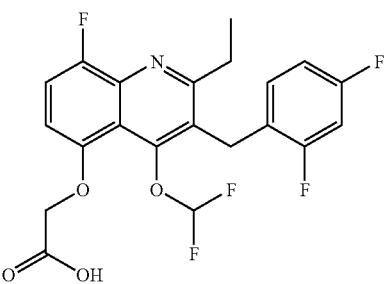

Preparation 53a

N-(2-fluoro-5-nitrophenyl)acetamide

Acetic anhydride (8.0 mL) was added dropwise over a period of 10 minutes to a mixture of 2-fluoro-5-nitrophenylamine (7.8 g) and acetic acid (50 mL) at reflux. The resulting mixture was heated at reflux for 30 minutes and cooled to 40° C. The mixture was poured into cold water (800 mL) and the resulting precipitate collected by filtration, washed with 1.0 M aqueous hydrochloric acid and water and dried to give title compound as a light brown solid, 9.2 g.

$^1$H NMR (DMSO-d6): δ 2.15 (s, 3H), 7.55 (dd, J=9.1, 10.3 Hz, 1H), 8.00-8.05 (ddd, J=2.9, 4.2, 9.1 Hz, 1H), 9.00 (dd, J=2.9, 6.8 Hz, 1H), 10.20 (s, 1H).

Preparation 53b

N-(5-amino-2-fluorophenyl)acetamide

A mixture of 2-fluoro-5-nitrophenylamine (2.0 g), palladium, 10 wt. % on activated carbon (0.10 g) and ethanol (20 mL) were stirred at room temperature for 2 hours under an atmosphere of hydrogen. The mixture was filtered through hyflo, washing with ethanol and the solvent removed under reduced pressure to afford title compound as a white solid, 1.7 g.

$^1$H NMR (DMSO-d6): δ 2.05 (s, 3H), 4.95 (s, 2H), 6.25 (m, 1H), 6.85 (dd, J=8.7, 10.9 Hz, 1H), 7.15 (dd, J=2.6, 6.7 Hz, 1H), 9.90 (s, 1H).

Preparation 53c

3-amino-4-fluorophenol

A solution of sodium nitrite (17.3 g) in water (40 mL) was added dropwise to a mixture of N-(5-amino-2-fluorophenyl) acetamide (36.7 g), sulfuric acid (50 mL) and water (270 mL) at 0-10° C. The mixture was stirred at 0-10° C. for 20 minutes and then a solution of urea (2.0 g) in water (20 mL) was added and the resulting mixture stirred at 0-10° C. for a further 20 minutes. The mixture was added dropwise over a period 75 minutes to a stirred solution of copper sulfate pentahydrate (131 g) in water (110 mL) at 130° C. and the resulting mixture heated at 130° C. for 2.5 hours. The mixture was cooled in an ice bath and the pH of the solution adjusted to 14 by the addition of 30% aqueous sodium hydroxide solution. The mixture was filtered through hyflo, washing with water. The pH of the filtrate was acidified by the addition of concentrated hydrochloric acid and extracted with ethyl acetate. The combined extracts were dried over magnesium sulfate and the solvent removed under reduced pressure to afford title compound as a brown solid, 22.1 g.

$^1$H NMR (DMSO-d6): δ 4.95 (br s, 2H), 5.8 (m, 1H), 6.15 (dd, J=2.9, 7.8 Hz, 1H), 6.70 (dd, J=8.7, 11.4 Hz, 1H), 8.85 (br s, 1H).

Preparation 53d

(3-amino-4-fluorophenoxy)acetic Acid Methyl Ester

3-Amino-4-fluorophenol (3.0 g) was added to a stirred suspension of sodium hydride (60% in oil, 0.94 g) in N,N-dimethylformamide (30 mL) at 0° C. The mixture was warmed to room temperature for 15 minutes and then cooled to 0° C. and this mixture was treated with bromoacetic acid methyl ester (3.3 g). The resulting mixture was warmed to room temperature and then stirred at this temperature for 2 hours. The mixture was diluted with dilute aqueous ammonium chloride solution and extracted with ethyl acetate. The combined extracts were washed with saturated aqueous sodium chloride solution and dried over magnesium sulfate. The solvent was removed under reduced pressure and purification of the residue by column chromatography on silica gel, eluting with a mixture of toluene, dichloromethane and ethyl acetate (2:1:0 to 0:1:0 to 0:20:1 by volume) gave title compound, 2.7 g.

$^1$H NMR (DMSO-d6): δ 3.70 (s, 3H), 4.65 (s, 2H), 5.15 (br s, 2H), 6.00 (dt, J=3.1, 8.8 Hz, 1H), 6.30 (dd, J=3.1, 7.6 Hz, 1H), 6.85 (dd, J=8.8, 11.2 Hz, 1H).

MS: ESI (+ve) (Method B): 200 (M+H)$^+$, Retention time 2.5 min.

Preparation 53e

2-(2,4-difluorobenzyl)-3-oxopentanoic Acid Methyl Ester

A suspension of potassium tert-butoxide (3.2 g) in anhydrous tetrahydrofuran (40 mL) at 0° C. was treated with a mixture of tert-butanol (0.15 mL) and 3-oxopentanoic acid methyl ester (3.8 g). The mixture was warmed to room temperature over 30 minutes and then a solution of 1-bromomethyl-2,4-difluorobenzene (6.0 g) in tetrahydrofuran (10 mL) was added and the resulting mixture stirred at room temperature for 72 hours. The mixture was diluted with water (10 mL) and the tetrahydrofuran removed under reduced pressure. The residue was partitioned between ethyl acetate and dilute aqueous ammonium chloride solution and the aqueous phase extracted with diethyl ether. The combined organic phases were dried over magnesium sulfate and the solvent removed under reduced pressure. The residue was purified by column chromatography on silica gel, eluting with a mixture of toluene, dichloromethane and ethyl acetate (4:1:0 to 0:1:0 to 0:25:1 by volume) to afford title compound as colourless oil, 4.5 g.

$^1$H NMR (DMSO-d6): δ 0.9 (t, J=7.2 Hz, 6H), 2.45-2.60 (m 4H), 3.05 (m, 2H), 3.30 (s, 2H), 3.60 (s, 6H), 4.00 (m, 1H), 7.00 (m, 2H), 7.20 (m, 2H), 7.30 (m, 2H).

Preparation 53f

[3-(2,4-difluorobenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (0.5 g), 2-(2,4-difluorobenzyl)-3-oxopentanoic acid methyl ester (0.64 g), polyphosphoric acid (2.5 mL) and dioxane (10 mL) was heated at 130° C. for 17 hours. The mixture was diluted with water and the pH adjusted to 4 by the addition of sodium acetate. The resulting precipitate was collected by filtration, washed with water and dried to give title compound as a creamy solid, 0.84 g.

MS: ESI (+ve) (Method B): 406 (M+H)$^+$, Retention time 3.2.

Preparation 53g

[3-(2,4-difluorobenzyl)-4-difluoromethoxy-2-ethyl-8-fluoroquinolin-5-yloxy]acetic Acid Methyl Ester The title compound was prepared by the method of Preparation 34e using [3-(2,4-difluorobenzyl)-2-ethyl-8-fluoro-4-oxo-1,4-dihydroquinolin-5-yloxy]acetic acid methyl ester.

¹H NMR (DMSO-d6): δ 1.20 (t, J=7.4 Hz, 3H), 2.85 (q, J=7.4 Hz, 2H), 3.75 (s, 3H), 4.30 (s, 2H), 5.00 (s, 2H), 6.85 (m, 1H), 6.95 (m, 1H), 7.05 (dd, J=3.7, 9.0 Hz, 1H), 7.20 (t, J=75 Hz, 1H), 7.25 (m, 1H), 7.55 (dd, J=8.9, 10.1 Hz, 1H).
MS: ESI (+ve) (Method B): 456 (M+H)⁺, Retention time 4.3 min.

Preparation 53h

[3-(2,4-difluorobenzyl)-4-difluoromethoxy-2-ethyl-8-fluoroquinolin-5-yloxy]acetic Acid A solution of [3-(2,4-difluorobenzyl)-4-difluoromethoxy-2-ethyl-8-fluoroquinolin-5-yloxy]acetic acid methyl ester (0.54 g), methanol (20 mL), water (1.0 mL) and 5.0 M aqueous lithium hydroxide solution (0.5 mL) was stirred at room temperature for 2 hours. The pH of the solution was adjusted to 5 by the addition of glacial acetic acid and the solvent removed under reduced pressure. The residue was diluted with water and the solid collected by filtration, washed with water and dried to afford title compound as a cream solid, 0.089 g.
¹H NMR (DMSO-d6): δ 1.2 (t, J=7.4 Hz, 3H), 2.85 (q, J=7.4 Hz, 2H), 4.25 (s, 2H), 4.50 (s, 2H), 6.80-6.85 (m, 2H), 6.95 (dt, J=2.3, 8.5 Hz, 1H), 7.25 (m, 1H), 7.45 (dd, J=8.9 Hz, 10.2 Hz, 1H), 7.95 (t, J=75 Hz, 1H).
MS: ESI (+ve) (Method A): 442 (M+H)⁺, Retention time 18.8 min.
MS: ESI (+ve) (Method B): 442 (M+H)⁺, Retention time 3.9 min.

Example 54

[3-(2,4-dichlorobenzyl)-4-difluoromethoxy-2-ethyl-8-fluoroquinolin-5-yloxy]acetic acid

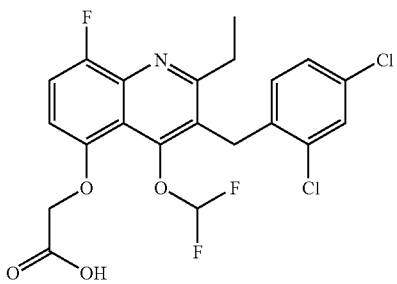

Preparation 54a 2-(2,4-dichlorobenzyl)-3-oxopentanoic Acid Methyl Ester

A suspension of potassium tert-butoxide (8.4 g) in anhydrous tetrahydrofuran (180 mL) at 0° C. was treated with a mixture of tert-butanol (0.4 mL) and 3-oxopentanoic acid methyl ester (9.8 g). After stirring at room temperature for 30 minutes a solution of 2,4-dichloro-1-chloromethylbenzene (14.7 g) in tetrahydrofuran (20 mL) was added and the resulting mixture warmed to room temperature and then stirred at this temperature for 6 days. The mixture was diluted with water (200 mL), extracted with ethyl acetate and the combined extracts washed with water and saturated aqueous sodium chloride solution and then dried over magnesium sulfate. The solvent was removed under reduced pressure and the residue purified by column chromatography on silica gel, eluting with a mixture of pentane and dichloromethane (1:0 to 1:1 by volume) to afford title compound as a white solid, 7.0 g.
¹H NMR (CDCl₃): δ 1.00 (t, J=6.9 Hz, 3H), 2.40 (m, 1H), 2.60 (m, 1H), 3.25 (m, 2H), 3.70 (s, 3H), 3.95 (t, J=7.5 Hz, 1H), 7.15-7.20 (m, 2H), 7.35 (m, 1H).

Preparation 54b

[3-(2,4-dichlorobenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (0.75 g), 2-(2,4-dichlorobenzyl)-3-oxopentanoic acid methyl ester (1.3 g), polyphosphoric acid (5 mL) and dioxane (25 mL) was heated at 120° C. for 17 hours. The mixture was cooled to room temperature, diluted with ethyl acetate and this mixture washed with water, saturated aqueous sodium hydrogen carbonate solution and saturated aqueous sodium chloride solution and then dried over magnesium sulfate. The solvent was removed under reduced pressure to afford title compound as a brown oil, 1.7 µg.
MS: ESI (+ve) (Method B): 438 (M+H)⁺, Retention time 3.6 min.

Preparation 54c

[3-(2,4-dichlorobenzyl)-4-difluoromethoxy-2-ethyl-8-fluoroquinolin-5-yloxy]acetic Acid Methyl Ester The title compound was prepared by the method of Preparation 34e using [3-(2,4-dichlorobenzyl)-2-ethyl-8-fluoro-4-oxo-1,4-dihydroquinolin-5-yloxy]acetic acid methyl ester.
¹H NMR (DMSO-d6): δ 1.20 (t, J=7.4 Hz, 3H), 2.80 (q, J=7.4 Hz, 2H), 3.75 (s, 3H), 4.35 (s, 2H), 5.00 (s, 2H), 6.65 (d, J=8.4 Hz, 1H), 7.05 (dd, J=3.7, 8.9 Hz, 1H), 7.20 (t, J=75 Hz, 1H), 7.25 (dd, J=2.2, 8.4 Hz, 1H), 7.55 (dd, J=8.9, 10.1 Hz, 1H), 7.70 (d, J=2.2 Hz, 1H).

Preparation 54d

[3-(2,4-dichlorobenzyl)-4-difluoromethoxy-2-ethyl-8-fluoroquinolin-5-yloxy]acetic Acid A solution of [3-(2,4-dichlorobenzyl)-4-difluoromethoxy-2-ethyl-8-fluoroquinolin-5-yloxy]acetic acid methyl ester (0.17 g), methanol (6 mL), water (0.3 mL) and 5.0 M aqueous sodium hydroxide solution (0.15 mL) was stirred at room temperature for 1 hour. The pH of the solution was adjusted to 5 by the addition of glacial acetic acid and the solvent removed under reduced pressure. The residue was diluted with water and the solid collected by filtration. Purification by column chromatography on silica gel, eluting with a mixture of dichloromethane and methanol (1:0 to 3:1 by volume) gave title compound as a white solid, 0.030 g.
¹H NMR (DMSO-d6): δ 1.20 (t, J=7.4 Hz, 3H), 2.75 (t, J=7.4 Hz, 2H), 4.30 (s, 2H), 4.50 (s, 2H), 6.60 (d, J=8.5 Hz, 1H), 6.85 (dd, J=3.7, 8.9 Hz, 1H), 7.25 (dd, J=2.1, 8.4 Hz, 1H), 7.50 (dd, J=8.9, 10.2 Hz, 1H), 7.70 (d, J=2.1 Hz, 1H), 8.00 (t, J=75 Hz, 1H).
MS: ESI (+ve) (Method A): 474 (M+H)⁺, Retention time 13.5 min.
MS: ESI (+ve) (Method B): 474 (M+H)⁺, Retention time 4.5 min.

Example 55

[3-(2,4-difluorobenzyl)-2-difluoromethoxy-8-fluoro-4-methylquinolin-5-yloxy]acetic acid

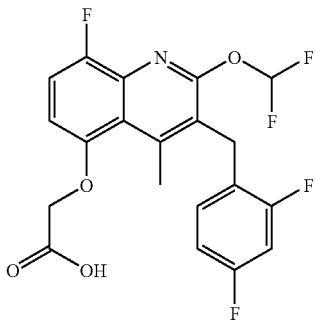

Preparation 55a 2-(2,4-difluorobenzyl)-3-oxothiobutyric acid S-tert-butyl Ester The title compound was prepared by the method of Preparation 34a using 1-bromomethyl-2,4-difluorobenzene and 3-oxothiobutyric acid S-tert-butyl ester
MS: ESI (−ve) (Method B): 323 (M−H)⁻, Retention time 4.2 min.

Preparation 55b 2-(2,4-difluorobenzyl)-N-(2-fluoro-5-hydroxyphenyl)-3-oxobutyramide The title compound was prepared by the method of Preparation 34b using 3-amino-4-fluorophenol and 2-(2,4-difluorobenzyl)-3-oxothiobutyric acid S-tert-butyl ester.
$^1$H NMR (DMSO-d6): δ 2.20 (s, 3H), 3.00 (m, 2H), 4.20 (dd, J=5.4, 9.4 Hz, 1H), 6.50 (m, 1H), 7.00 (m, 2H), 7.15-7.30 (m, 3H), 9.40 (s, 1H), 9.95 (s, 1H).
MS: ESI (+ve) (Method B): 338 (M+H)⁺, Retention time 3.1 min.

Preparation 55c 3-(2,4-difluorobenzyl)-8-fluoro-5-hydroxy-4-methyl-1H-quinolin-2-one The title compound was prepared by the method of Preparation 34c using 2-(2,4-difluorobenzyl)-N-(2-fluoro-5-hydroxyphenyl)-3-oxobutyramide.
$^1$H NMR (DMSO-d6): δ 2.55 (s, 3H), 4.00 (s, 2H), 6.50 (dd, J=4.4, 8.9 Hz, 1H), 6.95 (m, 1H), 7.00 (m, 1H), 7.15-7.25 (m, 2H), 10.15 (s, 1H), 11.40 (s, 1H).
MS: ESI (+ve) (Method B): 320 (M+H)⁺, Retention time 3.2 min.

Preparation 55d

[3-(2,4-difluorobenzyl)-8-fluoro-4-methyl-2-oxo-1,2-dihydroquinolin-5-yloxy]acetic Acid Methyl Ester The title compound was prepared by the method of Preparation 34d using 3-(2,4-difluorobenzyl)-8-fluoro-5-hydroxy-4-methyl-1H-quinolin-2-one.
$^1$H NMR (DMSO-d6): δ2.60 (s, 3H), 3.70 (s, 3H), 4.00 (s, 2H), 4.90 (s, 2H), 6.65 (dd, J=4.0, 9.1 Hz, 1H), 6.95 (dt, J=2.5, 8.5 Hz, 1H), 7.00 (m, 1H), 7.20 (m, 1H), 7.30 (m, 1H), 11.65 (br s, 1H).
MS: ESI (+ve) (Method B): 392 (M+H)⁺, Retention time 3.5 min.

Preparation 55e

[3-(2,4-difluorobenzyl)-2-difluoromethoxy-8-fluoro-4-methylquinolin-5-yloxy]acetic Acid Methyl Ester The title compound was prepared by the method of Preparation 34e using [3-(2,4-difluorobenzyl)-8-fluoro-4-methyl-2-oxo-1,2-dihydroquinolin-5-yloxy]acetic acid methyl ester.
$^1$H NMR (DMSO-d6): δ 2.60 (s, 3H), 3.70 (s, 3H), 4.00 (s, 2H), 4.90 (s, 2H) 6.65 (dd, J=4.1, 9.0 Hz, 1H), 6.95 (dt, J=2.5, 8.6 Hz, 1H), 7.00 (m, 1H), 7.20 (m, 1H), 7.30 (m, 1H), 11.65 (s, 1H).
MS: ESI (+ve) (Method B): 442 (M+H)⁺, Retention time 4.4 min.

Preparation 55f

[3-(2,4-difluorobenzyl)-2-difluoromethoxy-8-fluoro-4-methylquinolin-5-yloxy]acetic Acid A solution of [3-(2,4-difluorobenzyl)-2-difluoromethoxy-8-fluoro-4-methylquinolin-5-yloxy]acetic acid methyl ester (0.20 g), methanol (10 mL), water (0.8 mL) and 5.0 M aqueous sodium hydroxide solution (0.4 mL) was stirred at room temperature for 2 hour. The pH of the mixture was adjusted to 5 by the addition of glacial acetic acid and the solvent removed under reduced pressure. The residue was diluted with water and the solid collected by filtration, washed with water and dried to afford title compound as a white solid, 0.030 g.
$^1$H NMR (DMSO-d6): δ 2.90 (s, 3H), 4.15 (s, 2H), 4.80 (s, 2H), 6.90-7.00 (m, 3H), 7.25 (m, 1H), 7.500 (dd, J=8.9, 9.7 Hz, 1H), 7.85 (t, J=72 Hz, 1H).
MS: ESI (+ve) (Method A): 428 (M+H)⁺, Retention time 12.3 min.
MS: ESI (+ve) (Method B): 428 (M+H)⁺, Retention time 4.0 min.

Example 56

[3-(4-chloro-2-fluorobenzyl)-2-difluoromethoxy-8-fluoro-4-methylquinolin-5-yloxy]acetic Acid

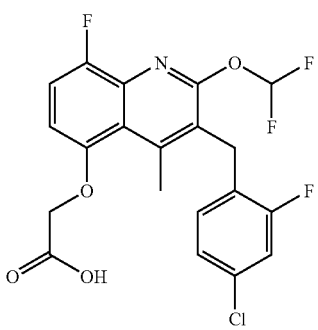

Preparation 56a

2-(4-chloro-2-fluorobenzyl)-3-oxothiobutyric acid S-tert-butyl Ester

The title compound was prepared by the method of Preparation 34a using 1-bromomethyl-4-chloro-2-fluorobenzene and 3-oxothiobutyric acid S-tert-butyl ester.

$^1$H NMR (CDCl$_3$): δ 1.40 (s, 9H), 1.45 (s, 9H), 1.80 (s, 3H), 2.20 (s, 3H), 3.05 (dd, J=8.4, 14.0 Hz, 1H), 3.15 (dd, J=6.6, 14.0 Hz, 1H), 3.65 (s, 2H), 3.90 (dd, J=6.6, 8.4 Hz, 1H), 7.00-7.15 (m, 6H).

Preparation 56b

2-(4-chloro-2-fluorobenzyl)-N-(2-fluoro-5-hydroxyphenyl)-3-oxobutyramide

The title compound was prepared by the method of Preparation 34b using 3-amino-4-fluorophenol and 2-(4-chloro-2-fluorobenzyl)-3-oxothiobutyric acid S-tert-butyl ester.

$^1$H NMR (CDCl$_3$): δ 2.25 (s, 3H), 3.25 (m, 2H), 3.85 (t, J=7.4 Hz, 1H), 6.40 (br s, 1H), 6.55 (m, 1H), 6.95 (dd, J=8.9, 10.4 Hz, 1H), 7.05 (m, 2H), 7.10 (t, J=8.1 Hz, 1H), 7.90 (dd, J=3.0, 6.3 Hz, 1H), 8.55 (br s, 1H).

MS: ESI (+ve) (Method B): 354 (M+H)$^+$, Retention time 3.2 min.

Preparation 56c

3-(4-chloro-2-fluorobenzyl)-8-fluoro-5-hydroxy-4-methyl-1H-quinolin-2-one

The title compound was prepared by the method of Preparation 34c using 2-(4-chloro-2-fluorobenzyl)-N-(2-fluoro-5-hydroxyphenyl)-3-oxobutyramide.

$^1$H NMR (CD$_3$OD): δ 2.65 (s, 3H), 4.10 (s, 2H), 6.55 (dd, J=4.2, 8.8 Hz, 1H), 6.95-7.15 (m, 4H).

MS: ESI (+ve) (Method B): 336 (M+H)$^+$, Retention time 3.4 min.

Preparation 56d

[3-(4-chloro-2-fluorobenzyl)-8-fluoro-4-methyl-2-oxo-1,2-dihydroquinolin-5-yloxy]acetic Acid Methyl Ester The title compound was prepared by the method of Preparation 34d using 3-(4-chloro-2-fluorobenzyl)-8-fluoro-5-hydroxy-4-methyl-1H-quinolin-2-one.

MS: ESI (+ve) (Method B): 408 (M+H)$^+$, Retention time 3.7 min.

Preparation 56e

[3-(4-chloro-2-fluorobenzyl)-2-difluoromethoxy-8-fluoro-4-methylquinolin-5-yloxy]acetic Acid Methyl Ester The title compound was prepared by the method of Preparation 34e using [3-(4-cloro-2-fluorobenzyl)-8-fluoro-4-methyl-2-oxo-1,2-dihydroquinolin-5-yloxy]acetic acid methyl ester.

$^1$H NMR (CDCl$_3$): δ 2.9 (s, 3H), 3.80 (s, 3H), 4.20 (s, 2H), 4.70 (s, 2H), 6.60 (dd, J=3.9, 8.8 Hz; 1H), 6.80 (t, J=8.2 Hz, 1H), 6.90 (dd, J=2.1, 8.8 Hz, 1H), 7.10 (dd, J=2.1, 9.7 Hz, 1H), 7.25 (m, 1H), 7.80 (t, J=73 Hz, 1H).

MS: ESI (+ve) (Method B): 458 (M+H)$^+$, Retention time 4.6 min.

Preparation 56f

[3-(4-chloro-2-fluorobenzyl)-2-difluoromethoxy-8-fluoro-4-methylquinolin-5-yloxy]acetic Acid A solution of [3-(4-chloro-2-fluorobenzyl)-2-difluoromethoxy-8-fluoro-4-methylquinolin-5-yloxy]acetic acid methyl ester (0.094 g), tetrahydrofuran (10 mL) and 1.0 M aqueous lithium hydroxide solution (0.22 mL) was stirred at room temperature for 1 hour. The solvent was removed under reduced pressure and the residue diluted with water. The pH of this mixture was adjusted to 4 by the addition of sodium dihydrogenphosphate and extracted with ethyl acetate. The combined extracts were dried over magnesium sulfate and the solvent removed under reduced pressure to afford title compound, 0.090 g.

$^1$H NMR (CDCl$_3$): δ 2.85 (s, 3H), 4.20 (s, 2H), 4.80 (s, 2H), 6.65 (dd, J=3.9, 8.7 Hz, 1H), 6.80 (m, 1H), 7.00 (m, 1H), 7.10 (dd, J=2.1, 9.8 Hz, 1H), 7.25 (m, 1H), 7.80 (t, J=72 Hz, 1H).

MS: ESI (+ve) (Method A): 444 (M+H)$^+$, Retention time 13.1 min.

Example 57

[8-chloro-3-(4-chlorobenzyl)-2-difluoromethoxy-4-methylquinolin-5-yloxy]acetic Acid

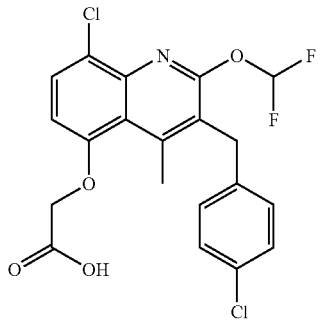

Preparation 57a

2-(4-chlorobenzyl)-3-oxothiobutyric acid S-tert-butyl Ester

The title compound was prepared by the method of Preparation 34a using 1-bromomethyl-4-chlorobenzene and 3-oxothiobutyric acid S-tert-butyl ester.

$^1$H NMR (CDCl$_3$): δ 1.40 (s, 9H), 2.20 (s, 3H), 3.05-3.15 (m, 2H), 3.80 (t, J=7.4 Hz, 1H), 7.10 (d, J=8.6 Hz, 2H), 7.25 (d, J=8.6 Hz, 2H).

Preparation 57b

2-(4-chlorobenzyl)-N-(2-chloro-5-hydroxyphenyl)-3-oxobutyramide

The title compound was prepared by the method of Preparation 34b using 3-amino-4-chlorophenol and 2-(4-chlorobenzyl)-3-oxothiobutyric acid S-tert-butyl ester.

MS: ESI (+ve) (Method B): 352 (M+H)⁺, Retention time 3.3 min.

Preparation 57c 8-chloro-3-(4-chlorobenzyl)-5-hydroxy-4-methyl-H-quinolin-2-one

The title compound was prepared by the method of Preparation 34c using 2-(4-chlorobenzyl)-N-(2-chloro-5-hydroxyphenyl)-3-oxobutyramide.

$^1$H NMR (DMSO-d6): δ 2.75 (s, 3H), 4.05 (s, 2H), 6.65 (d, J=8.7 Hz, 1H), 7.20-7.35 (m, 4H), 7.40 (d, J=8.7 Hz, 1H), 10.35 (br s, 1H), 10.50 (br s, 1H).

MS: ESI (+ve) (Method B): 334 (M+H)⁺, Retention time 3.6 min.

Preparation 57d

[8-chloro-3-(4-chlorobenzyl)-4-methyl-2-oxo-1,2-dihydroquinolin-5-yloxy]acetic Acid Methyl Ester The title compound was prepared by the method of Preparation 34d using 8-chloro-3-(4-chlorobenzyl)-5-hydroxy-4-methyl-1H-quinolin-2-one.

$^1$H NMR (DMSO-d6): δ 2.60 (s, 3H), 3.70 (s, 3H), 4.05 (s, 2H), 4.95 (s, 2H), 6.75 (d, J=8.9 Hz, 1H), 7.20 (d, J=8.5 Hz, 2H), 7.30 (d, J=8.5 Hz, 2H), 7.55 (d, J=8.9 Hz, 1H), 10.65 (br s, 1H).

MS: ESI (+ve) (Method B): 406 (M+H)⁺, Retention time 3.9 min.

Preparation 57e

[8-chloro-3-(4-chlorobenzyl)-2-difluoromethoxy-4-methylquinolin-5-yloxy]acetic Acid Methyl Ester The title compound was prepared by the method of Preparation 34e using [8-chloro-3-(4-chlorobenzyl)-4-methyl-2-oxo-1,2-dihydroquinolin-5-yloxy]acetic acid methyl ester.

$^1$H NMR (DMSO-d6): δ 2.85 (s, 3H), 3.75 (s, 3H), 4.20 (s, 2H), 5.00 (s, 2H), 7.00 (d, J=8.4 Hz, 1H), 7.15 (d, J=8.6 Hz, 2H), 7.35 (d, J=8.6 Hz, 2H), 7.80 (d, J=8.4 Hz, 1H), 7.85 (t, J=72 Hz, 1H).

MS: ESI (+ve) (Method B): 456 (M+H)⁺, Retention time 4.8 min.

Preparation 57f

[8-chloro-3-(4-chlorobenzyl)-2-difluoromethoxy-4-methylquinolin-5-yloxy]acetic Acid A solution of [8-chloro-3-(4-chlorobenzyl)-2-difluoromethoxy-4-methylquinolin-5-yloxy]acetic acid methyl ester (0.52 g), methanol (20 mL), water (2.0 mL) and 5.0 M aqueous sodium hydroxide solution (1.0 mL) was stirred at room temperature for 1 hour. The pH of the mixture was adjusted to 5 by the addition of glacial acetic acid and the solvent removed under reduced pressure. The residue was diluted with water and the solid collected by filtration, washed with water and acetonitrile and then dried to afford title compound as an off-white solid, 0.41 g.

$^1$H NMR (DMSO-d6): δ 2.90 (s, 3H), 4.20 (s, 2H), 4.30 (s, 2H), 6.80 (d, J=8.2 Hz, 1H), 7.15 (d, J=8.7 Hz, 2H), 7.30 (d, J=8.7 Hz, 2H), 7.70 (d, J=8.2 Hz, 1H), 7.85 (t, J=72 Hz, 1H).

MS: ESI (+ve) (Method A): 442 (M+H)⁺, Retention time 13.5 min.

MS: ESI (+ve) (Method B): 442 (M+H)⁺, Retention time 4.4 min.

Example 58

[3-(2-chloro-4-fluorobenzyl)-4-difluoromethoxy-2-ethyl-8-fluoroquinolin-5-yloxy]acetic Acid Preparation 58a 2-(2-chloro-4-fluorobenzyl)-3-oxopentanoic Acid Methyl Ester A suspension of potassium tert-butoxide (1.6 g) in anhydrous tetrahydrofuran (25 mL) at 0° C. was treated with a mixture of tert-butanol (1.0 mL) and 3-oxopentanoic acid methyl ester (1.5 g). After stirring at 0° C. for 45 minutes a solution of 1-bromomethyl-2-chloro-4-fluorobenzene (2.6 g) in tetrahydrofuran (5.0 mL) was added and the resulting mixture stirred at room temperature for 3 days. The mixture was diluted with water and the tetrahydrofuran removed under reduced pressure. The mixture was extracted with ethyl acetate and the combined extracts dried over magnesium sulfate and the solvent removed under reduced pressure to afford the title compound, 3.2 g.

MS: ESI (+ve) (Method B): 273 (M+H)⁺, Retention time 3.8 min.

Preparation 58b

[3-(2-chloro-4-fluorobenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (1.1 g), 2-(2-chloro-4-fluorobenzyl)-3-oxopentanoic acid methyl ester (2.4 g), polyphosphoric acid (5 g) and dioxane (10 mL) was heated at 130° C. for 17 hours. The mixture was cooled to room temperature, diluted with water and extracted with ethyl acetate. The combined extracts were washed with saturated aqueous sodium chloride solution and dried over magnesium sulfate. The solvent was removed under reduced pressure and the solid washed with diethyl ether and dried to afford title compound, 1.5 g.

MS: ESI (+ve) (Method B): 422 (M+H)⁺, Retention time 3.4 min.

Preparation 58c

[3-(2-chloro-4-fluorobenzyl)-4-difluoromethoxy-2-ethyl-8-fluoroquinolin-5-yloxy]acetic Acid Methyl Ester The title compound was prepared by the method of Preparation 34e using [3-(2-chloro-4-fluorobenzyl)-2-ethyl-8-fluoro-4-oxo-1,4-dihydroquinolin-5-yloxy]acetic acid methyl ester.

$^1$H NMR (CDCl$_3$): δ1.25 (t, J=7.5 Hz, 3H), 2.80 (q, J=7.5 Hz, 2H), 3.85 (s, 3H), 4.40 (s, 2H), 4.80 (s, 2H), 6.55 (dd, J=6.1, 8.5 Hz, 1H), 6.70 (dd, J=3.6, 8.9 Hz, 1H), 6.80 (dt, J=2.5, 8.4 Hz, 1H), 6.96 (t, J=75 Hz, 1H), 7.20 (dd, J=2.5, 8.4 Hz, 1H), 7.30 (t, J=8.9 Hz, 1H).

MS: ESI (+ve) (Method B): 472 (M+H)$^+$, Retention time 4.5 min.

Preparation 58d

[3-(2-chloro-4-fluorobenzyl)-4-difluoromethoxy-2-ethyl-8-fluoroquinolin-5-yloxy]acetic Acid A mixture of [3-(2-chloro-4-fluorobenzyl)-4-difluoromethoxy-2-ethyl-8-fluoroquinolin-5-yloxy]acetic acid methyl ester (1.2 g), tetrahydrofuran (10 mL) and 1.0 M aqueous lithium hydroxide solution (3.0 mL) was stirred at room temperature for 1 hour. The solvent was removed under reduced pressure and the pH of the residue adjusted to 4 by the addition of sodium dihydrogenphosphate. The mixture was extracted with ethyl acetate and the combined extracts dried over magnesium sulfate. The solvent was removed under reduced pressure to afford title compound, 1.1 g.

$^1$H NMR (DMSO-d6): δ 1.20 (t, J=7.4 Hz, 3H), 2.75 (q, J=7.4 Hz, 2H), 4.30 (s, 2H), 4.90 (s, 2H), 6.65 (dd, J=6.2, 8.7 Hz, 1H), 7.00-7.10 (m, 2H), 7.25 (t, J=75 Hz, 1H), 7.50-7.60 (m, 2H).

MS: ESI (+ve) (Method A): 458 (M+H)$^+$, Retention time 12.5 min.

Example 59

[3-(2-chloro-4-fluorobenzyl)-2-difluoromethoxy-8-fluoro-4-methylquinolin-5-yloxy]acetic Acid

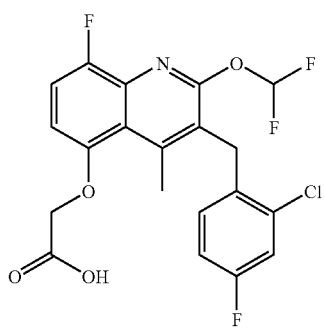

Preparation 59a 2-(2-chloro-4-fluorobenzyl)-3-oxothiobutyric acid S-tert-butyl Ester The title compound was prepared by the method of Preparation 34a using 1-bromomethyl-2-chloro-4-fluorobenzene and 3-oxothiobutyric acid S-tert-butyl ester.

Preparation 59b 2-(2-chloro-4-fluorobenzyl)-N-(2-fluoro-5-hydroxyphenyl)-3-oxobutyramide The title compound was prepared by the method of Preparation 34b using 3-amino-4-fluorophenol and 2-(2-chloro-4-fluorobenzyl)-3-oxothiobutyric acid S-tert-butyl ester.

MS: ESI (+ve) (Method B): 354 (M+H)$^+$, Retention time 3.2 min.

Preparation 59c 3-(2-chloro-4-fluorobenzyl)-8-fluoro-5-hydroxy-4-methyl-1H-quinolin-2-one The title compound was prepared by the method of Preparation 34c using 2-(2-chloro-4-fluorobenzyl)-N-(2-fluoro-5-hydroxyphenyl)-3-oxobutyramide.

$^1$H NMR (DMSO-d6): δ 2.50 (s, 3H), 4.00 (s, 2H), 6.55 (dd, J=4.3, 8.8 Hz, 1H), 6.85 (dd, J=6.4, 8.6 Hz, 1H), 7.05 (dt, J=2.7, 8.6 Hz, 1H), 7.20 (dd, J=8.8, 10.2 Hz, 1H), 7.45 (dd, J=2.7, 8.8 Hz, 1H), 10.20 (s, 1H), 11.45 (s, 1H).

MS: ESI (+ve) (Method B): 336 (M+H)$^+$, Retention time 3.3 min.

Preparation 59d

[3-(2-chloro-4-fluorobenzyl)-8-fluoro-4-methyl-2-oxo-1,2-dihydroquinolin-5-yloxy]acetic Acid Methyl Ester The title compound was prepared by the method of Preparation 36d using 3-(2-chloro-4-fluorobenzyl)-8-fluoro-5-hydroxy-4-methyl-1H-quinolin-2-one.

$^1$H NMR (DMSO-d6): δ2.55 (s, 3H), 3.70 (s, 3H), 4.05 (s, 2H), 4.90 (s, 2H), 6.70 (dd, J=4.0, 9.1 Hz, 1H), 6.90 (dd, J=6.2, 8.6 Hz, 1H), 7.05 (dt, J=2.7, 8.6 Hz, 1H), 7.35 (dd, J=9.1, 10.0 Hz, 1H), 7.45 (dd, J=2.7, 8.8 Hz, 1H), 11.70 (s, 1H).

MS: ESI (+ve) (Method B): 408 (M+H)$^+$, Retention time 3.7 min.

Preparation 59e

[3-(2-chloro-4-fluorobenzyl)-2-difluoromethoxy-8-fluoro-4-methylquinolin-5-yloxy]acetic Acid Methyl Ester The title compound was prepared by the method of Preparation 34e using [3-(2-chloro-4-fluorobenzyl)-8-fluoro-4-methyl-2-oxo-1,2-dihydroquinolin-5-yloxy]acetic acid methyl ester.

$^1$H NMR (CDCl$_3$): δ 2.8 (s, 3H), 3.8 (s, 3H), 4.25 (s, 2H), 4.75 (s, 2H), 6.60-6.65 (m, 2H), 6.80 (m, 1H), 7.20 (dd, J=2.6, 8.5 Hz, 1H), 7.25 (t, J=9.1 Hz, 1H), 7.80 (t, J=72.5 Hz, 1H).

MS: ESI (+ve) (Method B): 458 (M+H)$^+$, Retention time 4.6 min.

Preparation 59f

[3-(2-chloro-4-fluorobenzyl)-2-difluoromethoxy-8-fluoro-4-methylquinolin-5-yloxy]acetic Acid A mixture of [3-(2-chloro-4-fluorobenzyl)-2-difluoromethoxy-8-fluoro-4-methylquinolin-5-yloxy]acetic acid methyl ester (0.20 g), tetrahydrofuran (3.0 mL) and 1.0 M aqueous lithium hydroxide solution (0.45 mL) was stirred at room temperature for 1 hour. The solvent was removed under reduced pressure and the residue diluted with water. The pH of mixture was adjusted to 4 by the addition of sodium dihydrogenphosphate and the resulting precipitate collected by filtration and dried to afford title compound as a white solid, 0.18 g.

$^1$H NMR (DMSO-d6): δ 2.80 (s, 3H), 4.20 (s, 2H), 4.65 (s, 2H), 6.75 (dd, J=6.1, 8.8 Hz, 1H), 6.85 (dd, J=4.0, 8.8 Hz, 1H), 7.05 (dt, J=2.7, 8.5 Hz, 1H), 7.45-7.55 (m, 2H), 7.80 (t, J=72 Hz, 1H).

MS: ESI (+ve) (Method A): 444 (M+H)$^+$, Retention time 12.9 min.

Example 60

[4-difluoromethoxy-3-(4-ethanesulfonylbenzyl)-2-ethyl-8-fluoroquinolin-5-yloxy]acetic Acid

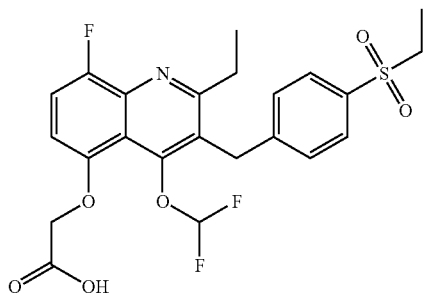

Preparation 60a 2-(4-ethanesulfonylbenzyl)-3-oxopentanoic Acid Methyl Ester

The title compound was prepared by the method of Preparation 34a using 1-bromomethyl-4-ethanesulfonylbenzene and 3-oxopentanoic acid methyl ester.

$^1$H NMR (CDCl$_3$): δ 1.00 (t, J=7.3 Hz, 3H), 1.25 (t, J=7.3 Hz, 3H), 2.40 (m, 1H), 2.60 (m, 1H), 3.10 (q, J=7.3 Hz, 2H), 3.25 (m, 2H), 3.80 (t, J=7.5 Hz, 1H), 3.70 (s, 3H), 7.40 (d, J=8.4 Hz, 2H), 7.80 (d, J=8.4 Hz, 2H).

Preparation 60b

[3-(4-ethanesulfonylbenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (0.90 g), 2-(4-ethanesulfonylbenzyl)-3-oxopentanoic acid methyl ester (1.4 g), polyphosphoric acid (10 g) and dioxane (10 mL) was heated at 120° C. for 17 hours. The mixture was cooled to room temperature, diluted with water and extracted with ethyl acetate. The combined extracts were washed with water, dried over magnesium sulfate and the solvent removed under reduced pressure to afford title compound, 1.9 g.

MS: ESI (+ve) (Method B): 462 (M+H)$^+$, Retention time 2.7 min.

Preparation 60c

[4-difluoromethoxy-3-(4-ethanesulfonylbenzyl)-2-ethyl-8-fluoroquinolin-5-yloxy]acetic Acid Methyl Ester A mixture of [3-(4-ethanesulfonylbenzyl)-2-ethyl-8-fluoro-4-oxo-1,4-dihydroquinolin-5-yloxy]acetic acid methyl ester (1.9 g), N,N-dimethylformamide (30 mL), potassium carbonate (1.7 g) and acetic acid chlorodifluoromethyl ester (2.2 mL) was stirred at 70° C. for 3 days. The mixture was diluted with saturated aqueous ammonium chloride solution, extracted with ethyl acetate and the combined extracts washed with saturated aqueous sodium chloride solution and then dried over magnesium sulfate. The solvent was removed under reduced pressure and purification of the residue by Isolute SCX2 column, eluting with methanol and then 2.0 M ammonia in methanol gave title compound, 0.090 g.

$^1$H NMR (CD$_3$OD): δ 1.20 (m, 6H), 2.90 (q, J=7.4 Hz, 2H), 3.20 (q, J=7.4 Hz, 2H), 3.80 (s, 3H), 4.55 (s, 2H), 4.95 (s, 2H), 6.95 (dd, J=3.7, 8.8 Hz, 1H), 7.10 (t, J=75 Hz, 1H), 7.35-7.50 (m, 3H), 7.80 (m, 2H).

Preparation 60d

[4-difluoromethoxy-3-(4-ethanesulfonylbenzyl)-2-ethyl-8-fluoroquinolin-5-yloxy]acetic Acid A mixture of [4-difluoromethoxy-3-(4-ethanesulfonylbenzyl)-2-ethyl-8-fluoroquinolin-5-yloxy]acetic acid methyl ester (0.080 g), methanol (2.0 mL), tetrahydrofuran (2.0 mL), water (2.0 mL) and lithium hydroxide (0.006 mg) was stirred at room temperature for 45 minutes. The mixture was acidified by the addition of 1.0 M aqueous hydrochloric acid and purified by preparative reverse-phase HPLC using a gradient over 30 minutes of acetonitrile in water to afford title compound as an off-white solid, 0.025 g.

$^1$H NMR (DMSO-d6): δ1.05 (t, J=7.4 Hz, 3H), 1.45 (t, J=7.4 Hz, 3H), 2.80 (q, J=7.4 Hz, 2H), 3.25 (q, J=7.4 Hz, 2H), 4.45 (s, 2H), 4.90 (s, 2H), 7.00 (dd, J=3.6, 8.8 Hz, 1H), 7.30 (t, J=75 Hz, 1H), 7.35 (d, J=8.3 Hz, 2H), 7.55 (dd, J=8.8, 10.0 Hz, 1H), 7.80 (d, J=8.3 Hz, 2H).

MS: ESI (+ve) (Method A): 498 (M+H)$^+$, Retention time 10.2 min.

Example 61

[2-difluoromethoxy-3-(4-ethanesulfonylbenzyl)-8-fluoro-4-methylquinolin-5-yloxy]acetic Acid

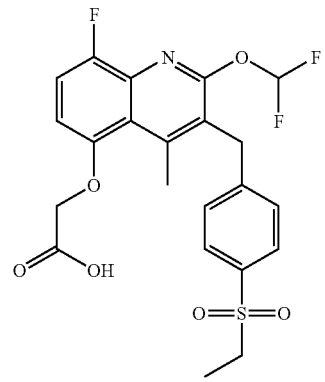

Preparation 61a

2-(4-ethanesulfonylbenzyl)-3-oxothiobutyric acid S-tert-butyl Ester

The title compound was prepared by the method of Preparation 34a using 1-bromomethyl-4-ethanesulfonylbenzene and 3-oxothiobutyric acid S-tert-butyl ester.

$^1$H NMR (CDCl$_3$): δ 1.30 (t, J=7.4 Hz, 3H), 1.50 (s, 9H), 1.80 (s, 3H), 3.10 (q, J=7.4 Hz, 2H), 3.80 (s, 2H), 7.40 (d, J=8.3 Hz, 2H), 7.80 (d, J=8.3 Hz, 2H).

Preparation 61b

2-(4-ethanesulfonylbenzyl)-N-(2-fluoro-5-hydroxyphenyl)-3-oxobutyramide

The title compound was prepared by the method of Preparation 34b using 3-amino-4-fluorophenol and 2-(4-ethanesulfonylbenzyl)-3-oxothiobutyric acid S-tert-butyl ester.

Preparation 61c

3-(4-ethanesulfonylbenzyl)-8-fluoro-5-hydroxy-4-methyl-1H-quinolin-2-one

The title compound was prepared by the method of Preparation 34c using 2-(4-ethanesulfonylbenzyl)-N-(2-fluoro-5-hydroxyphenyl)-3-oxobutyramide $^1$H NMR (DMSO-d6): δ 1.05 (t, J=7.3 Hz, 3H), 2.60 (s, 3H), 3.20 (q, J=7.3 Hz, 2H), 4.15 (s, 2H), 6.50 (dd, J=4.2, 8.7 Hz, 1H), 7.20 (m, 1H), 7.45 (d, J=8.2 Hz, 2H), 7.75 (d, J=8.2 Hz, 2H), 10.20 (br s, 1H), 11.45 (s 1H).

Preparation 61d

[3-(4-ethanesulfonylbenzyl)-8-fluoro-4-methyl-2-oxo-1,2-dihydroquinolin-5-yloxy]acetic Acid Methyl Ester The title compound was prepared by the method of Preparation 34d using 3-(4-ethanesulfonylbenzyl)-8-fluoro-5-hydroxy-4-methyl-1H-quinolin-2-one MS: ESI (+ve) (Method B): 448 (M+H)$^+$, Retention time 3.0 min.

Preparation 61e

[2-difluoromethoxy-3-(4-ethanesulfonylbenzyl)-8-fluoro-4-methylquinolin-5-yloxy]acetic Acid Methyl Ester A mixture of [3-(4-ethanesulfonylbenzyl)-8-fluoro-4-methyl-2-oxo-1,2-dihydroquinolin-5-yloxy]acetic acid methyl ester (0.33 g), N,N-dimethylformamide (5.0 mL), potassium carbonate (0.16 g) and acetic acid chlorodifluoromethyl ester (1.2 mL) was stirred at 70° C. for 3 days. The mixture was diluted with saturated aqueous ammonium chloride solution, extracted with ethyl acetate and the combined extracts washed with saturated aqueous sodium chloride solution and then dried over magnesium sulfate. The solvent was removed under reduced pressure and purification of the residue by column chromatography on silica gel, eluting with dichloromethane gave title as a white solid, 0.10 g.

$^1$H NMR (CDCl$_3$): δ 1.25 (t, J=7.4 Hz, 3H), 2.90 (s, 3H), 3.10 (q, J=7.4 Hz, 2H), 3.85 (s, 3H), 4.35 (s, 2H), 4.75 (s, 2H), 6.65 (dd, J=3.9, 8.8 Hz, 1H), 7.25 (m, 1H), 7.35 (d, J=8.4 Hz, 2H), 7.80 (d, J=8.4 Hz, 2H), 7.80 (t, J=73 Hz, 1H).

MS: ESI (+ve) (Method B): 498 (M+H)$^+$, Retention time 3.9 min.

Preparation 61f

[2-difluoromethoxy-3-(4-ethanesulfonylbenzyl)-8-fluoro-4-methylquinolin-5-yloxy]acetic Acid A mixture of [2-difluoromethoxy-3-(4-ethanesulfonylbenzyl)-8-fluoro-4-methylquinolin-5-yloxy]acetic acid methyl ester (0.10 g), methanol (2.0 mL), tetrahydrofuran (2.0 mL), water (2.5 mL) and lithium hydroxide (0.017 mg) was stirred at room temperature for 1 hour. The mixture was acidified by the addition of 1.0 M aqueous hydrochloric acid and purified by preparative reverse-phase HPLC, using a gradient over 30 minutes of acetonitrile in water to afford title compound as a white solid, 0.070 g.

$^1$H NMR (DMSO-d6): δ 1.05 (t, J=7.3 Hz, 3H), 2.90 (s, 3H), 3.25 (q, J=7.3 Hz, 2H), 4.35 (s, 2H), 4.80 (s, 2H), 6.95 (dd, J=4.0, 8.9 Hz, 1H), 7.40 (d, J=8.4 Hz, 2H), 7.50 (dd, J=8.9, 9.7 Hz, 1H), 7.80 (d, J=8.4 Hz, 2H), 7.85 (t, J=72 Hz, 1H).

MS: ESI (+ve) (Method A): 484 (M+H)$^+$, Retention time 10.8 min.

Example 62

[8-chloro-3-(4-chloro-2-fluorobenzyl)-4-difluoromethoxy-2-ethylquinolin-5-yloxy]acetic Acid

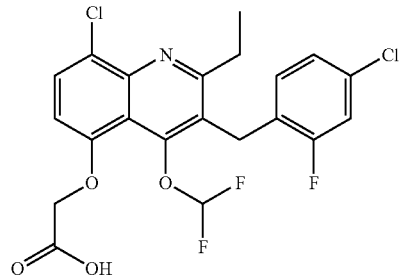

Preparation 62a

2-(4-chloro-2-fluorobenzyl)-3-oxopentanoic Acid Methyl Ester

A suspension of potassium tert-butoxide (1.6 g) in anhydrous tetrahydrofuran (75 mL) at 0° C. was treated with a mixture of tert-butanol (1.0 mL) and 3-oxopentanoic acid methyl ester (1.5 g). After stirring at 0° C. for 45 minutes a solution of 1-bromomethyl-4-chloro-2-fluorobenzene (2.6 g) in tetrahydrofuran (25 mL) was added and the resulting mixture stirred at room temperature for 17 hours. The mixture was diluted with water and the tetrahydrofuran removed under reduced pressure. The mixture was extracted with ethyl acetate and the combined extracts washed with saturated aqueous sodium chloride solution and then dried over magnesium sulfate. The solvent was removed under reduced pressure and the residue purified by column chromatography on silica gel, eluting with a mixture of ethyl acetate and cyclohexane (1:19 to 1:9 by volume) to afford title compound, 1.4 g.

MS: ESI (+ve) (Method B): 273 (M+H)⁺, Retention time 3.8 min.

Preparation 62b

[8-chloro-3-(4-chloro-2-fluorobenzyl)-2-ethyl-4-oxo-1,4-dihydroquinolin-5-yloxy]acetic Acid Methyl Ester A mixture of (3-amino-4-chlorophenoxy)acetic acid methyl ester (0.37 g), 2-(4-chloro-2-fluorobenzyl)-3-oxopentanoic acid methyl ester (0.60 g), polyphosphoric acid (3 g) and dioxane (10 mL) was heated at 120° C. for 23 hours. The reaction mixture was cooled to room temperature, diluted with water and extracted with ethyl acetate. The combined extracts were washed with water, dried over magnesium sulfate and the solvent removed under reduced pressure. The residue was purified by column chromatography on silica gel, eluting with a mixture of ethyl acetate and cyclohexane (1:4 to 1:1 by volume) to afford title compound, 0.082 g.

¹H NMR (CD₃OD): δ 1.25 (t, J=7.6 Hz, 3H), 2.85 (q, J=7.6 Hz, 2H), 3.75 (s, 3H), 4.00 (s, 2H), 4.85 (s, 2H), 6.70 (d, J=8.8 Hz, 1H), 7.00-7.10 (m, 2H), 7.15 (dd, J=1.8, 9.9 Hz, 1H), 7.65 (d, J=8.8 Hz, 1H).

MS: ESI (+ve) (Method B): 438 (M+H)⁺, Retention time 3.8 min.

Preparation 62c

[8-chloro-3-(4-chloro-2-fluorobenzyl)-4-difluoromethoxy-2-ethyl-quinolin-5-yloxy]acetic Acid Methyl Ester The title compound was prepared by the method of Preparation 34e using [8-chloro-3-(4-chloro-2-fluorobenzyl)-2-ethyl-4-oxo-1,4-dihydroquinolin-5-yloxy]acetic acid methyl ester MS: ESI (+ve) (Method B): 488 (M+H)⁺, Retention time 4.8 min.

Preparation 62d

[8-chloro-3-(4-chloro-2-fluorobenzyl)-4-difluoromethoxy-2-ethylquinolin-5-yloxy]acetic Acid A mixture of [8-chloro-3-(4-chloro-2-fluorobenzyl)-4-difluoromethoxy-2-ethyl-quinolin-5-yloxy]acetic acid methyl ester (0.075 g), tetrahydrofuran (2.0 mL) and 1.0 M aqueous lithium hydroxide solution (0.20 mL) was stirred at room temperature for 2 hour. The solvent was removed under reduced pressure and the residue diluted with water. The pH of mixture was adjusted to 4 by the addition of sodium dihydrogenphosphate and extracted with ethyl acetate. The combined extracts were dried over magnesium sulfate and solvent removed under reduced pressure. The residue was crystallised from a mixture of acetonitrile and water to afford title compound, 0.057 g.

¹H NMR (CDCl₃): δ 1.35 (t, J=7.4 Hz, 3H), 2.90 (q, J=7.4 Hz, 2H), 4.35 (s, 2H), 4.90 (s, 2H), 6.65 (d, J=8.1 Hz, 1H), 6.75 (d, J=8.6 Hz, 1H), 6.35 (t=J 75 Hz, 1H), 6.95 (m, 1H), 7.10 (m, 1H), 7.75 (d, J=8.6 Hz).

MS: ESI (+ve) (Method A): 474 (M+H)⁺, Retention time 13.8 min.

Example 63

[3-(4-chloro-2-fluorobenzyl)-4-difluoromethoxy-2-ethyl-8-fluoroquinolin-5-yloxy]acetic acid

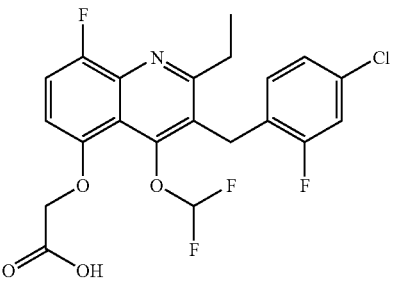

Preparation 63a

[3-(4-chloro-2-fluorobenzyl)-2-ethyl-8-fluoro-4-oxo-1,4-dihydroquinolin-5-yloxy]acetic Acid Methyl Ester A mixture of (3-amino-4-fluorophenoxy)acetic acid methyl ester (0.80 g), 2-(4-chloro-2-fluorobenzyl)-3-oxopentanoic acid methyl ester (1.4 g), polyphosphoric acid (5 g) and dioxane (10 mL) was heated at 120° C. for 23 hours. The reaction mixture was cooled to room temperature, diluted with water and extracted with ethyl acetate. The combined extracts were washed with water, dried over magnesium sulfate and the solvent removed under reduced pressure. The residue was purified by column chromatography on silica gel, eluting with a mixture of ethyl acetate and cyclohexane (3:7 to 7:10 by volume) to afford title compound, 0.20 g.

¹H NMR (CD₃OD): δ 1.20 (t, J=7.1 Hz, 3H), 2.08 (q, J=7.1 Hz, 2H), 3.75 (s, 3H), 4.00 (s, 2H), 4.80 (s, 2H), 6.65 (m 1H), 7.00-7.15 (m, 3H), 7.35 (t, J=9.7 Hz, 1H).

MS: ESI (+ve) (Method B): 424 (M+H)⁺, Retention time 3.4 min.

Preparation 63b

[3-(4-chloro-2-fluorobenzyl)-4-difluoromethoxy-2-ethyl-8-fluoroquinolin-5-yloxy]acetic Acid Methyl Ester A mixture of [3-(4-chloro-2-fluorobenzyl)-2-ethyl-8-fluoro-4-oxo-1,4-dihydroquinolin-5-yloxy]acetic acid methyl ester (0.20 g), N,N-dimethylformamide (3.0 mL), potassium carbonate (0.20 g) and acetic acid chlorodifluoromethyl ester (0.15 mL) was stirred at 80° C. for 4 days. The mixture was diluted with water and extracted with ethyl acetate. The combined extracts were washed with saturated aqueous sodium chloride solution, dried over magnesium sulfate and the solvent removed under reduced pressure. Purification of the residue by column chromatography on silica gel, eluting with a mixture of cyclohexane and dichloromethane (1:4 by volume) gave title compound, 0.071 g.

¹H NMR (CDCl₃): δ 1.30 (t, J=7.4 Hz, 3H), 2.90 (q, J=7.4 Hz, 2H), 3.80 (s, 3H), 4.35 (s, 2H), 4.80 (s, 2H), 6.65-6.75 (m, 2H), 6.95 (m, 1H), 7.10 (m, 1H), 7.25-7.35 (m, 2H).

Preparation 63

[3-(4-chloro-2-fluorobenzyl)-4-difluoromethoxy-2-ethyl-8-fluoroquinolin-5-yloxy]acetic Acid A mixture of [3-(4-chloro-2-fluorobenzyl)-4-difluoromethoxy-2-ethyl-8-fluoroquinolin-5-yloxy]acetic acid methyl ester (0.071 g), tetrahydrofuran (5.0 mL) and 1.0 M aqueous lithium hydroxide solution (0.30 mL) was stirred at room temperature for 2 hour. The solvent was removed under reduced pressure and the residue was diluted with water. The pH of mixture was adjusted to 4 by the addition of sodium dihydrogenphosphate and extracted with ethyl acetate. The combined extracts were dried over magnesium sulfate and the solvent removed under reduced pressure to afford title compound, 0.064 g.

$^1$H NMR (CDCl$_3$): δ 1.3 (t, J=7.5 Hz, 3H), 2.90 (q, J=7.5 Hz, 2H), 4.35 (s, 2H), 4.85 (s, 2H), 6.70 (m, 1H), 6.75 (dd, J=3.6, 8.7, Hz, 1H), 6.90 (t, J=75 Hz, 1H), 6.95 (m, 1H), 7.10 (dd, J=2.1, 9.7 Hz, 1H), 7.30 (t, J=9.3 Hz, 1H).

MS: ESI (+ve) (Method A): 458 (M+H)$^+$, Retention time 12.7 min.

Example 64

{4-difluoromethoxy-2-ethyl-8-fluoro-3-[4-(morpholine-4-sulfonyl)benzyl]quinolin-5-yloxy}acetic acid

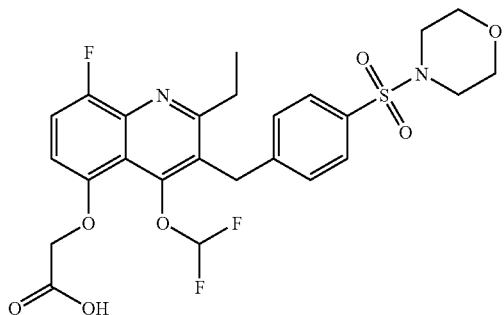

Preparation 64a 4-(4-bromomethylbenzenesulfonyl)morpholine

A solution of 4-bromomethylbenzenesulfonyl chloride (0.81 g) in anhydrous diethyl ether (5.0 mL) at −10° C. was treated with a solution of morpholine (0.26 mL) and triethylamine (0.46 mL) in anhydrous diethyl ether (5.0 mL). The resulting mixture was warmed to room temperature over 1 hour and then stirred at this temperature for 17 hours. The mixture was diluted with water, extracted with dichloromethane and the combined extracts washed with saturated aqueous sodium chloride solution and then dried over magnesium sulfate. The solvent was removed under reduced pressure and the residue purified by column chromatography on silica gel, eluting with a mixture of ethyl acetate and cyclohexane (3:7 by volume) to afford title compound, 0.53 g.

$^1$H NMR (CD$_3$OD): δ 2.95 (m, 4H), 3.70 (m, 4H), 4.65 (s, 2H), 7.70 (d, J=8.2 Hz, 2H), 7.75 (d, J=8.2 Hz, 2H).

Preparation 64b

2-[4-(morpholine-4-sulfonyl)benzyl]-3-oxopentanoic Acid Methyl Ester

A suspension of potassium tert-butoxide (0.26 g) in anhydrous tetrahydrofuran (40 mL) at 0° C. was treated with a mixture of tert-butanol (1.0 mL) and 3-oxopentanoic acid methyl ester (0.25 mL). The mixture was stirred at 0° C. for 45 minutes and then a solution of 4-(4-bromomethylbenzenesulfonyl)morpholine (0.53 g) in tetrahydrofuran (10 mL) was added and the resulting mixture warmed to room temperature over 1 hour and then stirred at this temperature for 17 hours. The mixture was concentrated under reduced pressure and the residue diluted with water and extracted with ethyl acetate. The combined extracts were washed with saturated aqueous sodium chloride solution and dried over magnesium sulfate. The solvent was removed under reduced pressure and the residue purified by column chromatography on silica gel, eluting with a mixture of ethyl acetate and cyclohexane (1:1 by volume) to afford title compound, 0.41 g.

MS: ESI (+ve) (Method B): 370 (M+H)$^+$, Retention time 3.2 min.

Preparation 64c

{2-ethyl-8-fluoro-3-[4-(morpholine-4-sulfonyl)benzyl]-4-oxo-1,4-dihydroquinolin-5-yloxy}acetic Acid Methyl Ester A mixture of (3-amino-4-fluorophenoxy)acetic acid methyl ester (0.22 g), 2-[4-(morpholine-4-sulfonyl)benzyl]-3-oxopentanoic acid methyl ester (0.41 g), polyphosphoric acid (1 g) and dioxane (20 mL) was heated at 130° C. for 18 hours. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of ethyl acetate, dichloromethane and methanol (1:4:0 to 1:1:0 to 0:9:1 by volume) to afford title compound, 0.14 g.

$^1$H NMR (DMSO-d6): δ 1.00 (t, J=7.3 Hz, 3H), 2.70 (q, J=7.3 Hz, 2H), 2.80 (m, 4H), 3.60 (m, 4H), 3.70 (s, 3H), 4.00 (s, 2H), 4.80 (s, 2H), 6.65 (m, 1H), 7.40 (m, 1H) 7.45 (d, J=8.2 Hz, 2H), 7.60 (d, J=8.2 Hz, 2H), 11.10 (br s, 1H).

Preparation 64d

{4-difluoromethoxy-2-ethyl-8-fluoro-3-[4-(morpholine-4-sulfonyl)benzyl]quinolin-5-yloxy}acetic Acid Methyl Ester A mixture of {2-ethyl-8-fluoro-3-[4-(morpholine-4-sulfonyl)benzyl]-4-oxo-1,4-dihydroquinolin-5-yloxy}acetic acid methyl ester (0.14 g), N,N-dimethylformamide (3.0 mL), potassium carbonate (0.12 g) and acetic acid chlorodifluoromethyl ester (0.15 mL) was stirred at 80° C. for 17 hours. The mixture was cooled to room temperature, diluted with water and extracted with ethyl acetate. The combined extracts were dried over magnesium sulfate and the solvent removed under reduced pressure. Purification of the residue by column chromatography on silica gel, eluting with a mixture of cyclohexane and dichloromethane (1:1 by volume) gave title compound, 0.092 g.

$^1$H NMR (CDCl$_3$): δ 1.30 (t, J=7.2 Hz, 3H), 2.90 (q, J=7.2 Hz, 2H), 2.95 (m, 4H), 3.70 (m, 4H), 3.85 (s, 3H), 4.45 (s, 2H), 4.85 (s, 2H), 6.70 (dd, J=3.7, 8.7 Hz, 1H), 7.00 (t, J=75 Hz, 1H), 7.25 (d, J=8.3 Hz, 2H), 7.30 (dd, J=8.7, 9.6 Hz, 1H), 7.65 (J=8.3 Hz, 2H).

Preparation 64e

{4-difluoromethoxy-2-ethyl-8-fluoro-3-[4-(morpholine-4-sulfonyl)benzyl]quinolin-5-yloxy}acetic Acid A mixture of {4-difluoromethoxy-2-ethyl-8-fluoro-3-[4-(morpholine-4-sulfonyl)benzyl]quinolin-5-yloxy}acetic acid methyl ester (0.16 g), tetrahydrofuran (5.0 mL) and 1.0 M aqueous lithium hydroxide solution (0.32 mL) was stirred at room temperature for 2 hour. The solvent was removed under reduced pressure and the residue was diluted with water. The pH of mixture was adjusted to 4 by the addition of sodium dihydrogenphosphate and extracted with ethyl acetate. The combined extracts were washed with saturated aqueous sodium chloride solution and dried over magnesium sulfate. The solvent was removed under reduced pressure and the residue triturated with a mixture of acetonitrile and water to afford title compound, 0.083 g.

$^1$H NMR (DMSO-d6): δ 1.15 (t, J=7.4 Hz, 3H), 2.80 (m, 6H), 3.60 (m, 4H), 4.45 (s, 2H), 4.90 (s, 2H), 7.00 (dd, J=3.7 Hz, 8.9 Hz, 1H), 7.30 (t, J=75 Hz, 1H), 7.35 (d, J=8.3 Hz, 2H), 7.55 (dd, J=8.9, 10.1 Hz, 1H), 7.65 (d, J=8.3 Hz, 2H).

MS: ESI (+ve) (Method A): 555 (M+H)$^+$, Retention time 10.0 min.

MS: ESI (+ve) (Method B): 555 (M+H)$^+$, Retention time 3.5 min.

Example 65

{4-difluoromethoxy-2-ethyl-8-fluoro-3-[4-(pyrrolidine-1-carbonyl)benzyl]quinolin-5-yloxy}acetic Acid

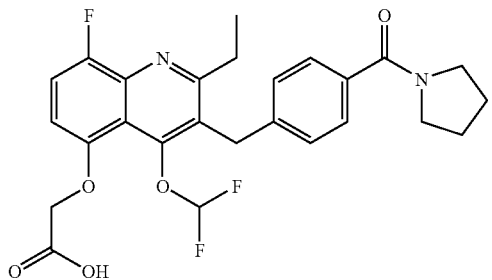

Preparation 65a (4-chloromethylphenyl)pyrrolidin-1-ylmethanone

A solution of 4-chloromethylbenzoyl chloride (5.0 g) and pyrrolidine (2.2 mL) in dichloromethane (30 mL) at 0° C. was treated with ethyldiisopropylamine (5.2 mL). The resulting mixture was warmed to room temperature over 1 hour and then stirred at this temperature for 2 hours. The mixture was diluted with 1.0 M aqueous hydrochloric acid, extracted with dichloromethane and the combined extracts washed with saturated aqueous sodium chloride solution and then dried over magnesium sulfate. The solvent was removed under reduced pressure to afford title compound, 6.0 g.

$^1$H NMR (CDCl$_3$): δ 1.85-2.00 (m, 4H), 3.40 (t, J=6.5 Hz, 2H), 3.60 (t, J=6.8 Hz, 2H), 4.60 (s, 2H), 7.40 (d, J=8.2 Hz, 2H), 7.50 (d, J=8.2 Hz, 2H).

Preparation 65b 3-oxo-2-[4-(pyrrolidine-1-carbonyl)benzyl]pentanoic Acid Methyl Ester A suspension of potassium tert-butoxide (1.4 g) in anhydrous tetrahydrofuran (40 mL) at 0° C. was treated with a mixture of tert-butanol (1.0 mL) and 3-oxopentanoic acid methyl ester (1.3 mL). The mixture was stirred at 0° C. for 45 minutes and then a solution of (4-chloromethylphenyl)pyrrolidin-1-ylmethanone (2.0 g) in tetrahydrofuran (10 mL) was added and the resulting mixture heated at 70° C. for 24 hours. The mixture was cooled to room temperature, diluted with water and the tetrahydrofuran removed under reduced pressure. The residue was extracted with ethyl acetate and the combined extracts washed with saturated aqueous sodium chloride solution and dried over magnesium sulfate. The solvent was removed under reduced pressure and the residue purified by column chromatography on silica gel, eluting with a mixture of ethyl acetate and cyclohexane (3:7 by volume) to afford title compound, 1.1 g.

MS: ESI (+ve) (Method B): 318 (M+H)$^+$, Retention time 3.0 min.

Preparation 65c

{2-ethyl-8-fluoro-4-oxo-3-[4-(pyrrolidine-1-carbonyl)benzyl]-1,4-dihydroquinolin-5-yloxy}acetic Acid Methyl Ester A mixture of (3-amino-4-fluorophenoxy)acetic acid methyl ester (0.39 g), 3-oxo-2-[4-(pyrrolidine-1-carbonyl) benzyl]pentanoic acid methyl ester (1.0 g), polyphosphoric acid (2 g) and dioxane (20 mL) was heated at 120° C. for 18 hours. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of dichloromethane and methanol (9:1 by volume) to afford title compound, 0.25 g.

MS: ESI (+ve) (Method B): 467 (M+H)$^+$, Retention time 2.7 min.

Preparation 65d

{4-difluoromethoxy-2-ethyl-8-fluoro-3-[4-(pyrrolidine-1-carbonyl)benzyl]quinolin-5-yloxy}acetic Acid Methyl Ester A mixture of {2-ethyl-8-fluoro-4-oxo-3-[4-(pyrrolidine-1-carbonyl)benzyl]-1,4-dihydroquinolin-5-yloxy}acetic acid methyl ester (0.25 g), N,N-dimethylformamide (5.0 mL), potassium carbonate (0.22 g) and acetic acid chlorodifluoromethyl ester (0.28 mL) was stirred at 80° C. for 17 hours. The mixture was cooled to room temperature, diluted with water and extracted with ethyl acetate. The combined extracts were dried over magnesium sulfate and the solvent removed under reduced pressure. Purification of the residue by column chromatography on silica gel, eluting with a mixture of cyclohexane and dichloromethane (1:1 by volume) gave title compound, 0.14 g.

MS: ESI (+ve) (Method B): 517 (M+H)$^+$, Retention time 3.7 min.

Preparation 65e

{4-difluoromethoxy-2-ethyl-8-fluoro-3-[4-(pyrrolidine-1-carbonyl)benzyl]quinolin-5-yloxy}acetic Acid A mixture of {4-difluoromethoxy-2-ethyl-8-fluoro-3-[4-(pyrrolidine-1-carbonyl)benzyl]quinolin-5-yloxy}acetic acid methyl ester (0.14 g), tetrahydrofuran (3.0 mL) and 1.0 M aqueous lithium hydroxide solution (0.55 mL) was stirred at room temperature for 2 hours. The solvent was removed under reduced pressure and the residue was diluted with water. The pH of mixture was adjusted to 4 by the addition of sodium dihydrogenphosphate and the resulting precipitate was collected by filtration, washed with water and dried to afford title compound, 0.11 g.

$^1$H NMR (DMSO-d6): δ 1.15 (t, J=7.4 Hz, 3H), 1.75 (m, 4H), 2.85 (q, J=7.4 Hz, 2H), 3.35 (t, J=6.4 Hz, 2H), 3.40 (t, J=6.8 Hz, 2H), 4.40 (s, 2H), 4.85 (s, 2H), 7.00 (dd, J=3.8, 8.8 Hz, 1H), 7.15 (d, J=8.2 Hz, 2H), 7.35 (t, J=75 Hz, 1H), 7.45 (d, J=8.2 Hz, 2H), 7.50 (dd, J=8.8, 10.1 Hz, 1H).

MS: ESI (+ve) (Method A): 503 (M+H)$^+$, Retention time 9.4 min.

Example 66

2-[8-chloro-3-(4-chlorobenzyl)-2-difluoromethoxy-4-methylquinolin-5-yloxy]-2-methylpropionic Acid

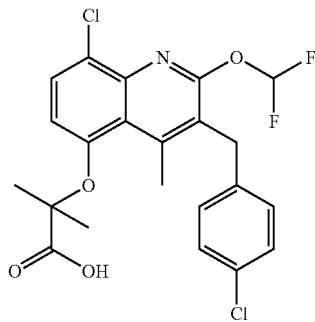

Preparation 66a

2-[8-chloro-3-(4-chlorobenzyl)-4-methyl-2-oxo-1,2-dihydroquinolin-5-yloxy]-2-methylpropionic Acid Methyl Ester A mixture of 8-chloro-3-(4-chlorobenzyl)-5-hydroxy-4-methyl-1H-quinolin-2-one (0.14 g), N,N-dimethylformamide (10 mL), sodium hydride (60% in oil, 0.020 g) and 2-bromo-2-methylpropionic acid methyl ester (0.11 g) was stirred at 100° C. for 3 days. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of ethyl acetate and cyclohexane (3:7 by volume) to afford title compound, 0.056 g.

MS: ESI (+ve) (Method B): 434 (M+H)$^+$, Retention time 4.3 min.

Preparation 66b

2-[8-chloro-3-(4-chlorobenzyl)-2-difluoromethoxy-4-methylquinolin-5-yloxy]-2-methylpropionic Acid Methyl Ester The title compound was prepared by the method of Preparation 65d using 2-[8-chloro-3-(4-chlorobenzyl)-4-methyl-2-oxo-1,2-dihydroquinolin-5-yloxy]-2-methylpropionic acid methyl ester.

MS: ESI (+ve) (Method B): 484 (M+H)$^+$, Retention time 5.0 min.

Preparation 66c

2-[8-chloro-3-(4-chlorobenzyl)-2-difluoromethoxy-4-methylquinolin-5-yloxy]-2-methylpropionic Acid A mixture of 2-[8-chloro-3-(4-chlorobenzyl)-2-difluoromethoxy-4-methylquinolin-5-yloxy]-2-methylpropionic acid methyl ester (0.030 g), tetrahydrofuran (2.0 mL) and 1.0 M aqueous lithium hydroxide solution (2.0 mL) was stirred at room temperature for 24 hours. The solvent was removed under reduced pressure, diluted with water and the pH adjusted to 4 by the addition of sodium dihydrogenphosphate. The mixture was extracted with ethyl acetate and the combined extracts dried over magnesium sulfate. The solvent was removed under reduced pressure to afford title compound, 0.027 g.

$^1$H NMR (CDCl$_3$): δ 1.75 (s, 6H), 2.85 (s, 3H), 4.20 (s, 2H), 6.60 (d, J=8.4 Hz, 1H), 7.05 (d, J=8.5 Hz, 2H), 7.25 (d, J=8.5 Hz, 2H), 7.55 (d, J=8.4 Hz, 1H), 7.85 (t, J=73 Hz, 1H).

MS: ESI (+ve) (Method A): 470 (M+H)$^+$, Retention time 13.7 min.

Example 67

2-[3-(2,4-dichlorobenzyl)-2-difluoromethoxy-8-fluoro-4-methylquinolin-5-yloxy]propionic Acid

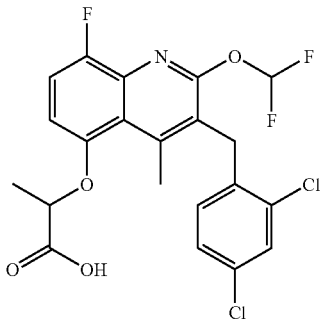

Preparation 67a

2-[3-(2,4-dichlorobenzyl)-8-fluoro-4-methyl-2-oxo-1,2-dihydroquinolin-5-yloxy]propionic Acid Methyl Ester The title compound was prepared by the method of Preparation 34d using 3-(2,4-dichlorobenzyl)-8-fluoro-5-hydroxy-4-methyl-1H-quinolin-2-one and 2-bromopropionic acid methyl ester.

MS: ESI (+ve) (Method B): 438 (M+H)$^+$, Retention time 4.2 min.

Preparation 67b

2-[3-(2,4-dichlorobenzyl)-2-difluoromethoxy-8-fluoro-4-methylquinolin-5-yloxy]propionic Acid Methyl Ester The title compound was prepared by the method of Preparation 65d using 2-[3-(2,4-dichlorobenzyl)-8-fluoro-4-methyl-2-oxo-1,2-dihydroquinolin-5-yloxy]propionic acid methyl ester.

MS: ESI (+ve) (Method B): 488 (M+H)$^+$, Retention time 5.0 min.

Preparation 67c

2-[3-(2,4-dichlorobenzyl)-2-difluoromethoxy-8-fluoro-4-methylquinolin-5-yloxy]propionic Acid A mixture of 2-[3-(2,4-dichlorobenzyl)-2-difluoromethoxy-8-fluoro-4-methylquinolin-5-yloxy]propionic acid methyl ester (0.15 g), methanol (5.0 mL), water (0.2 mL) and 5.0 M aqueous lithium hydroxide solution (0.090 mL) was stirred at room temperature for 24 hours. The mixture was filtered and the filtrate was concentrated under reduced pressure. The residue was acidified by the addition of glacial acetic acid and the resulting precipitate collected by filtration, washed with water and a mixture of water and methanol (1:1 by volume) and then dried to afford title compound as a white solid, 0.13 g.

$^1$H NMR (DMSO-d6): δ 1.50 (d, J=6.6 Hz, 3H), 2.75 (s, 3H), 4.15 (s, 2H), 4.95 (q, J=6.6 Hz, 1H), 6.70 (d, J=8.4 Hz, 1H), 6.80 (dd, J=2.2, 8.4 Hz, 1H), 7.20 (dd, J=2.2, 8.4 Hz, 1H), 7.40 (dd, J=9.0, 10 Hz, 1H), 7.65 (d, J=2.2 Hz, 1H), 7.75 (t, J=72 Hz, 1H).

MS: ESI (+ve) (Method A): 474 (M+H)$^+$, Retention time 14.0 min.

Example 68

(S)-2-[3-(2,4-dichlorobenzyl)-2-difluoromethoxy-8-fluoro-4-methylquinolin-5-yloxy]propionic Acid

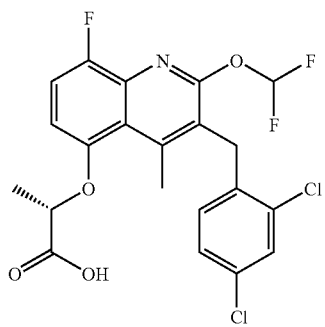

Preparation 68a

(S)-2-[3-(2,4-dichlorobenzyl)-8-fluoro-4-methyl-2-oxo-1,2-dihydroquinolin-5-yloxy]propionic Acid Methyl Ester A mixture of 3-(2,4-dichlorobenzyl)-8-fluoro-5-hydroxy-4-methyl-1H-quinolin-2-one (0.40 g), N,N-dimethylformamide (5.0 mL), potassium carbonate (0.17 g) and (R)-2-chloropropionic acid methyl ester (0.15 g) was stirred at 40° C. for 24 hours. The mixture was diluted with water and extracted with ethyl acetate. The combined extracts were washed saturated aqueous sodium chloride solution, dried over magnesium sulfate and the solvent removed under reduced pressure. The residue was purified by column chromatography on silica gel, eluting with a mixture of toluene, dichloromethane and ethyl acetate (1:1:0 to 0:1:0 to 0:10:1 by volume) to afford title compound as a cream solid, 0.21 g.

MS: ESI (+ve) (Method B): 438 (M+H)$^+$, Retention time 4.2 min.

Preparation 68b

(S)-2-[3-(2,4-dichlorobenzyl)-2-difluoromethoxy-8-fluoro-4-methylquinolin-5-yloxy]propionic Acid Methyl Ester The title compound was prepared by the method of Preparation 65d using (S)-2-[3-(2,4-dichlorobenzyl)-8-fluoro-4-methyl-2-oxo-1,2-dihydroquinolin-5-yloxy]propionic acid methyl ester.

MS: ESI (+ve) (Method B): 488 (M+H)$^+$, Retention time 5.0 min.

Preparation 68c

(S)-2-[3-(2,4-dichlorobenzyl)-2-difluoromethoxy-8-fluoro-4-methylquinolin-5-yloxy]propionic Acid A mixture of (S)-2-[3-(2,4-dichlorobenzyl)-2-difluoromethoxy 8-fluoro-4-methylquinolin-5-yloxy]propionic acid methyl ester (0.070 g), methanol (3.0 mL), water (0.1 mL) and 5.0 M aqueous lithium hydroxide solution (0.060 mL) was stirred at room temperature for 18 hours. The mixture was acidified by the addition of glacial acetic acid and concentrated under reduced pressure. The residue was triturated with water to afford title compound as a white solid, 0.067 g.

$^1$H NMR (DMSO-d6): δ 1.45 (d, J=6.6 Hz, 3H), 2.75 (s, 3H), 4.15 (s, 2H), 4.65 (q, J=6.6 Hz, 1H), 6.70 (d, 4=8.5 Hz, 1H), 6.75 (dd, J=4.2, 8.8 Hz, 1H), 7.20 (dd, J=2.2, 8.5 Hz, 1H), 7.40 (dd, J=8.8, 9.9 Hz, 1H), 7.65 (d, J=2.2 Hz, 1H), 7.75 (t, J=72 Hz, 1H).

MS: ESI (+ve) (Method A): 474 (M+H)$^+$, Retention time 14.0 min.

Example 69

2-[8-chloro-3-(4-chlorobenzyl)-2-difluoromethoxy-4-methylquinolin-5-yloxy]propionic Acid

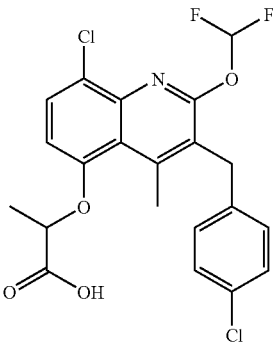

Preparation 69a

2-[8-chloro-3-(4-chlorobenzyl)-4-methyl-2-oxo-1,2-dihydroquinolin-5-yloxy]propionic acid methyl ester The title compound was prepared by the method of Preparation 34d using 8-chloro-3-(4-chlorobenzyl)-5-hydroxy-4-methyl-1H-quinolin-2-one and 2-bromopropionic acid methyl ester.

MS: ESI (+ve) (Method B): 420 (M+H)$^+$, Retention time 4.1 min.

Preparation 69b

2-[8-chloro-3-(4-chlorobenzyl)-2-difluoromethoxy-4-methylquinolin-5-yloxy]propionic Acid Methyl Ester The title compound was prepared by the method of Preparation 65d using 2-[8-chloro-3-(4-chlorobenzyl)-4-methyl-2-oxo-1,2-dihydroquinolin-5-yloxy]propionic acid methyl ester.

MS: ESI (+ve) (Method B): 470 (M+H)$^+$, Retention time 4.8 min.

Preparation 69c

2-[8-chloro-3-(4-chlorobenzyl)-2-difluoromethoxy-4-methylquinolin-5-yloxy]propionic Acid A mixture of 2-[8-chloro-3-(4-chlorobenzyl)-2-difluoromethoxy-4-methylquinolin-5-yloxy]propionic acid methyl ester (0.22 g), tetrahydrofuran (3.0 mL) and 1.0 M aqueous lithium hydroxide solution (1.0 mL) was stirred at room temperature for 3 hours. The mixture was acidified by the addition of sodium dihydrogenphosphate, concentrated under reduced pressure and the residue extracted with ethyl acetate. The combined extracts were washed with saturated aqueous sodium chloride solution, dried over magnesium sulfate and the solvent removed under reduced pressure to afford title compound, 0.20 g.

$^1$H NMR (DMSO-d6): δ1.60 (d, J=6.8 Hz, 3H), 2.85 (s, 3H), 4.20 (s, 2H), 5.10 (q, J=6.8 Hz, 1H), 6.90 (d, J=8.7 Hz, 2H), 7.15 (d, J=8.4 Hz, 2H), 7.35 (d, J=8.4 Hz, 2H), 7.80 (d, J=8.7 Hz, 1H), 7.90 (t, J=72 Hz, 1H).

MS: ESI (+ve) (Method A): 456 (M+H)$^+$, Retention time 13.8 min.

Example 70

(R)-2-[3-(2,4-dichlorobenzyl)-2-difluoromethoxy-8-fluoro-4-methylquinolin-5-yloxy]propionic Acid

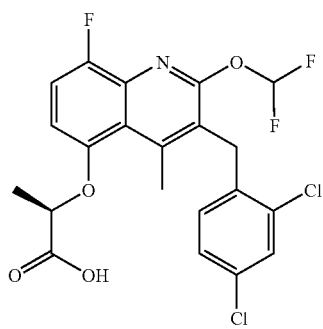

Preparation 70a

(R)-2-[3-(2,4-dichlorobenzyl)-8-fluoro-4-methyl-2-oxo-1,2-dihydroquinolin-5-yloxy]propionic Acid Methyl Ester A mixture of 3-(2,4-dichlorobenzyl)-8-fluoro-5-hydroxy-4-methyl-1H-quinolin-2-one (0.30 g), N,N-dimethylformamide (4.0 mL), potassium carbonate (0.13 g) and (S)-2-chloropropionic acid methyl ester (0.11 g) was stirred at 45° C. for 3 days. The mixture was diluted with water and extracted with ethyl acetate. The combined extracts were washed saturated aqueous sodium chloride solution, dried over magnesium sulfate and the solvent removed under reduced pressure. The residue was purified by column chromatography on silica gel, eluting with a mixture of dichloromethane and ethyl acetate (1:0 to 6:4 by volume) to afford title compound as a pale peach solid, 0.17 g.

MS: ESI (+ve) (Method B): 438 (M+H)$^+$, Retention time 4.2 min.

Preparation 70b

(R)-2-[3-(2,4-dichlorobenzyl)-2-difluoromethoxy-8-fluoro-4-methylquinolin-5-yloxy]propionic Acid Methyl Ester The title compound was prepared by the method of Preparation 65d using (R)-2-[3-(2,4-dichlorobenzyl)-8-fluoro-4-methyl-2-oxo-1,2-dihydroquinolin-5-yloxy]propionic acid methyl ester.

MS: ESI (+ve) (Method B): 488 (M+H)$^+$, Retention time 4.9 min.

Preparation 70c

(R)-2-[3-(2,4-dichlorobenzyl)-2-difluoromethoxy-8-fluoro-4-methylquinolin-5-yloxy]propionic Acid A mixture of (R)-2-[3-(2,4-dichlorobenzyl)-2-difluoromethoxy-8-fluoro-4-methylquinolin-5-yloxy]propionic acid methyl ester (0.054 g), methanol (2.0 mL), water (0.1 mL) and 5.0 M aqueous lithium hydroxide solution (0.044 mL) was stirred at room temperature for 15 hours. The mixture was acidified by the addition of glacial acetic acid, diluted with water and the resulting precipitate collected by filtration to afford title compound as a white solid, 0.048 g.

$^1$H NMR (DMSO-d6): δ 1.50 (d, J=6.7 Hz, 3H), 2.75 (s, 3H), 4.15 (s, 2H), 4.85 (q, J=6.7 Hz, 1H), 6.70 (d, J=8.4 Hz, 1H), 6.75 (dd, J=4.0, 9.0 Hz, 1H), 7.20 (dd, J=2.1, 8.4 Hz, 1H), 7.40 (dd, J=9.0, 9.7 Hz, 1H), 7.65 (d, J=2.1 Hz, 1H), 7.75 (t, J=72 Hz, 1H).

MS: ESI (+ve) (Method A): 474 (M+H)$^+$, Retention time 14.4 min.

Example 71

{8-chloro-4-difluoromethoxy-2-ethyl-3-[4-(pyrrolidine-1-carbonyl)benzyl]quinolin-5-yloxy}acetic Acid

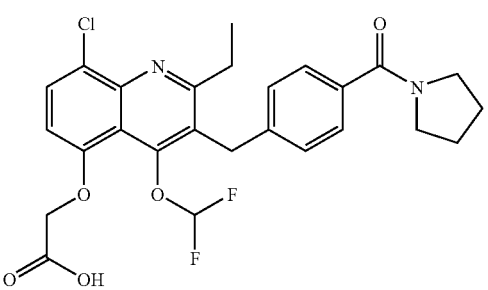

Preparation 70a

{8-chloro-2-ethyl-4-oxo-3-[4-(pyrrolidine-1-carbonyl)benzyl]-1,4-dihydroquinolin-5-yloxy}acetic Acid Methyl Ester A mixture of (3-amino-4-chlorophenoxy)acetic acid methyl ester (1.0 g), 3-oxo-2-[4-(pyrrolidine-1-carbonyl)benzyl]pentanoic acid methyl ester (1.9 g), polyphosphoric acid (6.0 g) and dioxane (20 mL) was heated at 120° C. for 18 hours. The mixture was cooled to room temperature, diluted with water and extracted with ethyl acetate. The combined extracts were dried over magnesium sulfate and the solvent removed under reduced pressure. The residue was purified by column chromatography on silica gel, eluting with a mixture of dichloromethane, ethyl acetate and methanol (9:1:0 to 0:9:1 by volume) to afford title compound, 0.079 g.

MS: ESI (+ve) (Method B): 483 (M+H)+, Retention time 3.0 min.

Preparation 70b

{8-chloro-4-difluoromethoxy-2-ethyl-3-[4-(pyrrolidine-1-carbonyl)benzyl]quinolin-5-yloxy}acetic Acid Methyl Ester The title compounds were prepared by the method of Preparation 65d using {8-chloro-2-ethyl-4-oxo-3-[4-(pyrrolidine-1-carbonyl)benzyl]-1,4-dihydroquinolin-5-yloxy}acetic acid methyl ester.

MS: ESI (+ve) (Method B): 533 (M+H)+, Retention time 4.1 min.

Preparation 70c

{8-chloro-4-difluoromethoxy-2-ethyl-3-[4-(pyrrolidine-1-carbonyl)benzyl]quinolin-5-yloxy}acetic Acid A mixture of {8-chloro-4-difluoromethoxy-2-ethyl-3-[4-(pyrrolidine-1-carbonyl)benzyl]quinolin-5-yloxy}acetic acid methyl ester (0.037 g), tetrahydrofuran (3.0 mL) and 1.0 M aqueous lithium hydroxide solution (1.0 mL) was stirred at room temperature for 1 hour. The mixture was concentrated under reduced pressure, acidified by the addition of sodium dihydrogenphosphate and extracted with ethyl acetate. The combined extracts were dried over magnesium sulfate and the solvent removed under reduced pressure to afford title compound, 0.034 g.

1H NMR (DMSO-d6): δ1.15 (t, J=7.3 Hz, 3H), 1.70-1.80 (m, 4H), 2.80 (q, J=7.3 Hz, 2H), 3.40 (m, 4H), 4.35 (s, 2H), 4.70 (s, 2H), 6.90 (d, J=8.5 Hz, 1H), 7.10 (d, J=8.3 Hz, 2H), 7.35 (d, J=8.3 Hz, 2H), 7.50 (m, 1H), 7.80 (d, J=8.5 Hz, 1H).

MS: ESI (+ve) (Method A): 519 (M+H)+, Retention time 11.1 min.

Example 72

{3-[2-chloro-4-(pyrrolidine-1-carbonyl)benzyl]-4-difluoromethoxy-2-ethyl-8-fluoroquinolin-5-yloxy}acetic Acid

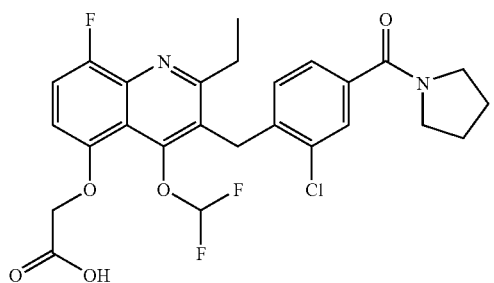

Preparation 72a 4-bromomethyl-3-chlorobenzonitrile

A mixture of 3-chloro-4-methylbenzonitrile (4.8 g), N-bromosuccinimide (5.5 g), dibenzoyl peroxide (0.43 g) and carbon tetrachloride (30 mL) was heated a reflux for 2 hours. The mixture was cooled to room temperature, filtered and washed with dichloromethane. The filtrated was washed with water, dried over sodium sulfate and the solvent removed under reduced pressure. Purification of the residue by column chromatography on silica gel, eluting with a mixture of cyclohexane and ethyl acetate (1:0 to 19:1 by volume) gave title compound, 4.1 g.

1H NMR (CDCl3): δ 4.55 (s, 2H), 7.55 (m, 2H), 7.70 (m, 1H).

Preparation 72b 4-bromomethyl-3-chlorobenzoic Acid

A mixture of 4-bromomethyl-3-chlorobenzonitrile (0.24 g) and hydrogen bromide:
solution (48 wt. % in water, 3.0 mL) was heated overnight in a sealed vial at 100° C.

The mixture was cooled to room temperature, diluted with water and extracted with ethyl acetate. The combined extracts were extracted with diluted aqueous potassium carbonate solution and the combined aqueous extracts were acidified by the addition of 1.0 M aqueous hydrochloric acid and then extracted with ethyl acetate. The combined extracts were dried over sodium sulfate and the solvent removed under reduced pressure to afford title compound as a white solid, 0.10 g.

MS: ESI (+ve) (Method B): 250 (M+H)+, Retention time 3.2 min.

Preparation 72c (4-bromomethyl-3-chlorophenyl)pyrrolidin-1-yl-methanone

A mixture of 4-bromomethyl-3-chlorobenzoic acid (0.090 g) and thionyl chloride (3.0 mL) was heated at 85° C. for 90 minutes. The mixture was cooled to room temperature and concentrated under reduced pressure. The residue was dissolved in dichloromethane and the resulting solution cooled to 0° C. and then treated with N,N-diisopropylethylamine, followed by pyrrolidine (0.030 mL). The mixture was stirred at 0° C. for 20 minutes, diluted with saturated aqueous sodium hydrogen carbonate solution and extracted with dichloromethane. The combined extracts were washed with water, dried over sodium sulfate and concentrated under reduced pressure. The residue was purified by column chromatography on silica gel, eluting with a mixture of cyclohexane and ethyl acetate (4:1 by volume) to afford title compound as a yellow oil, 0.070 g.

$^1$H NMR (CDCl$_3$): δ 1.90 (m, 4H), 3.40 (m, 2H), 3.65 (m, 2H), 4.70 (s, 2H), 7.40 (dd, J=1.6, 7.8 Hz, 1H), 7.50 (d, J=7.8 Hz, 1H), 7.55 (d, J=1.6 Hz, 1H).

Preparation 72d

2-[2-chloro-4-(pyrrolidine-1-carbonyl)benzyl]-3-oxopentanoic Acid Ethyl Ester

A solution of 3-oxopentanoic acid ethyl ester (14 mL) in 1,2-dimethoxyethane (25 mL) was added to a stirred suspension of sodium hydride (60% in oil, 3.7 g) in 1,2-dimethoxyethane (250 mL) and N,N-dimethylformamide (30 mL) at 0° C. and the resulting mixture was stirred at 0° C. for 10 minutes. A solution of (4-bromomethyl-3-chlorophenyl)pyrrolidin-1-ylmethanone (9.7 g) in 1,2-dimethoxyethane (25 mL) was added and the resulting mixture warmed to room temperature and then stirred at this temperature for 20 hours. The mixture was diluted with saturated aqueous ammonium chloride solution, extracted with diethyl ether and the combined extracts washed with saturated aqueous sodium chloride solution and then dried over magnesium sulfate. The solvent was removed under reduced pressure and the residue purified by column chromatography on silica gel, eluting with a mixture of cyclohexane and ethyl acetate (9:1 by volume) to afford title compound, 1.8 g.

MS: ESI (+ve) (Method B): 266 (M+H)$^+$, Retention time 3.4 min.

Preparation 72e

{3-[2-chloro-4-(pyrrolidine-1-carbonyl)benzyl]-2-ethyl-8-fluoro-4-oxo-1,4-dihydroquinolin-5-yloxy}acetic Acid Methyl Ester The title compound was prepared by the method of Preparation 65c using 2-[2-chloro-4-(pyrrolidine-1-carbonyl)benzyl]-3-oxopentanoic acid ethyl ester and (3-amino-4-fluorophenoxy)acetic acid methyl ester.

MS: ESI (+ve) (Method B): 501 (M+H)$^+$, Retention time 2.9 min.

Preparation 72f

{3-[2-chloro-4-(pyrrolidine-1-carbonyl)benzyl]-4-difluoromethoxy-2-ethyl-8-fluoroquinolin-5-yloxy}acetic Acid Methyl Ester The title compounds were prepared by the method of Preparation 65d using {3-[2-chloro-4-(pyrrolidine-1-carbonyl)benzyl]-2-ethyl-8-fluoro-4-oxo-1,4-dihydroquinolin-5-yloxy}acetic acid methyl ester.

MS: ESI (+ve) (Method B): 551 (M+H)$^+$, Retention time 3.5 min.

Preparation 72g

{3-[2-chloro-4-(pyrrolidine-1-carbonyl)benzyl]-4-difluoromethoxy-2-ethyl-8-fluoroquinolin-5-yloxy}acetic Acid A mixture of {3-[2-chloro-4-(pyrrolidine-1-carbonyl)benzyl]-4-difluoromethoxy-2-ethyl-8-fluoroquinolin-5-yloxy}acetic acid methyl ester (0.26 g), tetrahydrofuran (5.0 mL), water (5.0 mL) and lithium hydroxide (0.040 g) was stirred at room temperature for 20 minutes. The mixture was washed with ethyl acetate and the aqueous phase acidified by the addition of 1.0 M aqueous hydrochloric acid and then extracted with ethyl acetate. The combined extracts were dried over magnesium sulfate and the solvent removed under reduced pressure. Purification of the residue by preparative reverse-phase HPLC, using a gradient of acetonitrile in water gave title compound as an off-white solid, 0.13 g.

$^1$H NMR (DMSO-d6): δ 1.20 (t, J=7.4 Hz, 3H), 1.80-1.95 (m, 4H), 2.80 (q, J=7.4 Hz, 2H), 3.40 (t, J=6.4 Hz, 2H), 3.50 (t, J=7.0 Hz, 2H), 4.45 (s, 2H), 4.85 (s, 2H), 6.70 (d, J=8.0 Hz, 1H), 6.90 (dd, J=3.7, 8.8 Hz, 1H), 7.10 (t, J=75 Hz, 1H), 7.25 (dd, J=1.7, 8.0 Hz, 1H), 7.40 (dd, J=8.0, 10 Hz, 1H), 7.60 (d, J=1.7 Hz, 1H).

MS: ESI (+ve) (Method A): 537 (M+H)$^+$, Retention time 10.1 min.

MS: ESI (+ve) (Method B): 537 (M+H)$^+$, Retention time 3.6 min.

Example 73

(S)-2-{3-[2-chloro-4-(pyrrolidine-1-carbonyl)benzyl]-4-difluoromethoxy-2-ethyl-8-fluoroquinolin-5-yloxy}propionic Acid

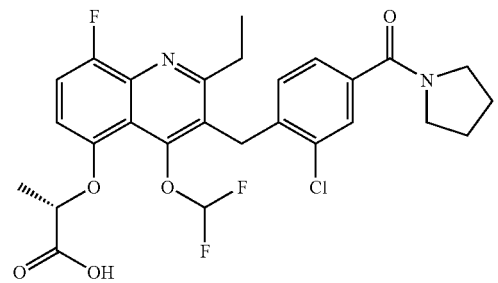

Preparation 73a (S)-2-{3-[2-chloro-4-(pyrrolidine-1-carbonyl)benzyl]-2-ethyl-8-fluoro-4-oxo-1,4-dihydroquinolin-5-yloxy}propionic Acid Methyl Ester The title compound was prepared by the method of Preparation 65c using 2-[2-chloro-4-(pyrrolidine-1-carbonyl)benzyl]-3-oxopentanoic acid ethyl ester and (S)-2-(3-amino-4-fluorophenoxy)propionic acid methyl ester.

MS: ESI (+ve) (Method B): 515 (M+H)+, Retention time 3.2 min.

Preparation 73b (S)-2-{3-[2-chloro-4-(pyrrolidine-1-carbonyl)benzyl]-4-difluoromethoxy-2-ethyl-8-fluoroquinolin-5-yloxy}propionic Acid Methyl Ester The title compounds were prepared by the method of Preparation 65d using (S)-2-{3-[2-chloro-4-(pyrrolidine-1-carbonyl)benzyl]-2-ethyl-8-fluoro-4-oxo-1,4-dihydroquinolin-5-yloxy}propionic acid methyl ester.

MS: ESI (+ve) (Method B): 565 (M+H)+, Retention time 3.7 min.

Preparation 73c (S)-2-{3-[2-chloro-4-(pyrrolidine-1-carbonyl)benzyl]-4-difluoromethoxy-2-ethyl-8-fluoroquinolin-5-yloxy}propionic Acid A mixture of (S)-2-{3-[2-chloro-4-(pyrrolidine-1-carbonyl)benzyl]-4-difluoromethoxy-2-ethyl-8-fluoroquinolin-5-yloxy}propionic acid methyl ester (0.75 g), tetrahydrofuran (20 mL), water (20 mL) and lithium hydroxide (0.11 g) was stirred at room temperature for 20 minutes. The mixture was washed with ethyl acetate and the aqueous phase acidified by the addition of 1.0 M aqueous hydrochloric acid and then extracted with ethyl acetate. The combined extracts were dried over magnesium sulfate and the solvent removed under reduced pressure. Purification of the residue by column chromatography on C-18 column, eluting with a mixture of water and methanol (4:1 to 0:1 by volume) gave title compound as an off-white solid, 0.20 g.

$^1$H NMR (DMSO-d6): δ 1.20 (t, J=7.5 Hz, 3H), 1.65 (d, J=6.8 Hz, 3H), 1.85-1.95 (m, 4H), 2.80 (m, 2H), 3.40 (t, J=6.4 Hz, 2H), 3.50 (t, J=6.9 Hz, 2H), 4.40 (d, J=17 Hz, 1H), 4.50 (d, J=17 Hz, 1H), 5.10 (q, J=6.8 Hz, 1H), 6.70 (d, J=8.0 Hz, 1H), 6.85 (dd, J=3.6, 8.8 Hz, 1H), 7.15 (dd, J=70, 81 Hz, 1H); 7.25 (dd, J=1.7, 8.0 Hz, 1H), 7.35 (dd, J=8.8, 10 Hz, 1H), 7.60 (d, J=1.7 Hz, 1H).

MS: ESI (+ve) (Method A): 551 (M+H)+, Retention time 10.6 min.

Example 74 and 75

(S)-2-[3-(2,4-dichlorobenzyl)-4-difluoromethoxy-2-ethyl-8-fluoroquinolin-5-yloxy]propionic Acid and (S)-2-[3-(2,4-dichlorobenzyl)-2-ethyl-8-fluoro-4-methoxyquinolin-5-yloxy]propionic Acid

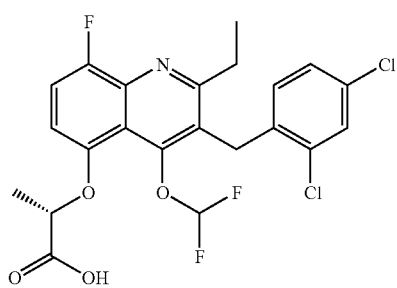

-continued

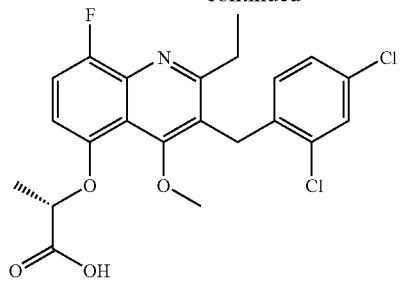

Preparation 74a and 75a (S)-2-(3-amino-4-fluorophenoxy)propionic Acid Methyl Ester A solution of 3-amino-4-fluorophenol (4.1 g) in N,N-dimethylformamide (15 mL) was added dropwise to a stirred suspension of sodium hydride (60% in oil, 1.3 g) in N,N-dimethylformamide (35 mL) at 0° C. The mixture was stirred a room temperature for 30 minutes, cooled 0° C. and then (R)-2-chloropropionic acid methyl ester (4.0 g) was added in one portion. The resulting mixture was stirred at room temperature overnight and then treated with saturated aqueous ammonium chloride solution. The mixture was extracted with ethyl acetate and the combined extracts, washed with saturated aqueous sodium chloride solution and then dried over magnesium sulfate. The solvent was removed under reduced pressure and purification of the residue by column chromatography on silica gel, eluting with a mixture of dichloromethane and ethyl acetate (1:0 to 3:2 by volume) to give the mixture of title compounds as golden oil, 2.5 g.

$^1$H NMR (CDCl$_3$): δ 1.55 (d, J=6.7 Hz, 3H), 3.75 (s, 3H), 4.65 (q, J=6.7 Hz, 1H), 6.15 (dt, J=3.0, 8.8 Hz, 1H), 6.35 (dd, J=3.0, 7.5 Hz, 1H), 6.85 (dd, J=8.8, 10.6 Hz, 1H).

Preparation 74b and 75b (S)-2-[3-(2,4-dichlorobenzyl)-2-ethyl-8-fluoro-4-oxo-1,4-dihydroquinolin-5-yloxy]propionic Acid Methyl Ester The title compounds were prepared by the method of Preparation 65c using (S)-2-(3-amino-4-fluorophenoxy)propionic acid methyl ester and 2-(2,4-dichlorobenzyl)-3-oxopentanoic acid methyl ester.

MS: ESI (+ve) (Method B): 452 (M+H)+, Retention time 3.8 min.

Preparation 74b and 75b (S)-2-[3-(2,4-dichlorobenzyl)-4-difluoromethoxy-2-ethyl-8-fluoroquinolin-5-yloxy]propionic Acid Methyl Ester and (S)-2-[3-(2,4-dichlorobenzyl)-2-ethyl-8-fluoro-4-methoxyquinolin-5-yloxy]propionic Acid Methyl Ester The title compounds were prepared by the method of Preparation 65d using (S)-2-[3-(2,4-dichlorobenzyl)-2-ethyl-8-fluoro-4-oxo-1,4-dihydroquinolin-5-yloxy]propionic acid methyl ester.

(S)-2-[3-(2,4-dichlorobenzyl)-4-difluoromethoxy-2-ethyl-8-fluoroquinolin-5-yloxy]propionic Acid Methyl Ester MS: ESI (+ve) (Method B): 502 (M+H)+, Retention time 4.5 min.

(S)-2-[3-(2,4-dichlorobenzyl)-2-ethyl-8-fluoro-4-methoxyquinolin-5-yloxy]propionic Acid Methyl Ester MS: ESI (+ve) (Method B): 466 (M+H)+, Retention time 4.3 min.

Preparation 74c and 75c (S)-2-[3-(2,4-dichlorobenzyl)-4-difluoromethoxy-2-ethyl-8-fluoroquinolin-5-yloxy]propionic Acid and (S)-2-[3-(2,4-dichlorobenzyl)-2-ethyl-8-fluoro-4-methoxyquinolin-5-yloxy]propionic Acid A mixture of (S)-2-[3-(2,4-dichlorobenzyl)-4-difluoromethoxy-2-ethyl-8-fluoroquinolin-5-yloxy]propionic acid methyl ester and (S)-2-[3-(2,4-dichlorobenzyl)-2-ethyl-8-fluoro-4-methoxyquinolin-5-yloxy]propionic acid methyl ester (0.58 g), methanol (10 mL), water (0.8 mL) and 5.0 M aqueous lithium hydroxide solution (0.40 mL) was stirred at room temperature overnight. The mixture was acidified by the addition of glacial acetic acid and concentrated under reduced pressure. Purification of the residue by column chromatography on C-18 column, eluting with a mixture of water and acetonitrile (4:1 to 0:1 by volume) gave (S)-2-[3-(2,4-dichlorobenzyl)-4-difluoromethoxy-2-ethyl-8-fluoroquinolin-5-yloxy]propionic acid as a while solid, 0.23 and (S)-2-[3-(2,4-dichlorobenzyl)-2-ethyl-8-fluoro-4-methoxyquinolin-5-yloxy]propionic acid as a white solid, 0.035 g.

(S)-2-[3-(2,4-dichlorobenzyl)-4-difluoromethoxy-2-ethyl-8-fluoroquinolin-5-yloxy]propionic Acid $^1$H NMR (DMSO-d6): δ 1.15 (t, J=7.4 Hz, 3H), 1.40 (d, J=6.7 Hz, 3H), 2.60-2.80 (m, 2H), 4.20 (d, J=17 Hz, 1H), 4.35 (d, J=17 Hz, 1H), 4.60 (d, J=6.7 Hz, 1H), 6.55 (d, J=8.4 Hz, 1H), 6.75 (dd, J=3.8, 9.1 Hz, 1H), 7.20 (dd, J=2.2, 8.4 Hz, 1H), 7.40 (dd, J=8.9, 10.4 Hz, 1H), 7.65 (d, J=2.2 Hz, 1H), 8.25 (dd, J=66, 86 Hz, 1H). MS: ESI (+ve) (Method A): 488 (M+H)+, Retention time 14.1 min.

(S)-2-[3-(2,4-dichlorobenzyl)-2-ethyl-8-fluoro-4-methoxyquinolin-5-yloxy]propionic Acid $^1$H NMR (DMSO-d6): δ 1.15 (t, J=7.3 Hz, 3H), 1.40 (d, J=6.7 Hz, 3H), 2.65 (m, 2H), 3.80 (s, 3H), 4.10 (d, J=17 Hz, 1H), 4.20 (d, J=17 Hz, 1H), 4.35 (q, J=6.7 Hz, 1H), 8.60 (m, 2H), 7.20 (dd, J=2.2, 8.4 Hz, 1H), 7.30 (dd, J=8.8, 11 Hz, 1H), 7.60 (d, J=2.2 Hz, 1H).

MS: ESI (+ve) (Method A): 452 (M+H)+, Retention time 12.7 min.

Example 76

[3-(2-chloro-4-cyclobutylcarbamoylbenzyl)-4-difluoromethoxy-2-ethyl-8-fluoroquinolin-5-yloxy]acetic Acid

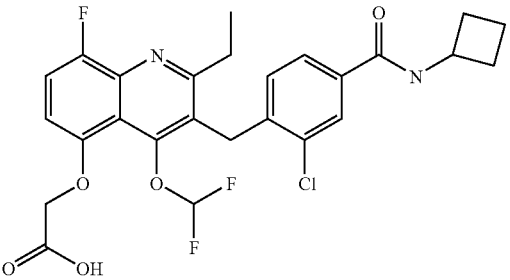

Preparation 76a 4-bromomethyl-3-chloro-N-cyclobutylbenzamide

A mixture of 4-bromomethyl-3-chlorobenzoic acid (1.4 g) and thionyl chloride (10 mL) was heated at reflux for 5 hours. The mixture was cooled to room temperature, diluted with toluene and concentrated under reduced pressure. The residue was dissolved in dichloromethane (10 mL) and the resulting solution cooled to 0° C. and then treated dropwise with a mixture of N,N-diisopropylethylamine (1.1 mL) and cyclobutylamine (0.48 mL). The resulting mixture was stirred at room temperature overnight, diluted dichloromethane and washed with saturated aqueous sodium hydrogen carbonate solution and saturated aqueous sodium chloride solution and then dried over magnesium sulfate. The solvent was removed under reduced pressure and the residue purified by column chromatography on silica gel, eluting with a mixture of dichloromethane and ethyl acetate (1:1 by volume) to afford title compound as an oil, 0.070 g.

MS: ESI (+ve) (Method B): 303 (M+H)+, Retention time 3.4 min.

Preparation 76b 2-(2-chloro-4-cyclobutylcarbamoyl-benzyl)-3-oxopentanoic Acid Ethyl Ester A suspension of potassium tert-butoxide (0.34 g) in anhydrous tetrahydrofuran (15 mL) at 0° C. was treated with a mixture of tert-butanol (1.0 mL) and 3-oxopentanoic acid ethyl ester (038 mL). The mixture was stirred at 0° C. for 45 minutes and then a solution of 4-bromomethyl-3-chloro-N-cyclobutylbenzamide (0.67 g) in tetrahydrofuran (5.0 mL) was added and the resulting mixture heated at 70° C. for 24 hours. The mixture was cooled to room temperature, diluted with water and the tetrahydrofuran removed under reduced pressure. The residue was extracted with ethyl acetate and the combined extracts washed With saturated aqueous sodium chloride solution and dried over magnesium sulfate. The solvent was removed under reduced pressure and the residue purified by column chromatography on silica gel, eluting with a mixture of ethyl acetate and cyclohexane (1:5 by volume) to afford title compound, 0.44 g.

MS: ESI (+ve) (Method B): 366 (M+H)+, Retention time 3.7 min.

Preparation 76c

[3-(8-chloro-4-cyclobutylcarbamoylbenzyl)-2-ethyl-8-fluoro-4-oxo-1,4-dihydroquinolin-5-yloxy]acetic Acid Methyl Ester The title compound was prepared by the method of Preparation 65c using 2-(2-chloro-4-cyclobutylcarbamoylbenzyl)-3-oxopentanoic acid ethyl ester and (3-amino-4-fluorophenoxy)acetic acid methyl ester.

MS: ESI (+ve) (Method B): 501 (M+H)$^+$, Retention time 2.9 min.

Preparation 76d

[3-(2-chloro-4-cyclobutylcarbamoylbenzyl)-4-difluoromethoxy-2-ethyl-8-fluoroquinolin-5-yloxy]acetic Acid Methyl Ester The title compounds were prepared by the method of Preparation 65d using [3-(2-chloro-4-cyclobutylcarbamoylbenzyl)-2-ethyl-8-fluoro-4-oxo-1,4-dihydroquinolin-5-yloxy]acetic acid methyl ester.

MS: ESI (+ve) (Method B): 551 (M+H)$^+$, Retention time 3.6 min.

Preparation 76e

[3-(2-chloro-4-cyclobutylcarbamoylbenzyl)-4-difluoromethoxy-2-ethyl-8-fluoroquinolin-5-yloxy]acetic Acid A mixture of [3-(2-chloro-4-cyclobutylcarbamoylbenzyl)-4-difluoromethoxy-2-ethyl-8-fluoroquinolin-5-yloxy]acetic acid methyl ester (0.23 g), tetrahydrofuran (5.0 mL) and 1.0 M aqueous lithium hydroxide solution (1.2 mL) was stirred at room temperature for 30 minutes. The mixture was concentrated under reduced pressure, acidified by the addition of sodium dihydrogenphosphate and extracted with ethyl acetate. The combined extracts were dried over magnesium sulfate and the solvent removed under reduced pressure. Purification of the residue by column chromatography on C-18 column, eluting with a mixture of water and methanol gave title compound as an off-white solid, 0.13 g.

$^1$H NMR (DMSO-d6): δ 1.15 (t, J=7.4 Hz, 3H), 1.60 (m, 2H), 2.00 (m, 2H), 2.15 (m, 2H), 2.70 (q, J=7.4 Hz, 2H), 4.35 (m, 3H), 4.80 (s, 2H), 6.65 (d, J=8.1 Hz, 1H); 6.95 (dd, J=3.8, 9.0 Hz, 1H), 7.25 (t, J=75 Hz, 1H), 7.50 (dd, J=9.0, 10 Hz, 1H), 7.55 (dd, J=1.7, 8.1 Hz, 1H), 7.95 (d, J=1.7 Hz, 1H), 8.65 (d, J=7.5 Hz, 1H).

MS: ESI (+ve) (Method A): 537 (M+H)$^+$, Retention time 10.9 min.

Example 77

(S)-2-[3-(2-chloro-4-cyclobutylcarbamoylbenzyl)-4-difluoromethoxy-2-ethyl-8-fluoroquinolin-5-yloxy] propionic acid

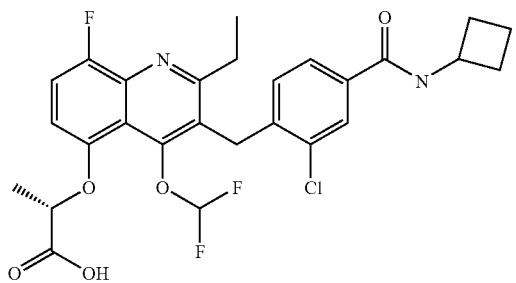

Preparation 77a (S)-2-[3-(2-chloro-4-cyclobutylcarbamoylbenzyl)-2-ethyl-8-fluoro-4-oxo-1,4-dihydroquinolin-5-yloxy] propionic Acid Methyl Ester The title compound was prepared by the method of Preparation 65c using 2-(2-chloro-4-cyclobutylcarbamoylbenzyl)-3-oxopentanoic acid ethyl ester and (S)-2-(3-amino-4-fluorophenoxy)propionic acid methyl ester.

MS: ESI (+ve) (Method B): 515 (M+H)$^+$, Retention time 2.9 min.

Preparation 77b (S)-2-[3-(2-chloro-4-cyclobutylcarbamoylbenzyl)-4-difluoromethoxy-2-ethyl-8-fluoroquinolin-5-yloxy] propionic Acid Methyl Ester The title compounds were prepared by the method of Preparation 65d using (S)-2-[3-(2-chloro-4-cyclobutylcarbamoylbenzyl)-2-ethyl-8-fluoro-4-oxo-1,4-dihydroquinolin-5-yloxy]propionic acid methyl ester.

MS: ESI (+ve) (Method B): 565 (M+H)$^+$, Retention time 3.8 min.

Preparation 77c (S)-2-[3-(2-chloro-4-cyclobutylcarbamoylbenzyl)-4-difluoromethoxy-2-ethyl-8-fluoroquinolin-5-yloxy] propionic Acid A mixture of (S)-2-[3-(2-chloro-4-cyclobutylcarbamoylbenzyl)-4-difluoromethoxy-2-ethyl-8-fluoroquinolin-5-yloxy]propionic acid methyl ester (0.18 g), tetrahydrofuran (5.0 mL) and 1.0 M aqueous lithium hydroxide solution (1.0 mL) was stirred at room temperature for 3 hours. The mixture was concentrated under reduced pressure, acidified by the addition of sodium dihydrogenphosphate and extracted with ethyl acetate. The combined extracts were dried over magnesium sulfate and the solvent removed under reduced pressure. Purification of the residue by column chromatography on C-18 column, eluting with a mixture of water and methanol (9:1 to 0:1 by volume) gave title compound as a pale yellow solid, 0.13 g.

$^1$H NMR (DMSO-d6): δ 1.20 (t, J=7.6 Hz, 3H), 1.60 (d, J=6.7 Hz, 3H), 1.65 (m, 2H), 2.05 (m, 2H), 2.20 (m, 2H), 2.75 (m, 2H), 4.40 (m, 3H), 5.10 (q, J=6.7 Hz, 1H), 6.70 (d, J=8.1 Hz, 1H), 6.90 (dd, J=3.4, 9.0 Hz, 1H), 7.35 (t, J=75 Hz, 1H), 7.55 (dd, J=9.0, 10 Hz, 1H), 7.60 (dd, J=1.8, 8.1 Hz, 1H), 8.00 (d, J=1.8 Hz, 1H), 8.70 (d, J=7.5 Hz, 1H).

MS: ESI (+ve) (Method A): 551 (M+H)$^+$, Retention time 10.9 min.

MS: ESI (+ve) (Method B): 551 (M+H)$^+$, Retention time 3.9 min.

Example 78

[3-(4-chlorobenzyl)-4,7-dimethylquinolin-5-yloxy]acetic Acid

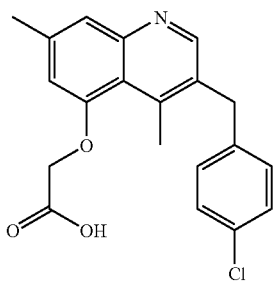

Preparation 78a 2-chloro-3-(4-chlorobenzyl)-4,7-dimethylquinolin-5-ol

A solution of 3-(4-chlorobenzyl)-5-hydroxy-4,7-dimethyl-1H-quinolin-2-one (1.8 g) in phosphorus oxychloride (9.0 mL) was heated at 180° C. in a microwave reactor for 15 minutes. The solution was poured onto a mixture of ice and water and the resulting precipitate collected by filtration, washed with water and then dried to afford title compound, 2.3 g.

Preparation 78b

[2-chloro-3-(4-chlorobenzyl)-4,7-dimethylquinolin-5-yloxy]acetic Acid Methyl Ester A mixture of 2-chloro-3-(4-chlorobenzyl)-4,7-dimethylquinolin-5-ol (1.7 g), N,N-dimethylformamide (25 mL), potassium carbonate (2.1 g) and bromoacetic acid methyl ester (1.1 g) was stirred at 60° C. overnight. The mixture was cooled to room temperature, diluted with water and the resulting precipitate collected by filtration, washed with water and then dried to afford title compound, 0.53 g.

MS: ESI (+ve) (Method B): 404 (M+H)$^+$, Retention time 4.4 min.

Preparation 78c

[3-(4-chlorobenzyl)-4,7-dimethylquinolin-5-yloxy]acetic Acid Methyl Ester

A mixture of [2-chloro-3-(4-chlorobenzyl)-4,7-dimethylquinolin-5-yloxy]acetic acid methyl ester (0.20 g), palladium (10 wt. % on activated carbon, 0.020 g), ethanol (7.0 mL) and 1.0 M aqueous hydrochloric acid (1.5 mL) was stirred at 40° C. for 17 hours under an atmosphere of hydrogen. The mixture was filtered through hyflo, washed with ethanol and the filtrate concentrated under reduced pressure to afford title compound, 0.18 g.

MS: ESI (+ve) (Method B): 370 (M+H)$^+$, Retention time 2.8 min.

Preparation 78d

[3-(4-chlorobenzyl)-4,7-dimethylquinolin-5-yloxy]acetic Acid

A mixture of [3-(4-chlorobenzyl)-4,7-dimethylquinolin-5-yloxy]acetic acid methyl ester (1.8 g), tetrahydrofuran and potassium trimethylsilanolate (0.19 g) was heated at 100° C. in a microwave reactor for 5 minutes. The mixture was concentrated under reduced pressure, diluted with water and acidified by the addition of concentrated hydrochloric acid. The resulting precipitate was collected by filtration and purified by preparative reverse-phase HPLC, using a gradient over 30 minutes of acetonitrile in water (35% to 95% organic modifier) to afford title compound, 0.015 g.

$^1$H NMR (DMSO-d6): δ 2.40 (s, 3H), 2.75 (s, 3H), 4.15 (s, 2H), 4.80 (s, 2H), 6.80 (s, 1H), 7.10 (d, J=8.5 Hz, 2H), 7.30 (d, J=8.5 Hz, 2H), 7.35 (m, 1H), 8.65 (s, 1H), 13.00 (br s, 1H).

MS: ESI (+ve) (Method A): 356 (M+H)$^+$, Retention time 7.3 min.

MS: ESI (+ve) (Method B): 356 (M+H)$^+$, Retention time 2.3 min.

Example 79

[3-(4-chlorobenzyl)-2-methylquinolin-5-yloxy]acetic Acid

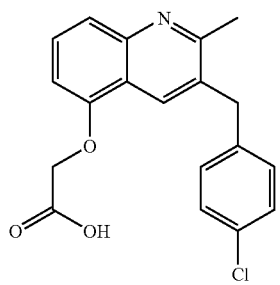

Preparation 79a

[3-(4-chlorobenzyl)-2-methylquinolin-5-yloxy]acetic Acid Methyl Ester

A mixture of [4,8-dichloro-3-(4-chlorobenzyl)-2-methylquinolin-5-yloxy]acetic acid methyl ester (0.13 g), palladium (5 wt. % on activated carbon, 0.010 g), ethanol (5.0 mL) and 1.0 M aqueous hydrochloric acid (1.0 mL) was stirred at room temperature for 17 hours under an atmosphere of hydrogen. The mixture was filtered through hyflo, washing with ethanol and water and the solvent removed under reduced pressure to afford title compound, 0.11 g.

Preparation 79b

[3-(4-chlorobenzyl)-2-methylquinolin-5-yloxy]acetic Acid

A solution of [3-(4-chlorobenzyl)-2-methylquinolin-5-yloxy]acetic acid methyl ester (0.11 g), ethanol (6.0 mL), water (2.0 mL) and saturated aqueous lithium hydroxide solution (2.0 mL) was stirred at room temperature for 5 hours. The ethanol was removed under reduced pressure and the pH of the residue adjusted to 4 by the addition of glacial acetic acid. The resulting precipitate was collected by filtration, washed with water and purification by preparative reverse-phase HPLC using a gradient over 37 minutes of acetonitrile in water (20% to 95% of organic modifier) gave title compound as a yellow gum, 0.028 mg.

$^1$H NMR (DMSO-d6): δ 2.70 (s, 3H), 4.30 (s, 2H), 5.00 (s, 2H), 7.10 (d, J=8.1 Hz, 1H), 7.25 (d, J=8.5 Hz, 2H), 7.40 (d, J=8.5 Hz, 2H), 7.65 (d, J=8.5 Hz, 1H), 7.80 (t, J=8.1 Hz, 1H), 8.65 (s, 1H).

MS: ESI (+ve) (Method A): 342 (M+H)$^+$, Retention time 6.9 min.

MS: ESI (+ve) (Method B): 342 (M+H)$^+$, Retention time 2.2 min.

Biological Methods

Compounds of the invention of formula [1] were tested using the following biological test methods to determine their ability to displace PGD$_2$ from the CRTH2 receptor and for their ability to antagonise the functional effects of PGD$_2$ at the CRTH2 receptor in a whole cell system.

Radioligand Binding Assay

The receptor binding assay is performed in a final volume of 200 μL binding buffer [10 mM BES (pH 7.4), 1 mM EDTA, 10 mM manganese chloride, 0.01% BSA] and 1 nM [$^3$H]-PGD$_2$ (Amersham Biosciences UK Ltd). Ligands are added in assay buffer containing a constant amount of DMSO (1% by volume). Total binding is determined using 1% by volume of DMSO in assay buffer and non-specific binding is determined using 10 μM of unlabeled PGD$_2$ (Sigma). Human embryonic kidney (HEK) cell membranes (3.5 μg) expressing the CRTH2 receptor are incubated with 1.5 mg wheatgerm agglutinin SPA beads and 1 nM [$^3$H]-PGD$_2$ (Amersham Biosciences UK Ltd) and the mixture incubated for 3 hours at room temperature. Bound [$^3$H]-PGD$_2$ is detected using a Microbeta TRILUX liquid scintillation counter (Perkin Elmer). Compound IC$_{50}$ value is determined using a 6-point dose response curve in duplicate with a semi-log compound dilution series. IC$_{50}$ calculations are performed using Excel and XLfit (Microsoft), and this value is used to determine a Ki value for the test compound using the Cheng-Prusoff equation.

Compounds of the invention that have been tested in the binding assay are, illustrated below in the following Table.

| Example | |
|---|---|
| 1 | +++ |
| 2 | +++ |
| 3 | +++ |
| 4 | ++ |
| 5 | ++ |
| 6 | +++ |
| 7 | +++ |
| 8 | +++ |
| 9 | +++ |
| 10 | ++ |
| 11 | +++ |
| 12 | +++ |
| 13 | ++ |
| 14 | + |
| 15 | +++ |
| 16 | +++ |
| 17 | +++ |
| 18 | +++ |
| 19 | +++ |
| 20 | +++ |
| 21 | +++ |
| 22 | +++ |
| 23 | + |
| 24 | +++ |
| 25 | ++ |
| 26 | +++ |
| 27 | +++ |
| 28 | ++ |
| 29 | +++ |
| 30 | +++ |
| 31 | ++ |
| 32 | ++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | + |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | + |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | + |
| 79 | + |

Key:
"+++" CRTH2 Ki < 100 nM;
"++" Ki < 1 μM;
"+" Ki < 10 μM

Functional Assay: Calcium Mobilisation

Stable CHO-K1 cells co-expressing the CRTH2 receptor and the G-protein Gα16 are seeded (40,000 cells per well in a plating volume of 75 μL in F-12 Hams supplemented with 1% foetal bovine serum) into collagen-coated 96-well plates 24 hours prior to the assay. The cells are then loaded with a fluorescence-imaging plate reader (FLIPR) calcium kit dye (Calcium 3 kit, Molecular Devices Ltd) containing 5 mM final concentration of probenecid and incubated at 37° C. for 1 hour in a 5% $CO_2$ atmosphere. The fluorescence emission caused by intracellular calcium mobilization elicited by the $PGD_2$ at the CRTH2 receptor is determined with a FLEXstation benchtop scanning and integrated fluid transfer workstation (Molecular Devices Ltd). To detect antagonists and determine compound $IC_{50}$, compounds are pre-incubated at varying concentrations with the loaded cells for 15 minutes at 37° C., 5% $CO_2$, prior to the addition of the agonist at its $EC_{80}$ value. Compounds and agonist are added in Hanks balanced salt solution containing 20 mM HEPES and 0.1% BSA). The fractional response values for each well are calculated by subtracting the basal response from the peak response. Results are calculated as the mean of triplicate wells using Excel and XLfit (Microsoft).

As an illustration, the following compounds were shown to have $IC_{50}$s of <1 μM in this assay: 20, 42; and the following compounds had $IC_{50}$s<100 nM in this assay: 12, 18.

The invention claimed is:

1. A compound of formula [1] or a pharmaceutically acceptable salt or N-oxide thereof:

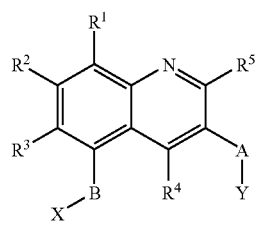

[1]

in which:
R$^1$ is hydrogen, $C_1$-$C_6$alkyl, fully or partially fluorinated $C_1$-$C_6$alkyl, cyclopropyl, halo, —S(O)$_n$R$^6$, —SO$_2$NR$^7$R$^8$, —NR$^7$R$^8$, —NR$^7$C(O)R$^6$, —CO$_2$R$^7$, —C(O)NR$^7$R$^8$, —C(O)R$^6$, —NO$_2$, or —CN;
R$^2$, R$^3$, R$^4$ and R$^5$ are independently hydrogen, $C_1$-$C_6$alkyl, fully or partially fluorinated $C_1$-$C_6$alkyl, cyclopropyl, halo, —S(O)$_n$R$^6$, —SO$_2$NR$^7$R$^8$, —NR$^7$R$^8$, —NR$^7$C(O)R$^6$, —CO$_2$R$^7$, —C(O)NR$^7$R$^8$, —C(O)R$^6$, —NO$_2$, or —CN or a group —OR$^9$;
wherein each R$^6$ is independently $C_1$-$C_6$alkyl, fully or partially fluorinated $C_1$-$C_6$alkyl, cycloalkyl, aryl, or heteroaryl;
R$^7$, R$^8$ are independently $C_1$-$C_6$alkyl, fully or partially fluorinated $C_1$-$C_6$alkyl, cycloalkyl, cycloalkyl-($C_1$-$C_6$alkyl)-, aryl, heteroaryl or hydrogen;
R$^9$ is $C_1$-$C_6$alkyl, fully or partially fluorinated $C_1$-$C_6$alkyl, cycloalkyl, cycloalkyl-($C_1$-$C_6$alkyl)-, or a group —SO$_2$R$^6$;
A is —CHR$^{10}$—, —C(O)—, —S(O)$_n$—, —O—, or —NR$^{10}$— wherein n is an integer from 0-2 and R$^{10}$ is hydrogen, $C_1$-$C_3$alkyl, or fully or partially fluorinated $C_1$-$C_3$alkyl group;
B is a divalent radical selected from —CH$_2$—, —CH$_2$CH$_2$—, —CHR$^{11}$—, —CR$^{11}$R$^{12}$—, —CH$_2$CHR$^{11}$— in either orientation, —CH$_2$CR$^{11}$R$^{12}$— in either orientation, —OCH(CH$_3$)— or —OCH$_2$— wherein the oxygen is attached to the ring carrying R$^1$, R$^2$ and R$^3$;
—CHR$^{11}$CHR$^{12}$— in either orientation, and —(CR$^{11}$R$^{12}$)$_p$—Z— wherein Z is attached to the ring carrying R$^1$, R$^2$ and R$^3$; wherein
R$^{11}$ is $C_1$-$C_3$alkyl, cyclopropyl, or fully or partially fluorinated $C_1$-$C_3$alkyl;
R$^{12}$ is methyl or fully or partially fluorinated methyl;
p is independently 1 or 2; and
Z is —O—, —NH—, or —S(O)$_n$—, wherein n is an integer from 0-2;
X is a carboxylic acid, tetrazole, 3-hydroxyisoxazole, hydroxamic acid, phosphinate, phosphonate, phosphonamide, or sulfonic acid group, or a group of formula C(=O)NHSO$_2$R$^6$ or SO$_2$NHC(=O)R$^6$; and
Y is aryl, heteroaryl, aryl-fused-heterocycloalkyl, heteroaryl-fused-cycloalkyl, heteroaryl-fused-heterocycloalkyl or aryl-fused-cycloalkyl group;
wherein R$^4$ and R$^5$ are not simultaneously hydrogen.

2. The compound as claimed in claim 1, wherein R$^1$ is fluoro or chloro; R$^2$ and R$^3$ are hydrogen; R$^4$ is methyl, ethyl, methoxy or difluoromethoxy; R$^5$ is methyl, ethyl, ethoxy, isopropoxy, difluoromethoxy or cyano; A is —CH$_2$—, —O— or —S(O)$_n$— wherein n is 0, 1 or 2; B is —CH$_2$—, —OCH(CH$_3$)— or —OCH$_2$— wherein the oxygen is attached to the ring carrying R$^1$, R$^2$ and R$^3$; X is —CO$_2$H; and Y is 4-fluorophenyl, 4-chlorophenyl, 4-methanesulfonylphenyl, 4-ethanesulfonylphenyl, 4-(morpholine-4-sulfonyl)phenyl, 4-(pyrrolidine-1-carbonyl)phenyl, 2,4-difluorophenyl, 2,4-dichlorophenyl, 2-chloro-2-fluorophenyl, 2-chloro-4-fluorophenyl, 2-chloro-4-methanesulfonylphenyl, 2-chloro-4-(pyrrolidine-1-carbonyl)phenyl or 2-chloro-4-cyclobutylcarbamoyl.

3. A compound selected from the group consisting of:
[8-chloro-3-(4-chlorobenzyl)-4-difluoromethoxy-2-ethylquinolin-5-yloxy]acetic acid,
[3-(4-chlorobenzyl)-4-difluoromethoxy-2-ethyl-8-fluoroquinolin-5-yloxy]acetic acid,
[3-(2,4-dichlorobenzyl)-2-difluoromethoxy-8-fluoro-4-methylquinolin-5-yloxy]acetic acid,
[4-difluoromethoxy-2-ethyl-8-fluoro-3-(4-fluorobenzyl)quinolin-5-yloxy]acetic acid,
[3-(2,4-difluorobenzyl)-4-difluoromethoxy-2-ethyl-8-fluoroquinolin-5-yloxy]acetic acid,
[3-(2,4-dichlorobenzyl)-4-difluoromethoxy-2-ethyl-8-fluoroquinolin-5-yloxy]acetic acid,
[3-(4-chloro-2-fluorobenzyl)-2-difluoromethoxy-8-fluoro-4-methylquinolin-5-yloxy]acetic acid,
[8-chloro-3-(4-chlorobenzyl)-2-difluoromethoxy-4-methylquinolin-5-yloxy]acetic acid,
[3-(2-chloro-4-fluorobenzyl)-4-difluoromethoxy-2-ethyl-8-fluoroquinolin-5-yloxy]acetic acid,
[3-(2-chloro-4-fluorobenzyl)-2-difluoromethoxy-8-fluoro-4-methylquinolin-5-yloxy]acetic acid,
[8-chloro-3-(4-chloro-2-fluorobenzyl)-4-difluoromethoxy-2-ethylquinolin-5-yloxy]acetic acid,
[3-(4-chloro-2-fluorobenzyl)-4-difluoromethoxy-2-ethyl-8-fluoroquinolin-5-yloxy]acetic acid,
{4-difluoromethoxy-2-ethyl-8-fluoro-3-[4-(morpholine-4-sulfonyl)benzyl]quinolin-5-yloxy}acetic acid,
{4-difluoromethoxy-2-ethyl-8-fluoro-3-[4-(pyrrolidine-1-carbonyl)benzyl]quinolin-5-yloxy}acetic acid,
2-[3-(2,4-dichlorobenzyl)-2-difluoromethoxy-8-fluoro-4-methylquinolin-5-yloxy]propionic acid,
(S)-2-[3-(2,4-dichlorobenzyl)-2-difluoromethoxy-8-fluoro-4-methylquinolin-5-yloxy]propionic acid,
2-[8-chloro-3-(4-chlorobenzyl)-2-difluoromethoxy-4-methylquinolin-5-yloxy]propionic acid,
{8-chloro-4-difluoromethoxy-2-ethyl-3-[4-(pyrrolidine-1-carbonyl)benzyl]-quinolin-5-yloxy}acetic acid, {3-[2-chloro-4-(pyrrolidine-1-carbonyl)benzyl]-4-difluoromethoxy-2-ethyl-8-fluoroquinolin-5-yloxy}acetic acid,
(S)-2-{3-[2-chloro-4-(pyrrolidine-1-carbonyl)benzyl]-4-difluoromethoxy-2-ethyl-8-fluoroquinolin-5-yloxy}propionic acid,
(S)-2-[3-(2,4-dichlorobenzyl)-4-difluoromethoxy-2-ethyl-8-fluoroquinolin-5-yloxy]propionic acid,
[3-(2-chloro-4-cyclobutylcarbamoylbenzyl)-4-difluoromethoxy-2-ethyl-8-fluoroquinolin-5-yloxy]acetic acid; and
(S)-2-[3-(2-chloro-4-cyclobutylcarbamoylbenzyl)-4-difluoromethoxy-2-ethyl-8-fluoroquinolin-5-yloxy]propionic acid;
and pharmaceutically acceptable salts or N-oxides thereof.

4. The compound as claimed in claim 1, wherein $R^1$ is Cl, $R^2$ and $R^3$ are H, $R^4$ is difluoromethoxy, $R^5$ is ethyl, A is —$CH_2$—, B is —O—$CH_2$—, X is carboxylic acid and Y is 4-chlorophenyl.

5. A pharmaceutical composition comprising
i) a compound of formula [1] or a pharmaceutically acceptable salt or N-oxide thereof:

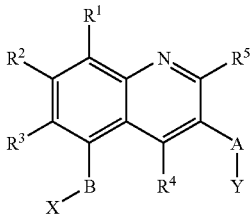

[1]

in which:
R$^1$ is hydrogen, $C_1$-$C_6$alkyl, fully or partially fluorinated $C_1$-$C_6$alkyl, cyclopropyl, halo, —S(O)$_n$R$^6$, —SO$_2$NR$^7$R$^8$, —NR$^7$R$^8$, —NR$^7$C(O)R$^6$, —CO$_2$R$^7$, —C(O)NR$^7$R$^8$, —C(O)R$^6$, —NO$_2$, or —CN;
R$^2$, R$^3$, R$^4$ and R$^5$ are independently hydrogen, $C_1$-$C_6$alkyl, fully or partially fluorinated $C_1$-$C_6$alkyl, cyclopropyl, halo, —S(O)$_n$R$^6$, —SO$_2$NR$^7$R$^8$, —NR$^7$R$^8$, —NR$^7$C(O)R$^6$, —CO$_2$R$^7$, —C(O)NR$^7$R$^8$, —C(O)R$^6$, —NO$_2$, or —CN or a group —OR$^9$;
wherein each R$^6$ is independently $C_1$-$C_6$alkyl, fully or partially fluorinated $C_1$-$C_6$alkyl, cycloalkyl, aryl, or heteroaryl;
R$^7$, R$^8$ are independently $C_1$-$C_6$alkyl, fully or partially fluorinated $C_1$-$C_6$alkyl, cycloalkyl, cycloalkyl-($C_1$-$C_6$alkyl)-, aryl, heteroaryl or hydrogen;
R$^9$ is $C_1$-$C_6$alkyl, fully or partially fluorinated $C_1$-$C_6$alkyl, cycloalkyl, cycloalkyl-($C_1$-$C_6$alkyl)-, or a group —SO$_2$R$^6$;
A is —CHR$^{10}$—, —C(O)—, —S(O)$_n$—, —O—, or —NR$^{10}$— wherein n is an integer from 0-2 and R$^{10}$ is hydrogen, $C_1$-$C_3$alkyl, or fully or partially fluorinated $C_1$-$C_3$alkyl group;
B is a divalent radical selected from —CH$_2$—, —CH$_2$CH$_2$—, —CHR$^{11}$—, —CR$^{11}$R$^{12}$—, —CH$_2$CHR$^{11}$— in either orientation, —CH$_2$CR$^{11}$R$^{12}$— in either orientation, —OCH(CH$_3$)— or —OCH$_2$— wherein the oxygen is attached to the ring carrying R$^1$, R$^2$ and R$^3$;
—CHR$^{11}$CHR$^{12}$— in either orientation, and —(CR$^{11}$R$^{12}$)$_p$—Z— wherein Z is attached to the ring carrying R$^1$, R$^2$ and R$^3$; wherein
R$^{11}$ is $C_1$-$C_3$alkyl, cyclopropyl, or frilly or partially fluorinated $C_1$-$C_3$alkyl;

R$^{12}$ is methyl or fully or partially fluorinated methyl;
p is independently 1 or 2; and
Z is —O—, —NH—, or —S(O)$_n$—, wherein n is an integer from 0-2;
X is a carboxylic acid, tetrazole, 3-hydroxyisoxazole, hydroxamic acid, phosphinate, phosphonate, phosphonamide, or sulfonic acid group, or a group of formula C(=O)NHSO$_2$R$^6$ or SO$_2$NHC(=O)R$^6$; and
Y is aryl, heteroaryl, aryl-fused-heterocycloalkyl, heteroaryl-fused-cycloalkyl, heteroaryl-fused-heterocycloalkyl or aryl-fused-cycloalkyl group; or
ii) a compound selected from the group consisting of:
[8-chloro-3-(4-chlorobenzyl)-4-difluoromethoxy-2-ethylquinolin-5-yloxy]acetic acid,
[3-(4-chlorobenzyl)-4-difluoromethoxy-2-ethyl-8-fluoroquinolin-5-yloxy]acetic acid,
[3-(2,4-dichlorobenzyl)-2-difluoromethoxy-8-fluoro-4-methylquinolin-5-yloxy]acetic acid,
[4-difluoromethoxy-2-ethyl-8-fluoro-3-(4-fluorobenzyl)quinolin-5-yloxy]acetic acid,
[3-(2,4-difluorobenzyl)-4-difluoromethoxy-2-ethyl-8-fluoroquinolin-5-yloxy]acetic acid,
[3-(2,4-dichlorobenzyl)-4-difluoromethoxy-2-ethyl-8-fluoroquinolin-5-yloxy]acetic acid,
[3-(4-chloro-2-fluorobenzyl)-2-difluoromethoxy-8-fluoro-4-methylquinolin-5-yloxy]acetic acid,
[8-chloro-3-(4-chlorobenzyl)-2-difluoromethoxy-4-methylquinolin-5-yloxy]acetic acid,
[3-(2-chloro-4-fluorobenzyl)-4-difluoromethoxy-2-ethyl-8-fluoroquinolin-5-yloxy]acetic acid,
[3-(2-chloro-4-fluorobenzyl)-2-difluoromethoxy-8-fluoro-4-methylquinolin-5-yloxy]acetic acid,
[8-chloro-3-(4-chloro-2-fluorobenzyl)-4-difluoromethoxy-2-ethylquinolin-5-yloxy]acetic acid,
[3-(4-chloro-2-fluorobenzyl)-4-difluoromethoxy-2-ethyl-8-fluoroquinolin-5-yloxy]acetic acid,
{4-difluoromethoxy-2-ethyl-8-fluoro-3-[4-(morpholine-4-sulfonyl)benzyl]quinolin-5-yloxy}acetic acid,
{4-difluoromethoxy-2-ethyl-8-fluoro-3-[4-(pyrrolidine-1-carbonyl)benzyl]quinolin-5-yloxy}acetic acid,
2-[3-(2,4-dichlorobenzyl)-2-difluoromethoxy-8-fluoro-4-methylquinolin-5-yloxy]propionic acid,
(S)-2-[3-(2,4-dichlorobenzyl)-2-difluoromethoxy-8-fluoro-4-methylquinolin-5-yloxy]propionic acid,
2-[8-chloro-3-(4-chlorobenzyl)-2-difluoromethoxy-4-methylquinolin-5-yloxy]propionic acid,
{8-chloro-4-difluoromethoxy-2-ethyl-3-[4-(pyrrolidine-1-carbonyl)benzyl]-quinolin-5-yloxy}acetic acid,
{3-[2-chloro-4-(pyrrolidine-1-carbonyl)benzyl]-4-difluoromethoxy-2-ethyl-8-fluoroquinolin-5-yloxy}acetic acid,
(S)-2-{3-[2-chloro-4-(pyrrolidine-1-carbonyl)benzyl]-4-difluoromethoxy-2-ethyl-8-fluoroquinolin-5-yloxy}propionic acid,
(S)-2-[3-(2,4-dichlorobenzyl)-4-difluoromethoxy-2-ethyl-8-fluoroquinolin-5-yloxy]propionic acid,
[3-(2-chloro-4-cyclobutylcarbamoylbenzyl)-4-difluoromethoxy-2-ethyl-8-fluoroquinolin-5-yloxy]acetic acid; and
(S)-2-[3-(2-chloro-4-cyclobutylcarbamoylbenzyl)-4-difluoromethoxy-2-ethyl-8-fluoroquinolin-5-yloxy]propionic acid;
and pharmaceutically acceptable salts and N-oxides thereof;
together with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,858,640 B2 | Page 1 of 1 |
| APPLICATION NO. | : 12/066603 | |
| DATED | : December 28, 2010 | |
| INVENTOR(S) | : Michael Colin Cramp et al. | |

It is certified that error appears in the above-identified patent and that said Letters Patent is hereby corrected as shown below:

Column 133,
Line 64 (Claim 5), "frilly" should read --fully--

Signed and Sealed this
Eighth Day of March, 2011

David J. Kappos
*Director of the United States Patent and Trademark Office*